US006897305B2

(12) United States Patent
Ji et al.

(10) Patent No.: US 6,897,305 B2
(45) Date of Patent: May 24, 2005

(54) CALCIUM CHANNEL DRUGS AND USES

(75) Inventors: Yu-Hua Ji, Redwood City, CA (US); Maya Natarajan, San Diego, CA (US); John H. Griffin, Atherton, CA (US); Thomas E. Jenkins, La Honda, CA (US)

(73) Assignee: Theravance, Inc., South San Francisco, CA (US)

( * ) Notice: Subject to any disclaimer, the term of this patent is extended or adjusted under 35 U.S.C. 154(b) by 109 days.

(21) Appl. No.: 09/456,429

(22) Filed: Dec. 8, 1999

(65) Prior Publication Data

US 2003/0073127 A1 Apr. 17, 2003

Related U.S. Application Data

(63) Continuation-in-part of application No. 09/325,557, filed on Jun. 4, 1999, now abandoned.
(60) Provisional application No. 60/103,866, filed on Oct. 12, 1998.

(51) Int. Cl.$^7$ .................... C07D 515/02; C07D 279/16; C07D 231/56; G01N 33/53
(52) U.S. Cl. ...................... 540/491; 435/7.1; 435/7.2; 436/501; 436/518; 544/51; 544/358; 544/359; 544/392; 544/396; 548/361.1; 514/211.04; 514/211.05; 514/211.06; 514/211.07
(58) Field of Search .................. 435/7.1, 7.2; 436/501; 436/518; 544/51, 388, 359, 392, 396; 548/361.1; 540/491; 514/211.04–211.07

(56) References Cited

U.S. PATENT DOCUMENTS

| | | | |
|---|---|---|---|
| 3,845,770 A | | 11/1974 | Theeuwes et al. |
| 4,326,525 A | | 4/1982 | Swanson et al. |
| 4,532,248 A | | 7/1985 | Franckowiak et al. |
| 4,725,597 A | * | 2/1988 | Devlin et al. ............... 514/252 |
| 4,771,057 A | | 9/1988 | Knaus et al. |
| 4,808,605 A | * | 2/1989 | Branca et al. ............... 514/394 |
| 4,902,514 A | | 2/1990 | Barclay et al. |
| 4,992,445 A | | 2/1991 | Lawter et al. |
| 5,001,139 A | | 3/1991 | Lawter et al. |
| 5,011,472 A | | 4/1991 | Aebischer et al. |
| 5,023,252 A | | 6/1991 | Hseih |
| 5,120,730 A | * | 6/1992 | Pifferi et al. ............... 514/211 |
| 5,378,698 A | * | 1/1995 | Yamamori et al. ........... 514/211 |
| 5,462,936 A | * | 10/1995 | Yamamori et al. ........... 514/211 |
| 5,463,564 A | | 10/1995 | Agrafiotis et al. |
| 5,571,827 A | | 11/1996 | Barberich et al. |
| 5,616,345 A | | 4/1997 | Geoghegan et al. |
| 5,686,495 A | | 11/1997 | Goldin et al. |
| 5,723,618 A | * | 3/1998 | Leung-Toung et al. ..... 546/121 |
| 5,767,131 A | * | 6/1998 | Gluchowski et al. ....... 514/318 |
| 5,846,839 A | | 12/1998 | Gallop et al. |
| 5,891,643 A | | 4/1999 | Fesik et al. |
| 6,420,560 B1 | * | 7/2002 | Numerof et al. ............ 544/362 |

FOREIGN PATENT DOCUMENTS

| | | |
|---|---|---|
| CA | 1 179 342 | 12/1984 |
| CA | 2240325 | 6/1998 |
| EP | 0052300 B1 | 5/1982 |
| EP | 0052300 A1 | 5/1982 |
| EP | 0 122 488 A1 * | 10/1984 |
| EP | 0 266 549 A1 * | 5/1988 |
| WO | WO 92/05802 | 4/1992 |
| WO | WO 93/06121 | 4/1993 |
| WO | 96/33972 | 10/1996 |
| WO | WO 97/21445 | 1/1997 |
| WO | WO 98/00439 | 1/1998 |
| WO | WO 98/34948 | 8/1998 |

OTHER PUBLICATIONS

Inoue et al. J. Med. Chem., 1991, vol. 34, No. 2, pp. 675–687.*

Nagao et al. Chem. Pharm. Bull., 1973, vol. 21, No. 1, pp. 92–97.*

Van Albada et al. Accession No.: 1995:776400; CAPLUS database on STN (Inorg. Chem. (1995), 34(19), pp. 4910–4917); Abstract only.*

Joslyn, A.F., et al. "Dimeric 1,4–dihydropryidines as calcium channel antagonists." *J. Med. Chem.* 31(8): 1489–1492 (1988).

Alker, D., et al. "Formation, Synthetic Utility and Structure Elucidation of a 2–Bromomethyl 1,4–Dihydropyridine." *Tetrahedron Letts.* 31: 1479–1482 (1990).

Arrowsmith, et al. "Long–Acting Dihydropyridine Calcium Antagonists. 1. 2–Alkoxymethyl Derivatives Incorporating Basic Substituents." *J. Med. Chem.* 29: 1696–1702 (1986).

Balboni, B., et al. "Calcium Antagonists: Vinylogues and bivalent ligands related to nifedipine." *Pharmazie.* 43: 318 (1988).

Bezprozvanny, I., et al. "Voltage–Dependent Blockade of Diverse Types of Voltage–Gated $Ca^{2+}$Channels Expressed in Xenopus Oocytes by the $Ca^{2+}$Channel Antagonist Mibefradil (Ro 40–5967)." *Molec. Pharmacol.* 48: 540–549 (1995).

Bossert, et al. "4–Aruldihydropyridines, a New Class of Highly Active Calcium Antagonists."*Angew. Chem. Int. Ed.* 20: 762–769 (1997).

Brittain, et al. "Relaxation of $K^+$Contracted Rabbit Aortic Strips Implies Calcium Channel Blockade." *Physiologist*, 28: 325 (1985).

(Continued)

Primary Examiner—Maurie Garcia Baker
(74) Attorney, Agent, or Firm—Jeffrey A. Hagenah; Roberta P. Saxon; Joyce G. Cohen

(57) ABSTRACT

Novel multibinding compounds are disclosed. The compounds of this invention comprise 2–10 ligands covalently connected, each of the ligands being capable of binding to a ligand binding site in a $Ca^{++}$ channel, thereby modulating the biological activities thereof.

3 Claims, 101 Drawing Sheets

OTHER PUBLICATIONS

Brenner, et al. "Encoded combinatorial chemistry." *Proc. Natl. Acad. Sci., USA*, 89: 5181 (1992).

Cremers, et al. "Effects of the Novel T–Type Calcium Channel Antagonist Mibefradil on Human Myocardial Contractility in Comparison with Nifedipine and Verapamil." *J. Cardiovasc. Pharmacol.* 29: 692–696 (1997).

Cross, PE., et al. "Selective Class III Antiarrhythmic Agents. 1. Bis(arylalkyl)amines." *J. Med. Chem.* 33(4): 1151 (1989).

Denyer, et al. "HTS Approaches to Voltage–Gated Ion Channel Drug Discovery." *Drug Discovery today*. 3(7):323–332 (1998).

Eltze, et al. "Stereoselective Inhibition of Thromboxane–Induced Coronary Vasoconstriction by 1,4–Dihydropyridine Calcium Channel Antagonists." *Chirality*, 2: 233–240 (1990).

Gordeev, et al. "A General and Efficient Solid Phase Synthesis of Qynazoline–2,4–diones." *Tetrahedron Lett.* 38(10): 1729–1732 (1997).

Gordeev, et al. "Approaches to Combinatorial synthesis of Heterocycles: A Solid Phase Synthesis of 1,4–Dihydropyridines." *J. Org. Chem.* 61: 924–928 (1996).

Hess, et al. "Different modes of Ca channel gating behaviour favoured by dihydropyridine Ca agonists and antagonists." *Nature* 311: 538–544 (1984).

Hockerman, et al. "Molecular Determinants of Drug Binding and Action on L–Type Calcium Channels." *Annu. Rev. Pharmacol. Toxicol.* 37: 361–96 (1997).

Joslyn, et al. "Dimeric 1,4–Dihydropyridines as Calcium Channel Antagonists." *J. Med. Chem.* 31: 1489–1492 (1988).

Kenny, et al. "The Application of High–throughput Screening to Novel Lead Discovery." Progress in Drug Research. Edited by Ernst Jucker. Herhauser Verlag: Basel, 1998, vol. 1, 246–269.

Kokubun, et al., "Studies on Ca Channels in Intact Cardiac Cells: Voltage–Dependent Effects and Cooperative Interactions of Dihydropyridine Enantiomers.." *Molec. Pharmacol.* 30: 571–584 (1986).

Liang, R., et al. "Parallel synthesis and screening of a solid phase carbohydrate library." *Science*, 274: 1520 (1996).

Osterrieder, W., et al. "In Vitro Phamacologic profile of Ro 40–5967, a Novel $Ca^{2+}$Channel Blocker with Potent Vasodilator but Weak Inotropic Action." *Cardiovasc. Pharmacol.* 13: 754–9 (1989).

PD–029361. Current drug report.

Portoghese, P.S. "The Role of Concepts in Structure–Activity Relationship Studies of Opioid Ligands." *J. Med. Chem.* 35(11): 1927–1937 (1992).

Rampe, D., et al., "New synthetic ligands for L–type voltage–gated calcium channels." *Prog. Drug. Res.* 40: 191–238 (1993).

Rovnyak, G.C., et al. "Dihydropyrimidine Calcium Channel Blockers. 4. Basic 3–Substituted–4–aryl–1, 4–dihydropyrimidine–5–carboxylic Acid Ester. Potent Antihypertensive Agents." *J. Med. Chem.* 35: 3254–3263 (1992).

Shuker, S.B., et al. "Discovering High–Affinity Ligands for Proteins, SAR by NMR." Science. 274: 1531–1534 (1996).

Tokuma, Y., et al. "Stereoselective pharmacokinetics of dihydropyridine calcium antagonists." *J. Chromatography A.*, 694: 181–193 (1995).

Yuen, P., et al. "Synthesis and SAR of sibustituted 1,2,3, 4–tetrahydroisoquinoloines as N type Calcium channel blockers." *Bioorg and Med. Chem. Lett.* 8: 2415 (1998).

Zeng, et al. "Automated Analytical/Preparative High Performance Liquid Chromatography–Mass Spectrometry System for the Rapid Characterization and Purification of Compound Libraries." *J. Chrom. A.* 794:3–13 (1998).

* cited by examiner

◯ = ligand
n+m+core<100 atoms

FIG. 21-1
Multivalent Calcium Antagonist Subunits
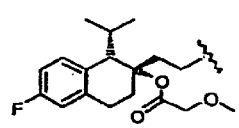
A
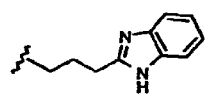
B
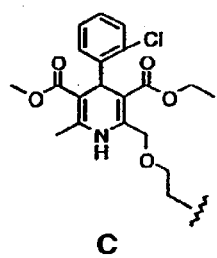
C
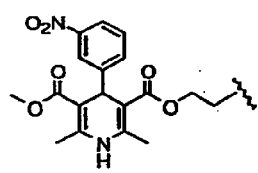
D
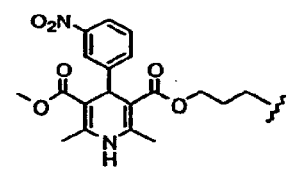
E
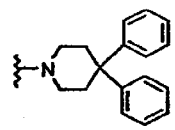
F
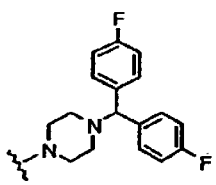
G
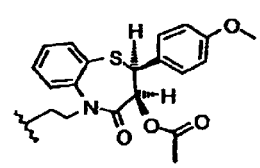
H Multibinding Calcium Channel Antagonist Table
| Cmpd | Subunit 1 | Linker | Subunit 2 |
|---|---|---|---|
| 1 | A | 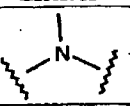 | A |
| 2 | A |  | A |
| 3 | A | 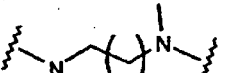 | A |
| 4 | A | 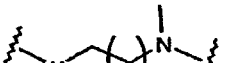 | A |
| 5 | A | 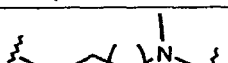 | A |
| 6 | A | 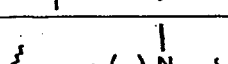 | A |
| 7 | A |  | A |
| 8 | A | 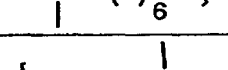 | A |
| 9 | A | 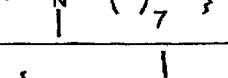 | A |
| 10 | A | 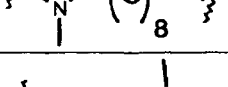 | A |
*FIG. 21-2*

| 11 | A | 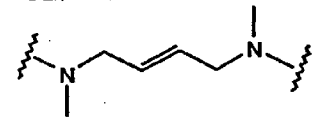 | A |
|----|---|---|---|
| 12 | A |  | A |
| 13 | A | 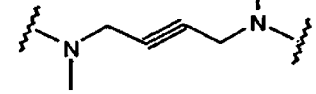 | A |
| 14 | A | 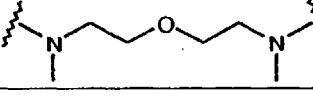 | A |
| 15 | A | 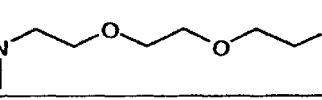 | A |
| 16 | A | 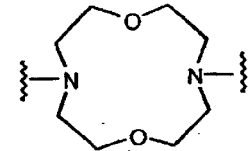 | A |
| 17 | A | 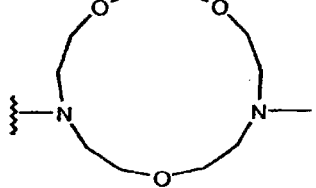 | A |
| 18 | A | 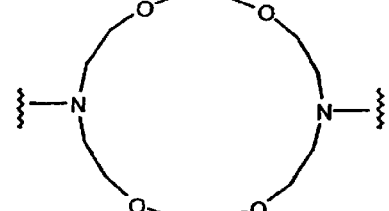 | A |
*FIG. 21-3*

| 19 | A | 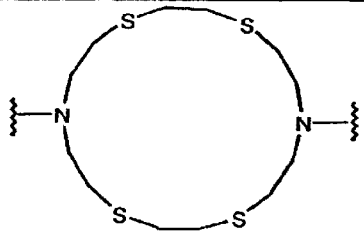 | A |
| 20 | A | 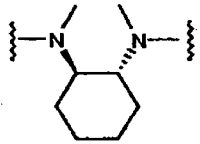 | A |
| 21 | A | 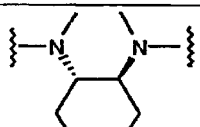 | A |
| 22 | A | 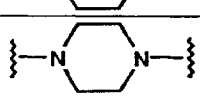 | A |
| 23 | A |  | A |
| 24 | A | 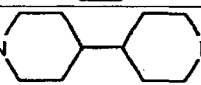 | A |
| 25 | A |  | A |
| 26 | A | 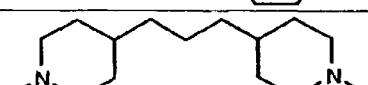 | A |
| 27 | A | 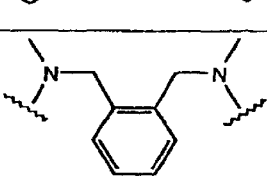 | A |
| 28 | A | 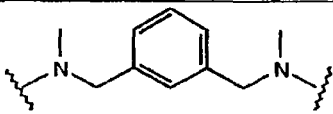 | A |
*FIG. 21-4*

| 29 | A | 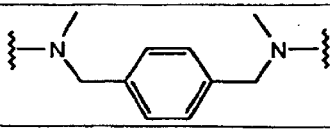 | A |
|---|---|---|---|
| 30 | A | 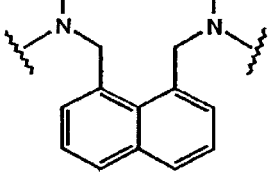 | A |
| 31 | A | 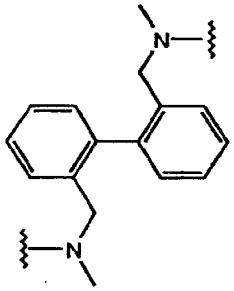 | A |
| 32 | A | 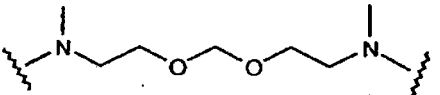 | A |
| 33 | A | 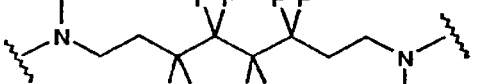 | A |
| 33 | A | 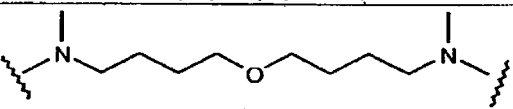 | A |
| 34 | A | 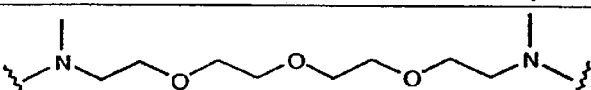 | A |
| 35 | A | 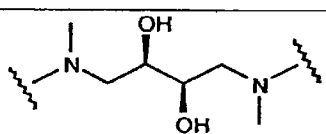 | A |
| 36 | A | 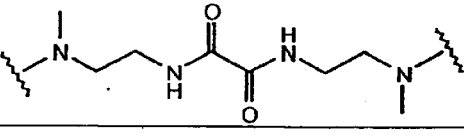 | A |
*FIG. 21-5*

| # | | | |
|---|---|---|---|
| 37 | A | ![N-(CH2)1-N] | B |
| 38 | A | ![N-(CH2)2-N] | B |
| 39 | A | ![N-(CH2)3-N] | B |
| 41 | A | ![N-(CH2)4-N] | B |
| 42 | A | ![N-(CH2)5-N] | B |
| 43 | A | ![N-(CH2)6-N] | B |
| 44 | A | ![N-(CH2)7-N] | B |
| 45 | A | ![N-(CH2)8-N] | B |
| 46 | A | ![N-(CH2)9-N] | B |
| 47 | A | ![N-CH2-CH=CH-CH2-N (trans)] | B |
| 48 | A | ![N-CH2-CH=CH-CH2-N (cis)] | B |

*FIG. 21-6*

| # | | | |
|---|---|---|---|
| 49 | A | [structure: N-CH2-C≡C-CH2-N with methyl groups] | B |
| 50 | A | [structure: N-CH2CH2-O-CH2CH2-N with methyl groups] | B |
| 51 | A | [structure: N-CH2CH2-O-CH2CH2-O-CH2CH2-N with methyl groups] | B |
| 52 | A | [structure: diaza crown ether with 2 oxygens] | B |
| 53 | A | [structure: diaza crown ether with 3 oxygens] | B |
| 54 | A | [structure: diaza crown ether with 4 oxygens] | B |
| 55 | A | [structure: diaza-tetrathia macrocycle] | B |
| 56 | A | [structure: trans-1,2-diaminocyclohexane moiety] | B |

FIG. 21-7

| 57 | A | 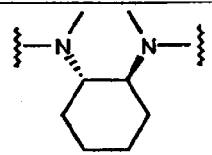 | B |
| 58 | A |  | B |
| 59 | A | 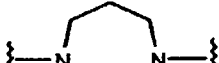 | B |
| 60 | A |  | B |
| 61 | A | 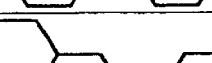 | B |
| 62 | A |  | B |
| 63 | A |  | B |
| 64 | A |  | B |
| 65 | A |  | B |
| 66 | A | 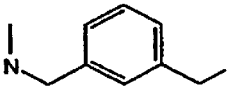 | B |
*FIG. 21-8*

| 67 | A | ![structure: biphenyl with two CH2-N groups] | B |
| 68 | A | ~N-CH2CH2-O-CH2-O-CH2CH2-N~ | B |
| 69 | A | ~N-CH2CH2-CF2-CF2-CF2-CF2-CH2CH2-N~ | B |
| 70 | A | ~N-(CH2)3-O-(CH2)3-N~ | B |
| 71 | A | ~N-CH2CH2-O-CH2CH2-O-CH2CH2-O-CH2CH2-N~ | B |
| 72 | A | ~N-CH2-CH(OH)-CH(OH)-CH2-N~ | B |
| 73 | A | ~N-CH2CH2-NH-C(O)-C(O)-NH-CH2CH2-N~ | B |
| 75 | A | ~N~ | C |
| 76 | A | ~N-(—)$_1$-N~ | C |
| 77 | A | ~N-(—)$_2$-N~ | C |

FIG. 21-9

| 78 | A | 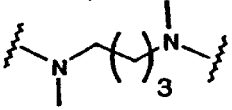 | C |
| 79 | A | 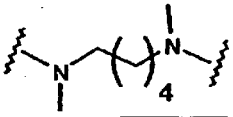 | C |
| 80 | A | 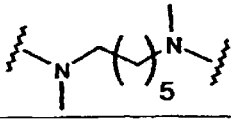 | C |
| 81 | A | 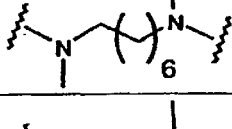 | C |
| 82 | A | 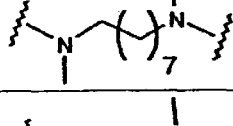 | C |
| 83 | A | 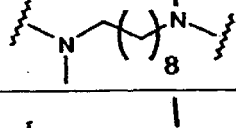 | C |
| 84 | A | 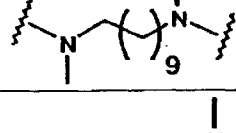 | C |
| 85 | A | 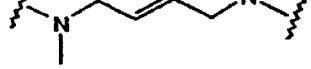 | C |
| 86 | A | 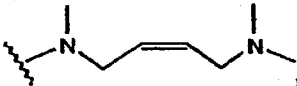 | C |
| 87 | A |  | C |
| 88 | A | 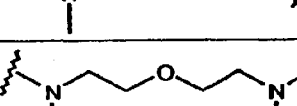 | C |
FIG. 21-10

| 89 | A | ⸝N(CH₃)CH₂CH₂OCH₂CH₂OCH₂CH₂N(CH₃)⸝ | C |
|----|---|---|---|
| 90 | A | (diazacrown with 2 O) | C |
| 91 | A | (diazacrown with 3 O) | C |
| 92 | A | (diazacrown with 4 O) | C |
| 93 | A | (diazadithia macrocycle) | C |
| 94 | A | (trans-1,2-diaminocyclohexane) | C |
| 95 | A | (trans-1,2-diaminocyclohexane) | C |
| 96 | A | (piperazine) | C |

FIG. 21-11

| 97 | A |  | C |
| 98 | A | 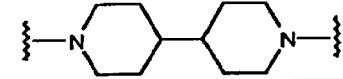 | C |
| 99 | A | 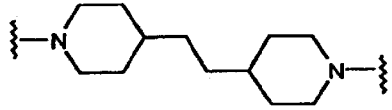 | C |
| 100 | A | 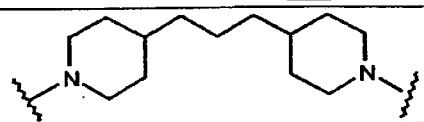 | C |
| 101 | A | 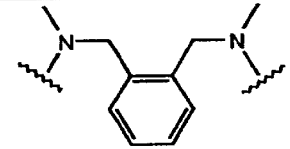 | C |
| 102 | A | 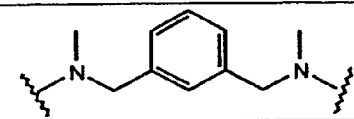 | C |
| 103 | A | 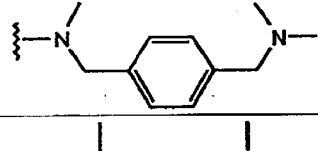 | C |
| 104 | A | 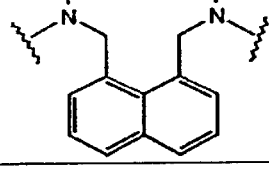 | C |
| 105 | A | 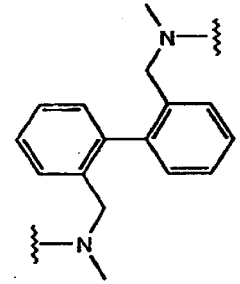 | C |
FIG. 21-12

| 106 | A | 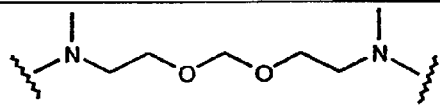 | C |
| 107 | A | 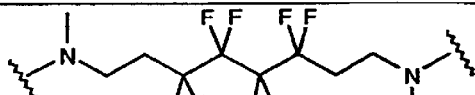 | C |
| 108 | A | 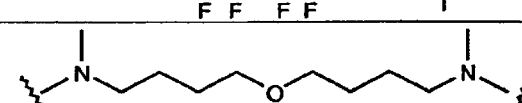 | C |
| 109 | A | 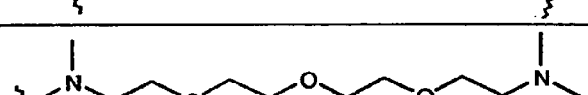 | C |
| 110 | A | 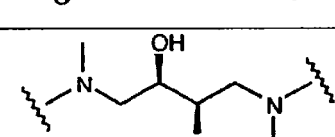 | C |
| 111 | A | 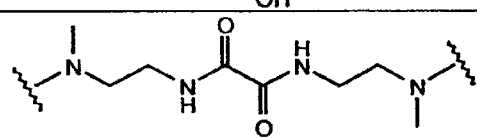 | C |
| 112 | A | 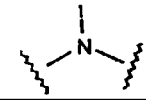 | D |
| 113 | A | 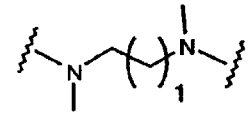 | D |
| 114 | A | 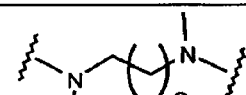 | D |
| 115 | A | 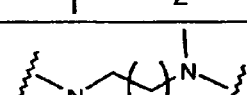 | D |
| 116 | A | 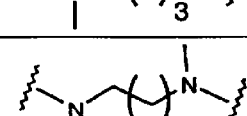 | D |
FIG. 21–13

| # | | | |
|---|---|---|---|
| 117 | A | ⸨N-(CH₂)₅-N⸩ | D |
| 118 | A | ⸨N-(CH₂)₆-N⸩ | D |
| 119 | A | ⸨N-(CH₂)₇-N⸩ | D |
| 120 | A | ⸨N-(CH₂)₈-N⸩ | D |
| 121 | A | ⸨N-(CH₂)₉-N⸩ | D |
| 122 | A | ⸨N-CH₂-CH=CH-CH₂-N⸩ (trans) | D |
| 123 | A | ⸨N-CH₂-CH=CH-CH₂-N⸩ (cis) | D |
| 124 | A | ⸨N-CH₂-C≡C-CH₂-N⸩ | D |
| 125 | A | ⸨N-CH₂CH₂-O-CH₂CH₂-N⸩ | D |
| 126 | A | ⸨N-CH₂CH₂-O-CH₂CH₂-O-CH₂CH₂-N⸩ | D |
| 127 | A | diaza-crown ether (N-CH₂CH₂-O-CH₂CH₂-N-CH₂CH₂-O-CH₂CH₂ cyclic) | D |

FIG. 21-14

| | | | |
|---|---|---|---|
| 128 | A | 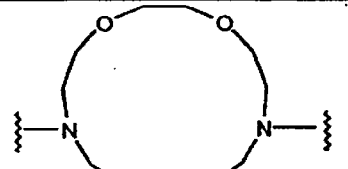 | D |
| 129 | A | 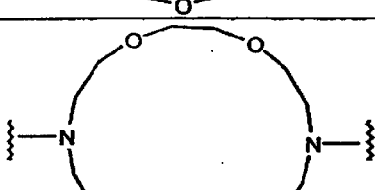 | D |
| 130 | A | 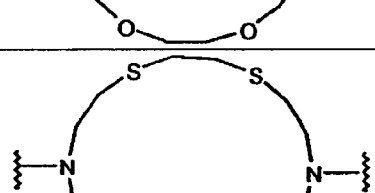 | D |
| 131 | A | 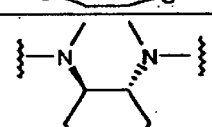 | D |
| 132 | A | 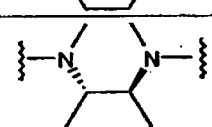 | D |
| 133 | A | 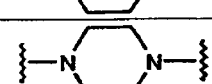 | D |
| 134 | A |  | D |
| 135 | A | 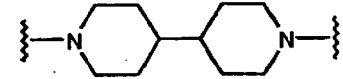 | D |
*FIG. 21-15*

| 136 | A |  | D |
| 137 | A | 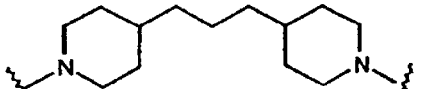 | D |
| 138 | A | 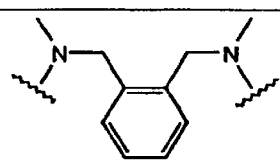 | D |
| 139 | A | 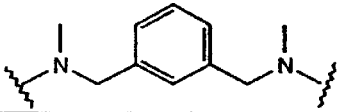 | D |
| 140 | A | 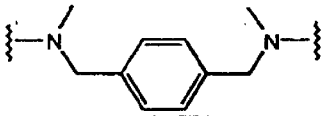 | D |
| 141 | A | 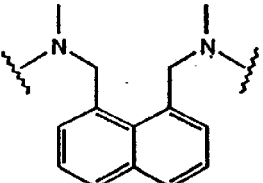 | D |
| 142 | A | 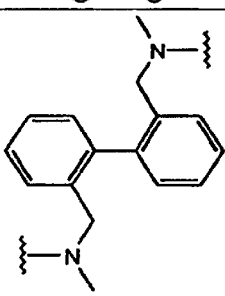 | D |
| 143 | A | 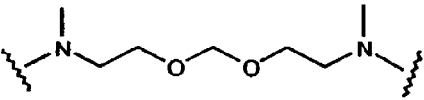 | D |
| 144 | A | 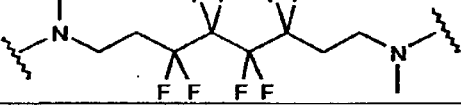 | D |
*FIG. 21-16*

| # | | Structure | |
|---|---|---|---|
| 145 | A | ~N-(CH2)3-O-(CH2)3-N~ (with methyl on each N) | D |
| 146 | A | ~N-CH2CH2-O-CH2CH2-O-CH2CH2-O-CH2CH2-N~ (with methyl on each N) | D |
| 147 | A | ~N-CH2-CH(OH)-CH(OH)-CH2-N~ (with methyl on each N) | D |
| 148 | A | ~N-CH2CH2-NH-C(O)-C(O)-NH-CH2CH2-N~ (with methyl on each N) | D |
| 149 | A | ~N~ (with methyl on N) | E |
| 150 | A | ~N-(CH2)1-N~ (with methyl on each N) | E |
| 151 | A | ~N-(CH2)2-N~ (with methyl on each N) | E |
| 152 | A | ~N-(CH2)3-N~ (with methyl on each N) | E |
| 153 | A | ~N-(CH2)4-N~ (with methyl on each N) | E |
| 154 | A | ~N-(CH2)5-N~ (with methyl on each N) | E |
| 155 | A | ~N-(CH2)6-N~ (with methyl on each N) | E |

FIG. 21-17

| 156 | A | 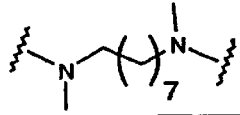 | E |
| 157 | A | 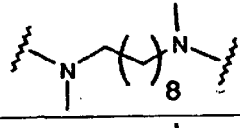 | E |
| 158 | A | 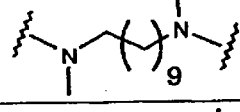 | E |
| 159 | A | 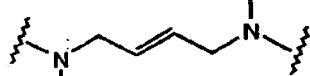 | E |
| 160 | A | 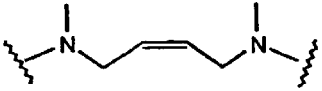 | E |
| 161 | A | 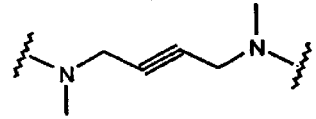 | E |
| 162 | A | 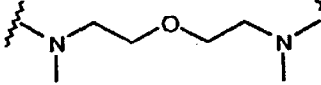 | E |
| 163 | A | 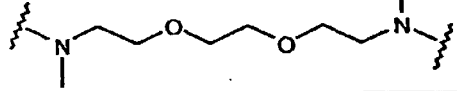 | E |
| 164 | A | 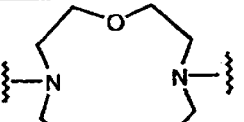 | E |
| 165 | A | 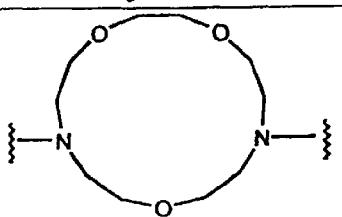 | E |
*FIG. 21-18*

| 166 | A | 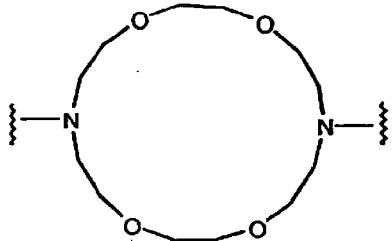 | E |
| 167 | A | 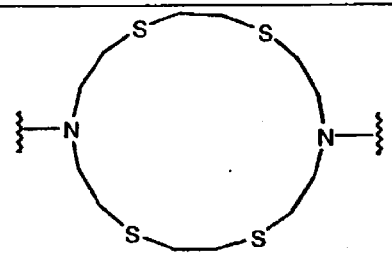 | E |
| 168 | A | 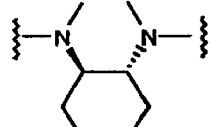 | E |
| 169 | A | 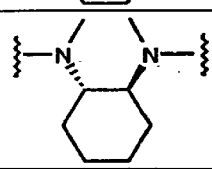 | E |
| 170 | A |  | E |
| 171 | A | 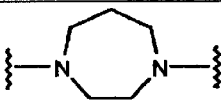 | E |
| 172 | A |  | E |
| 173 | A | 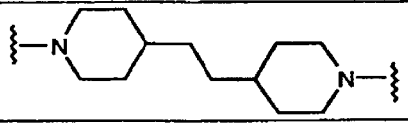 | E |
| 174 | A |  | E |
*FIG. 21-19*

| 175 | A | 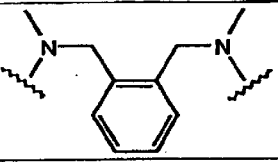 | E |
| 176 | A | 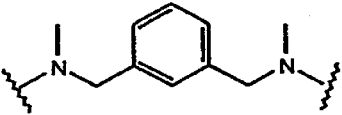 | E |
| 177 | A | 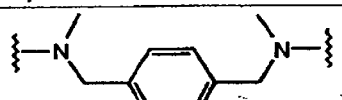 | E |
| 178 | A | 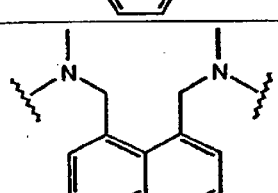 | E |
| 179 | A | 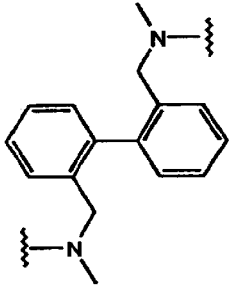 | E |
| 180 | A | 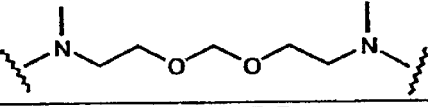 | E |
| 181 | A |  | E |
| 182 | A | 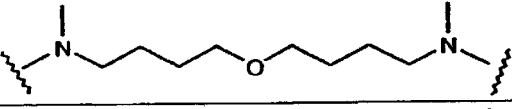 | E |
| 183 | A | 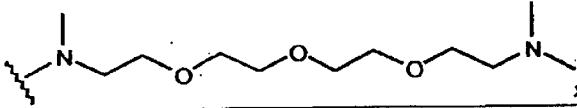 | E |
*FIG. 21-20*

| | | | |
|---|---|---|---|
| 184 | A |  | E |
| 185 | A |  | E |
| 186 | A |  | H |
| 187 | A |  | H |
| 188 | A |  | H |
| 189 | A |  | H |
| 190 | A |  | H |
| 191 | A |  | H |
| 192 | A |  | H |
| 193 | A |  | H |
| 194 | A |  | H |

| 195 | A | 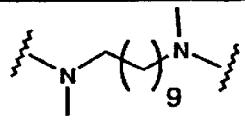 | H |
| 196 | A | 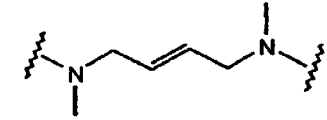 | H |
| 197 | A | 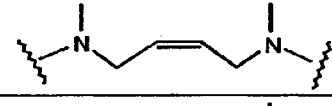 | H |
| 198 | A |  | H |
| 199 | A | 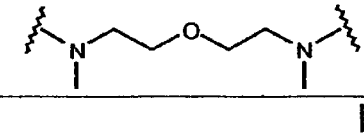 | H |
| 200 | A | 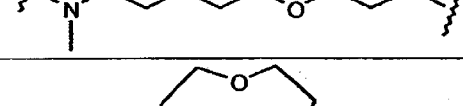 | H |
| 201 | A | 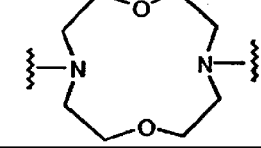 | H |
| 202 | A |  | H |
| 203 | A | 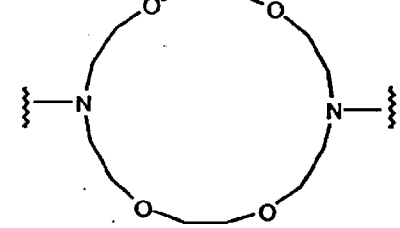 | H |
*FIG. 21-22*

| 204 | A | (macrocycle with two N and four S) | H |
| 205 | A | (trans-cyclohexane-1,2-diyl bis-N) | H |
| 206 | A | (cis-cyclohexane-1,2-diyl bis-N) | H |
| 207 | A | (piperazine) | H |
| 208 | A | (1,4-diazepane) | H |
| 209 | A | (4,4'-bipiperidine) | H |
| 210 | A | (1,2-bis(piperidin-4-yl)ethane) | H |
| 211 | A | (1,3-bis(piperidin-4-yl)propane) | H |
| 212 | A | (o-xylylenediamine, N,N'-dimethyl) | H |
| 213 | A | (m-xylylenediamine, N,N'-dimethyl) | H |

FIG. 21-23

| 214 | A | 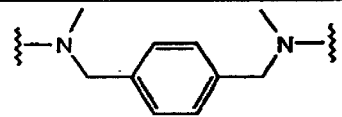 | H |
| 215 | A | 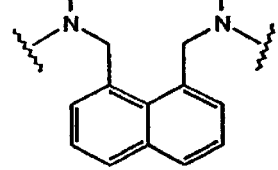 | H |
| 216 | A | 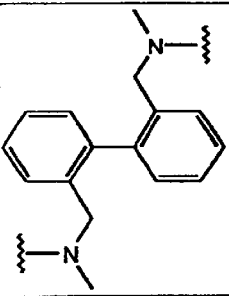 | H |
| 217 | A | 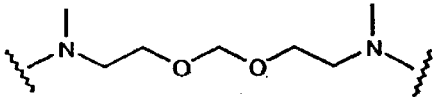 | H |
| 218 | A | 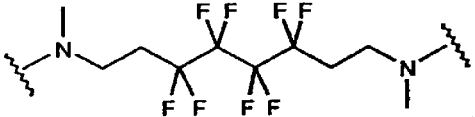 | H |
| 219 | A | 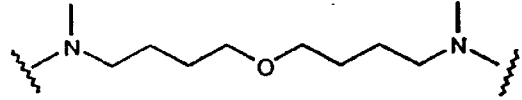 | H |
| 220 | A | 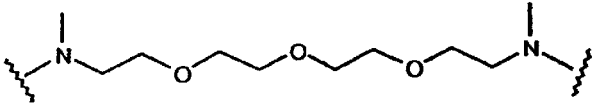 | H |
| 221 | A | 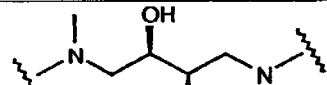 | H |
| 222 | A | 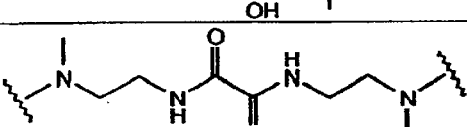 | H |
*FIG. 21-24*

| | | | |
|---|---|---|---|
| 223 | B | 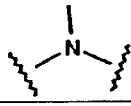 | C |
| 224 | B | 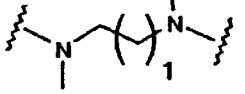 | C |
| 225 | B | 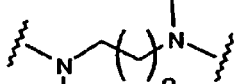 | C |
| 226 | B | 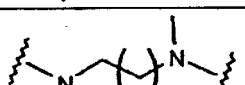 | C |
| 227 | B | 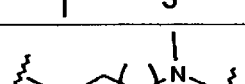 | C |
| 228 | B | 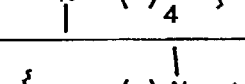 | C |
| 229 | B | 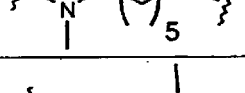 | C |
| 230 | B | 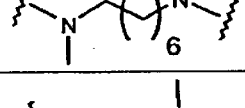 | C |
| 231 | B |  | C |
| 232 | B | 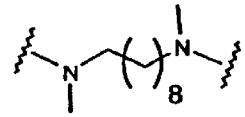 | C |
| 233 | B | 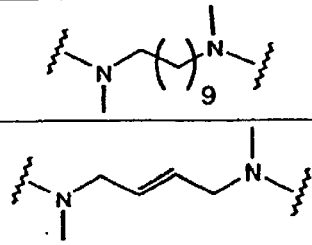 | C |
FIG. 21–25

| 234 | B | 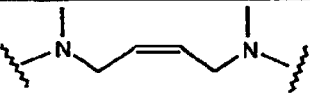 | C |
| 235 | B | 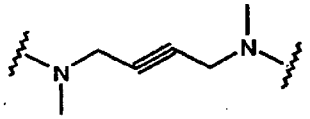 | C |
| 236 | B | 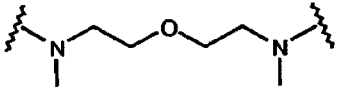 | C |
| 237 | B | 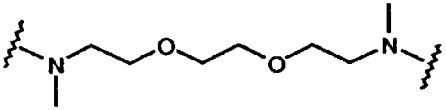 | C |
| 238 | B |  | C |
| 239 | B | 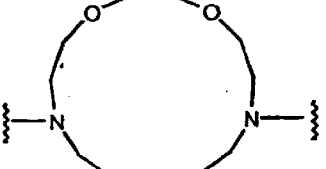 | C |
| 249 | B | 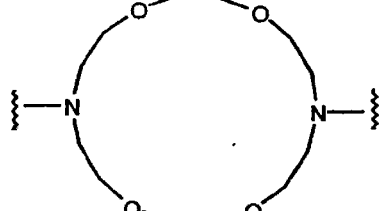 | C |
| 250 | B | 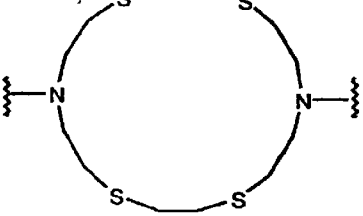 | C |
FIG. 21-26

| 251 | B | 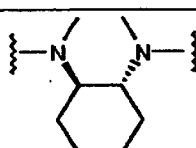 | C |
| 252 | B | 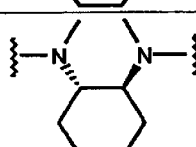 | C |
| 253 | B | 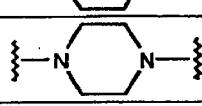 | C |
| 254 | B | 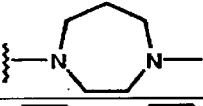 | C |
| 255 | B | 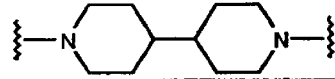 | C |
| 256 | B | 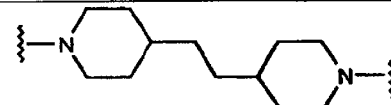 | C |
| 257 | B | 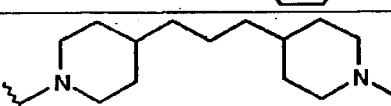 | C |
| 258 | B | 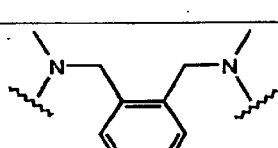 | C |
| 259 | B | 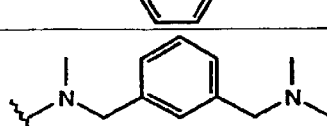 | C |
| 260 | B | 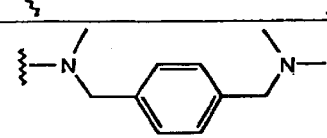 | C |
FIG. 21-27

| 261 | B | 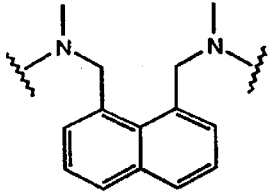 | C |
| 262 | B | 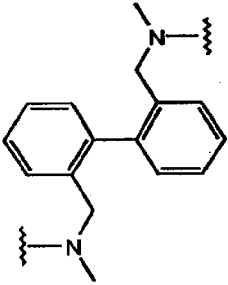 | C |
| 263 | B | 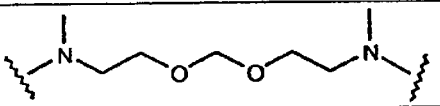 | C |
| 264 | B | 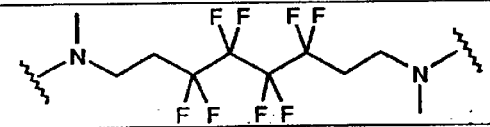 | C |
| 265 | B | 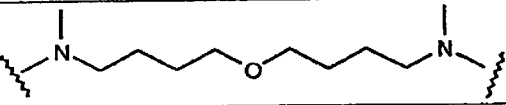 | C |
| 266 | B | 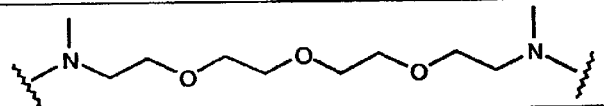 | C |
| 267 | B | 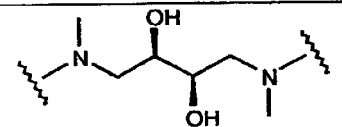 | C |
| 268 | B | 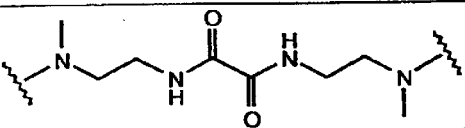 | C |
| 269 | B | 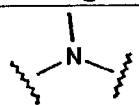 | D |
FIG. 21-28

| 270 | B | 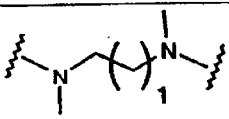 | D |
| 271 | B | 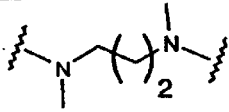 | D |
| 272 | B | 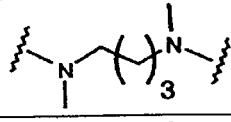 | D |
| 273 | B | 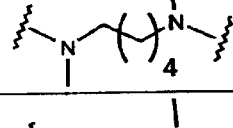 | D |
| 274 | B | 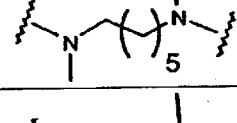 | D |
| 275 | B | 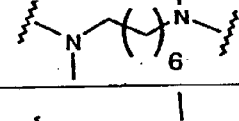 | D |
| 276 | B | 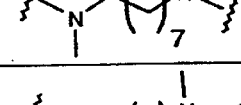 | D |
| 277 | B | 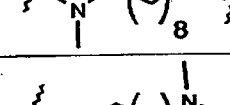 | D |
| 278 | B | 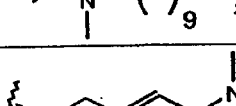 | D |
| 279 | B |  | D |
| 280 | B | 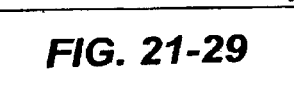 | D |
FIG. 21-29

| | | | |
|---|---|---|---|
| 281 | B | 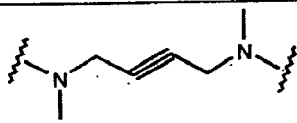 | D |
| 282 | B | 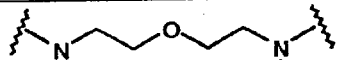 | D |
| 283 | B | 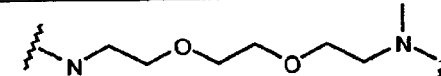 | D |
| 284 | B | 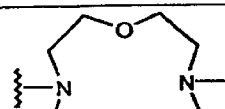 | D |
| 285 | B | 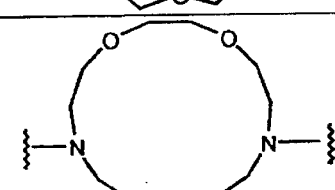 | D |
| 286 | B | 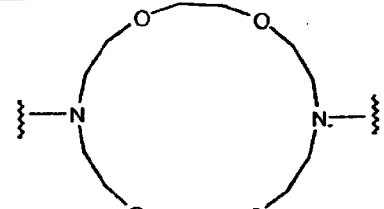 | D |
| 287 | B | 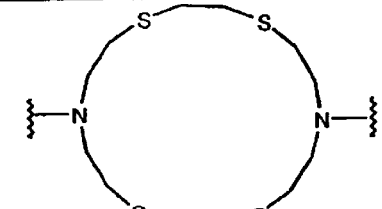 | D |
| 288 | B | 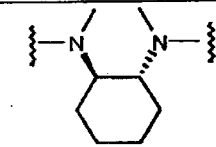 | D |
*FIG. 21-30*

| 289 | B | 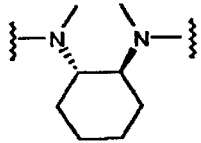 | D |
| 290 | B | 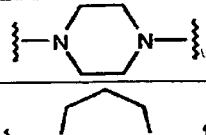 | D |
| 291 | B | 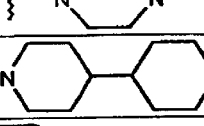 | D |
| 292 | B | 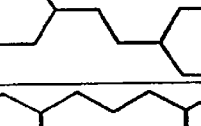 | D |
| 293 | B |  | D |
| 294 | B | 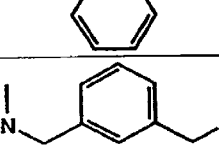 | D |
| 295 | B | 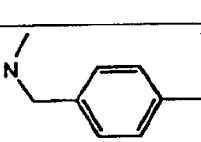 | D |
| 296 | B | 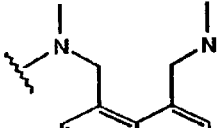 | D |
| 297 | B | 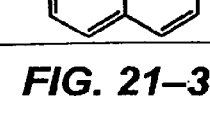 | D |
| 298 | B |  | D |
*FIG. 21–31*

| 299 | B | 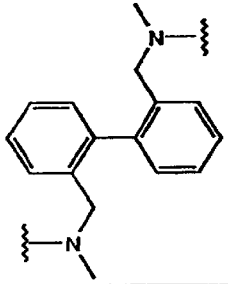 | D |
| 300 | B | 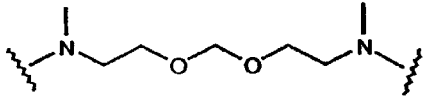 | D |
| 301 | B | 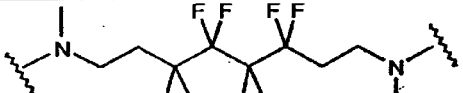 | D |
| 302 | B | 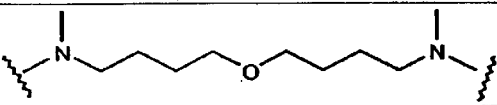 | D |
| 303 | B | 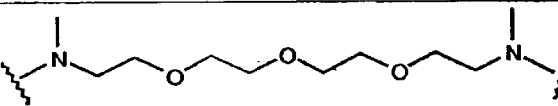 | D |
| 304 | B | 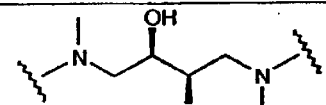 | D |
| 305 | B | 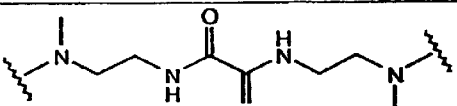 | D |
| 306 | B | 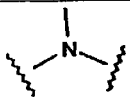 | E |
| 307 | B | 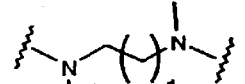 | E |
| 308 | B | 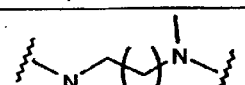 | E |
*FIG. 21-32*

| # | | Structure | |
|---|---|---|---|
| 309 | B | ⁓N-(CH₂)₃-N⁓ | E |
| 310 | B | ⁓N-(CH₂)₄-N⁓ | E |
| 311 | B | ⁓N-(CH₂)₅-N⁓ | E |
| 312 | B | ⁓N-(CH₂)₆-N⁓ | E |
| 313 | B | ⁓N-(CH₂)₇-N⁓ | E |
| 314 | B | ⁓N-(CH₂)₈-N⁓ | E |
| 315 | B | ⁓N-(CH₂)₉-N⁓ | E |
| 316 | B | ⁓N-CH₂-CH=CH-CH₂-N⁓ (trans) | E |
| 317 | B | ⁓N-CH₂-CH=CH-CH₂-N⁓ (cis) | E |
| 318 | B | ⁓N-CH₂-C≡C-CH₂-N⁓ | E |
| 319 | B | ⁓N-CH₂CH₂-O-CH₂CH₂-N⁓ | E |

*FIG. 21-33*

| | | | |
|---|---|---|---|
| 320 | B | 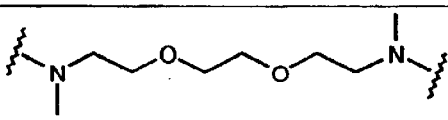 | E |
| 321 | B | 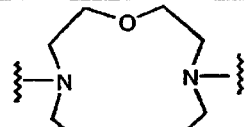 | E |
| 322 | B | 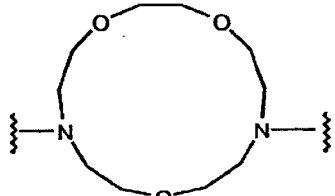 | E |
| 323 | B | 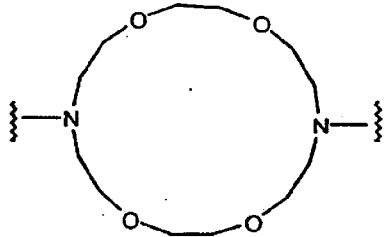 | E |
| 324 | B | 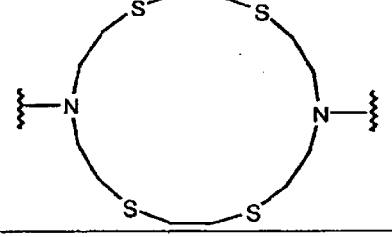 | E |
| 325 | B | 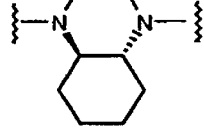 | E |
| 326 | B | 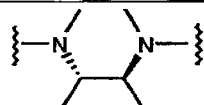 | E |
| 327 | B | 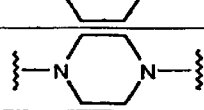 | E |
*FIG. 21–34*

| # | | Structure | |
|---|---|---|---|
| 328 | B | ⟨diazepane linker⟩ | E |
| 329 | B | ⟨4,4'-bipiperidine linker⟩ | E |
| 330 | B | ⟨bis-piperidinyl ethane linker⟩ | E |
| 331 | B | ⟨bis-piperidinyl propane linker⟩ | E |
| 332 | B | ⟨ortho-xylylenediamine (N-Me) linker⟩ | E |
| 333 | B | ⟨meta-xylylenediamine (N-Me) linker⟩ | E |
| 334 | B | ⟨para-xylylenediamine (N-Me) linker⟩ | E |
| 335 | B | ⟨1,8-bis(aminomethyl)naphthalene (N-Me) linker⟩ | E |
| 336 | B | ⟨2,2'-bis(aminomethyl)biphenyl (N-Me) linker⟩ | E |

FIG. 21-35

| | | | |
|---|---|---|---|
| 337 | B | 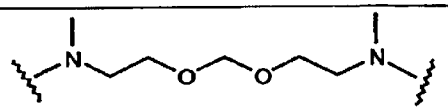 | E |
| 338 | B | 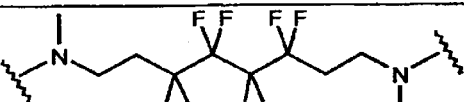 | E |
| 339 | B | 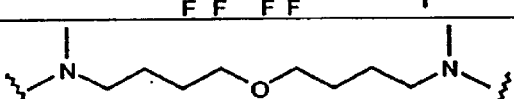 | E |
| 340 | B | 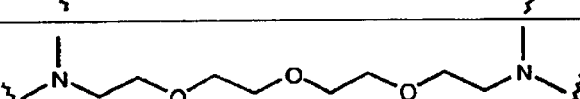 | E |
| 341 | B | 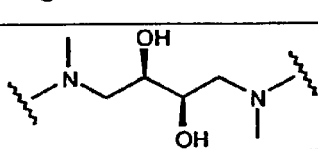 | E |
| 342 | B | 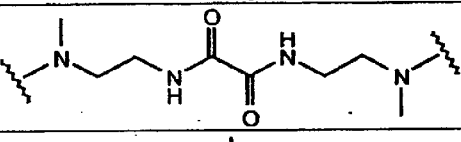 | E |
| 343 | B | 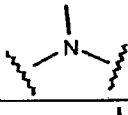 | H |
| 344 | B | 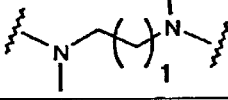 | H |
| 345 | B | 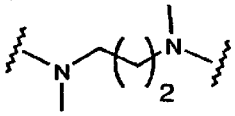 | H |
| 346 | B | 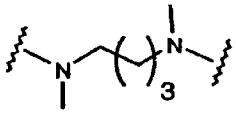 | H |
| 347 | B | 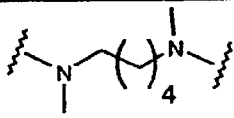 | H |
FIG. 21-36

| 348 | B | 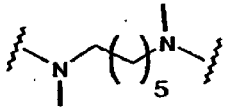 | H |
|---|---|---|---|
| 349 | B | 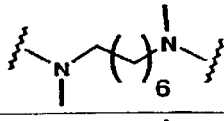 | H |
| 350 | B | 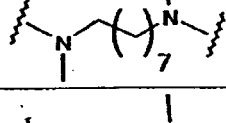 | H |
| 351 | B | 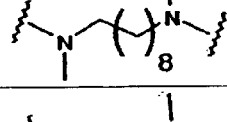 | H |
| 352 | B | 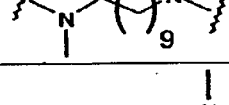 | H |
| 353 | B | 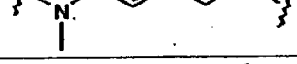 | H |
| 354 | B | 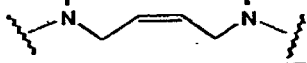 | H |
| 355 | B | 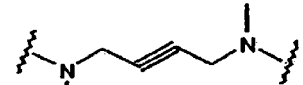 | H |
| 356 | B | 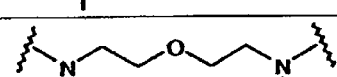 | H |
| 357 | B |  | H |
| 358 | B | 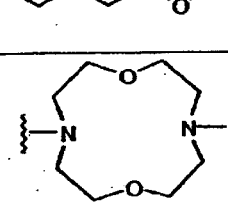 | H |
*FIG. 21-37*

| | | | |
|---|---|---|---|
| 359 | B | 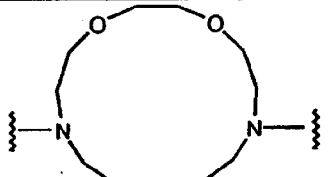 | H |
| 360 | B | 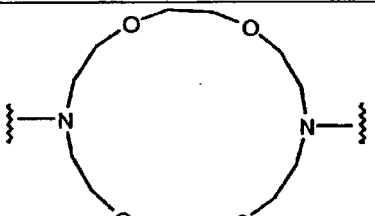 | H |
| 361 | B | 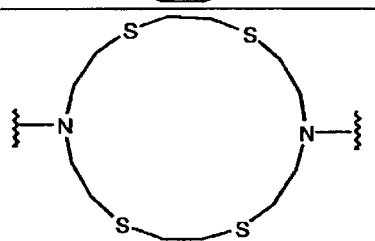 | H |
| 362 | B | 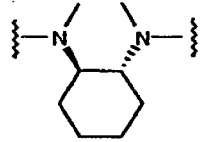 | H |
| 363 | B | 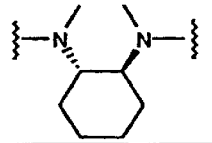 | H |
| 364 | B | 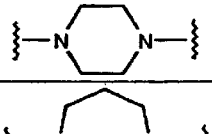 | H |
| 365 | B | 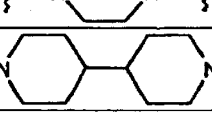 | H |
| 366 | B | 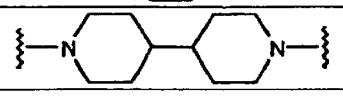 | H |
FIG. 21-38

| | | | |
|---|---|---|---|
| 367 | B | 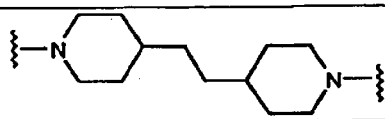 | H |
| 368 | B | 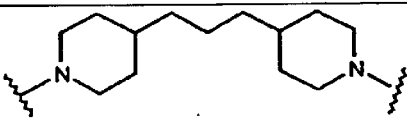 | H |
| 369 | B | 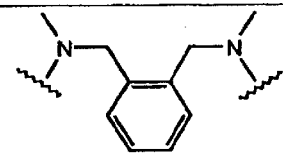 | H |
| 370 | B | 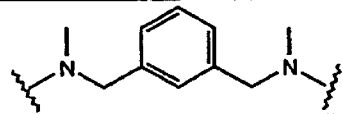 | H |
| 371 | B | 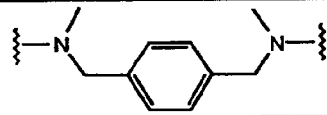 | H |
| 372 | B | 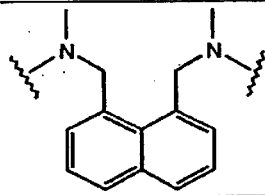 | H |
| 373 | B | 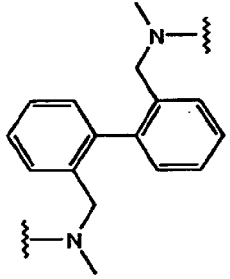 | H |
| 374 | B | 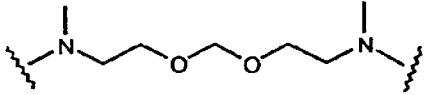 | H |
| 375 | B |  | H |
*FIG. 21-39*

| 376 | B | 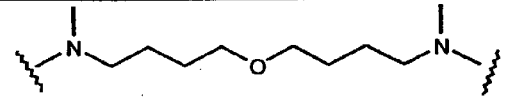 | H |
|---|---|---|---|
| 377 | B | 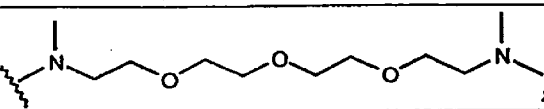 | H |
| 378 | B | 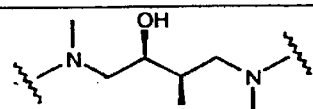 | H |
| 379 | B | 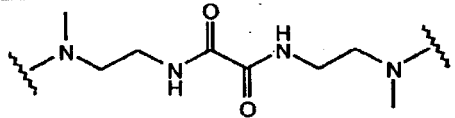 | H |
| 380 | C | 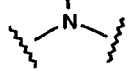 | H |
| 381 | C | 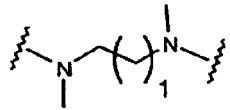 | H |
| 382 | C | 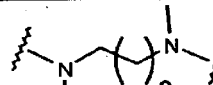 | H |
| 383 | C | 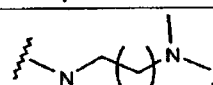 | H |
| 384 | C | 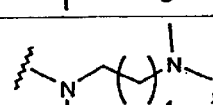 | H |
| 385 | C | 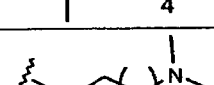 | H |
| 386 | C | 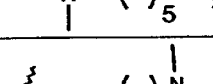 | H |
*FIG. 21-40*

| 387 | C | 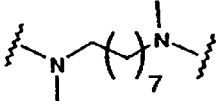 | H |
| 388 | C | 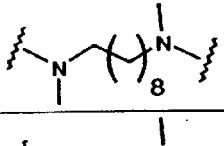 | H |
| 389 | C | 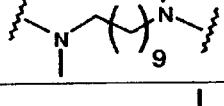 | H |
| 390 | C | 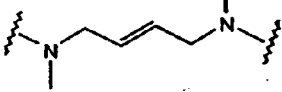 | H |
| 391 | C |  | H |
| 392 | C | 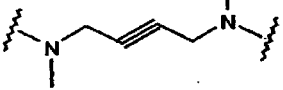 | H |
| 393 | C | 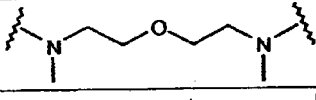 | H |
| 394 | C | 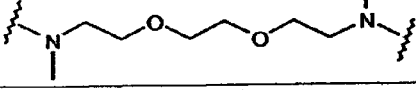 | H |
| 395 | C | 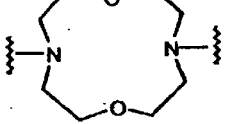 | H |
| 396 | C | 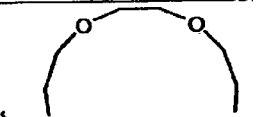 | H |
FIG. 21-41

| 397 | C | 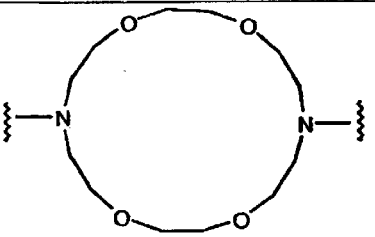 | H |
| 398 | C | 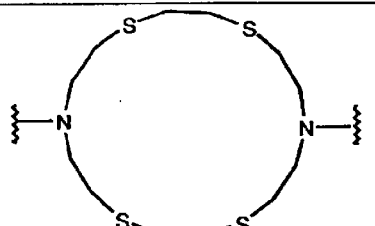 | H |
| 399 | C | 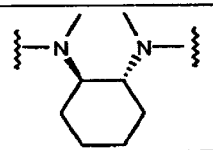 | H |
| 400 | C | 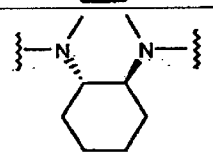 | H |
| 401 | C |  | H |
| 402 | C | 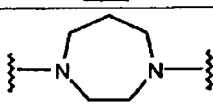 | H |
| 403 | C | 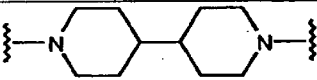 | H |
| 404 | C | 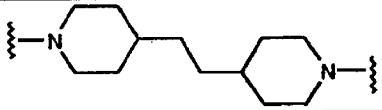 | H |
| 405 | C | 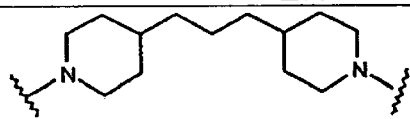 | H |
FIG. 21-42

| 406 | C | 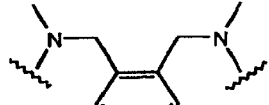 | H |
| 407 | C | 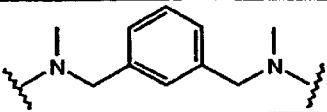 | H |
| 408 | C | 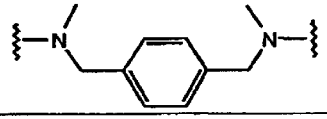 | H |
| 409 | C | 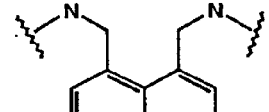 | H |
| 410 | C | 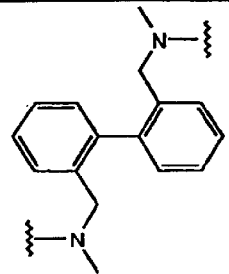 | H |
| 411 | C | 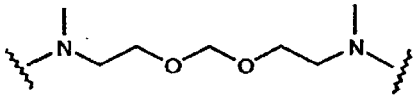 | H |
| 412 | C |  | H |
| 413 | C | 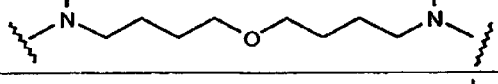 | H |
| 414 | C | 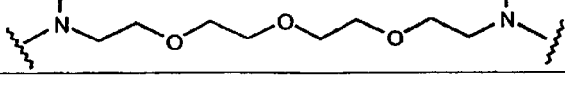 | H |
FIG. 21-43

| 415 | C | 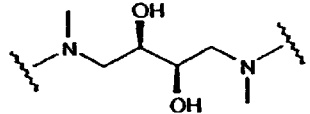 | H |
|---|---|---|---|
| 416 | C | 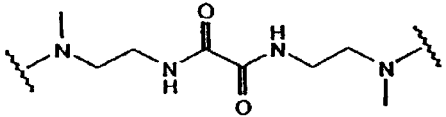 | H |
| 417 | D | 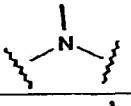 | H |
| 418 | D | 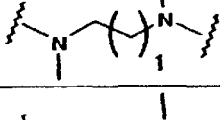 | H |
| 419 | D | 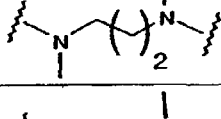 | H |
| 420 | D | 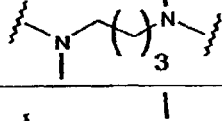 | H |
| 421 | D | 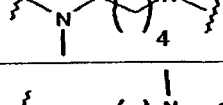 | H |
| 422 | D | 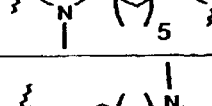 | H |
| 423 | D | 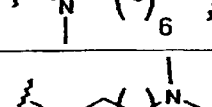 | H |
| 424 | D | 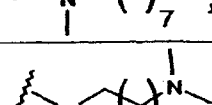 | H |
| 425 | D | 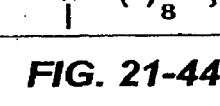 | H |
*FIG. 21-44*

| # | | Structure | |
|---|---|---|---|
| 426 | D | [N-(CH2)9-N structure] | H |
| 427 | D | [N-CH2-CH=CH-CH2-N trans structure] | H |
| 428 | D | [N-CH2-CH=CH-CH2-N cis structure] | H |
| 429 | D | [N-CH2-C≡C-CH2-N structure] | H |
| 430 | D | [N-CH2CH2-O-CH2CH2-N structure] | H |
| 431 | D | [N-CH2CH2-O-CH2CH2-O-CH2CH2-N structure] | H |
| 432 | D | [cyclic diaza-dioxa ring] | H |
| 433 | D | [cyclic diaza-trioxa ring] | H |
| 434 | D | [cyclic diaza-tetraoxa (cryptand-like) ring] | H |

FIG. 21-45

| 435 | D | 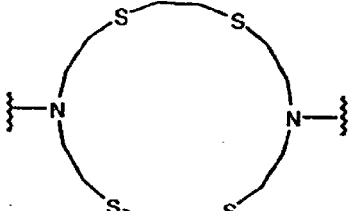 | H |
| 436 | D |  | H |
| 437 | D | 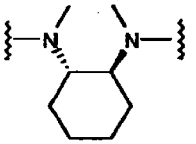 | H |
| 438 | D |  | H |
| 439 | D | 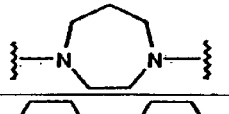 | H |
| 440 | D |  | H |
| 441 | D | 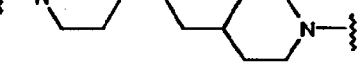 | H |
| 442 | D |  | H |
| 443 | D | 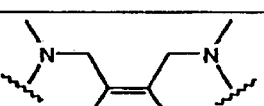 | H |
| 444 | D | 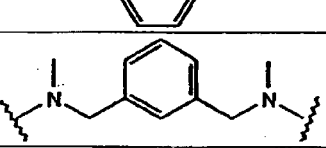 | H |
*FIG. 21-46*

| 445 | D | 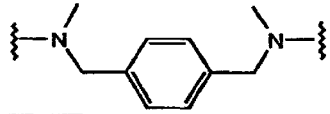 | H |
| 446 | D | 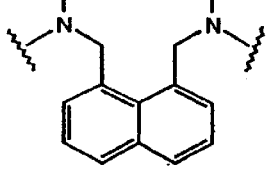 | H |
| 447 | D | 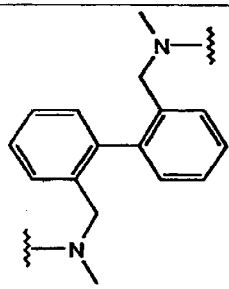 | H |
| 448 | D | 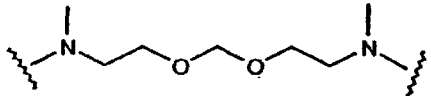 | H |
| 449 | D | 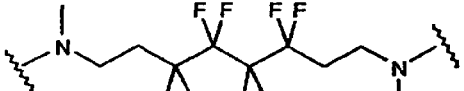 | H |
| 450 | D | 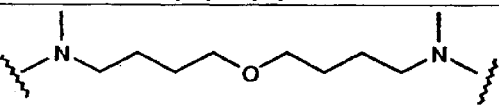 | H |
| 451 | D | 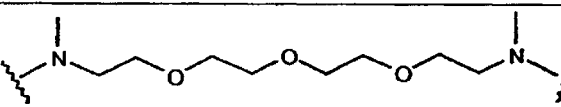 | H |
| 452 | D | 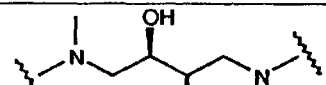 | H |
| 453 | D | 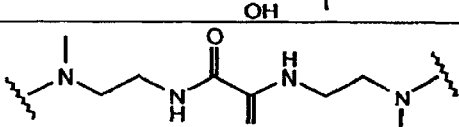 | H |
FIG. 21-47

| 454 | E | 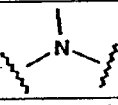 | H |
| 455 | E |  | H |
| 456 | E | 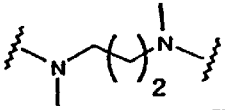 | H |
| 457 | E | 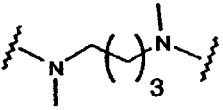 | H |
| 458 | E | 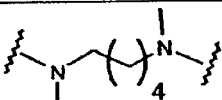 | H |
| 459 | E | 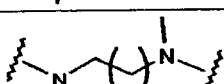 | H |
| 460 | E | 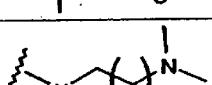 | H |
| 461 | E | 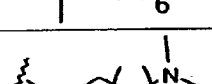 | H |
| 462 | E | 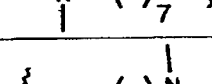 | H |
| 463 | E | 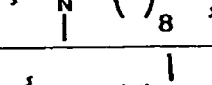 | H |
| 464 | E | 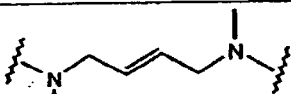 | H |
FIG. 21-48

| | | | |
|---|---|---|---|
| 465 | E | ⸯN−CH₂−CH=CH−CH₂−Nⸯ (cis) | H |
| 466 | E | ⸯN−CH₂−C≡C−CH₂−Nⸯ | H |
| 467 | E | ⸯN−CH₂CH₂−O−CH₂CH₂−Nⸯ | H |
| 468 | E | ⸯN−CH₂CH₂−O−CH₂CH₂−O−CH₂CH₂−Nⸯ | H |
| 469 | E | diaza-crown (2 N, 2 O) | H |
| 470 | E | diaza-crown (2 N, 3 O) | H |
| 471 | E | diaza-crown (2 N, 4 O) | H |
| 472 | E | diaza-crown (2 N, 4 S) | H |

FIG. 21-49

| 473 | E | 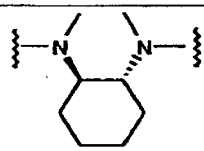 | H |
| 474 | E | 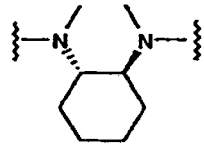 | H |
| 475 | E |  | H |
| 476 | E |  | H |
| 477 | E | 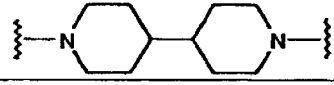 | H |
| 478 | E | 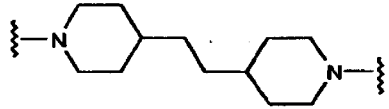 | H |
| 479 | E | 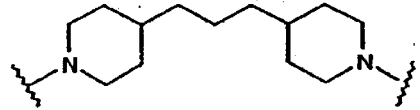 | H |
| 480 | E | 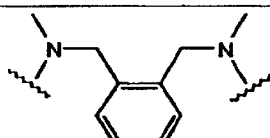 | H |
| 481 | E | 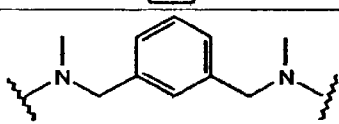 | H |
| 482 | E | 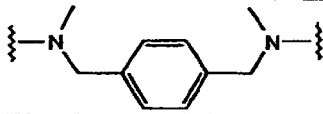 | H |
*FIG. 21-50*

| # | | | |
|---|---|---|---|
| 483 | E | 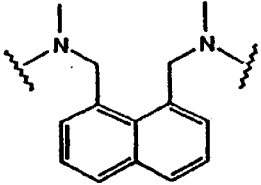 | H |
| 484 | E | 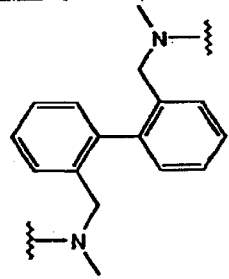 | H |
| 485 | E | 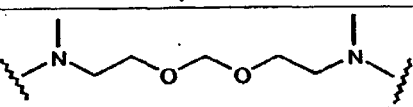 | H |
| 486 | E | 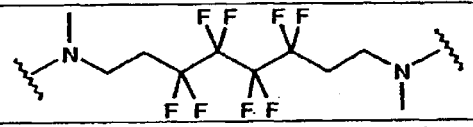 | H |
| 487 | E | 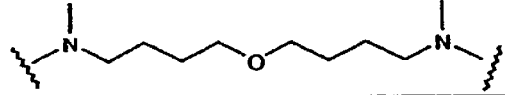 | H |
| 488 | E | 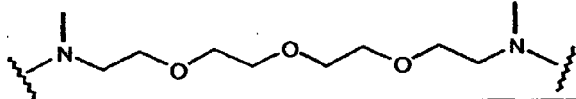 | H |
| 489 | E | 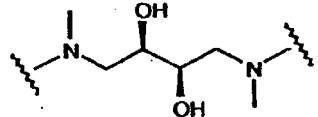 | H |
| 490 | E | 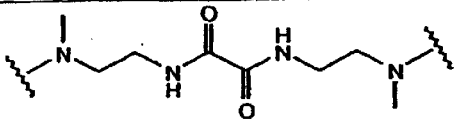 | H |
| 491 | F | None | A |
| 492 | F | 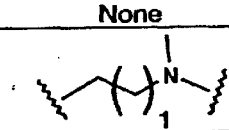 | A |
*FIG. 21-51*

| 493 | F | 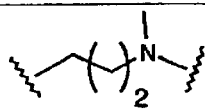 | A |
| 494 | F |  | A |
| 495 | F | 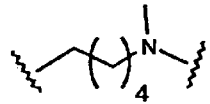 | A |
| 496 | F | 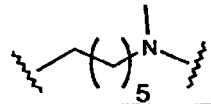 | A |
| 497 | F | 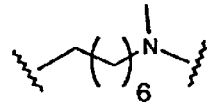 | A |
| 498 | F |  | A |
| 499 | F |  | A |
| 500 | F | 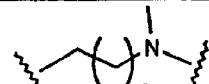 | A |
| 501 | F | 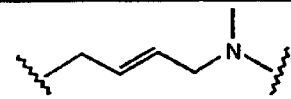 | A |
| 502 | F | 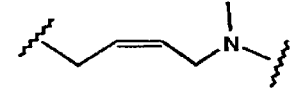 | A |
| 503 | F | 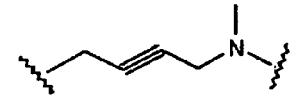 | A |
| 504 | F | 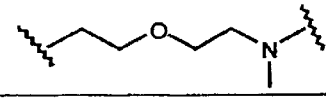 | A |
| 505 | F | 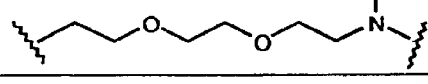 | A |
*FIG. 21-52*

| 506 | F | 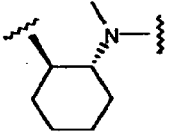 | A |
| 507 | F | 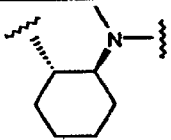 | A |
| 508 | F | 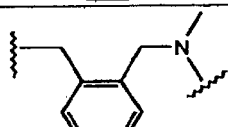 | A |
| 509 | F | 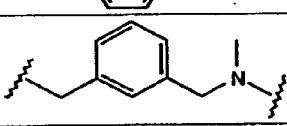 | A |
| 510 | F | 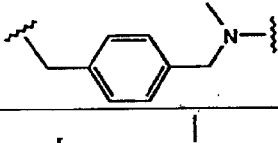 | A |
| 511 | F | 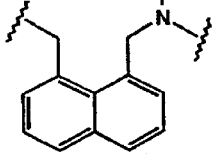 | A |
| 512 | F | 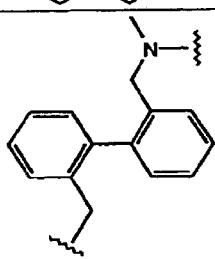 | A |
| 513 | F | 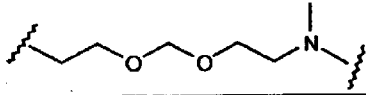 | A |
*FIG. 21–53*

| 514 | F | 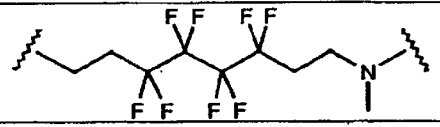 | A |
| 515 | F | 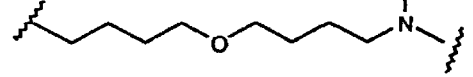 | A |
| 516 | F | 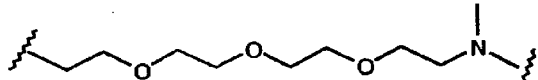 | A |
| 517 | F | 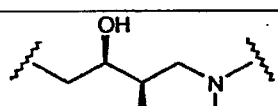 | A |
| 518 | F | 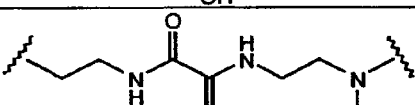 | A |
| 491 | F | None | C |
| 492 | F | 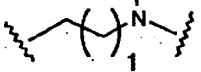 | C |
| 493 | F |  | C |
| 494 | F | 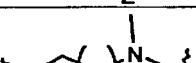 | C |
| 495 | F | 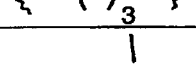 | C |
| 496 | F |  | C |
| 497 | F | 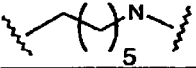 | C |
| 498 | F |  | C |
*FIG. 21-54*

| 499 | F | 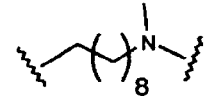 | C |
| 500 | F |  | C |
| 501 | F | 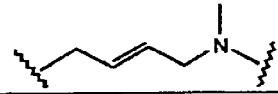 | C |
| 502 | F |  | C |
| 503 | F | 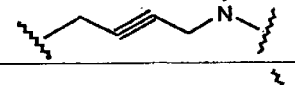 | C |
| 504 | F |  | C |
| 505 | F | 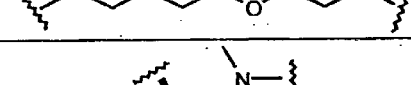 | C |
| 506 | F | 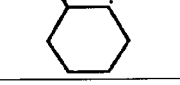 | C |
| 507 | F |  | C |
| 508 | F |  | C |
| 509 | F | 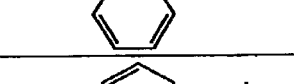 | C |
FIG. 21-55

| 510 | F | 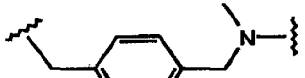 | C |
| 511 | F | 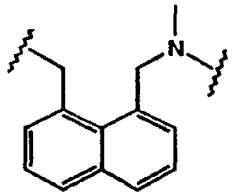 | C |
| 512 | F | 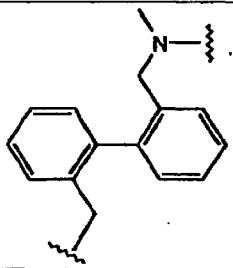 | C |
| 513 | F | 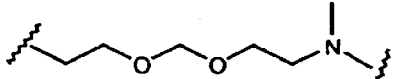 | C |
| 514 | F | 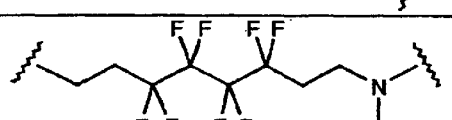 | C |
| 515 | F | 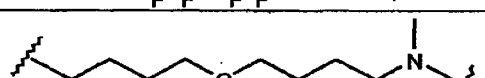 | C |
| 516 | F | 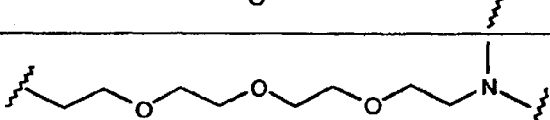 | C |
| 517 | F | 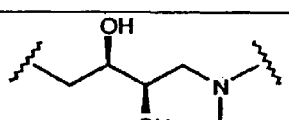 | C |
| 518 | F | 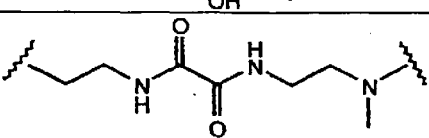 | C |
| 519 | F | None | D |
FIG. 21-56

| 520 | F | 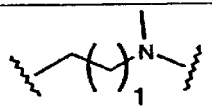 | D |
| 521 | F | 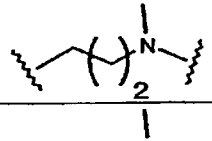 | D |
| 522 | F | 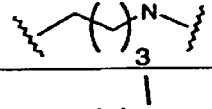 | D |
| 523 | F | 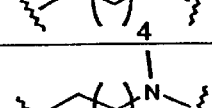 | D |
| 524 | F | 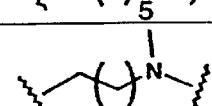 | D |
| 525 | F | 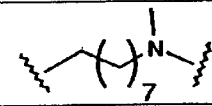 | D |
| 526 | F | 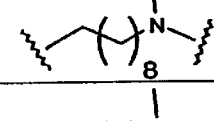 | D |
| 527 | F | 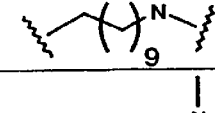 | D |
| 528 | F |  | D |
| 529 | F | 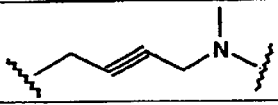 | D |
| 530 | F | 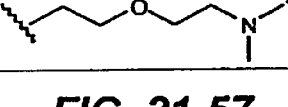 | D |
| 531 | F |  | D |
| 532 | F | | D |
*FIG. 21-57*

| 533 | F | 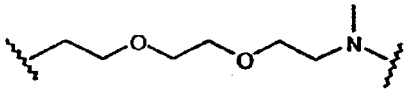 | D |
| 534 | F |  | D |
| 535 | F | 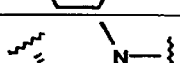 | D |
| 536 | F | 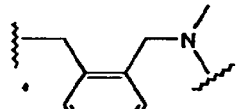 | D |
| 537 | F | 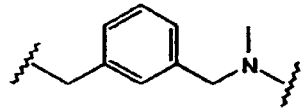 | D |
| 538 | F |  | D |
| 539 | F | 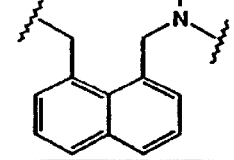 | D |
| 540 | F | 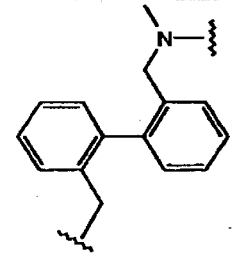 | D |
| 541 | F | 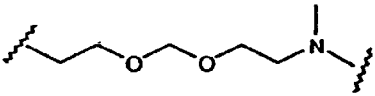 | D |
FIG. 21-58

| 542 | F | 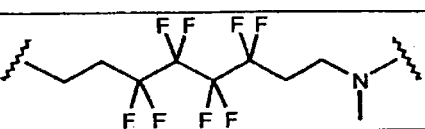 | D |
| 543 | F | 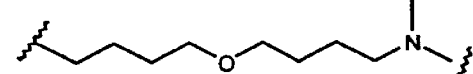 | D |
| 544 | F | 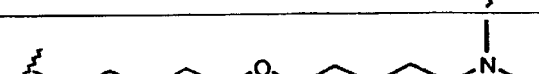 | D |
| 545 | F | 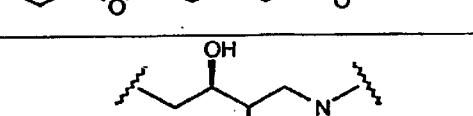 | D |
| 546 | F | 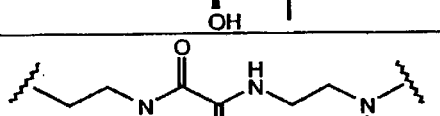 | D |
| 547 | F | 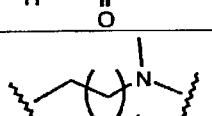 | E |
| 548 | F | 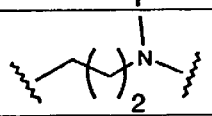 | E |
| 549 | F | 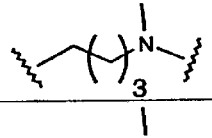 | E |
| 550 | F | 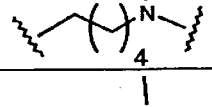 | E |
| 551 | F | 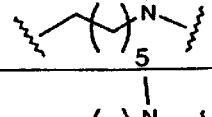 | E |
| 552 | F | 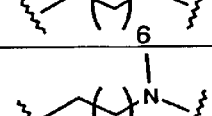 | E |
| 553 | F | 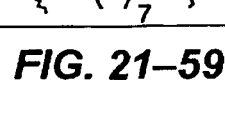 | E |
*FIG. 21–59*

| 554 | F | 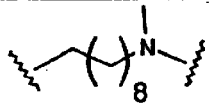 | E |
| 555 | F | 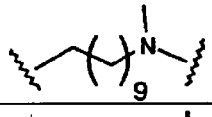 | E |
| 556 | F | 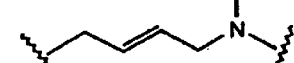 | E |
| 557 | F | 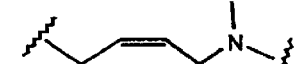 | E |
| 558 | F | 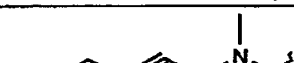 | E |
| 559 | F | 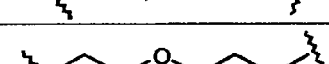 | E |
| 560 | F | 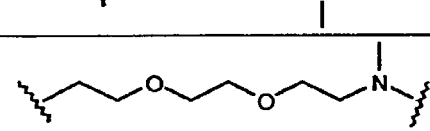 | E |
| 561 | F | 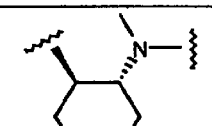 | E |
| 562 | F | 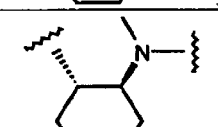 | E |
| 563 | F | 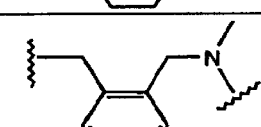 | E |
| 564 | F | 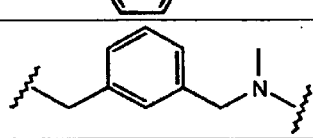 | E |
*FIG. 21-60*

| 565 | F | 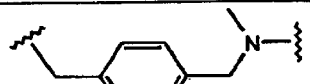 | E |
| 566 | F | 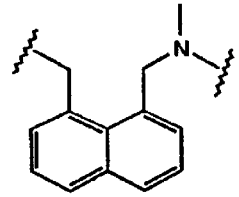 | E |
| 567 | F | 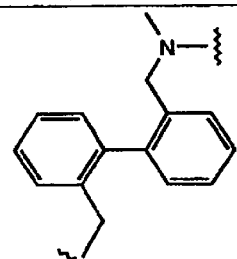 | E |
| 568 | F | 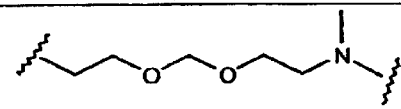 | E |
| 569 | F | 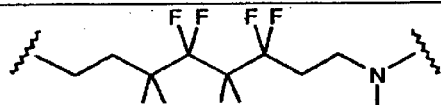 | E |
| 570 | F | 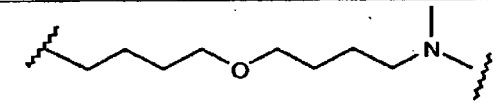 | E |
| 571 | F | 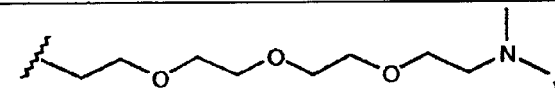 | E |
| 572 | F | 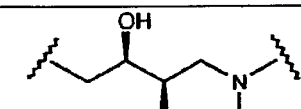 | E |
| 573 | F | 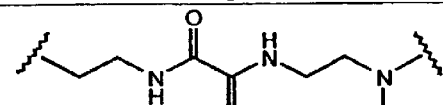 | E |
| 574 | F | None | H |
*FIG. 21-61*

| # | | | |
|---|---|---|---|
| 575 | F | ⁓(CH₂)₁N⁓ | H |
| 576 | F | ⁓(CH₂)₂N⁓ | H |
| 577 | F | ⁓(CH₂)₃N⁓ | H |
| 578 | F | ⁓(CH₂)₄N⁓ | H |
| 579 | F | ⁓(CH₂)₅N⁓ | H |
| 580 | F | ⁓(CH₂)₆N⁓ | H |
| 581 | F | ⁓(CH₂)₇N⁓ | H |
| 582 | F | ⁓(CH₂)₈N⁓ | H |
| 583 | F | ⁓(CH₂)₉N⁓ | H |
| 584 | F | ⁓CH₂CH=CHCH₂N⁓ (trans) | H |
| 585 | F | ⁓CH₂CH=CHCH₂N⁓ (cis) | H |
| 586 | F | ⁓CH₂C≡CCH₂N⁓ | H |
| 587 | F | ⁓CH₂CH₂OCH₂CH₂N⁓ | H |

*FIG. 21–62*

| 588 | F | 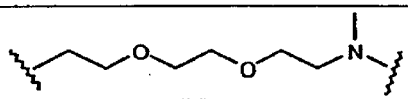 | H |
| 589 | F | 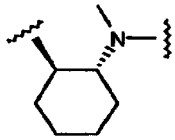 | H |
| 590 | F | 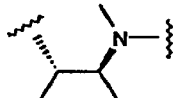 | H |
| 591 | F | 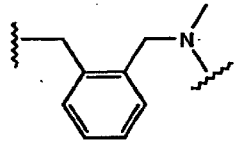 | H |
| 592 | F | 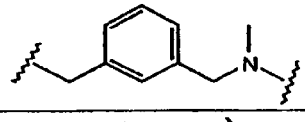 | H |
| 593 | F | 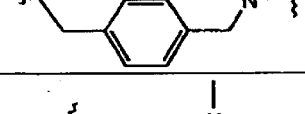 | H |
| 594 | F | 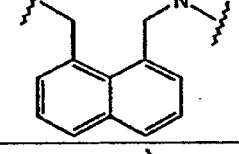 | H |
| 595 | F | 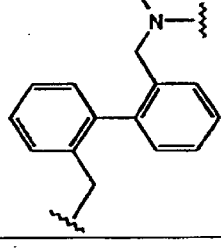 | H |
| 596 | F | 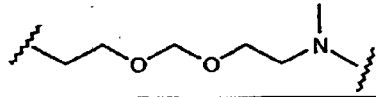 | H |
FIG. 21-63

| 597 | F | 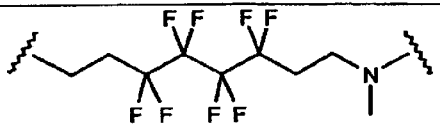 | H |
| --- | --- | --- | --- |
| 598 | F | 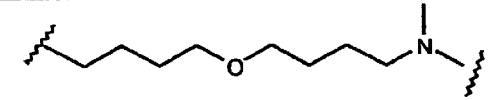 | H |
| 599 | F | 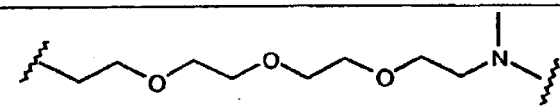 | H |
| 600 | F | 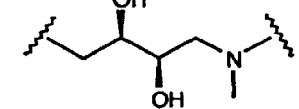 | H |
| 601 | F | 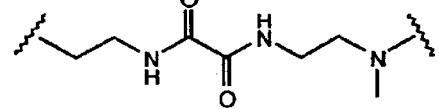 | H |
| 602 | G | None | A |
| 603 | G |  | A |
| 604 | G |  | A |
| 605 | G | 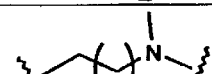 | A |
| 606 | G | 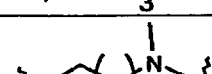 | A |
| 607 | G | 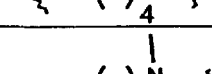 | A |
| 608 | G | 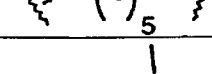 | A |
| 609 | G | 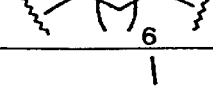 | A |
*FIG. 21-64*

| | | | |
|---|---|---|---|
| 610 | G | [structure: chain-(CH₂)₈-N-chain] | A |
| 611 | G | [structure: chain-(CH₂)₉-N-chain] | A |
| 612 | G | [structure: chain-CH₂-CH=CH-CH₂-N-chain (trans)] | A |
| 613 | G | [structure: chain-CH₂-CH=CH-CH₂-N-chain (cis)] | A |
| 614 | G | [structure: chain-CH₂-C≡C-CH₂-N-chain] | A |
| 615 | G | [structure: chain-CH₂CH₂-O-CH₂CH₂-N-chain] | A |
| 616 | G | [structure: chain-CH₂CH₂-O-CH₂CH₂-O-CH₂CH₂-N-chain] | A |
| 617 | G | [structure: cis-1,2-disubstituted cyclohexane with N] | A |
| 618 | G | [structure: trans-1,2-disubstituted cyclohexane with N] | A |
| 619 | G | [structure: 1,2-disubstituted benzene-CH₂-N] | A |
| 620 | G | [structure: 1,3-disubstituted benzene-CH₂-N] | A |

FIG. 21-65

| 621 | G | 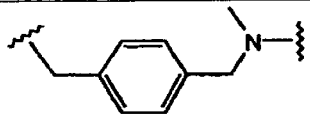 | A |
| 622 | G | 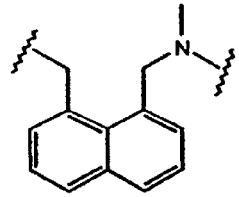 | A |
| 623 | G | 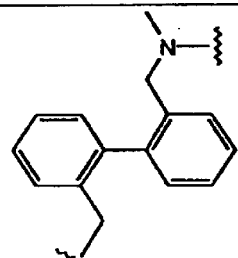 | A |
| 624 | G | 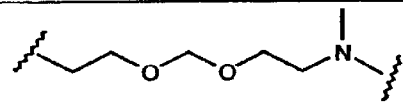 | A |
| 625 | G | 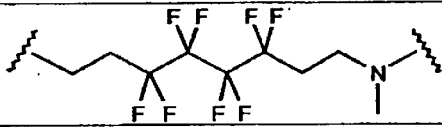 | A |
| 626 | G | 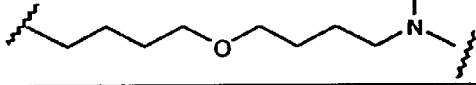 | A |
| 627 | G | 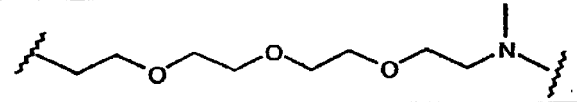 | A |
| 628 | G | 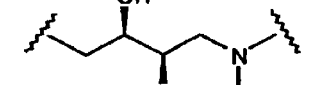 | A |
| 629 | G | 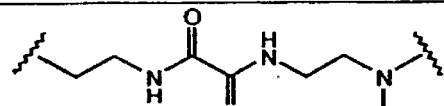 | A |
| 630 | G | None | C |
*FIG. 21-66*

| 631 | G |  | C |
| 632 | G | 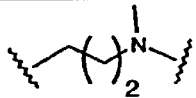 | C |
| 633 | G | 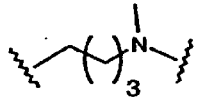 | C |
| 634 | G | 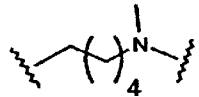 | C |
| 635 | G | 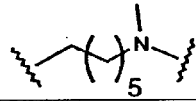 | C |
| 636 | G | 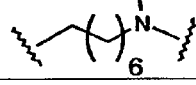 | C |
| 637 | G | 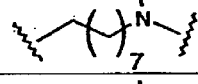 | C |
| 638 | G | 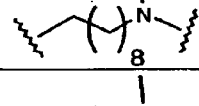 | C |
| 639 | G | 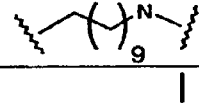 | C |
| 640 | G | 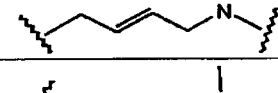 | C |
| 641 | G | 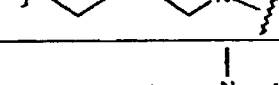 | C |
| 642 | G | 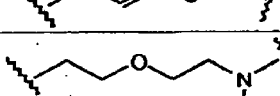 | C |
| 643 | G | 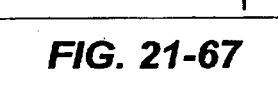 | C |
FIG. 21-67

| 644 | G | 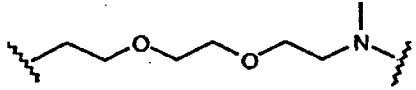 | C |
| 645 | G | 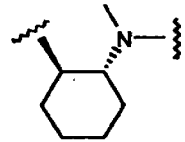 | C |
| 646 | G | 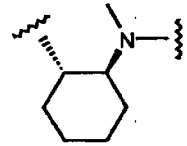 | C |
| 647 | G | 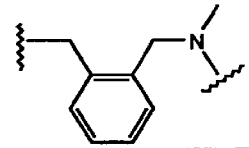 | C |
| 648 | G | 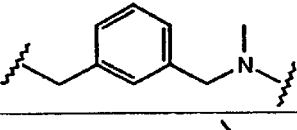 | C |
| 649 | G | 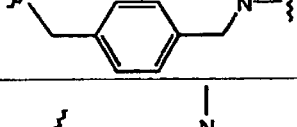 | C |
| 650 | G | 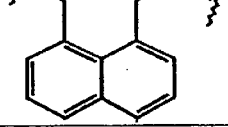 | C |
| 651 | G | 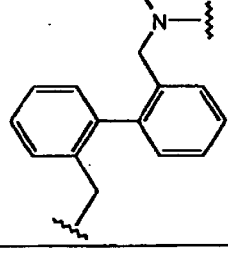 | C |
| 652 | G | 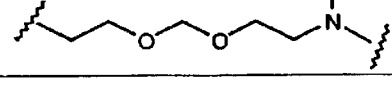 | C |
*FIG. 21-68*

| 653 | G | 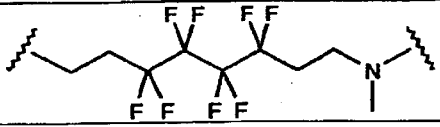 | C |
|---|---|---|---|
| 654 | G | 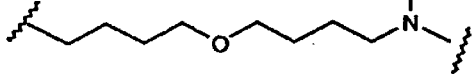 | C |
| 655 | G | 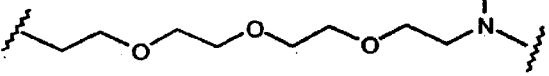 | C |
| 656 | G | 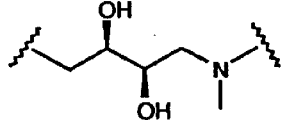 | C |
| 657 | G | 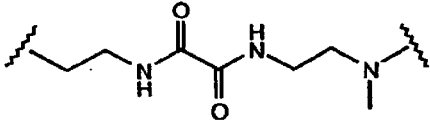 | C |
| 658 | G | None | D |
| 659 | G |  | D |
| 660 | G |  | D |
| 661 | G |  | D |
| 662 | G |  | D |
| 663 | G |  | D |
| 664 | G |  | D |
| 665 | G | 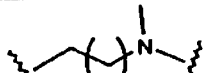 | D |
FIG. 21-69

| 666 | G | 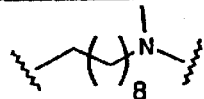 | D |
| 667 | G | 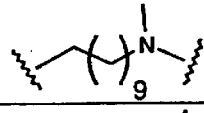 | D |
| 668 | G | 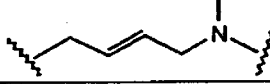 | D |
| 669 | G | 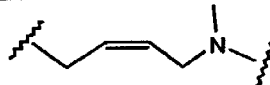 | D |
| 670 | G | 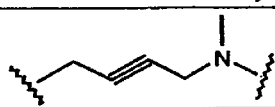 | D |
| 671 | G | 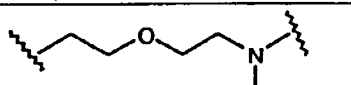 | D |
| 672 | G | 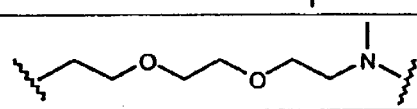 | D |
| 673 | G | 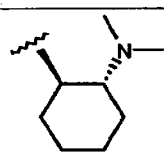 | D |
| 674 | G | 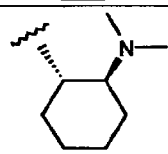 | D |
| 675 | G | 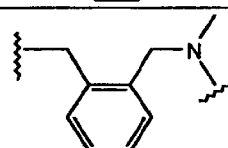 | D |
| 676 | G | 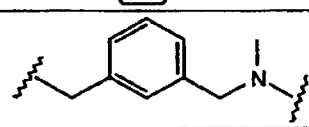 | D |
FIG. 21-70

| 677 | G |  | D |
| 678 | G | 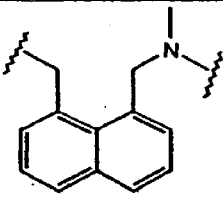 | D |
| 679 | G | 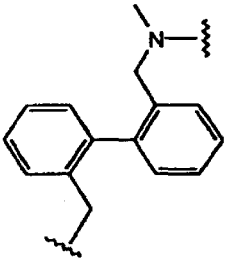 | D |
| 680 | G | 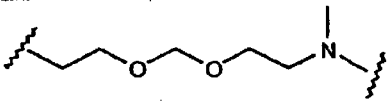 | D |
| 681 | G | 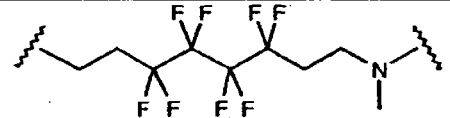 | D |
| 682 | G | 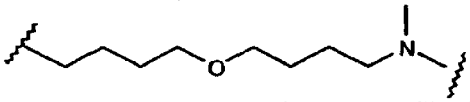 | D |
| 683 | G | 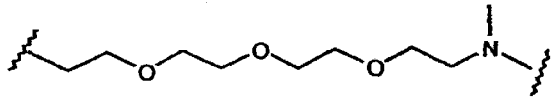 | D |
| 684 | G | 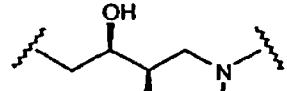 | D |
| 685 | G | 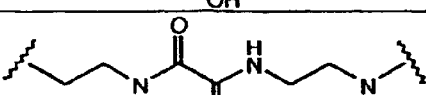 | D |
| 686 | G | None | E |
FIG. 21-71

| 687 | G | 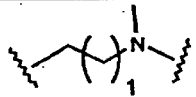 | E |
| 688 | G | 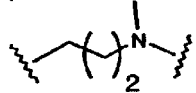 | E |
| 689 | G | 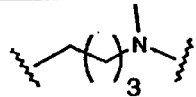 | E |
| 690 | G | 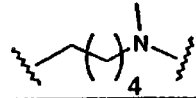 | E |
| 691 | G | 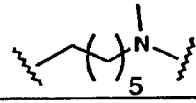 | E |
| 692 | G | 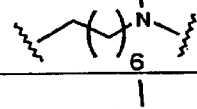 | E |
| 693 | G | 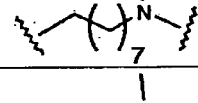 | E |
| 694 | G | 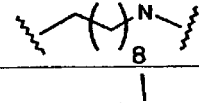 | E |
| 695 | G | 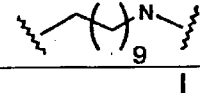 | E |
| 696 | G | 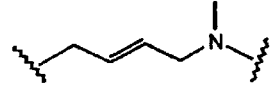 | E |
| 697 | G |  | E |
| 698 | G |  | E |
| 699 | G | 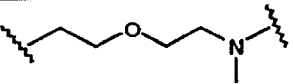 | E |
FIG. 21-72

| 700 | G | ~~~O~~~O~~~N~~~ | E |
| 701 | G | (trans-cyclohexane-1,2-diyl with N-methyl) | E |
| 702 | G | (cis-cyclohexane-1,2-diyl with N-methyl) | E |
| 703 | G | 1,2-bis(methylene)benzene with N-methyl | E |
| 704 | G | 1,3-bis(methylene)benzene with N-methyl | E |
| 705 | G | 1,4-bis(methylene)benzene with N-methyl | E |
| 706 | G | 1,8-bis(methylene)naphthalene with N-methyl | E |
| 707 | G | 2,2'-bis(methylene)biphenyl with N-methyl | E |
| 708 | G | ~~~O~CH2~O~~~N~~~ | E |

FIG. 21-73

| 709 | G | 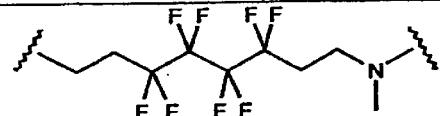 | E |
| 710 | G | 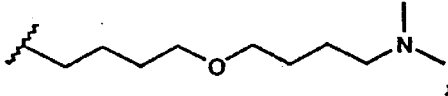 | E |
| 711 | G | 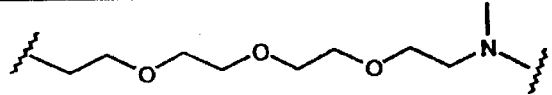 | E |
| 712 | G | 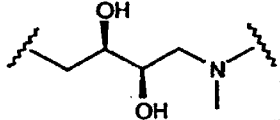 | E |
| 713 | G | 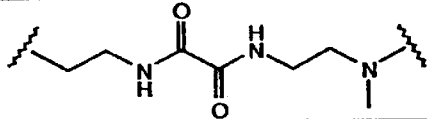 | E |
| 714 | G | None | H |
| 715 | G | 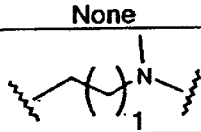 | H |
| 716 | G | 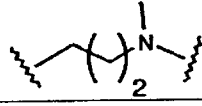 | H |
| 717 | G | 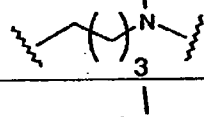 | H |
| 718 | G | 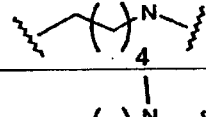 | H |
| 719 | G | 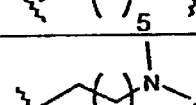 | H |
| 720 | G | 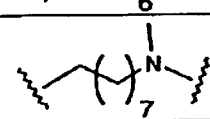 | H |
| 721 | G |  | H |
FIG. 21-74

| 722 | G | 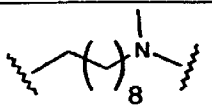 | H |
| 723 | G | 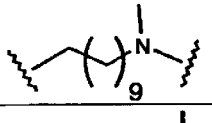 | H |
| 724 | G | 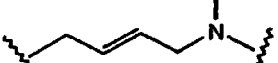 | H |
| 725 | G | 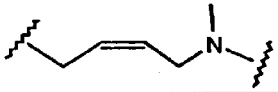 | H |
| 726 | G |  | H |
| 727 | G | 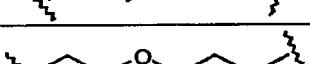 | H |
| 728 | G |  | H |
| 729 | G | 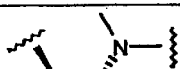 | H |
| 730 | G | 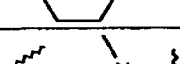 | H |
| 731 | G |  | H |
| 732 | G | 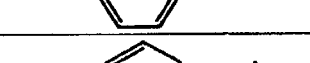 | H |
*FIG. 21-75*

| 733 | G | 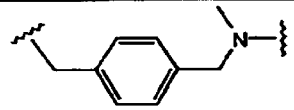 | H |
| 734 | G | 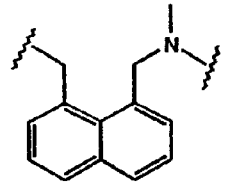 | H |
| 735 | G | 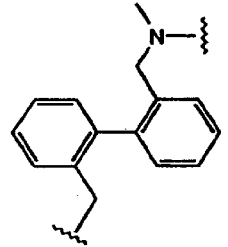 | H |
| 736 | G | 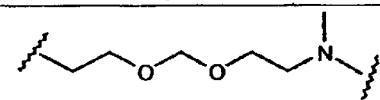 | H |
| 737 | G |  | H |
| 738 | G | 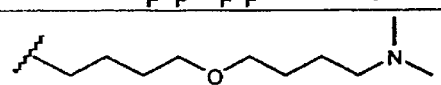 | H |
| 739 | G | 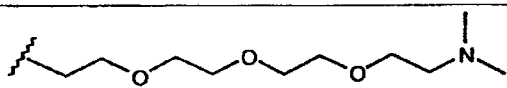 | H |
| 740 | G | 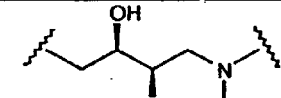 | H |
| 741 | G | 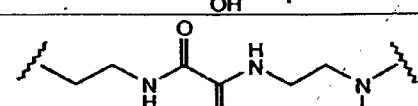 | H |
*FIG. 21-76*

CALCIUM CHANNEL DRUGS AND USES

CONTINUING APPLICATION DATA

This on is a continuation-in-part of U.S. application Ser. No. 09/325,557, filed Jun. 4, 1999, now abandoned, which, in turn, claims the benefit of U.S. Provisional Application Ser. No. 60/103,866 filed Oct. 12, 1998.

BACKGROUND

1. Field of the Invention

This invention relates to novel multibinding compounds that bind to $Ca^{++}$ channels and modulate their activity. The compounds of this invention comprise 2–10 $Ca^{++}$ channel ligands covalently connected by a linker or linkers, wherein the ligands in their monovalent (i.e. unlinked) state bind to and are capable of modulating the activity of one or more types of $Ca^{++}$ channel. The manner of linking the ligands together is such that the multibinding agents thus formed demonstrate an increased biologic and/or therapeutic effect as compared to the same number of unlinked ligands made available for binding to the $Ca^{++}$ channel. The invention also relates to methods of using such compounds and to methods of preparing them.

The compounds of this invention are particularly useful for treating diseases and conditions of mammals that are mediated by $Ca^{++}$ channels. Accordingly, this invention also relates to pharmaceutical compositions comprising a pharmaceutically acceptable excipient and an effective amount of a compound of this invention.

2. State of the Art

Voltage-gated $Ca^{++}$ channels mediate the influx of $Ca^{++}$ into cells in response to changes in membrane potential. Because of their central roles in ion homeostasis and in cell signaling events, these channels are involved in a wide variety of physiological activities, e.g., muscle contraction, cardiovascular function, hormone and neurotransmitter secretion, and tissue growth and remodeling processes.

At least six types of calcium channels have been identified and characterized (Table 1, Appendix). The high-voltage activated $Ca^{++}$ channels are formed by the heteromeric association of membrane proteins comprising at least three subunits $\alpha$ ($\alpha_1$, $\alpha_2$), $\delta$, $\beta$ (and y in skeletal muscle). The $\alpha_1$ subunit alone is sufficient to form a functional channel, although the functional properties of the channel are subject to modification, particularly by the $\beta$ subunit. The $\alpha_1$ subunit is organized into four homologous domains (I–IV), each domain including 6 transmembrane segments (S1–S6) (FIG. 1, Appendix). It is thought that the channel pore is formed from S5, S6 and the region between them, and that the voltage sensor resides in S4.

These channels exist in resting (closed), activated (open) or inactivated (desensitized) states. The resting channels open in response to depolarization of the membrane, then transition to an inactivated state.

Repolarization is required for return to the resting state. As shown in Table 1, channels differ in their activation and inactivation properties.

Not surprisingly, $Ca^{++}$ channels are recognized as important targets for drug therapy. They are implicated in a variety of pathologic conditions, including, e.g., essential hypertension, angina, congestive heart failure, arrythmias, migraine and pain.

Calcium channel antagonists are potent vasodilators and are widely used in the treatment of hypertension and angina pectoris. The compounds approved for clinical use in the U.S. fall into several chemical classes: the dihydropyridines (e.g., amlodipine, felodipine, nifedipine, nicardipine, isradipine, nimodipine); the benzothiazepines (e.g., diltiazem), phenylalkylamines (e.g., verapamil); and diaryaminopropylamine ether (e.g., bepridil).

The dihydropyridines, benzothiazepines and phenylalkylamines bind to distinct, but functionally coupled, sites on the $\alpha_1$ subunit of L-type channels at the interface of the IIIS6 and IVS6 transmembrane segments, such that the binding of any one class of drug can allosterically modulate the binding of drugs in the other two classes and the high affinity $Ca^{++}$ binding site in the channel (see G H Hockerman et al, *Annu. Rev. Pharmacol. Toxicol.* 37. 361–96 (1997)). It has been suggested that more than one high affinity binding site may exist for dihydropyridines in voltage-dependent calcium channels (Kokubun et al, *Molec. Pharmacol.* 30: 571–584 (1986)). However, studies reported in the scientific literature cast doubt on this hypothesis. In particular, the antagonist activities of a series of 1,n-alkanediylbis(1,4-dihydropyridines) was reported to be essentially independent of the bridging carbon chain length, and similar to that of the monomeric drugs (Joslyn et al., *J. Med. Chem.* 31: 1489–1492(1988)).

The clinical shortcomings of drugs in current usage are considerable. Various benzothiazepines and phenylalkylamines, for example, weaken cardiac contractility and are therefore contraindicated in patients with left ventricular dysfunction. Other $Ca^{++}$ channel antagonists cause AV block, reflex tachycardia, excessive vasodilation and gastrointestinal problems. Their most common adverse side effects include headache, flushing, hypotension, nausea, dizziness, fatigue, edema, abdominal pain, constipation, and the like. With few exceptions, the currently used drugs have a short duration of action and must be administered frequently for sustained effects.

Thus, there continues to exist a need for novel compounds with greater tissue selectivity, increased efficacy, reduced side effects and a more favorable duration of action.

SUMMARY OF THE INVENTION

This invention is directed to novel multibinding compounds that bind to $Ca^{++}$ channels in mammalian tissues and can be used to treat diseases and conditions mediated by such channels.

Accordingly, in one of its composition aspects, this invention is directed to a multibinding compound and salts thereof comprising 2 to 10 ligands which may be the same or different and which are covalently attached to a linker or linkers, which may be the same or different, each of said ligands comprising a ligand domain capable of binding to a $Ca^{++}$ channel.

The multibinding compounds of this invention are preferably represented by Formula I:

$$(L)_p(X)_q \qquad \text{I}$$

where each L is a ligand that may be the same or different at each occurrence;
X is a linker that may be the same or different at each occurrence;
p is an integer of from 2 to 10; and
q is an integer of from 1 to 20;
wherein each of said ligands comprises a ligand domain capable of binding to a $Ca^{++}$ channel.

Preferably q is less than p.

More preferably the linker is represented by the following formula:

—X'-Z-(Y'-Z)$_m$-Y"-Z-X'— in which:

m is an integer of from 0 to 20;

X' at each separate occurrence is —O—, —S—, —S(O)—, —S(O)$_2$—, —NR—, —N$^+$RR'—, —C(O)—, —C(O)O—, —C(O)NH—, —C(S), —C(S)O—, —C(S)NH— or a covalent bond, where R and R' at each separate occurrence are as defined below for R' and R";

Z is at each separate occurrence selected from alkylene, substituted alkylene, alkylalkoxy, cycloalkylene, substituted cycloalkylene, alkenylene, substituted alkenylene, alkynylene, substituted alkynylene, cycloalkenylene, substituted alkenylene, arylene, substituted arylene, heteroarylene, heterocyclene, substituted heterocyclene, crown compounds, or a covalent bond;

Y' and Y' at each separate occurrence are selected from —S—S— or a covalent bond;

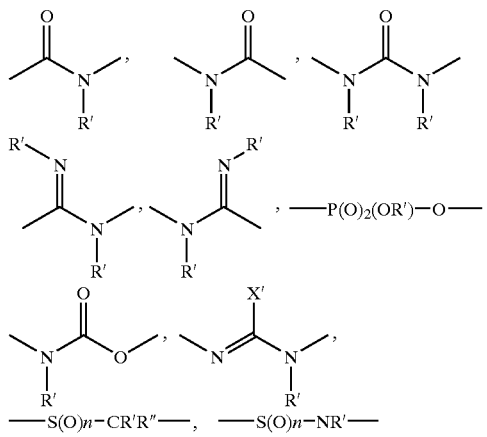

—S(O)$n$—CR'R"—, —S(O)$n$—NR'— in which:

n is 0, 1 or 2; and

R' and R" at each separate occurrence are selected from hydrogen, alkyl, substituted alkyl, cycloalkyl, substituted cycloalkyl, alkenyl, substituted alkenyl, alkynyl, substituted alkynyl, aryl, heteroaryl or heterocyclic.

Even more preferably, the ligands are selected from Ca$^{++}$ channel modulators such as A-53930A, AE-0047, AGN-190604, AGN-190744, AH-1058, AHR-12742, AHR-16303B, AHR-16462B, AIT-110, AIT-111, AJ-3941, AM-336, amlopidine (including S(-), R-(+), and racemic), anipamil, AP-1067, aranidipine, atosiban, azelnidipine, barnidipine, Bay-t-7207, Bay-y-5959, Bay-z-4406, BBR-2160, belfosdil, BIII-890-CL, bisaramil, BMS-181102, BMS-188107, BMY-43011, BRL-32872, buflomedil, CD-349, CD-832, CERM-12816, CGP-28932, cilnidipine, dentiazem, clevidipine, CNS-1067, CNS-1237, CNS-2103, CP-060S, CPC-301, CPC-317, CPU-86017, D-2024, darodipine, DHP-218, diftiazem, diperdipine, dopropidil, dotarazine, dronedarone, DTZ-323, E-047/1, efonidipine, EGIS-7229, elgodipine, emopamil, etomoxir, F-0401, fantofarone, fasudil, FCE-24265, FCE-26262, FCE-27335, FCE-27892, FCE-28718, felodipine, FPL-64176, FR-172516, FRG-8701, fumidipine, GS-386, iganidipine, ipenoxazone, isradipine, JTV-591, KP-840, KT-362, L-366682, lacidipine, LAS-0538, LCB-2514, lemildipine, lercanidipine, leualacin, lifarizine, LOE-908, lomerizine, lubeluzole, LY-042826, manidipine, McN-6186, mibefradil, monatepil, MR-14134, N-3601, NCC-1048, nefiracetam, nexopamil, nifedipine, nifedipine, Nifelan, nilvadipine, nimodipine, NNC-09-0026, NPS-568, NS-638, NS-649, NS-696, NS-7, OPC-8490, Org-13061, Org-30029, oxodipine, P-5, palonidipine, PCA-50922, PCA-50938, PCA-50941, PD-029361, PD-157667, PD-158143, PD-176078, pranidipine, QX-314, ranolazine, RHG-2716, RingCap, Ro-11-2933, RS-5773, RU-43945, RWJ-22108, RWJ-22726, RWJ-29009, RWJ-37868, S-12968, S-2150, S-312-d, SANK-71996, SB-201823, SB-206284A, SB-23736, SD-3212, semotiadil, SIB-1281, siratiazem, SKFA-45675, SKF-96365, SKT-M-26, SL-34.0829, SL-87.0495, SM-6586, SNX-124, SNX-236, SNX-239, SNX-325, SNX-482, SQ-31727, SQ-33351, SQ-34399, SR-33805, TA-993, tamolarizine, TDN-345, temiverine, terodiline, TH-9229, TN-871, U-88999, U-92032, U-92798, UCL-1439, UK-1656, UK-55444, UK-56593, UK-84149, verapamil, Verelan, vexibinol, VUF-8929, WAY-141520, XB-513, XT-044, Y-22516, YH-334, YM-1615-4, YM-430, Z-6568, zatebradine, ziconotide, and ZM-224832.

Particularly preferred Ca$^{++}$ channel modulators include verapamil, diltiazem, benziazem clentiazem, nicardipine, nifedipine, nilvadipine, nitredipine, nimodipine, isradipine, lacidipine, amlodipine, nisoldipine, isradipine, mibefradil, amlodipine, felodipine, nimodipine, bepridil, SQ 32,910 and SQ 32,428.

In a second embodiment, this invention is directed to a pharmaceutical composition comprising a pharmaceutically acceptable excipient and a therapeutically effective amount of one or more multibinding compounds (or pharmaceutically acceptable salts thereof) comprising 2 to 10 ligands which may be the same or different and which are covalently attached to a linker or linkers, which may be the same or different, each of said ligands comprising a ligand domain capable of binding to a Ca$^{++}$ channel of a cell mediating mammalian diseases or conditions, thereby modulating the diseases or conditions.

In a third embodiment, this invention is directed to a pharmaceutical composition comprising a pharmaceutically acceptable excipient and a therapeutically effective amount of one or more multibinding compounds represented by Formula I, $$(L)_p(X)_q \qquad \qquad I$$

or pharmaceutically acceptable salts thereof, where each L is a ligand that may be the same or different at each occurrence;

X is a linker that may be the same or different at each occurrence;

p is an integer of from 2 to 10; and q is an integer of from 1 to 20;

wherein each of said ligands comprises a ligand domain capable of binding to a Ca$^{++}$ channel of a cell mediating mammalian diseases or conditions, thereby modulating the diseases or conditions, Preferably q is less than p.

In a fourth embodiment, this invention is directed to a method for modulating the activity of a Ca$^{++}$ channel in a biologic tissue, which method comprises contacting a tissue having a Ca$^{++}$ channel with a multibinding compound (or pharmaceutically acceptable salts thereof) under conditions sufficient to produce a change in the activity of the channel in said tissue, wherein the multibinding compound comprises 2 to 10 ligands which may be the same or different and which are covalently attached to a linker or linkers, which may be the same or different, each of said ligands comprising a ligand domain capable of binding to a Ca$^{++}$ channel.

In a fifth embodiment, this invention is directed to a method for treating a disease or condition in a mammal resulting from an activity of a $Ca^{++}$ channel, which method comprises administering to said mammal a therapeutically effective amount of a pharmaceutical composition comprising a pharmaceutically acceptable excipient and one or more multibinding compounds (or pharmaceutically acceptable salts thereof) comprising 2 to 10 ligands which may be the same or different and which are covalently attached to a linker or linkers, which may be the same or different, each of said ligands comprising a ligand domain capable of binding to a $Ca^{++}$ channel of a cell mediating mammalian diseases or conditions.

In a sixth embodiment, this invention is directed to a method for treating a disease or condition in a mammal resulting from an activity of a $Ca^{++}$ channel, which method comprises administering to said mammal a therapeutically effective amount of a pharmaceutical composition comprising a pharmaceutically acceptable excipient and one or more multibinding compounds represented by Formula I,

  I and pharmaceutically acceptable salts thereof,
where each L is a ligand that may be the same or different at each occurrence;
X is a linker that may be the same or different at each occurrence;
p is an integer of from 2 to 10; and
q is an integer of from 1 to 20:
wherein each of said ligands comprises a ligand domain capable of binding to a $Ca^{++}$ channel of a cell mediating mammalian diseases or conditions. Preferably q is less than p.

In a seventh embodiment, this invention relates to processes for preparing the multibinding agents of Formula I.

In an eighth aspect, this invention is directed to general synthetic methods for generating large libraries of diverse multimeric compounds which multimeric compounds are candidates for possessing multibinding properties. The diverse multimeric compound libraries provided by this invention are synthesized by combining a linker or linkers with a ligand or ligands to provide for a library of multimeric compounds wherein the linker and ligand each have complementary functional groups permitting covalent linkage. The library of linkers is preferably selected to have diverse properties such as valency, linker length, linker geometry and rigidity, hydrophilicity or hydrophobicity, amphiphilicity, acidity, basicity and polarization. The library of ligands is preferably selected to have diverse attachment points on the same ligand, different functional groups at the same site of otherwise the same ligand, and the like.

This invention is also directed to libraries of diverse multimeric compounds which multimeric compounds are candidates for possessing multibinding properties. These libraries are prepared via the methods described above and permit the rapid and efficient evaluation of what molecular constraints impart multibinding properties to a ligand or a class of ligands targeting a receptor.

Accordingly, in one of its method aspects, this invention is directed to a method for identifying multimeric ligand compounds possessing multibinding properties which method comprises:
(a) identifying a ligand or a mixture of ligands wherein each ligand contains at least one reactive functionality;
(b) identifying a library of linkers wherein each linker in said library comprises at least two functional groups having complementary reactivity to at least one of the reactive functional groups of the ligand;
(c) preparing a multimeric ligand compound library by combining at least two stoichiometric equivalents of the ligand or mixture of ligands identified in (a) wit the library of linkers identified in (b) under conditions wherein the complementary functional groups react to form a covalent linkage between said linker and at least two of said ligands; and
(d) assaying the multimeric ligand compounds produced in (c) above to identify multimeric ligand compounds possessing multibinding properties.

In another of its method aspects, this invention is directed to a method for identifying multimeric ligand compounds possessing multibinding properties which method comprises:
(a) identifying a library of ligands wherein each ligand contains at least one reactive functionality;
(b) identifying a linker or mixture of linkers wherein each linker comprises at least two functional groups having complementary reactivity to at least one of the reactive functional groups of the ligand;
(c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands; and
(d) assaying the multimeric ligand compounds produced in (c) above to identify multimeric ligand compounds possessing multibinding properties.

The preparation of the multimeric ligand compound library is achieved by either the sequential or concurrent combination of the two or more stoichiometric equivalents of the ligands identified in (a) with the linkers identified in (b). Sequential addition is preferred when a mixture of different ligands is employed to ensure heterodimeric or multimeric compounds are prepared. Concurrent addition of the ligands occurs when at least a portion of the multimer comounds prepared are homomultimeric compounds.

The assay protocols recited in (d) can be conducted on the multimeric ligand compound library produced in (c) above, or preferably, each member of the library is isolated by preparative liquid chromatography mass spectrometry (LCMS).

In one of its composition aspects, this invention is directed to a library of multimeric ligand compounds which may possess multivalent properties which library is prepared by the method comprising:
(a) identifying a ligand or a mixture of ligands wherein each ligand contains at least one reactive functionality;
(b) identifying a library of linkers wherein each linker in said library comprises at least two functional groups having complementary reactivity to at least one of the reactive functional groups of the ligand; and
(c) preparing a multimeric ligand compound library by combining at least two stoichiometric equivalents of the ligand or mixture of ligands identified in (a) with the library of linkers Identified in (b) under conditions wherein the complementary functional groups react to form a covalent linkage between said linker and at least two of said ligands.

In another of its composition aspects, this invention is directed to a library of multimeric ligand compounds which may possess multivalent properties which library is prepared by the method comprising:
(a) identifying a library of ligands wherein each ligand contains at least one reactive functionality;
(b) identifying a linker or mixture of linkers wherein each linker comprises at least two functional groups having complementary reactivity to at least one of the reactive functional groups of the ligand; and (c) preparing a multimeric ligand compound library by combining at least two stoichiometric equivalents of the library of ligands identified in (a) with the linker or mixture of linkers identified in (b) under conditions wherein the complementary functional groups react to form a covalent linkage between said linker and at least two of said ligands.

In a preferred embodiment, the library of linkers employed in either the methods or the library aspects of this invention is selected from the group comprising flexible linkers, rigid linkers, hydrophobic linkers, hydrophilic linkers, linkers of different geometry, acidic linkers, basic linkers, linkers of different polarization and amphiphilic linkers. For example, in one embodiment, each of the linkers in the linker library may comprise linkers of different chain length and/or having different complementary reactive groups. Such linker lengths can preferably range from about 2 to 100 Å.

In another preferred embodiment, the ligand or mixture of ligands is selected to have reactive functionality at different sites on said ligands in order to provide for a range of orientations of said ligand on said multimeric ligand compounds. Such reactive functionality includes, by way of example, carboxylic acids, carboxylic acid halides, carboxyl esters, amines, halides, isocyanates, vinyl unsaturation, ketones, aldehydes, thiols, alcohols, anhydrides, and precursors thereof. It is understood, of course, that the reactive functionality on the ligand is selected to be complementary to at least one of the reactive groups on the linker so that a covalent linkage can be formed between the linker and the ligand.

In other embodiments, the multimeric ligand compound is homomeric (ie., each of the ligands is the same, although it may be attached at different points) or heterodimeric (i.e., at least one of the ligands is different from the other ligands).

In addition to the combinatorial methods described herein, this invention provides for an iterative process for rationally evaluating what molecular constraints impart multibinding properties to a class of multimeric compounds or ligands targeting a receptor. Specifically, this method aspect is directed to a method for Identifying multimeric ligand compounds possessing multibinding properties which method comprises:

(a) preparing a first collection or iteration of multimeric compounds which is prepared by contacting at least two stoichiometric equivalents of the ligand or mixture of ligands which target a receptor with a linker or mixture of linkers wherein said ligand or mixture of ligands comprises at least one reactive functionality and said linker or mixture of linkers comprises at least two functional groups having complementary reactivity to at least one of the reactive functional groups of the ligand wherein said contacting is conducted under conditions wherein the complementary functional groups react to form a covalent linkage between said linker and at least two of said ligands;

(b) assaying said first collection or iteration of multimeric compounds to assess which if any of said multimeric compounds possess multibinding properties;

(c) repeating the process of (a) and (b) above until at least one multimeric compound is found to possess multibinding properties;

(d) evaluating what molecular constraints imparted multibinding properties to the multimeric compound or compounds found in the first iteration recited in (a)–(c) above;

(e) creating a second collection or iteration of multimeric compounds which elaborates upon the particular molecular constraints imparting multibinding properties to the multimeric compound or compounds found in said first iteration;

(f) evaluating what molecular constraints imparted enhanced multibinding properties to the multimeric compound or compounds found in the second collection or iteration recited in (e) above;

(g) optionally repeating steps (e) and (f) to further elaborate upon said molecular constraints.

Preferably, steps (e) and (f) are repeated at least two times, more preferably at from 2–50 times, even more preferably from 3 to 50 times, and still more preferably at least 5–50 times.

DETAILED DESCRIPTION OF THE INVENTION

Figure 1:
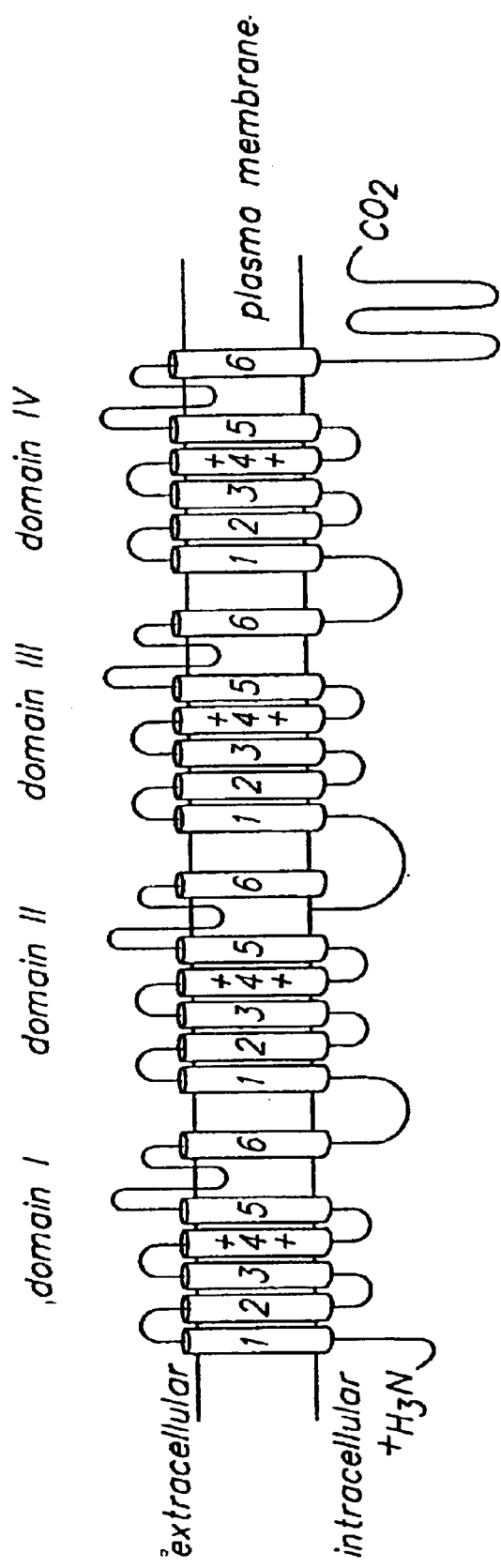
FIG. 1 is a highly schematic illustration of the transmembrane organization of the α1 subunit of the voltage-gated $Ca^{++}$ channel.
Figure 2A:
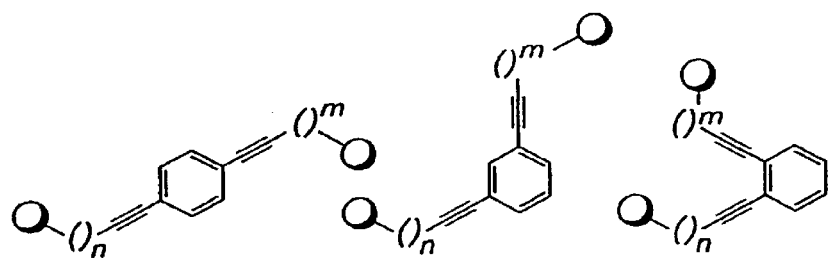
FIG. 2 illustrates a method for optimizing the linker geometry for presentation of ligands (filled circles) in bivalent compounds:
A. phenyldiacetylene core structure
B. cyclohexane dicarboxylic acid core structure
Figure 2B:
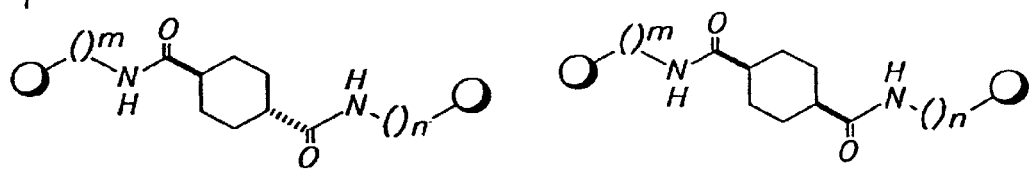
Figure 2B:
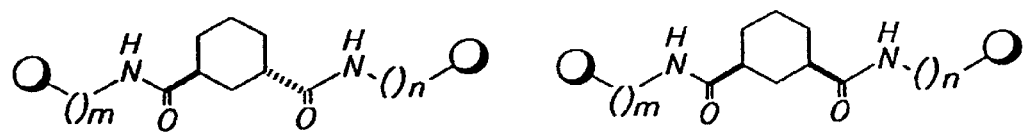
Figure 2B:
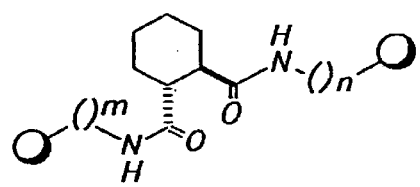
Figure 2B:
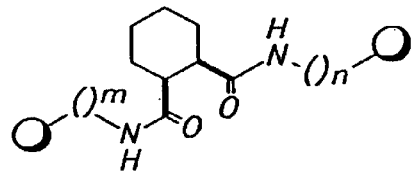

Biological systems in general are controlled by molecular interactions between bioactive ligands and their receptors, in which the receptor "reognizes" a molecule or a portion thereof (ie., a ligand domain) to produce a biological effect. The voltage-gated $Ca^{++}$ channels are considered to be pharmacological receptors: they possess specific binding sites for ligands having agonist and antagonist activities; the binding of ligands to such sites allosterically modulates $Ca^{++}$ flux through the channel; the channel properties (i.e., gating and ion selectivity) are regulatable; and various channels are known to associate with G-proteins (D. Rampe and D. J. Triggle, *Prog. Drug Res.* 40: 191–238 (1993). Accordingly, diseases or conditions that involve, or are mediated by, $Ca^{++}$ channels can be treated with pharmacologically active ligands that interact with such channels to initiate, modulate or abrogate transporter activity.

The interaction of a $Ca^{++}$ channel and a $Ca^{++}$ channel-binding ligand may be described in terms of "affinity" and "specificity". The "affinity" and "specificity" of any given ligand-$Ca^{++}$ channel interaction is dependent upon the complementarity of molecular binding surfaces and the energetic costs of complexation (i.e., the net difference in free energy $\Delta G$ between bound and free states). Affinity may be quantified by the equilibrium constant of complex formation, the ratio of on/off rate constants, and/or by the free energy of complex formation. Specificity relates to the difference in binding affinity of a ligand for different receptors.

The net free energy of interaction of such ligands with a $Ca^{++}$ channel is the difference between energetic gains (enthalpy gained through molecular complementarity and entropy gained through the hydrophobic effect) and energetic costs (enthalpy lost through decreased salvation and entropy lost through reduced translational, rotational and conformational degrees of freedom).

The compounds of this invention comprise 2 to 10 $Ca^{++}$ channel-binding ligands covalently linked together and capable of acting as multibinding agents. Without wishing to be bound by theory, the enhanced activity of these compounds is believed to arise at least in part from their ability to bind in a multivalent manner with multiple ligand binding sites on a $Ca^{++}$ channel or channels, which gives rise to a more favorable net free energy of binding. Multivalent interactions differ from collections of individual monovalent (univalent) interactions by being capable of providing enhanced biologic and/or therapeutic effect. Multivalent binding can amplify binding affinities and differences in binding affinities, resulting in enhanced binding specificity as well as affinity.

Definitions

As used herein:

The term "alkyl" refers to a monoradical branched or unbranched saturated hydrocarbon chain, preferably having from 1 to 40 carbon atoms, preferably 1–10 carbon atoms, more preferably 1–6 carbon atoms, such as methyl, ethyl, n-propyl, isopropyl, n-butyl, secondary butyl, tert-butyl, n-hexyl, n-octyl, n-decyl, n-dodecyl, 2-ethyldodecyl, tetradecyl, and the like, unless otherwise indicated.

The term "substituted alkyl" refers to an alkyl group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, hetararyloxy, heterocyclic, heterocyclooxy, hydroxyamino, alkoxyamino, nitro, —SO-alkyl, —SO-aryl, —SO-heteroaryl, —SO$_2$-alkyl, —O$_2$-aryl, —SO$_2$-heteroaryl, and —NR$^a$R$^b$, wherein R$^a$ and R$^b$ may be the same or different and and are chosen from hydrogen, optionally substituted alkyl, cycloalkyl, alkenyl, cycloalkenyl, alkynyl, aryl, heteroaryl and heterocyclic.

The term "alkylene" refers to a diradical of a branched or unbranched saturated hydrocarbon chain, preferably having from 1 to 40 carbon atoms, preferably 1–10 carbon atoms, more preferably 1–6 carbon atoms. This term is exemplified by groups such as methylene (—CH$_2$—), ethylene (—CH$_2$CH$_2$—), the propylene isomers (e.g., —CH$_2$CH$_2$CH$_2$— and —CH(CH$_3$)CH$_2$—) and the like.

The term "substituted alkylene" refers to an alkylene group as defined above having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkylene groups include those where 2 substituents on the alkylene group are fused to form one or more cycloalkyl, substituted cycloalkyl, cycloalkenyl, substituted cycloalkenyl, aryl, heterocyclic or heteroaryl groups fused to the alkylene group. The term "substituted alkylene" optionally includes an alkylene chain as defined above in which the carbon chain is interrupted by one or more atoms chosen from O, S or N (e.g., ethers, sulfides and amines).

The term "alkaryl" or "aralkyl" refers to the groups -alkylene-aryl and -substituted alkylene-aryl in which alkylene and aryl are as defined herein. Such alkaryl groups are exemplified by benzyl, phenethyl and the like.

The term "alkoxy" refers to the groups alkyl-O—, alkenyl-O—, cycloalkyl-O—, cycloalkenyl-O—, and alkynyl-O—, where alkyl, alkenyl, cycloalkyl, cycloalkenyl, and alkynyl are as defined herein. Preferred alkoxy groups are alkyl-O— and include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

"Alkenyl" refers to a monoradical of a branched or unbranched unsaturated hydrocarbon preferably having from 2 to 40 carbon atoms, preferably 2–10 carbon atoms, more preferably 2–6 carbon atoms, and preferably having 1–6 double bonds. This term is further exemplified by such radicals as vinyl, prop-2-enyl, pent-3-enyl, hex-5-enyl, 5-ethyldodec-3,6-dienyl, and the like.

The term "substituted alkenyl" refers to an alkenyl group as defined above having from 1 to 5 substituents selected from the group consisting of alkoxy, substituted alkoxy, acyl, acylamino, acyloxy, amino, aminoacyl, aminoacyloxy, oxyaminoacyl, azido, cyano, halogen, hydroxyl, keto, thioketo, carboxyl, carboxylalkyl, thiol, thioalkoxy, substituted thioalkoxy, aryl, heteroaryl, heterocydic, aryloxy, thioaryloxy, heteroaryloxy, thioheteroaryloxy, heterocyclooxy, thioheterocyclooxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and —NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkenylene" refers to a diradical of an unsaturated hydrocarbon, preferably having from 2 to 40 carbon atoms, preferably 2–10 carbon atoms, more preferably 2–6 carbon atoms, and preferably having 1–6 double bonds. This term is further exemplified by such radicals as 1,2-ethenyl, 1,3-prop-2-enyl, 1,5-pent-3enyl, 1,4-hex-5-enyl, 5-ethyl-1,12-dodec-3,6-dienyl, and the like.

The term "substituted alkenylene" refers to an alkenylene group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxylalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocyclooxy, nitro, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Additionally, such substituted alkenylene groups include those where 2 substituents on the alkenylene group are fused to form one or more cycloalkyl, substituted cycloalkyl, cycloalkenyl, substituted cycloalkenyl, aryl, heterocyclic or heteroaryl groups fused to the alkenylene group.

"Alkynyl" refers to a monoradical of an unsaturated hydrocarbon, preferably having from 2 to 40 carbon atoms, preferably 2–10 carbon atoms, more preferably 2–6 carbon atoms, and preferably having 1–6 triple bonds. This term is further exemplified by such radicals as acetylenyl, prop-2-ynyl, pent-3-ynyl, hex-5-ynyl, "ethyldodec-3,6-diynyl, and the like.

The term "substituted alkynyl" refers to an alkynyl group as defined above having from 1 to 5 substituents, selected from the group consisting of alkoxy, substituted alkoxy, acyl, acylamino, acyloxy, amino, aminoacyl, aminoacyloxy, oxyacylamino, azido, cyano, halogen, hydroxyl, keto, thioketo, carboxyl, carboxyalkyl, thiol, thioalkoxy, substituted thioalkoxy, aryl, aryloxy, thioaryloxy, heteroaryl, heteroaryloxy, thioheteroaryloxy, heterocyclic, heterocyclooxy, thioheterocycloxy, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, SO$_2$-heterocyclic, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

"Alkynylene" refers to a diradical of an unsaturated hydrocarbon radical, preferably having from 2 to 40 carbon atoms, preferably 2–10 carbon atoms, more preferably 2–6 carbon atoms, and preferably having 1–6 triple bonds. This term is further exemplified by such radicals as 1,3-prop-2-ynyl, 1,5-pent-3-ynyl, 1,4-hex-5-ynyl, 5-ethyl-1,12-dodec-3,6-diynyl, and the like.

The term "acyl" refers to the groups —CHO, alkyl-C(O)—, substituted alkyl-C(O)—, cycloalkyl-C(O)—, substituted cycloalkyl-C(O)—, cycloalkenyl-C(O)—, substituted cycloalkenyl-C(O)—, aryl-C(O)—, heteroaryl-C(O)— and heterocyclic-C(O)— where alkyl, substituted alkyl, cycloalkyl, substituted cycloalkyl, cycloalkenyl, substituted cycloalkenyl, aryl, heteroaryl and heterocyclic are as defined herein.

The term "acylamino" refers to the group —C(O)NRR where each R is independently hydrogen, alkyl, substituted alkyl, aryl, heteroaryl, heterocyclic or where both R groups are joined to form a heterocyclic group (e.g., morpholine) wherein alkyl, substituted alkyl, aryl, heteroaryl and heterocyclic are as defined herein.

The term "aminoacyl" refers to the group —NRC(O)R where each R is independently hydrogen, alkyl, substituted alkyl, aryl, heteroaryl, or heterocyclic wherein alkyl, substituted alkyl, aryl, heteroaryl and heterocyclic are as defined herein.

The term "aminoacyloxy" refers to the group —NRC(O)OR where each R is independently hydrogen, alkyl, substituted alkyl, aryl, heteroaryl, or heterocyclic wherein alkyl, substituted alkyl, aryl, heteroaryl and heterocyclic are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclic-C(O)O— wherein alkyl, substituted alkyl, cycloalkyl, substituted cycloalkyl, aryl, heteroaryl, and heterocyclic are as defined herein.

The term "aryl" refers to an unsaturated aromatic carbocydic group of from 6 to 20 carbon atoms having a single ring (e.g., phenyl) or multiple condensed (fused) rings (e.g., naphthyl or anthryl).

Unless otherwise constrained by the definition for the aryl substituent, such aryl groups can optionally be substituted with from 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Preferred aryl substituents include alkyl, alkoxy, halo, cyano, nitro, trihalomethyl, and thioalkoxy.

The term "aryloxy" refers to the group aryl-O— wherein the aryl group is as defined above including optionally substituted aryl groups as also defined above.

The term "arylene" refers to a diradical derived from aryl or substituted aryl as defined above, and is exemplified by 1,2-phenylene, 1,3-phenylene, 1,4-phenylene, 1,2-naphthylene and the like.

The term "carboxyalkyl" refers to the group "—C(O)Oalkyl" where alkyl is as defined above.

The term "cycloalkyl" refers to cyclic alkyl groups of from 3 to 20 carbon atoms having a single cyclic ring or multiple condensed rings. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents selected from the group consisting of alkoxy, substituted alkoxy, cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "cycloalkenyl" refers to cyclic alkenyl groups of from 4 to 20 carbon atoms having a single cyclic ring or fused rings and at least one point of internal unsaturation. Examples of suitable cycloalkenyl groups include, for instance, cyclobut-2-enyl, cyclopent-3-enyl, cyclooct-3-enyl and the like.

The term "substituted cycloalkenyl" refers to cycloalkenyl groups having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic.

The term "halo" or "halogen" refers to fluoro, chloro, bromo and iodo.

The term "heteroaryl" refers to an aromatic group of from 1 to 15 carbon atoms and 1 to 4 heteroatoms selected from oxygen, nitrogen and sulfur within at least one ring (if there is more than one ring).

Unless otherwise constrained by the definition for the heteroaryl substituent, such heteroaryl groups can be optionally substituted with 1 to 5 substituents selected from the group consisting of acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, aminoacyl, acylamino, alkaryl, aryl, aryloxy, azido, carboxyl, carboxylalkyl, cyano, halo, nitro, heteroaryl, heteroaryloxy, heterocyclic, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, trihalomethyl, mono-and di-alkylamino, mono- and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocydic. Preferred heteroaryls nclude pyridyl, pyrrolyl and furyl.

The term "heteroaryloxy" refers to the group heteroaryl-O—.

The term "heteroarylene" refers to the diradical group derived from heteroaryl or substituted heteroaryl as defined above, and is exemplified by the groups 2,6-pyridylene, 2,4-pyridiylene, 1,2-quinolinylene, 1,8-quinolinylene, 1,4-benzofuranylene, 2,5-pyridinylene, 1,3-morpholinylene, 2,5-indolenyl, and the like.

The term "heterocycle" or "heterocyclic" refers to a monoradical saturated or unsaturated group having a single ring or multiple condensed rings, from 1 to 40 carbon atoms and from 1 to 10 hetero atoms, preferably 1 to 4 heteroatoms, selected from nitrogen, sulfur, phosphorus, and/or oxygen within the ring.

Unless otherwise constrained by the definition for the heterocyclic substituent, such heterocyclic groups can be optionally substituted with 1 to 5, and preferably 1 to 3 substituents, selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclic, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl, and NR$^a$R$^b$, wherein R$^a$ and R$^b$ may be the same or different and are chosen from hydrogen, optionally substituted alkyl, cycloalkyl, alkenyl, cycloalkenyl, alkynyl, aryl, heteroaryl and heterocyclic. Such heterocyclic groups can have a single ring or multiple condensed rings.

Examples of nitrogen heterocycles and heteroaryls include, but are not limited to, pyrrole, imidazole, pyrazole, pyridine, pyrazine, pyrmidine, pyridazine, indolizine, isoindole, indole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, morpholino, piperidinyl, tetrahydrofuranyl, and the like as well as N-alkoxy-nitrogen containing heterocycles.

A preferred class of heterocyclics include "crown compounds" which refers to a specific class of heterocyclic compounds having one or more repeating units of the formula [—(CH$_2$—)$_m$Y—] where m is equal to or greater than 2, and Y at each separate occurrence can be O, N, S or P. Examples of crown compounds include, by way of example only, [—(CH$_2$)$_3$—NH—]$_3$, [—((CH$_2$)$_2$—O)$_4$—((CH$_2$)$_2$)—NH)$_2$] and the like. Typically such crown compounds can have from 4 to 10 heteroatoms and 8 to 40 carbon atoms.

The term "heterocyclooxy" refers to the group heterocyclic-O—.

The term "thioheterocyclooxy" refers to the group heterocydic-S—.

The term "heterocyclene" refers to the diradical group derived from a heterocycle as defined herein, and is exemplified by the groups 2,6-morpholino, 2,5-morpholino and the like.

The term "oxyacylamino" refers to the group —OC(O)NRR where each R is independently hydrogen, alkyl, substituted alkyl, aryl, heteroaryl, or heterocyclic wherein alkyl, substituted alkyl, aryl, heteroaryl and heterocydic are as defined herein.

The term "thiol" refers to the group —SH.

The term "thioalkoxy" refers to the group —S-alkyl.

The term "substituted thioalkoxy" refers to the group —S-substituted alkyl.

The term "thioaryloxy" refers to the group aryl-S— wherein the aryl group is as defined above including optionally substituted aryl groups also defined above.

The term "thioheteroaryloxy" refers to the group heteroaryl-S— wherein the heteroaryl group is as defined above including optionally substituted aryl groups as also defined above.

As to any of the above groups which contain one or more substituents, it is understood, of course, that such groups do not contain any substitution or substitution patterns which are sterically impractical and/or synthetically non-feasible. In addition, the compounds of this invention include all stereochemical isomers arising from the substitution of these compounds.

"Alkyl optionally interrupted by 1–5 atoms chosen from O, S, or N" refers to alkyl as defined above in which the carbon chain is interrupted by O, S, or N, Within the scope are ethers, sulfides, and amines, for example 1-methoxydecyl, 1-pentyloxynonane, 1-(2-isopropoxyethoxy)-4-methylnonane, 1-(2-ethoxyethoxy) dodecyl, 2-(t-butoxy)heptyl, 1-pentylsulfanylnonane, nonylpentylamine, and the like.

"Heteroarylalkyl" refers to heteroaryl as defined above linked to alkyl as defined above, for example pyrid-2-ylmethyl, 8-quinolinylpropyl, and the like.

"Optional" or "optionally" means that the subsequently described event or circumstance may or may not occur, and that the description includes instances where said event or circumstance occurs and instances in which it does not. For example, optionally substituted alkyl means that alkyl may or may not be substituted by those groups enumerated in the definition of substituted alkyl.

The term "pharmaceutically acceptable salt" refers to salts which retain the biological effectiveness and properties of the multibinding compounds of this invention and which are not biologically or otherwise undesirable. In many cases, the multibinding compounds of this invention are capable of forming acid and/or base salts by virtue of the presence of amino and/or carboxyl groups or groups similar thereto.

Pharmaceutically acceptable base addition salts can be prepared from inorganic and organic bases. Salts derived from inorganic bases, include by way of example only, sodium, potassium, lithium, ammonium, calcium and magnesium salts. Salts derived from organic bases include, but are not limited to, salts of primary, secondary and tertiary amines, such as alkyl amines, dialkyl amines, trialkyl amines, substituted alkyl amines, di(substituted alkyl) amines, tri(substituted alkyl) amines, alkenyl amines, dialkenyl amines, trialkenyl amines, substituted alkenyl amines, di(substituted alkenyl) amines, tri(substituted alkenyl) amines, cycloalkyl amines, di(cycloalkyl) amines, tri(cycloalkyl) amines, substituted cycloalkyl amines, disubstituted cycloalkyl amine, trisubstituted cycloalkyl amines, cycloalkenyl amines, di(cycloalkenyl) amines, tri(cycloalkenyl) amines, substituted cycloalkenyl amines, disubstituted cycloalkenyl amine, trisubstituted cycloalkenyl amines, aryl amines, diaryl amines, triaryl amines, heteroaryl amines, diheteroaryl amines, triheteroaryl amines, heterocyclic amines, diheterocyclic amines, triheterocyclic amines, mixed di- and tri-amines where at least two of the substituents on the amine are different and are selected from the group consisting of alkyl, substituted alkyl, alkenyl, substituted alkenyl, cycloalkyl, substituted cycloalkyl, cycloalkenyl, substituted cycloalkenyl, aryl, heteroaryl, heterocyclic, and the like. Also included are amines where the two or three substituents, together with the amino nitrogen, form a heterocyclic or heteroaryl group.

Examples of suitable amines include, by way of example only, isopropylamine, trimethyl amine, diethyl amine, tri(isopropyl) amine, tri(n-propyl) amine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, morpholine, N-ethylpiperdine, and the like. It should also be understood that other carboxylic acid derivatives would be useful in the practice of this invention, for example, carboxylic acid amides, including carboxamides, lower alkyl carboxamides, dialkyl carboxamides, and the like.

Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like.

The term "library" refers to at least 3, preferably from $10^2$ to $10^9$ and more preferably from $10^2$ to $10^4$ multimeric compounds. Preferably, these compounds are prepared as a multiplicity of compounds in a single solution or reaction mixture which permits facile synthesis thereof. In one embodiment, the library of multimeric compounds can be directly assayed for multibinding properties. In another embodiment, each member of the library of multimeric compounds is first isolated and, optionally, characterized. This member is then assayed for multibinding properties.

The term "collection" refers to a set of multimeric compounds which are prepared either sequentially or concurrently (e.g., combinatorially). The collection comprises at least 2 members: preferably from 2 to $10^9$ members and still more preferably from 10 to $10^4$ members.

The term "multimeric compound" refers to compounds comprising from 2 to 10 ligands covalently connected through at least one linker which compounds may or may not possess multibinding properties (as defined herein).

The term "pseudohalide" refers to functional groups which react in displacement reactions in a manner similar to a halogen. Such functional groups include, by way of example, mesyl, tosyl, azido and cyano groups.

The term "protecting group" or "blocking group" refers to any group which when bound to one or more hydroxyl, thiol, amino or carboxyl groups of the compounds prevents reactions from occurring at these groups and which protecting group can be removed by conventional chemical or enzymatic steps to reestablish the hydroxyl, thiol, amino or carboxyl group. See, generally, T. W. Greene & P. G. M. Wuts "Protective Groups in Organic Synthesis," $2^{nd}$ Ed, 1991, John Wiley and Sons, N.Y.

The particular removable blocking group employed is not critical and preferred removable hydroxyl blocking groups include conventional substituents such as allyl, benzyl, acetyl, chloroacetyl, thiobenzyl, benzylidine, phenacyl, t-butyl-diphenylsilyl and any other group that can be introduced chemically onto a hydroxyl functionality and later selectively removed either by chemical or enzymatic methods in mild conditions compatible with the nature of the product.

Preferred removable amino blocking groups include conventional substituents such as t-butyoxycarbonyl (t-BOC), benzyloxycarbonyl (CBZ), fluorenylmethoxycarbonyl (FMOC), allyloxycarbonyl (ALOC) and the like, which can be removed by conventional conditions compatible with the nature of the product.

Preferred carboxyl protecting groups include esters such as methyl, ethyl, propyl, t-butyl etc. which can be removed by mild hydrolysis conditions compatible with the nature of the product.

As used herein, the terms "inert organic solvent" or "inert solvent" mean a solvent inert under the conditions of the reaction being described in conjunction therewith [including, for example, benzene, toluene, acetonitrile, tetrahydrofuran ("THF"), dimethylformamide ("DMF"), chloroform ("$CHCl_3$"), methylene chloride (or dichloromethane or "$CH_2Cl_2$"), diethyl ether, ethyl acetate, acetone, methylethyl ketone, methanol, ethanol, propanol, isopropanol, tert-butanol, dioxane, pyridine, and the like]. Unless specified to the contrary, the solvents used in the reactions of the present invention are inert solvents.

The term "$Ca^{++}$ channel" refers to a structure comprised of integral membrane proteins that functions to allow $Ca^{++}$ to equilibrate across a membrane according to its electrochemical gradient and at rates that are diffusion-limited. Examples of various types of $Ca^{++}$ channels are given in Table 1 (Appendix).

"Ligand" as used herein denotes a compound that is a binding partner for a $Ca^{++}$ channel receptor, and is bound thereto, for example, by complementarity. The specific region or regions of the ligand molecule that is recognized by the ligand binding site of a $Ca^{++}$ channel receptor is designated as the "ligand domain". A ligand may be either capable of binding to a receptor by itself, or may require the presence of one or more non-ligand components for binding (e.g. ions, a lipid molecule, a solvent molecule, and the like).

Ligands useful in this invention comprise $Ca^{++}$ channel modulators such as verapamil (a phenylalkylamine), diltiazem (a benzothiazepine), nicardipine, nifedipine, isradipine, amlodipine, mibefradil, felodipine and nimodipine (dihydropyridines), and bepridil (a diarylaminopropylamine ether). See Tables 4 and 5, Appendix for structures of various dihydropyridine, phenylalkylamine, and benzothiazepine ligands.

While it is contemplated that many calcium channel ligands that are currently known can be used in the preparation of multibinding compounds of this invention (see Table 2 (Appendix)), it should be understood that portions of the ligand structure that are not essential for molecular recognition and binding activity (i.e., that are not part of the ligand domain) may be varied substantially, replaced with unrelated structures and, in some cases, omitted entirely without affecting the binding interaction. Accordingly, it should be understood that the term "ligand" is not intended to be limited to compounds known to be useful as $Ca^{++}$ channel receptor-binding compounds (e.g., known drugs), in that ligands that exhibit marginal activity or lack useful activity as monomers can be highly active as multibinding compounds, because of the biological benefit conferred by multivalency. The primary requirement for a ligand as defined herein is that it has a ligand domain, as defined above, which is available for binding to a recognition site on a $Ca^{++}$ channel.

For purposes of the present invention, the term "ligand" or "ligands" is intended to include the racemic ligands as well as the individual stereoisomers of the ligands, including pure enantiomers and non-racemic mixtures thereof. A large number of known calcium channel ligands have at least one chiral center and show stereoselective pharmacokinetics and pharmacologic activity (reviewed in Tokuma, Y and Noguchi, H., J. Chromatography A, 694: 181–193 (1995)). The scope of the invention as described and claimed encompasses the racemic forms of the ligands as well as the individual enantiomers and non-racemic mixtures thereof.

The term "ligand binding site" as used herein denotes a site on a $Ca^{++}$ channel receptor that recognizes a ligand domain and provides a binding partner for the ligand. The ligand binding site may be defined by monomeric or multimeric structures. This interaction may be capable of producing a unique biological effect, for example agonism, antagonism, modulation, or may maintain an ongoing biological event, and the like.

It should be recognized that the ligand binding sites of $Ca^{++}$ channel receptors that participate in biological multivalent binding interactions are constrained to varying degrees by their intra- and intermolecular associations. For example, $Ca^{++}$ channel ligand binding sites may be covalently joined in a single structure, nonchalantly associated in one or more multimeric structures, embedded in a membrane or biopolymer matrix, and so on, and therefore have less translational and rotational freedom than if the same sites were present as monomers in solution.

The terms "agonism" and "antagonism" are well known in the art. As used herein, the term "agonist" refers to a ligand that when bound to a $Ca^{++}$ channel stimulates its activity. The term "antagonist" refers to a ligand that when bound to a $Ca^{++}$ channel inhibits its activity. Channel block or activation may result from allosteric effects of ligand binding to the channel rather than occupancy of the channel pore. These allosteric effects may produce changes in protein conformation that affect $Ca^{++}$ binding sites, gating mechanisms and/or the pore region (i.e., ion permeation).

A channel can exist in three modes: mode 0 (where the channel has zero probability of opening); mode 1 (where the channel opens frequently but transiently) and mode 2, where the channel remains open for relatively long periods of time (Hess et al, Nature 311: 538–544 (1984)). The probability that a channel will exist in one of these three states changes with voltage. A given ligand may have different binding affinities for different states, and thereby be capable of producing agonist or antagonist activity.

The term "modulatory effect" is intended to refer to the ability of a ligand to change the activity of a $Ca^{++}$ channel through binding to the channel.

"Multibinding agent" or "multibinding compound" refers herein to a compound that has from 2 to 10 $Ca^{++}$ channel ligands as defined herein (which may be the same or different) covalenty bound to one or more linkers (which may be the same or different), and is capable of multivalency, as defined below.

A multibinding compound provides an improved biologic and/or therapeutic effect compared to that of the same number of unlinked ligands available for binding to the ligand binding sites on a $Ca^{++}$ channel or channels. Examples of improved "biologic and/or therapeutic effect" include increased ligand-receptor binding interactions (e.g., increased affinity, increased ability to elicit a functional change in the target, improved kinetics), increased selectivity for the target, increased potency, increased efficacy, decreased toxicity, increased therapeutic index, improved duration of action, improved bioavailability, improved pharmacokinetics, improved activity spectrum, and the like. The multibinding compounds of this invention will exhibit at least one, and preferably more than one, of the above-mentioned effects.

"Univalency" as used herein refers to a single binding interaction between one ligand with one ligand binding site as defined herein. It should be noted that a compound having multiple copies of a ligand (or ligands) exhibits univalency when only one ligand of that compound interacts with a ligand binding site. Examples of univalent interactions are depicted below.

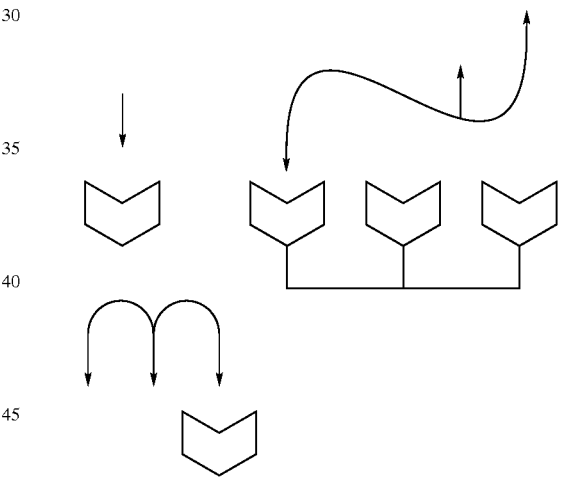

"Multivalency" as used herein refers to the concurrent binding of from 2 to 10 linked ligands, which may be the same or different, and two or more corresponding ligand binding sites, which may be the same or different. An example of trivalent binding is depicted below for illustrative purposes.

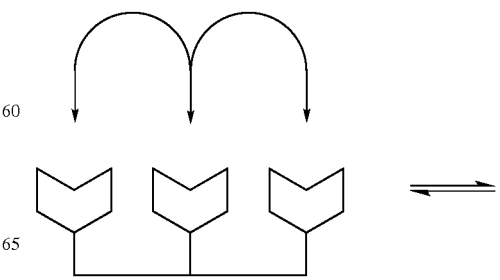

-continued

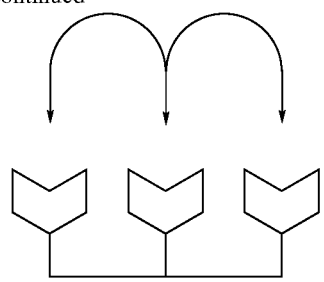

It should be understood that not all compounds that contain multiple copies of a ligand attached to a linker necessarily exhibit the phenomena of multivalency, i.e., that the biologic and/or therapeutic effect of the multibinding agent is greater than that of the same number of unlinked ligands made available for binding to the ligand binding sites. For multivalency to occur, the ligand domains of the ligands that are linked together must be presented to their cognate ligand binding sites by the linker or linkers in a specific manner in order to bring about the desired ligand-orienting result, and thus produce a multibinding interaction.

The term "linker", identified where appropriate by the symbol X, refers to a group or groups that covalently links from 2 to 10 ligands (as defined above) in a manner that provides a multibinding compound capable of multivalency. The linker is a ligand-orienting entity that permits attachment of multiple copies of a ligand (which may be the same or different) thereto.

The term "linker" includes everything that is not considered to be part of the ligand, e.g., ancillary groups such as solubilizing groups, lipophilic groups, groups that alter pharmacodynamics or pharmacokinetics, groups that modify the diffusability of the multibinding compound, spacers that attach the ligand to the linker, groups that aid the ligandorienting function of the linker, for example, by imparting flexibility or rigidity to the linker as a whole, or to a portion thereof, and so on. The term "linker" does not, however, cover solid inert supports such as beads, glass particles, rods, and the like, but it is to be understood that the multibinding compounds of this invention can be attached to a solid support if desired, for example, for use in separation and purification processes and for similar applications.

The extent to which the previously discussed enhanced activity of multibinding compounds is realized in this invention depends upon the efficiency with which the linker or linkers that joins the ligands presents them to their array of ligand binding sites. Beyond presenting these ligands for multivalent interactions with ligand binding sites, the linker spatially constrains these interactions to occur within dimensions defined by the linker.

The linkers used in this invention are selected to allow multivalent binding of ligands to any desired ligand binding sites of a $Ca^{++}$ channel, whether such sites are located interiorly (e.g., within a channel/translocation pore), both interiorly and on the periphery of a channel, at the boundary region between the lipid bilayer and the channel, or at any intermediate position thereof. The preferred linker length will vary depending on the distance between adjacent ligand binding sites, and the geometry, flexibility and composition of the linker. The length of the linker will preferably be in the range of about 2 Å to about 100 Å, more preferably from about 2 Å to about 50 Å and even more preferably from about 3 Å to about 10 Å.

The ligands are covalently attached to the linker or linkers using conventional chemical techniques. The reaction chemistries resulting in such linkage are well known in the art and involve the use of reactive functional groups present on the linker and ligand. Preferably, the reactive functional groups on the linker are selected relative to the functional groups available on the ligand for coupling, or which can be introduced onto the ligand for this purpose. Again, such reactive functional groups are well known in the art. For example, reaction between a carboxylic acid of either the linker or the ligand and a primary or secondary amine of the ligand or the linker in the presence of suitable well-known activating agents results in formation of an amide bond covalently linking the ligand to the linker; reaction between an amine group of either the linker or the ligand and a sulfonyl halide of the ligand or the linker results in formation of a sulfonamide bond covalently linking the ligand to the linker; and reaction between an alcohol or phenol group of either the linker or the ligand and an alkyl or aryl halide of the ligand or the linker results in formation of an ether bond covalenty linking the ligand to the linker. Table 3 (Appendix) illustrates numerous reactive functional groups and the resulting bonds formed by reaction therebetween. Where functional groups are lacking, they can be created by suitable chemistries that are described in standard organic chemistry texts such as J. March, "*Advanced Organic Chemistry*", $4^{th}$ *Edition*, (Wiley-interscience (New York), 1992.

The relative orientation in which the ligand domains are displayed depends both on the particular point or points of attachment of the ligands to the linker, and on the framework geometry. The determination of where acceptable substitutions can be made on a ligand is typically based on prior knowledge of structure-activity relationships of the ligand and/or congeners and/or structural information about ligand-receptor complexes (e.g., X-ray crystallography. NMR, and the like). Such positions and synthetic protocols for linkage are well known in the art and can be determined by those with ordinary skill in the art (see Methods of Preparation and FIGS. 4–20 of the Appendix), Following attachment of a ligand to the linker or linkers, or to a significant portion thereof (e.g., 2–10 atoms of linker), the linker-ligand conjugate may be tested for retention of activity in a relevant assay system (see Utility and Testing below for representative assays).

At present, it is preferred that the multibinding compound is a bivalent compound in which two ligands are covalently linked, or a trivalent compound, in which three ligands are covalently linked. Linker design is further discussed under Methods of Preparation.

"Potency" as used herein refers to the minimum concentration at which a ligand is able to achieve a desirable biological or therapeutic effect. The potency of a ligand is typically proportional to its affinity for its receptor. In some cases, the potency may be non-linearly correlated with its affinity. In comparing the potency of two drugs, e.g., a multibinding agent and the aggregate of its unlinked ligand, the dose-response curve of each is determined under identical test conditions (e.g. in an in vitro or in vivo assay, in an appropriate animal model). The finding that the multibinding agent produces an equivalent biologic or therapeutic effect at a lower concentration than the aggregate unlinked ligand (e.g. on a per weight, per mole or per ligand basis) is indicative of enhanced potency.

"Selectivity" or "specificity" is a measure of the binding preferences of a ligand for different receptors. The selectivity of a ligand with respect to its target receptor relative to another receptor is given by the ratio of the respective values of $K_d$ (i.e., the dissociation constants for each ligand-receptor complex) or, in cases where a biological effect is observed below the $K_d$, the ratio of the respective $EC_{50}$s or $IC_{50}$s (i.e., the concentrations that produce 50% of the maximum response for the ligand interacting with the two distinct receptors).

The term "treatment" refers to any treatment of a disease or condition in a mammal, particularly a human, and includes:

(i) preventing the disease or condition from occurring in a subject which may be predisposed to the condition but has not yet been diagnosed with the condition and, accordingly, the treatment constitutes prophylactic treatment for the pathologic condition;

(ii) inhibiting the disease or condition, i.e., arresting its development;

(iii) relieving the disease or condition, i.e., causing regression of the disease or condition; or (iv) relieving the symptoms resulting from the disease or condition without addressing the underlying disease or condition, e.g., relieving symptoms of angina pectoris and other conditions of ischemia but not an underlying cause such as, for example, atherosclerotic disease or hypertension.

The phrase "disease or condition which is modulated by treatment with a multibinding $Ca^{++}$ channel ligand" covers all disease states and/or conditions that are generally acknowledged in the art to be usefully treated with a ligand for a $Ca^{++}$ channel in general, and those disease states and/or conditions that have been found to be usefully treated by a specific multibinding compound of our invention, i.e., the compounds of Formula I. Such disease states include, by way of example only, hypertension, angina pectoris (particularly vasospastic angina and unstable angina), cerebral ischemia, cardiac arrythmias (particularly, arrythmias resulting from calcium-related changes in membrane potential and conduction), cardiac hypertrophy due to systolic or diastolic overload, congestive heart failure, migraine, Raynaud's disease, acute renal failure due to prolonged renal ischemia, and the like.

The term "therapeutically effective amount" refers to that amount of multibinding compound that is sufficient to effect treatment, as defined above, when administered to a mammal in need of such treatment. The therapeutically effective amount will vary depending upon the subject and disease condition being treated, the weight and age of the subject, the severity of the disease condition, the manner of administration and the like, which can readily be determined by one of ordinary skill in the art.

The term "pharmaceutically acceptable excipient" is intended to include vehicles and carriers capable of being coadministered with a multibinding compound to facilitate the performance of its intended function. The use of such media for pharmaceutically active substances is well known in the art. Examples of such vehicles and carriers include solutions, solvents, dispersion media, delay agents, emulsions and the like. Any other conventional carrier suitable for use with the multibinding compounds also falls within the scope of the present invention.

Methods of Preparation

Linkers

The linker or linkers, when covalently attached to multiple copies of the ligands, provides a biocompatible, substantially non-immunogenic multibinding compound. The biological activity of the multibinding $Ca^{++}$ channel compound is highly sensitive to the geometry, composition, size, length, flexibility or rigidity, the presence or absence of anionic or cationic charge, the relative hydrophobicity/hydrophilicity, and similar properties of the linker. Accordingly, the linker is preferably chosen to maximize the biological activity of the compound. The linker may be biologically "neutral," i.e., not itself contribute any additional biological activity to the multibinding compound, or it may be chosen to further enhance the biological activity of the compound. In general, the linker may be chosen from any organic molecule construct that orients two or more ligands for binding to the receptors to permit multivalency. In this regard, the linker can be considered as a "framework" on which the ligands are arranged in order to bring about the desired ligand-orienting result, and thus produce a multibinding compound.

For example, different orientations of ligands can be achieved by varying the geometry of the framework (linker) by use of mono- or polycyclic groups, such as aryl and/or heteroaryl groups, or structures incorporating one or more carbon-carbon multiple bonds (alkenyl, alkenylene, alkynyl or alkynylene groups). The optimal geometry and composition of frameworks (linkers) used in the multibinding compounds of this invention are based upon the properties of their intended receptors. For example, it is preferred to use rigid cyclic groups (e.g., aryl, heteroaryl), or non-rigid cyclic groups (e.g., cycloalkyl or crown groups) to reduce conformational entropy when such may be necessary to achieve energetically coupled binding.

Different hydrophobic/hydrophilic characteristics of the linker as well as the presence or absence of charged moieties can readily be controlled by the skilled artisan. For example, the hydrophobic nature of a linker derived from hexamethylene diamine ($H_2N(CH_2)_6NH_2$) or related polyamines can be modified to be substantially more hydrophilic by replacing the alkylene group with a poly(oxyalkylene) group such as found in the commercially available "Jeffamines" (class of surfactants).

Different frameworks can be designed to provide preferred orientations of the ligands. The identification of an appropriate framework geometry for ligand domain presentation is an important first step in the construction of a multi binding agent with enhanced activity. Systematic spatial searching strategies can be used to aid in the identification of preferred frameworks through an iterative process. FIG. 2 (Appendix) illustrates a useful strategy for determining an optimal framework display orientation for ligand domains and can be used for preparing the bivalent compounds of this invention. Various alternative strategies known to those skilled in the art of molecular design can be substituted for the one described here.

As shown in FIG. 2, the ligands (shown as filled circles) are attached to a central core structure such as phenyldiacetylene (Panel A) or cyclohexane dicarboxylic acid (Panel B). The ligands are spaced apart from the core by an attaching moiety of variable lengths m and n. If the ligand possesses multiple attachment sites (see discussion below), the orientation of the ligand on the attaching moiety may be varied as well. The positions of the display vectors around the central core structures are varied, thereby generating a collection of compounds. Assay of each of the individual compounds of a collection generated as described will lead to a subset of compounds with the desired enhanced activities (e.g., potency, selectivity). The analysis of this subset using a technique such as Ensemble Molecular Dynamics will suggest a framework orientation that favors the properties desired.

The process may require the use of multiple copies of the same central core stricture or combinations of different types of display cores. It is to be noted that core structures other than those shown here can be used for determining the optimal framework display orientation of the ligands. The above-described technique can be extended to trivalent compounds and compounds of higher-order valency.

A wide variety of linkers is commercially available (see, e.g., Chem Sources USA and Chem Sources international; the ACD electronic database; and Chemical Abstracts). Many of the linkers that are suitable for use in this invention fall into this category. Others can be readily synthesized by methods known in the art, and as described below. Examples of linkers include aliphatic moieties, aromatic moieties, steroidal moieties, peptides, and the like. Specific examples are peptides or polyamides, hydrocarbons, aromatics, heterocyclics, ethers, lipids, cationic or anionic groups, or a combination thereof.

Figure 3A:
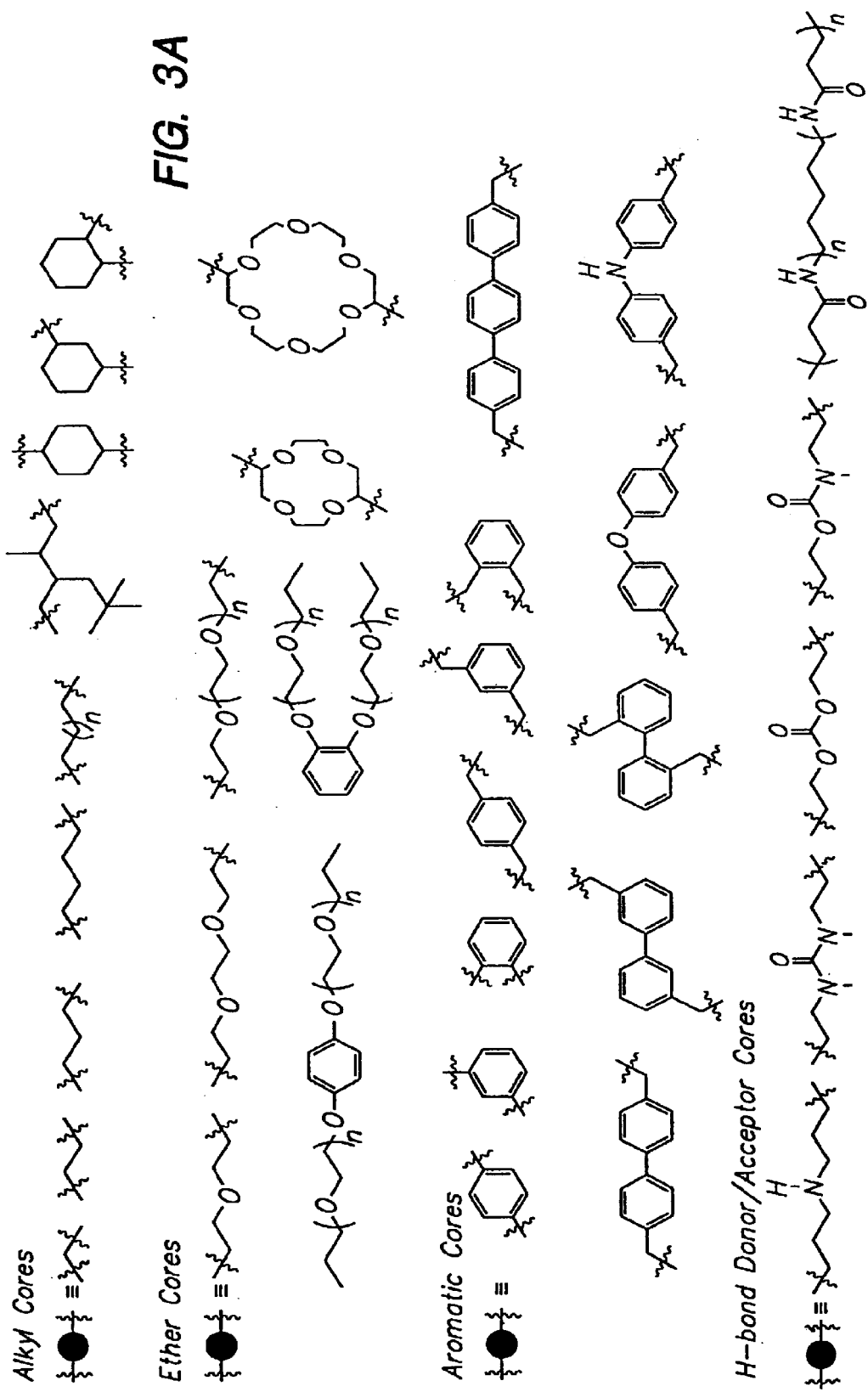
FIG. 3 shows exemplary linker "core" structures.
Figure 3B:
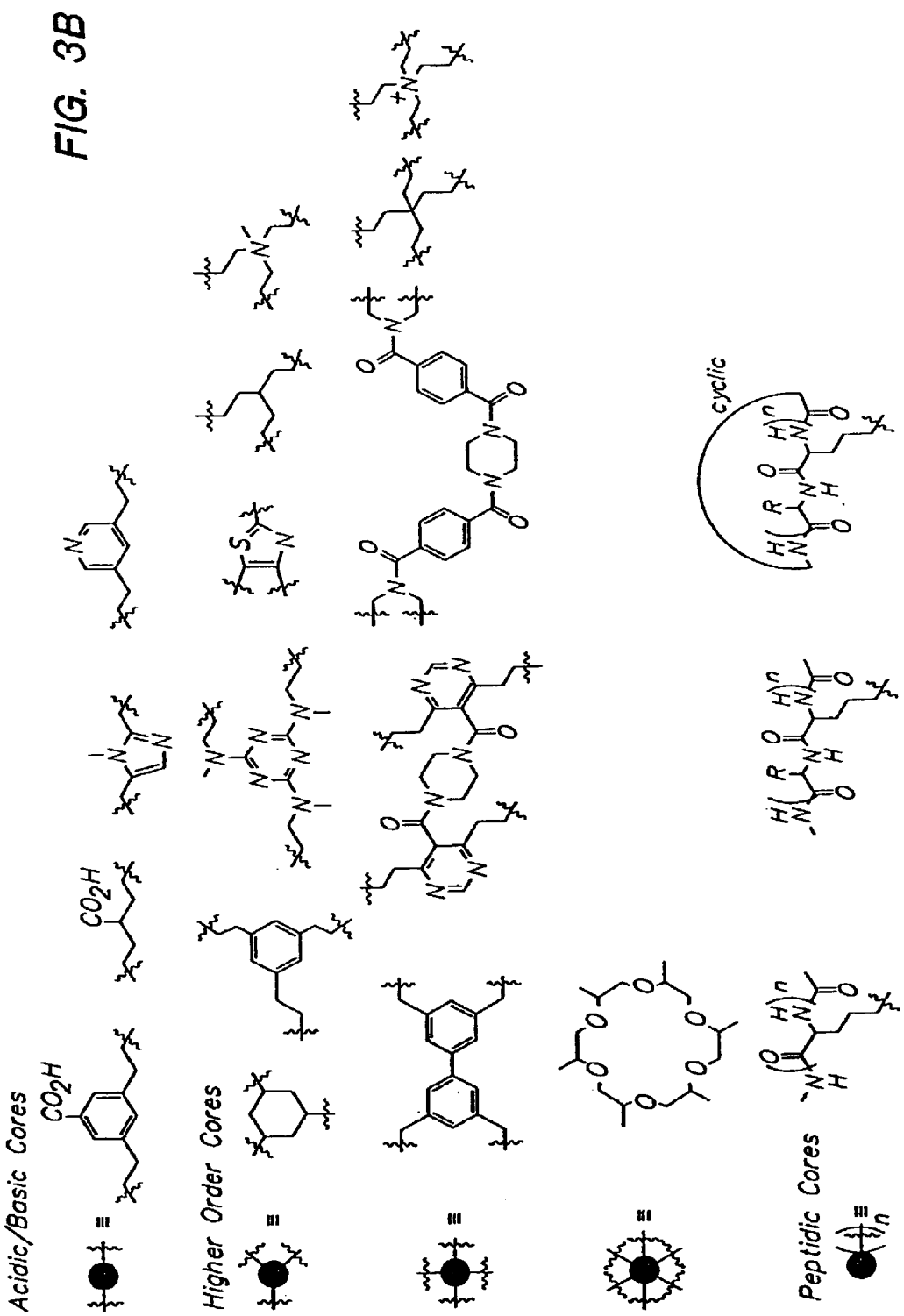

Examples are given below and in FIG. 3 (Appendix), but it should be understood that various changes may be made and equivalents may be substituted without departing from the true spirit and scope of the invention. For example, properties of the linker can be modified by the addition or insertion of ancillary groups into the linker, for example, to change the solubility of the multibinding compound (in water, fats, lipids, biological fluids, etc.), hydrophobicity, hydrophilicity, linker flexibility, antigenicity, stability, and the like. For example, the introduction of one or more poly(ethylene glycol) (PEG) groups onto the linker enhances the hydrophilicity and water solubility of the multibinding compound, increases both molecular weight and molecular size and, depending on the nature of the unPEGylated linker, may increase the in vivo retention time. Further, PEG may decrease antigenicity and potentially enhances the overall rigidity of the linker.

Ancillary groups that enhance the water solubility/hydrophilicity of the linker, and accordingly, the resulting multibinding compounds, are useful in practicing this invention. Thus, it is within the scope of the present invention to use ancillary groups such as, for example, small repeating units of ethylene glycols, alcohols, polyols, (e.g., glycerin, glycerol propoxylate, saccharides, including mono-, oligosaccharides, etc.) carboxylates (e.g., small repeating units of glutamic acid, acrylic acid, etc.), amines (e.g., tetraethylenepentamine), and the like to enhance the water solubility and/or hydrophilicity of the multibinding compounds of this invention. In preferred embodiments, the ancillary group used to improve water solubility/hydrophilicity will be a polyether. In particularly preferred embodiments, the ancillary group will contain a small number of repeating ethylene oxide (—$CH_2CH_2O$—) units.

The incorporation of lipophilic ancillary groups within the structure of the linker to enhance the lipophilicity and/or hydrophobicity of the compounds of Formula I is also within the scope of this invention. Lipophilic groups useful with the linkers of this invention include, but are not limited to, lower alkyl, aromatic groups and polycyclic aromatic groups. The aromatic groups may be either unsubstituted or substituted with other groups, but are at least substituted with a group which allows their covalent attachment to the linker. As used herein the term "aromatic groups" incorporates both aromatic hydrocarbons and heterocydic aromatics. Other lipophilic groups useful with the linkers of this invention include fatty acid derivatives which may or may not form micelles in aqueous medium and other specific lipophilic groups which modulate interactions between the multibinding compound and biological membranes.

Also within the scope of this invention is the use of ancillary groups which result in the compound of Formula I being incorporated into a vesicle, such as a liposome, or a micelle. The term "lipid" refers to any fatty acid derivative that is capable of forming a bilayer or micelle such that a hydrophobic portion of the lipid material orients toward the bilayer while a hydrophilic portion orients toward the aqueous phase. Hydrophilic characteristics derive from the presence of phosphate, carboxylic, sulfato, amino, sulfhydryl, nitro and other like groups well known in the art. Hydrophobicity could be conferred by the inclusion of groups that include, but are not limited to, long chain saturated and unsaturated aliphatic hydrocarbon groups of up to 20 carbon atoms and such groups substituted by one or more aryl, heteroaryl, cycloalkyl, and/or heterocyclic group(s). Preferred lipids are phosphoglycerides and sphingolipids, representative examples of which include phosphatidylcholine, phosphatidylethanolamine, phosphatidylserine, phosphatidylinositol, phosphatidic acid, palmitoyleoyl phosphatidylcholine, lysophosphatidylcholine, lysophosphatidyl-ethanolamine, dipalmitoylphosphatidylcholine, dioleoylphosphatidylcholine, distearoyl-phosphafidylcholine and dilinoleoylphosphatidylcholine. Other compounds lacking phosphorus, such as sphingolipid and glycosphingolipid families, are also within the group designated as lipid. Additionally, the amphipathic lipids described above may be mixed with other lipids including triglycerides and sterols.

The flexibility of the linker can be manipulated by the inclusion of ancillary groups which are bulky and/or rigid. The presence of bulky or rigid groups can hinder free rotation about bonds in the linker, or bonds between he linker and the ancillary group(s), or bonds between the linker and the functional groups. Rigid groups can include, for example, those groups whose conformational freedom is restrained by the presence of rings and/or n-bonds, for example, aryl, heteroaryl and heterocyclic groups. Other groups which can impart rigidity include polypeptide groups such as oligo- or polyproline chains.

Rigidity can also be imparted electrostatically. Thus, if the ancillary groups are either positively or negatively charged, the similarly charged ancillary groups will force the linker into a configuration affording the maximum distance between each of the like charges. The energetic cost of bringing the like-charged groups closer to each other, which is inversely related to the square of the distance between the groups, will tend to hold the linker in a configuration that maintains the separation between the like-charged ancillary groups. Further, ancillary groups bearing opposite charges will tend to be attracted to their oppositely charged counterparts and potentially may enter into both inter- and intramolecular ionic bonds. This non-covalent mechanism will tend to hold the linker in a conformation which allows bonding between the oppositely charged groups. The addition of ancillary groups which are charged, or alternatively, protected groups that bear a latent charge which is unmasked, following addition to the linker, by deprotection, a change in pH, oxidation, reduction or other mechanisms known to those skilled in the art, is within the scope of this invention. Bulky groups can include, for example, large atoms, ions (e.g., iodine, sulfur, metal ions, etc.) or groups containing large atoms, polycyclic groups, including aromatic groups, non-aromatic groups and structures incorporating one or more carbon-carbon n-bonds (i.e., alkenes and alkynes). Bulky groups can also include oligomers and polymers which are branched- or straight-chain species. Species that are branched are expected to increase the rigidity of the structure more per unit molecular weight gain than are straight-chain species.

In preferred embodiments, rigidity (entropic control) is imparted by the presence of alicyclic (e.g., cycloalkyl), aromatic and heterocyclic groups. In other preferred embodiments, this comprises one or more six-membered rings. In still further preferred embodiments, the ring is an aryl group such as, for example, phenyl or naphthyl, or a macrocyclic ring such as, for example, a crown compound.

In view of the above, it is apparent that the appropriate selection of a linker group providing suitable orientation, entropy and physico-chemical properties is well within the skill of the art.

Eliminating or reducing antigenicity of the multibinding compounds described herein is also within the scope of this invention. In certain cases, the antigenicity of a multibinding compound may be eliminated or reduced by use of groups such as, for example, poly(ethylene glycol).

Compounds of Formula I

As explained above, the multibinding compounds described herein comprise 2–10 ligands attached covalently to a linker that links the ligands in a manner that allows their multivalent binding to ligand binding sites of $Ca^{++}$ channels. The linker spatially constrains these interactions to occur within dimensions defined by the linker. This and other factors increases the biologic and/or therapeutic effect of the multibinding compound as compared to the same number of ligands used in monobinding form. The compounds of this invention are preferably represented by the empirical formula $(L)_p(X)_q$ where L, X, p and q are as defined above. This is intended to include the several ways in which the ligands can be linked together in order to achieve the objective of multivalency, and a more detailed explanation is provided below.

As noted previously, the linker may be considered as a framework to which ligands are attached. Thus, it should be recognized that the ligands can be attached at any suitable position on this framework, for example, at the termini of a linear chain or at any intermediate position thereof.

The simplest and most preferred multibinding compound is a bivalent compound which can be represented as L-X-L, where L is a ligand and is the same or different and X is the linker. A trivalent compound could also be represented in a linear fashion, i.e., as a sequence of repeated units L-X-L-X-L, in which L is a ligand and is the same or different at each occurrence, as is X. However, a trivalent compound can also comprise three ligands attached to a central core, and thus be represented as $(L)_3X$, where the linker X could include, for example, an aryl or cycloalkyl group. Tetravalent compounds can be represented in a linear array, L-X-L-X-L-X-L, or a branched array,

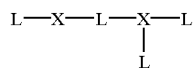

i.e., a branched construct analogous to the isomers of butane (n-butyl, iso-butyl, sec-butyl, and t-butyl). Alternatively, it could be represented as an aryl or cycloalkyl derivative as described above with four (4) ligands attached to the core linker.

The same considerations apply to higher multibinding compounds of this invention containing from 5–10 ligands. However, for multibinding agents attached to a central linker such as an aryl, cycloalkyl or heterocyclyl group, or a crown compound, there is a self-evident constraint that there must be sufficient attachment sites on the linker to accommodate the number of ligands present; for example, a benzene ring could not accommodate more than 6 ligands, whereas a multi-ring linker (e.g., biphenyl) could accommodate a larger number of ligands.

The formula $(L)_p(X)_q$ is also intended to represent a cyclic compound of formula $(-L-X-)_n$, where n is 2–10.

All of the above variations are intended to be within the scope of the invention defined by the formula $(L)_p(X)_q$. Examples of bivalent and higher-order valency compounds of this invention are provided in FIGS. 4–20. With the foregoing in mind, a preferred linker may be represented by the following formula:

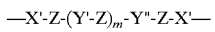

in which:

m is an integer of from 0 to 20;

X' at each separate occurrence is —O—, —S—, —S(O)—, —S(O)$_2$—, —NR—, —N$^+$RR'—, —C(O)—, —C(O)O—, —C(O)NH—, —C(S), —C(S)O—, —C(S)NH— or a covalent bond, where R and R' at each separate occurrence are as defined below for R' and R",;

Z is at each separate occurrence selected from alkylene, substituted alkylene, alkylalkoxy, cycloalkylene, substituted cycloalkylene, alkenylene, substituted alkenylene, alkynylene, substituted alkynylene, cycloalkenylene, substituted alkenylene, arylene, substituted arylene, heteroarylene, heterocyclene, substituted heterocyclene, crown compounds, or a covalent bond;

Y' and Y' at each separate occurrence are selected from —S—S— or a covalent bond;

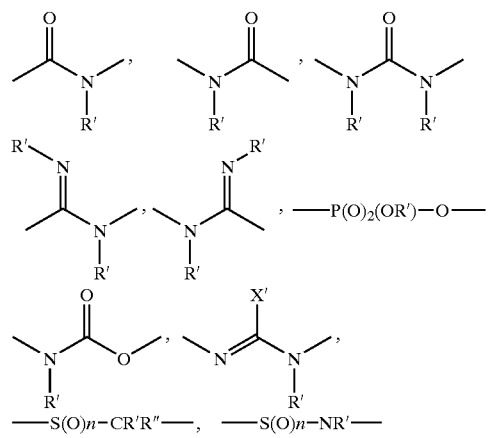

in which:

n is 0, 1 or 2; and

R' and R" at each separate occurrence are selected from hydrogen, alkyl, substituted alkyl, cycloalkyl, substituted cycloalkyl, alkenyl, substituted alkenyl, alkynyl, substituted alkynyl, aryl, heteroaryl or heterocyclic. Additionally, the linker moiety can be optionally substituted at any atom therein by one or more alkyl, substituted alkyl, cycloalkyl, substituted cycloalkyl, alkenyl, substituted alkenyl, alkynyl, substituted alkynyl, aryl, heteroaryl and heterocyclic group.

As indicated above, the simplest (and preferred) construct is a bivalent compound which can be represented as L-X-L, where L is a $Ca^{++}$ channel ligand that is the same or different at each occurrence, and X is the linker. Accordingly, examples of the preparation of a bivalent ligand are given below as an illustration of the manner in which multibinding compounds of Formula I are obtained.

The reaction schemes that follow illustrate preferred linking strategies for linking dihydropyridine, benzothiazepine and phenylalkylamine classes of calcium channel modulators. These strategies are intended to apply as well to any $Ca^{++}$ channel ligand that includes, or can be functionalized with groups compatible with the chosen linker (e.g., mibefradil).

As was previously discussed, the linker or linkers can be attached to different positions on the ligand molecule to achieve different orientations of the ligand domains and thereby facilitate multivalency. For example, the positions that are potentially available for linking a dihydropyridine of formula (1), a benzothiazepine of formula (2) verapamil, a phenylalkylamine (3) and mibefradil, a tetralol derivative and selective T-channel ligand (4) are indicated by arrows in the structures shown below.

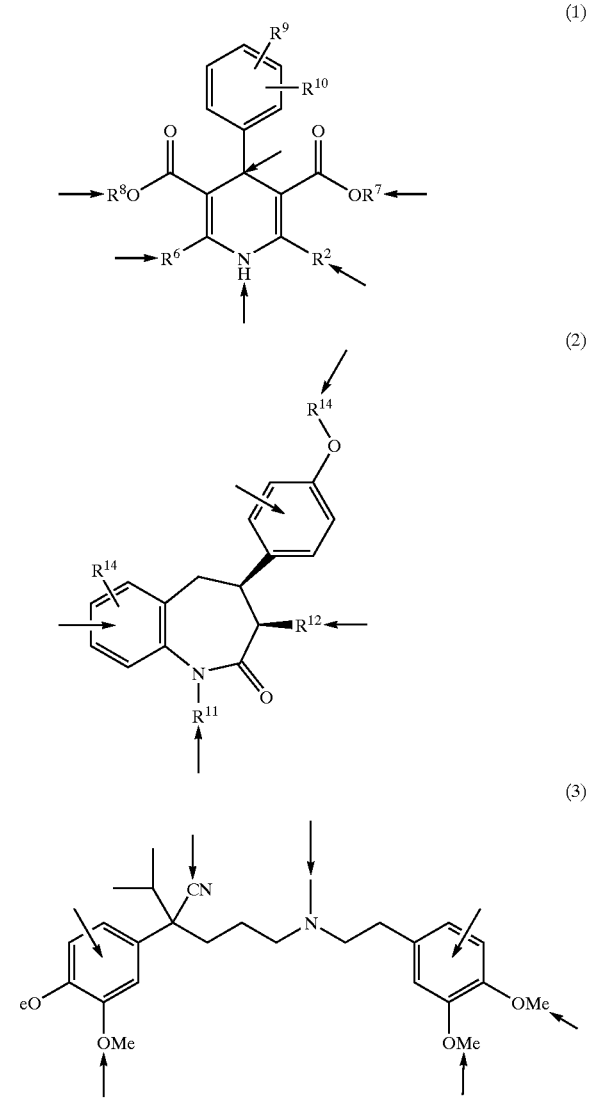

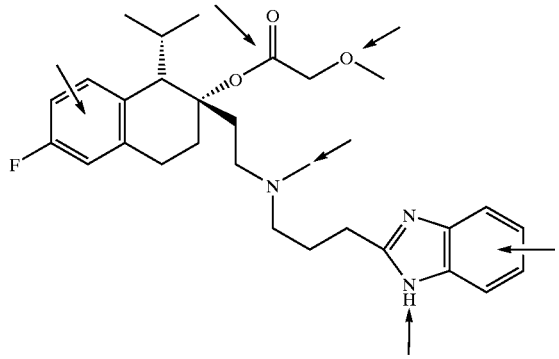

Preferred positions of attachment suggested by known SAR are illustrated in the reaction schemes of FIGS. 4–20. The R groups shown above are numbered to correspond to structures shown in the reaction schemes. Examples of ligands are shown in Tables 4 and 5 (Appendix).

It should be understood that a large number of $Ca^{++}$ channel ligands are chiral and exhibit stereoselectivity. The most active enantiomers are preferably used as ligands in the multibinding compounds of this invention. The chiral resolution of enantiomers is accomplished by well known procedures that result in the formation of diastereomeric derivatives or salts, followed by conventional separation by chromatographic procedures or by fractional crystallization (see, e.g., Bossert et al, *Angew. Chem. Int. Ed.* 20: 762–769 (1981) and U.S. Pat. No. 5,571,827 and references cited therein).

The ligands are covalently attached to the linker using conventional chemical techniques. The reaction chemistries resulting in such linkage are well known in the art and involve the coupling of reactive functional groups present on the linker and ligand. In some cases, it may be necessary to protect portions of the ligand that are not involved in linking reactions. Protecting groups for this purpose are well known in the art and are indicated generally in the reaction schemes by the symbols PG and PG'. Preferably, the reactive functional groups on the linker are selected relative to the functional groups on the ligand that are available for coupling, or can be introduced onto the ligand for this purpose. In some embodiments, the linker is coupled to ligand precursors, with the completion of ligand synthesis being carried out in a subsequent step (see, e.g., FIG. 7, Appendix). Where functional groups are lacking, they can be created by suitable chemistries that are described in standard organic chemistry texts such as J. March, "*Advanced Organic Chemistry*", 4$^{th}$ Edition (Wiley-Interscience, N.Y., 1992). Examples of the chemistry for connecting ligands by a linker are shown in Table 3 (Appendix), where $R^1$ and $R^2$ represent a ligand and/or the linking group. One skilled in the art will appreciate that synthetically equivalent coupling reactions can be substituted for the reactions illustrated herein.

The linker to which the ligands or ligand precursors are attached comprises a "core" molecule having two or more functional groups with reactivity that is complementary to that of the functional groups on the ligand. FIG. 3 illustrates the diversity of "cores" that are useful for varying the linker size, shape, length, orientation, rigidity, acidity/basicity, hydrophobicity/hydrophilicity, hydrogen bonding characteristics and number of ligands connected. This pictorial representation is intended only to illustrate the invention, and not to limit its scope to the structures shown. In the Figures and reaction schemes that follow, a solid circle is used to generically represent a core molecule. The solid circle is equivalent to a linker as defined above after reaction.

Syntheses of Bivalent Compounds

The preferred compounds of Formula I are bivalent Accordingly, and for the purpose of simplicity, the figures and reaction schemes below illustrate the synthesis of bivalent $Ca^{++}$ channel modulators. It should be noted, however, that the same techniques can be used to generate higher order multibinding compounds, i.e., the compounds of the invention where p is 3–10.

Reactions performed under standard amide coupling conditions are carried out in an inert polar solvent (e.g., DMF, DMA) in the presence of a hindered base (e.g., TEA, DIPEA) and standard amide coupling reagents (e.g., DPPA, PyBOP, HATU, DCC).

Preparation of Dihydropyridine (DHP) Bivalent Compounds

Figure 4A:
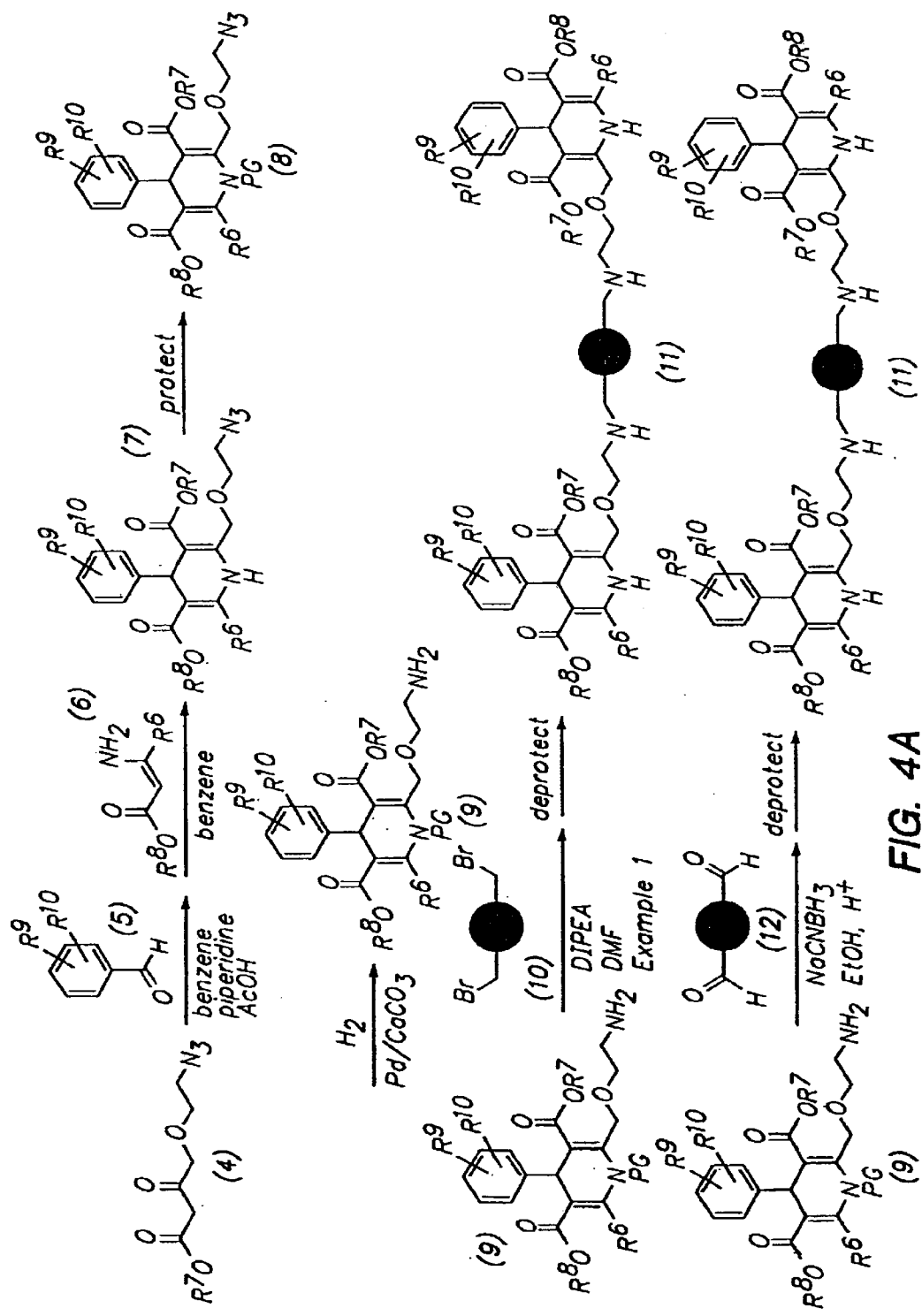
FIGS. 4–20 illustrate convenient methods for preparing the multibinding compounds of this invention.
Figure 4B:
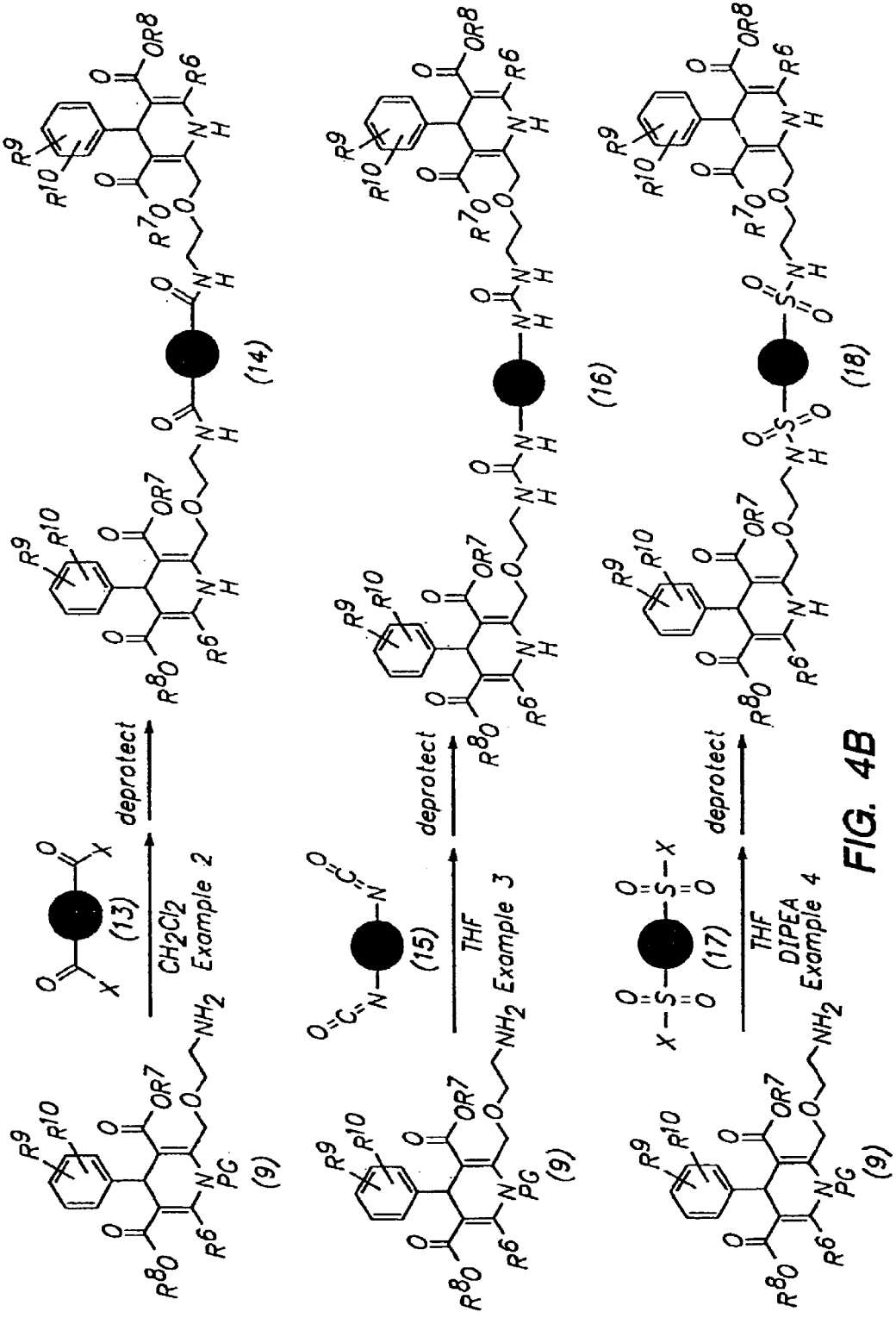

FIG. 4 illustrates a preferred method for linking molecules at positions $R^2$ ($R^6$) of the dihydropyridine ring. As exemplified here for amlodipine and structurally analogous molecules, a multistep Hantzsch DHP-cyclization is used to introduce the appropriate groups [see, e.g., Arrowsmith et al, *J. Med. Chem.* 29: 1696–1702 (1986); Bossert et al, *Angew. Chem. Int. Ed. Engl.* 20: 762–769 (1981)).

The starting materials are a compound of formula (4) having an azide-substituted β-keto ester and a substituted benzaldehyde (5). These compounds are reacted in benzene in the presence of piperidine and acetic acid to yield an intermediate product, which, when reacted with a compound of formula (6) in benzene yields DHP (7), where $R^2$ is $CH_2OCH_2CH_2N_3$. The ring nitrogen is protected to yield the compound of formula (8), following which the azide is reduced to an amine compound (9) using hydrogen and an appropriate catalyst, such as palladium/calcium carbonate. Amine (9) can then be coupled to a core molecule using a variety of well known reactions, examples of which are shown in FIG. 4 and described below. The compound of formula (9) is reacted with a bifunctional alkylating core (e.g. a dibromide linker (10)) in an inert solvent (e.g. DMF) with a hindered base (e.g. DIPEA) to produce, after deprotection, the amine linked compound of Formula I (11). Compound (11) can also be formed by reacting (9) with a dialdehyde core (12) under standard reductive amination conditions (e.g. sodium cyanoborohydride in ethanol with acid), followed by deprotection. In yet another type of coupling reaction, the compound of form (9) is reacted with an activated diacid core (13) in a polar inert solvent (e.g. $CH_2Cl_2$) to yield, after deprotection, the amide-linked compound of Formula I (14). The diacid may be preactivated (e.g. by using the acid chloride), or activated in situ using conventional coupling conditions (e.g. DCC, DMAP, THF). Alternatively, the compound of formula (9) can be reacted with a diisocyanate core (15) in an inert solvent (e.g. THF) to yield, after deprotection, the urea-linked compound of Formula I (16). The compound of formula (9) can also be reacted with an activated sulfonate core (17) in an inert solvent (e.g. THF) with a hindered base (e.g. DIPEA) to yield, after deprotection, the sulfonamide linked compound of Formula I (18).

Figure 5A:
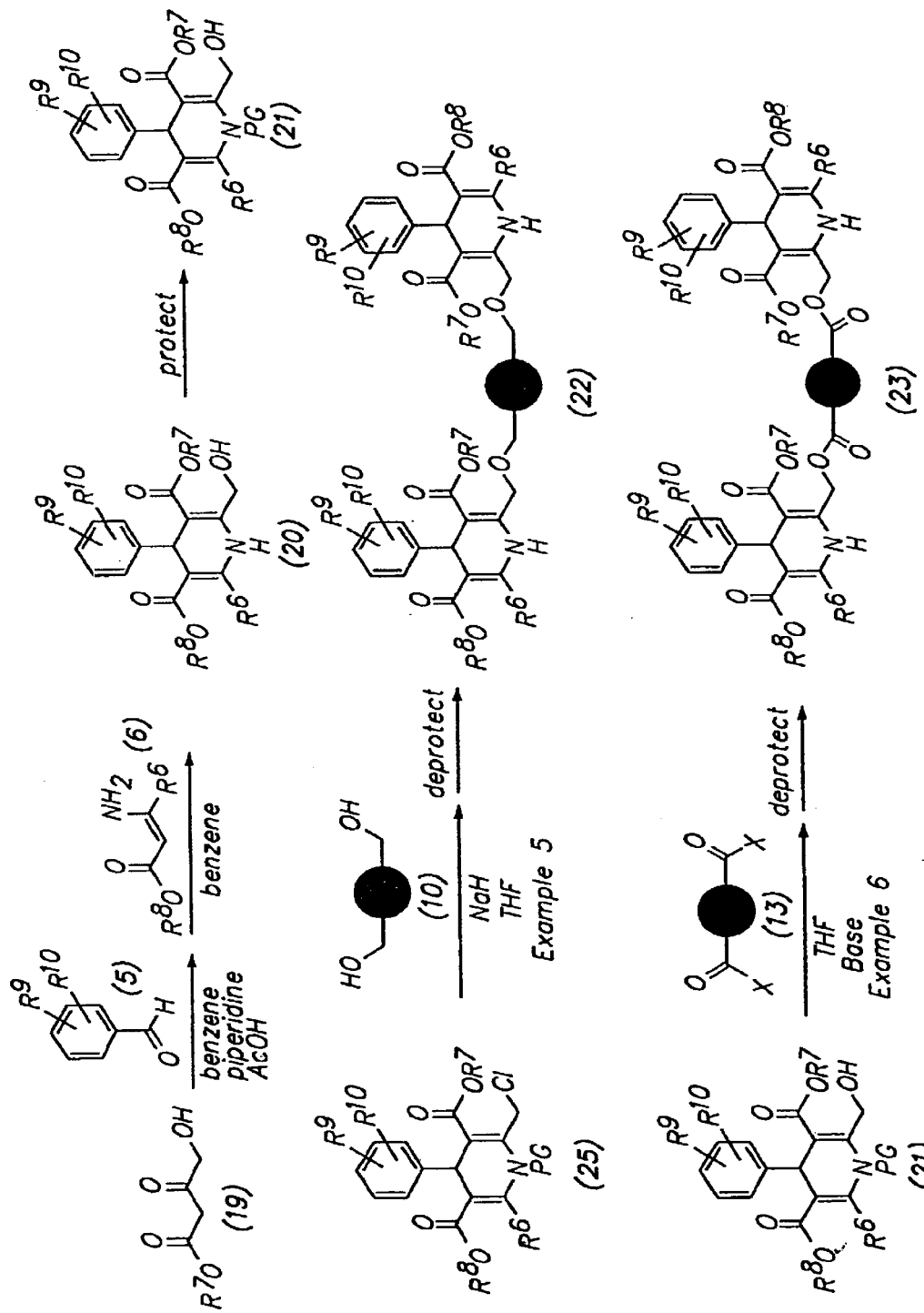
Figure 5B:
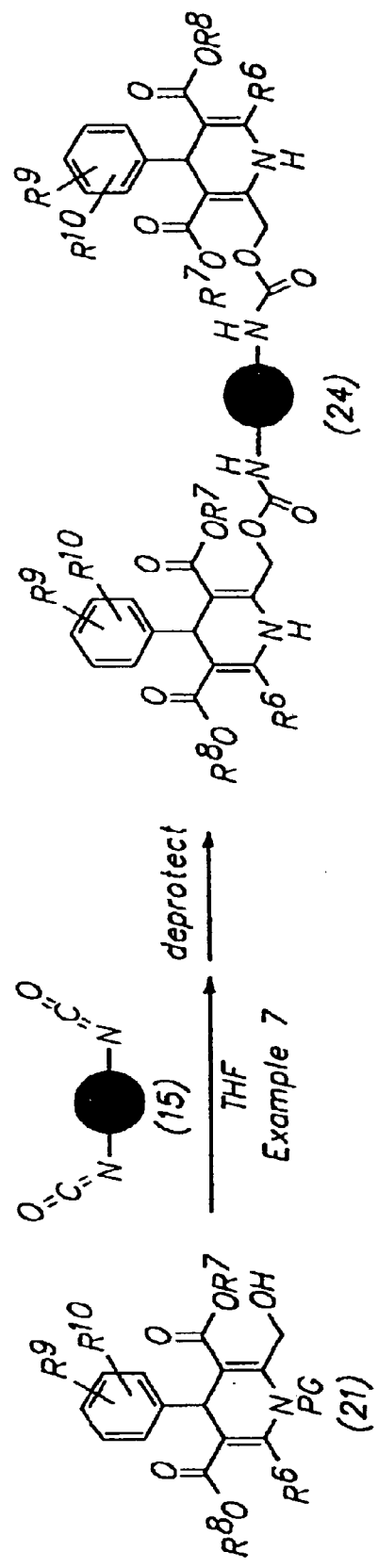
Figure 6:
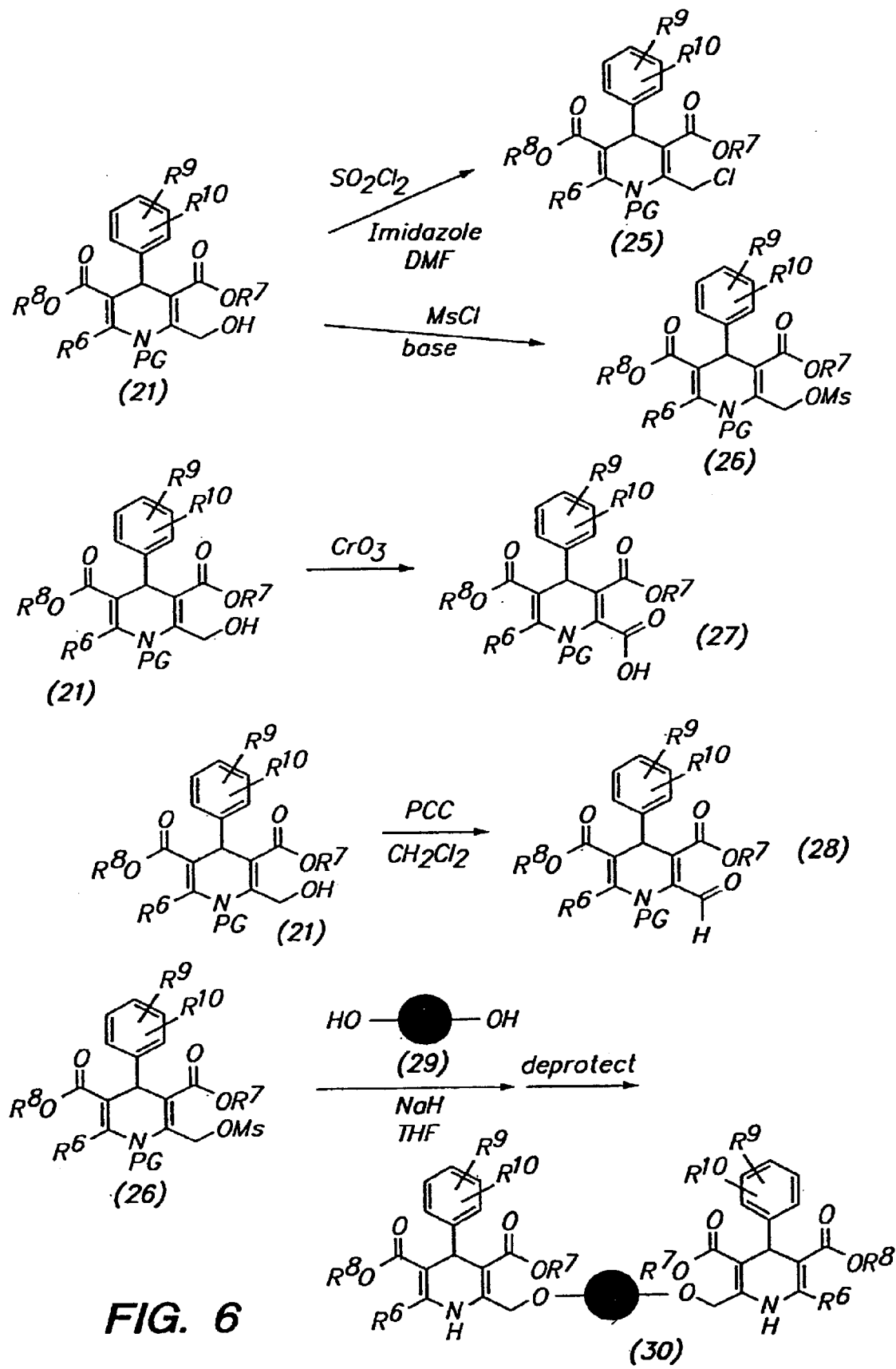

FIGS. 5 and 6 illustrate the preparation of dihydropyridine compounds of Formula I having different functional linking groups at positions $R^2$ ($R^6$) of the dihydropyridine ring.

As shown in FIG. 5, a dihydropyridine with an alcohol side chain at $R^2$ is prepared by reacting a compound of formula (19) with (5) and (6) (using the same conditions as above), to make a compound of formula (20). After protection with a suitable amine-protecting group, the compound of formula (21) can be coupled to various cores, as exemplified in FIG. 5. Alternatively, a compound of formula (21) can be prepared as described in Alker, D and Denton, S. M., *Tetrahedron*, 46, 3693–3702, (1990).

The compound of formula (25) is reacted with a bifunctional alkylating core (e.g., a diol (10)) in an inert solvent (e.g. THF) with a strong deprotonating base (e.g. NaH) to produce, after deprotection, an ether linked compound of Formula I (22). Alternatively, the compound of formula (21) is reacted with an activated diacid core (13) in a polar inert solvent (e.g. THF) with base to yield, after deprotection, an ester-linked compound of Formula I (23). Alternatively, the compound of formula (21) is reacted with a diisocyanate core (15) in an inert solvent (e.g. THF) to yield, after deprotection, a carbamic ester-linked compound of Formula I (24).

FIG. 6 illustrates reactions for converting a nucleophilic side chain into an electrophilic one. For example, the compound of formula (21) is reacted under standard chlorinating conditions (e.g. $SO_2Cl_2$ in the presence of a suitable base such as imidazole in DMF) to yield chloride (25). The compound of formula (21) is reacted with mesyl chloride in an inert solvent (e.g., THF) in the presence of a base to yield mesylate (26). The compound of formula (21) is reacted with oxidating agents (e.g. $CrO_3$) to yield acid (27). The compound of form (21) is reacted under mild oxidating conditions (e.g. $PCC/CH_2Cl_2$) to yield aldehyde (28).

The electrophilic groups thus generated can then be used in standard coupling reactions such as those shown in FIGS. 4 and 5, for example, the reaction illustrated in FIG. 6 (bottom). In this reaction, a molar equivalent of a diol core (29) is reacted with 2 molar equivalents of a mesylated dihydropyridine (26) in an inert solvent with a base to yield, after deprotection, an ether-linked compound of Formula I (30).

Figure 7:
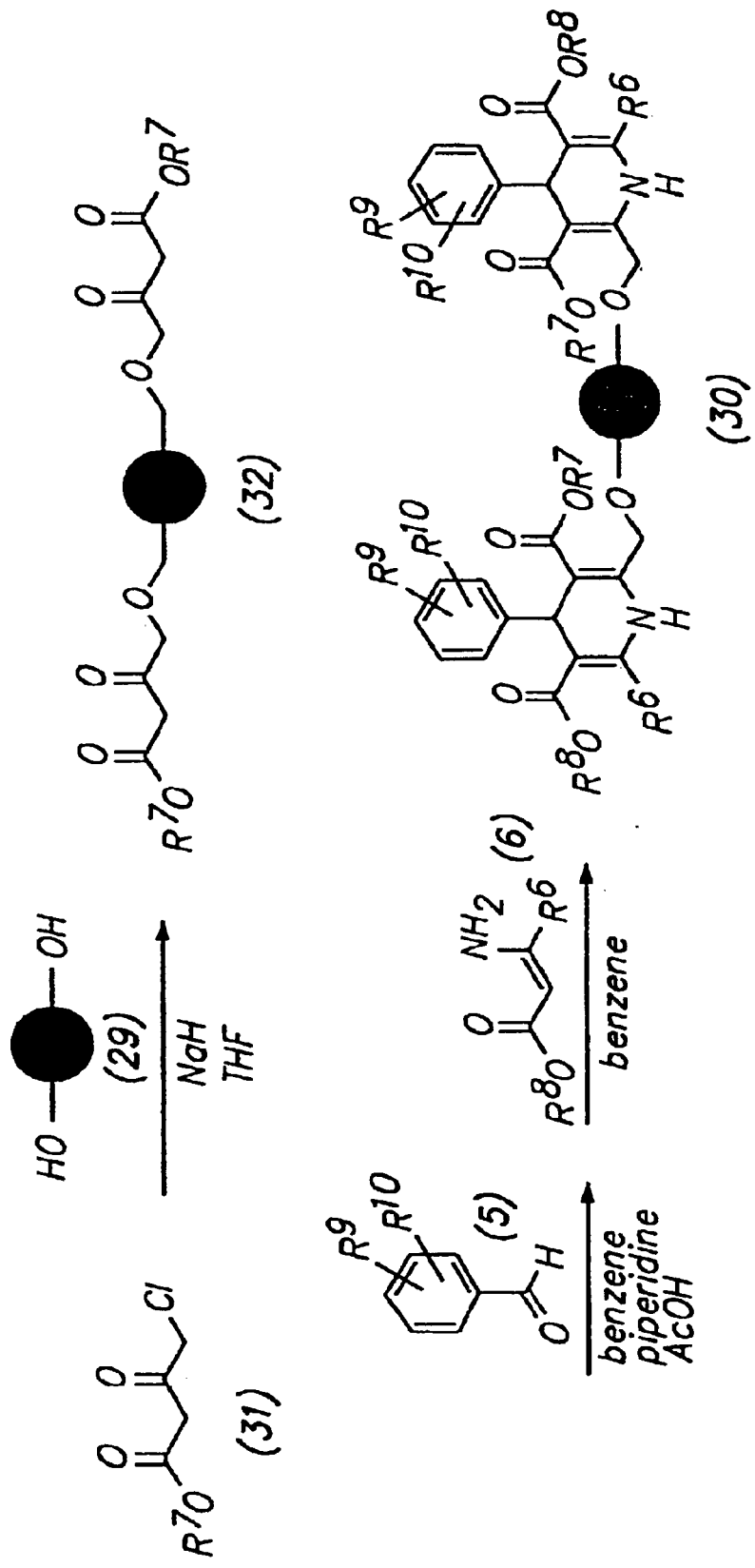

FIG. 7 illustrates a preferred method for forming bivalent DHP compounds, which involves coupling of the linker to ligand precursors, followed by synthesis of the ligand. As shown here, a molar equivalent of a diol core (29) is coupled with approximately two molar equivalents of a chloride-substituted β diketone (31) in an inert solvent (e.g. DMF) in the presence of a strong base (e.g. NaH) to yield an ether-linked compound of formula (32). Compound (32) is reacted with (5) and (6), as described above with reference to FIGS. 4 and 5, to form an ether-linked compound of Formula I (30).

Figure 8:
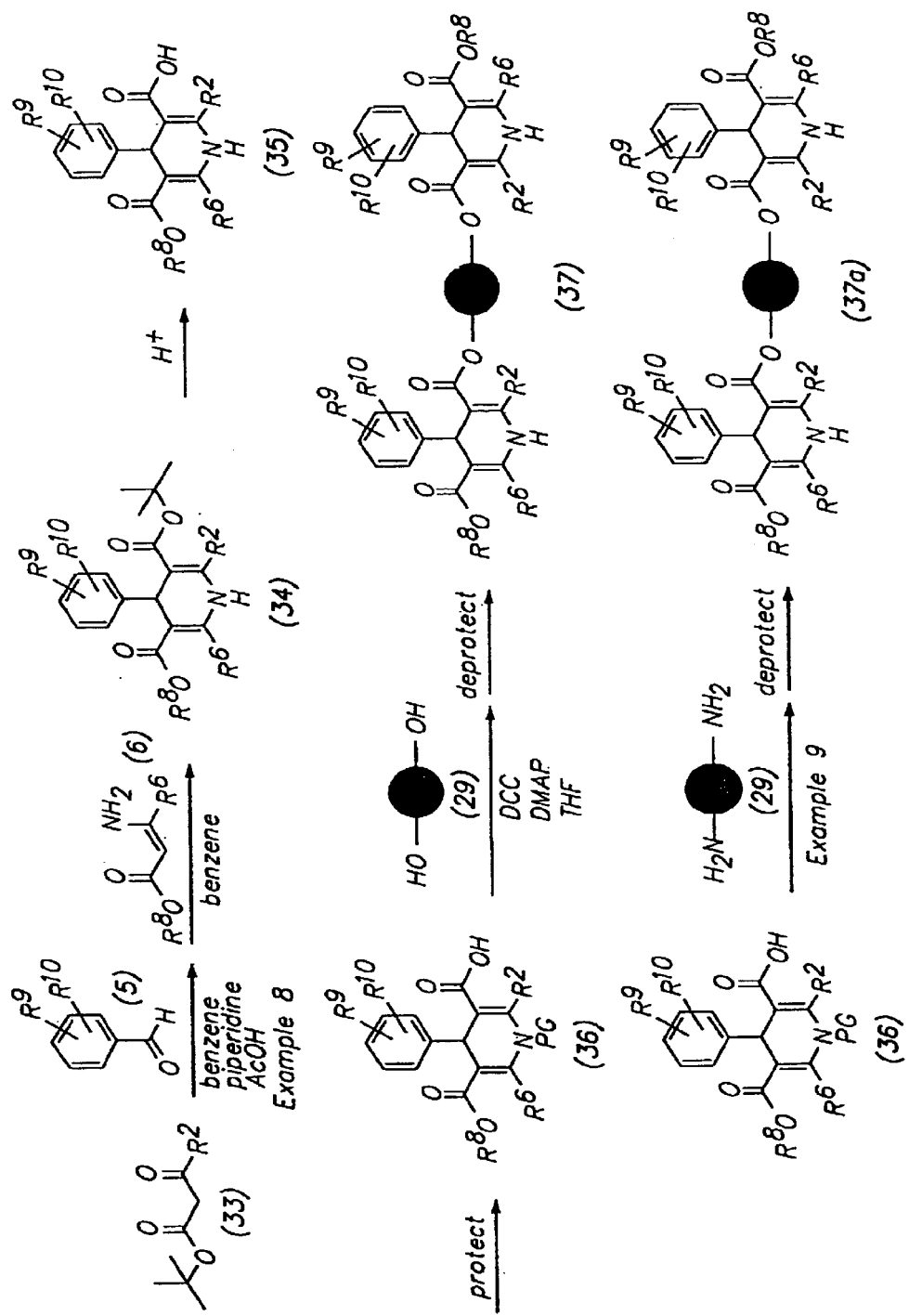

Dihydropyridine dimers may be linked through an ester linkage at $R^7$ or $R^8$, as is shown in FIG. 8. The starting material, a t-butyl ester of formula (33) is reacted with compounds (5) and (6) as described previously with reference to FIGS. 4 and 5, to yield a dihydropyridine of formula (34). Cleavage of the t-butyl group of (34) with dilute acid yields (35), which is then amine-protected to form (36). Standard activation techniques (e.g. DCC/DMAP/FHF) are used to couple the acid to a nucleophile core as previously described, for example to a diol core (29), to yield, after deprotection, an ester-linked compound of Formula I (37).

Figure 9:
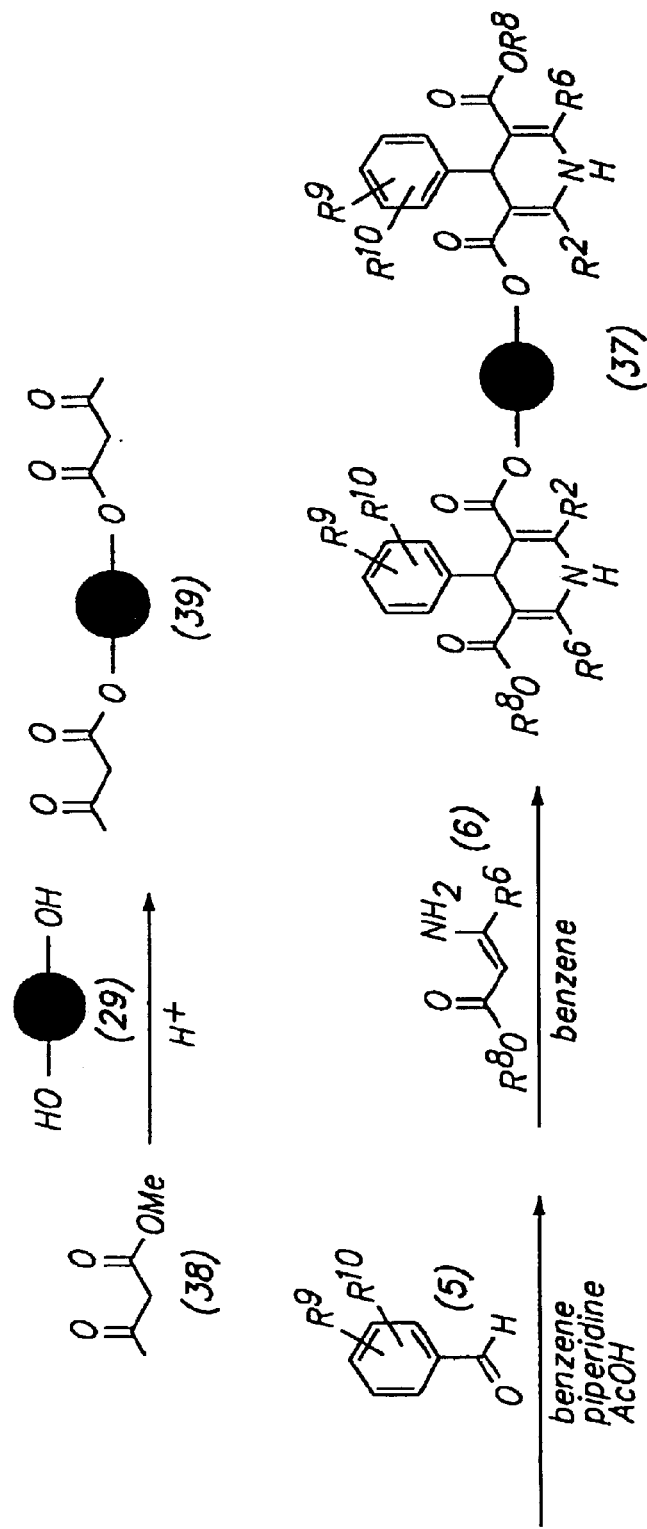

FIG. 9 illustrates another procedure for synthesizing an ester-inked dihydropyridine compound of Formula I. Here, a molar equivalent of a diol core (29) is coupled with two molar equivalents of a diketone compound of formula (38) in an acid-catalyzed transesterification reaction to form a compound of formula (39). Reaction of (39) with (5) and (6), as described above, yields ester-linked (37).

Preparation of Benzothiazepine (BZT) Bivalent Compounds

Figure 10:
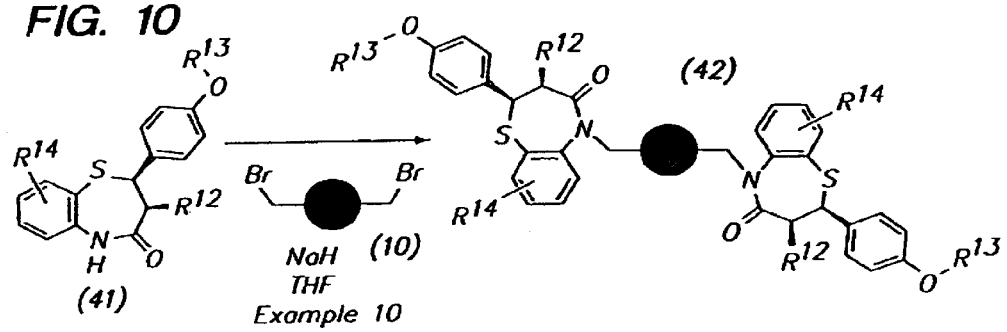
Figure 10:
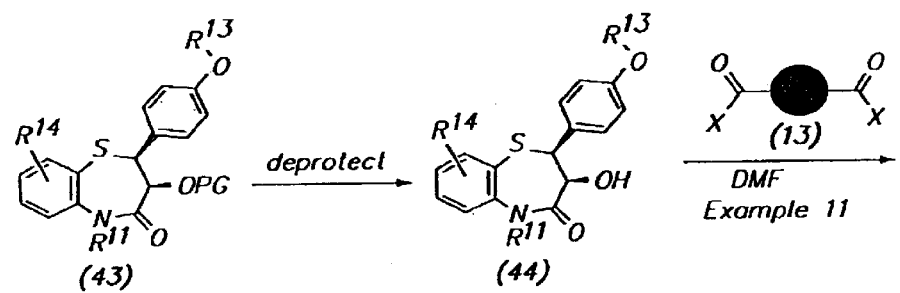
Figure 10:
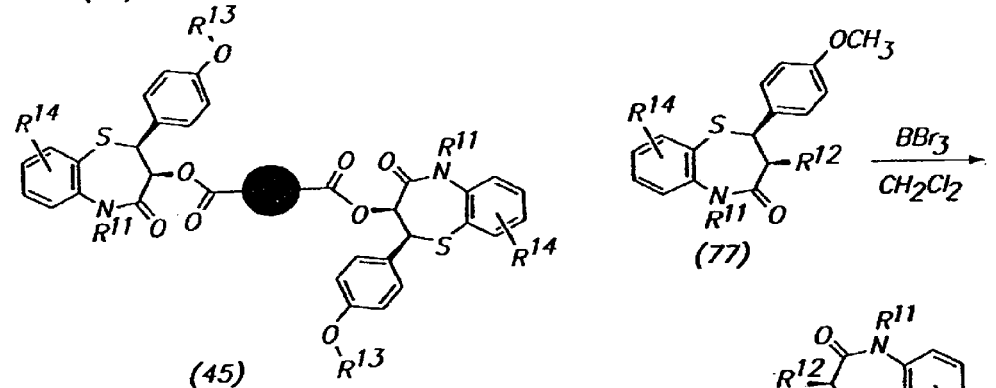
Figure 10:
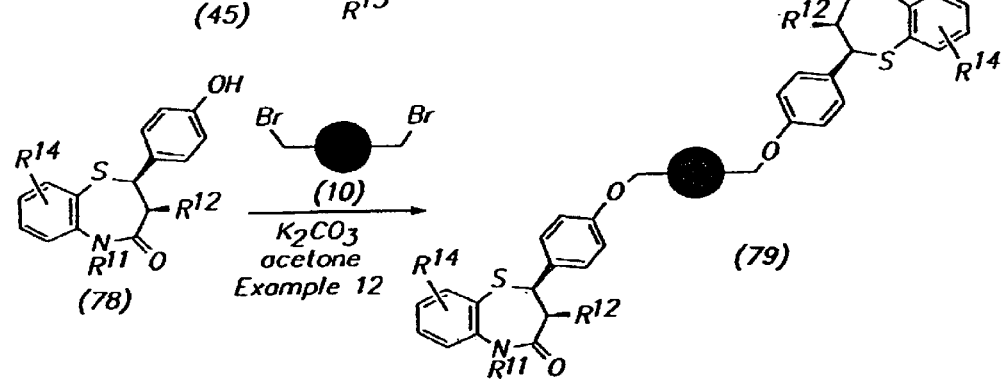

Several methods for preparing bivalent benzothiazepine compounds are illustrated in the reaction schemes shown in FIG. 10 (Appendix). According to FIG. 10, the starting material, a compound of formula (41) is prepared as described in U.S. Pat. No. 4,552,695. Compound (41) is reacted with a dihalide core (10). In an inert solvent (e.g. THF) in the presence of a strong base (e.g. NaH) to form an amide N-linked compound of Formula I (42). Following the linking step, the $R^{12}$ side chain can be deprotected if necessary and acylated as described in the above-mentioned patent.

Alternative coupling reactions are possible, including those shown in FIG. 4. In such instances, those skilled in the art will know how to modify the reaction conditions to compensate for the reduced nucleophilicity of the amide nitrogen.

Alternatively, the starting material is a compound of formula (43) (where $R^{12}$ is an ether-protected hydroxyl group), which is prepared as described in the above-referenced patent. Deprotection of this compound yields the alcohol (44), which can be reacted with an activated diacid core (13) in an inert solvent (e.g. DMF) to yield ester-inked (45) as shown here. Alternative coupling reactions can be used, such as those shown in FIG. 5.

Alternatively, a compound of formula (77) may be prepared as described in the above-referenced patent. Treatment of compound (77) with $BBr_3$ in $CH_2Cl_2$ affords cleavage of the aryl ether to phenol (78). Compound (78) can be selectively alkylated at the phenolic hydroxyl group by reaction with dihalide (10) in $K_2CO_3$/acetone solution to yield ether-linked (79).

Preparation of Phenylalkylamine (PAA) Bivalent Compounds

Figure 11:
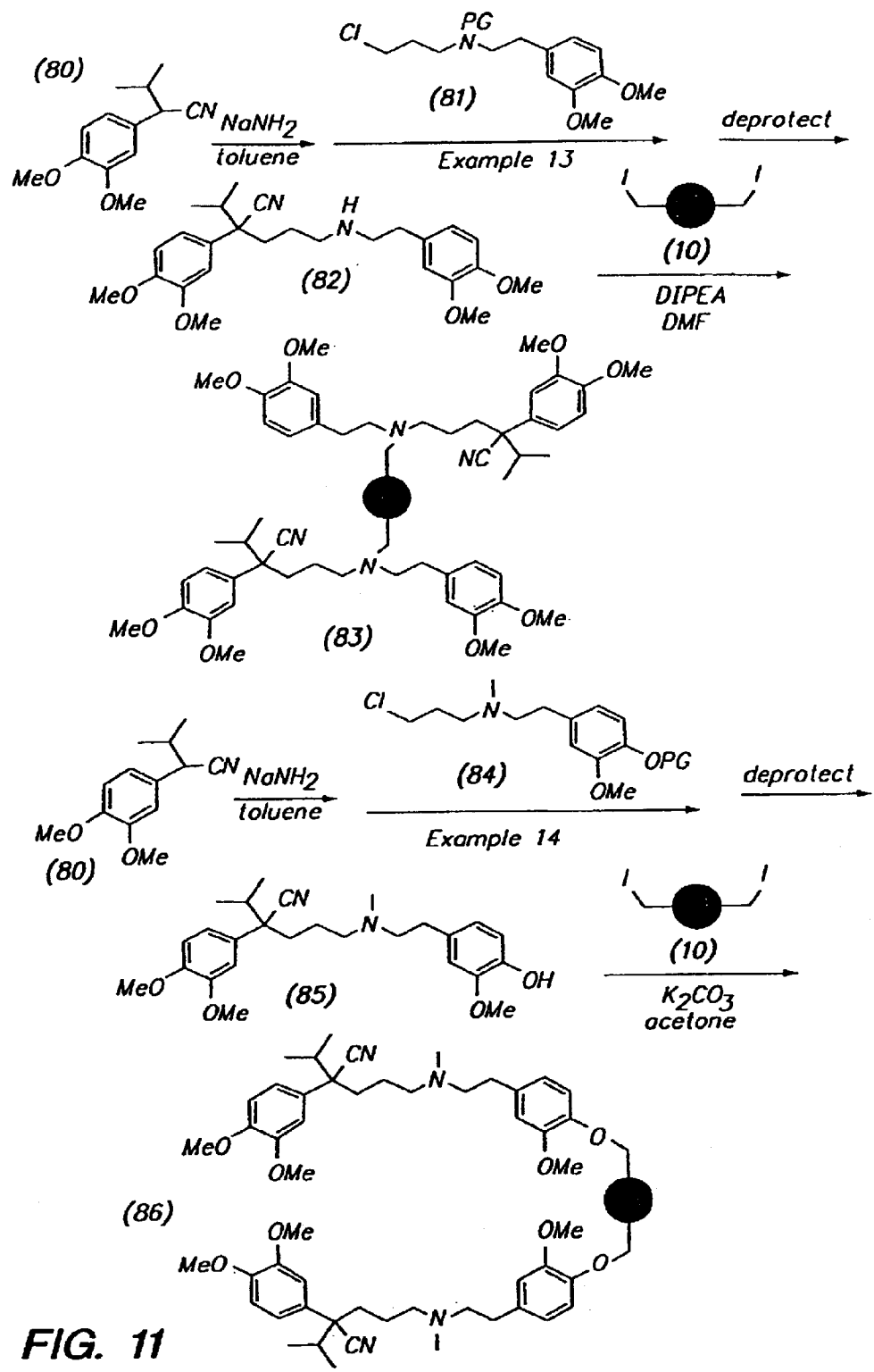

FIG. 11 illustrates methods for linking PAA molecules (as exemplified by verapamil) (mibefradil is also considered herein to be part of the category of phenylalkylamines). Phenyl acetonitrile (80) is treated with a basic condensing agent (e.g. sodium amide) in an inert solvent (e.g. toluene). N-protected (81) is slowly added to the amidine salt, as described in U.S. Pat. No. 3,261,859. After deprotection, compound (82) is coupled to an electrophilic core, for example, with a dihalide core (10) in an inert solvent (e.g. DMF) in the presence of a hindered base (e.g. DIPEA) to form an amine-linked compound of Formula I (83). Other coupling reactions may be substituted for the one shown here, e.g., those shown in FIG. 4.

Alternatively, the amidine salt of (80), is coupled to O-protected (84). After deprotection, the resulting compound (85) is reacted with a dihalide core (10), in a $K_2CO_3$/acetone solution to form an ether linked compound of Formula I (86). Other coupling reactions such as those shown in FIG. 5 may be substituted for the one shown here.

Figure 12:
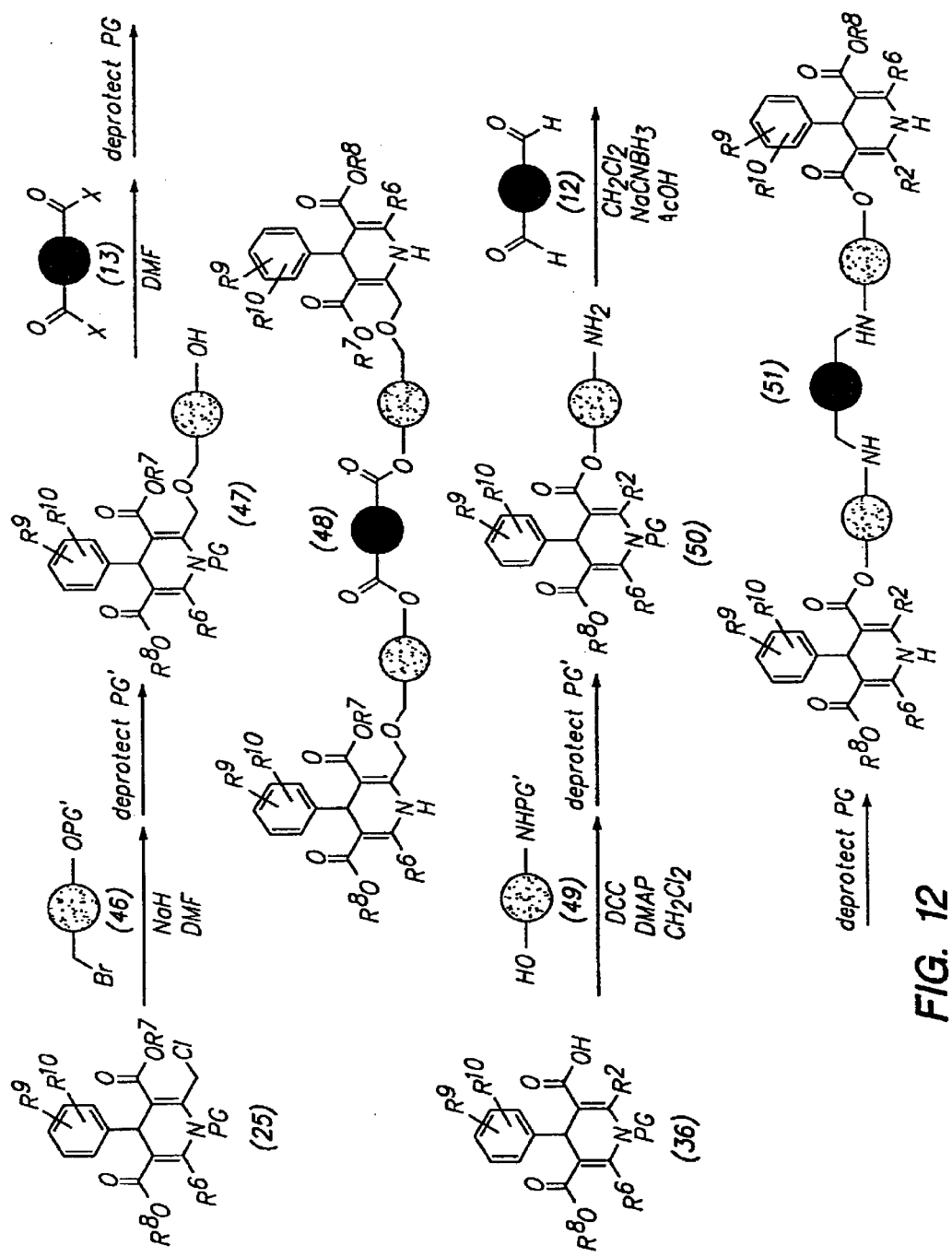
Figure 13A:
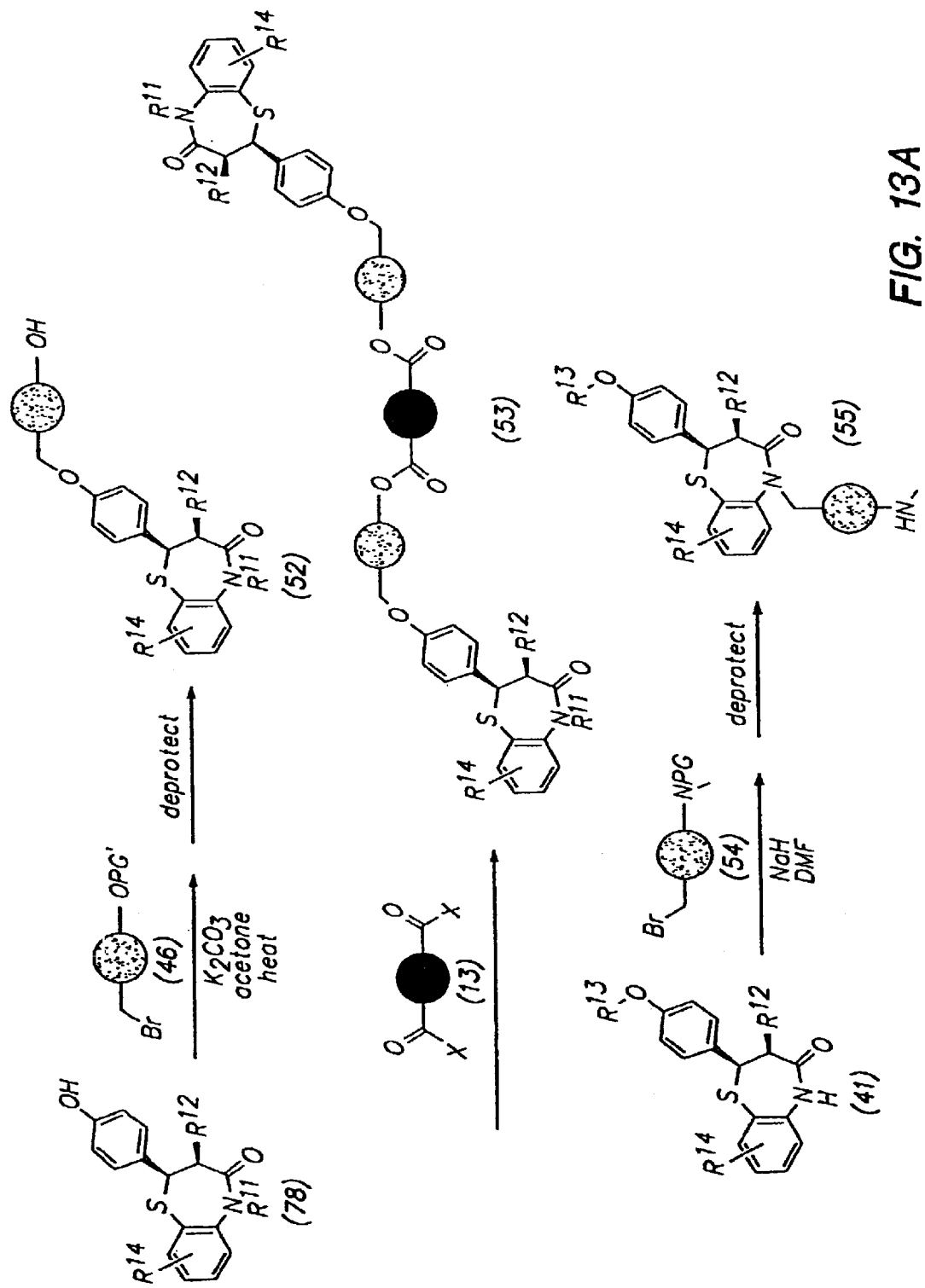
Figure 13B:
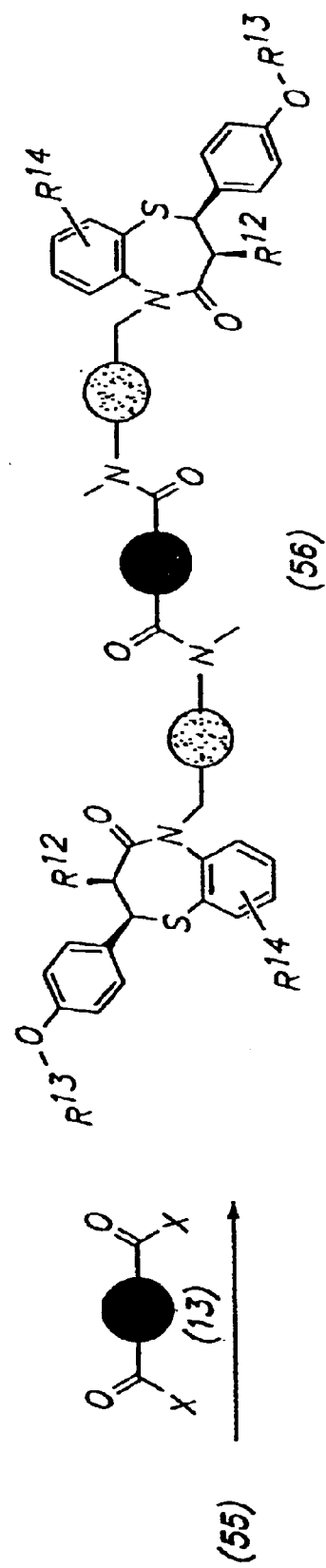

The strategies for preparing compounds of Formula I discussed above involve coupling the ligand directly to a homobifunctional core. Another strategy that can be used with all ligands, and for the preparation of both bivalent and higher order multibinding compounds, is to introduce a 'spacer' before coupling to a central core. Such a spacer can itself be selected from the same set as the possible core compounds. Examples of this linking strategy are shown in FIGS. 12 and 13, where the spacer is represented by a gray circle. As defined herein, the linker comprises the spacer+ core.

Referring to FIG. 12, a dihydropyridine compound of formula (21), synthesized according to FIG. 5 above, is coupled to a heterobifunctional spacer (46) having an electrophilic group (e.g., Br) and a masked nucleophilic group (e.g., protected alcohol). The protecting groups, PG and PG' are different (e.g., PG is Boc and PG' is Cbz) and are capable of selective removal. The reaction is carried out in an inert solvent (e.g. DMF) in the presence of a strong base (e.g. NaH). After removal of PG', the unmasked nucleophile (49) is coupled to an activated diacid core (13). The ring nitrogen is then deprotected to yield an ether-linked compound of Formula I (48). Core molecules with different functional groups may be substituted for the one shown here (see, e.g., FIG. 5).

In another example, a dihydropyridine compound of formula (36) is coupled to heterobifunctional spacer (49) under standard coupling conditions (e.g. DCC/DMAP/ $CH_2Cl_2$). After removal of the spacer protecting group, the unmasked nucleophile (50) is coupled to a dialdehyde core (12) by reductive amination (or to another core with chemically compatible functional groups). After removal of the protecting group from the ring nitrogen, an ester-inked compound of formula I (51) is obtained.

FIG. 13 Illustrates the use of spacers to make bivalent benzothiazepine compounds. As shown in FIG. 13, a compound of formula (78) is coupled to a heterobifunctional spacer (46) in basic conditions (e.g. $K_2CO_3$ in acetone). After removal of the spacer protecting group, the unmasked nucleophile (52) is coupled to an activated diacid core (13) using standard coupling conditions to yield an ether-linked compound of Formula I (53). In another example, compound (41) is coupled to heterobifunctional spacer (54) in an inert solvent solvent (e.g. DMF) in the presence of strong base (e.g. NaH). After removal of the spacer protecting group, the resulting compound (55) is coupled to an activated diacid core (13) to yield an N-alkylated compound of Formula I (56). Of course, other suitable cores may be substituted if desired.

Compounds of Formula I where p=3–10

Figure 14A:
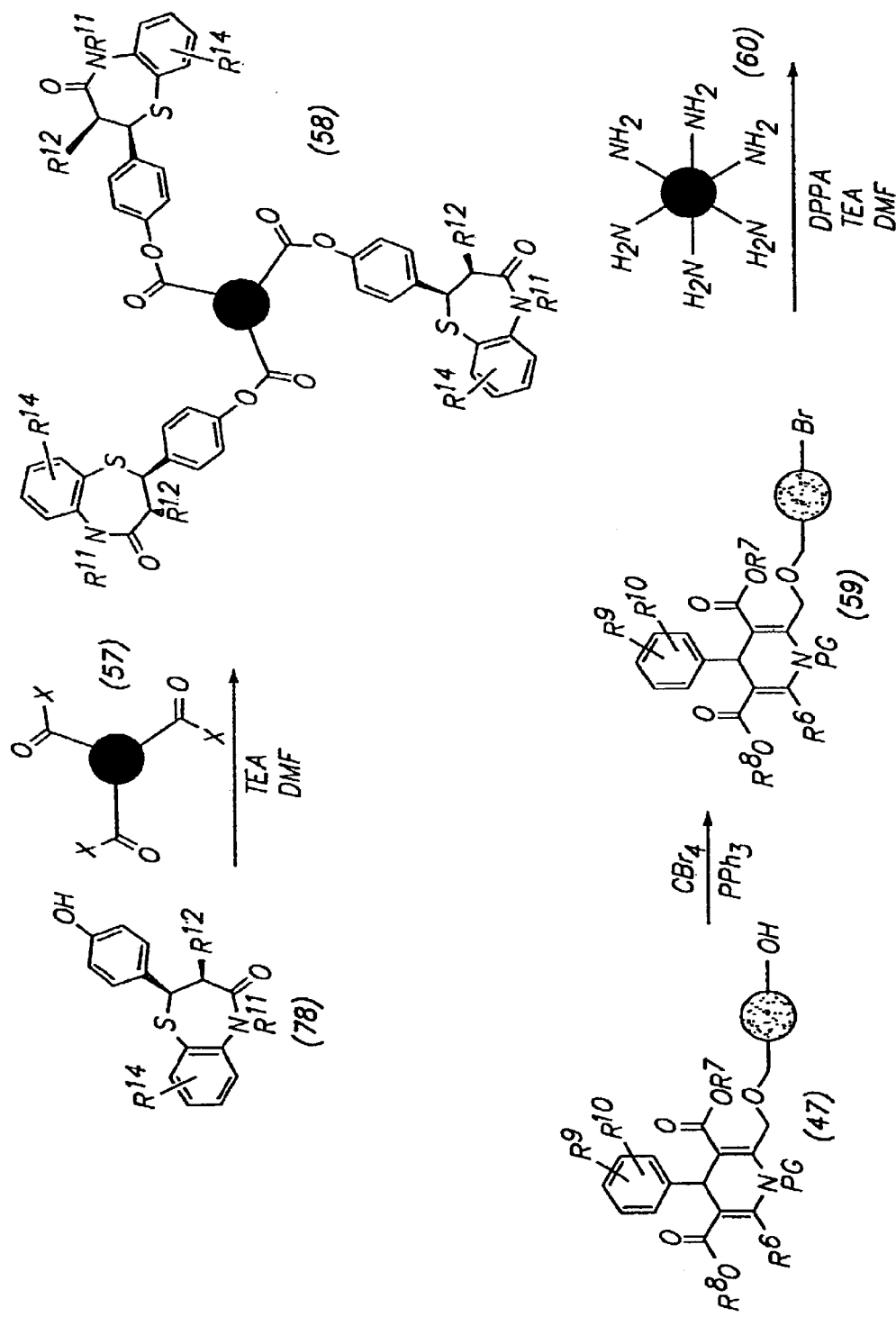
Figure 14B:
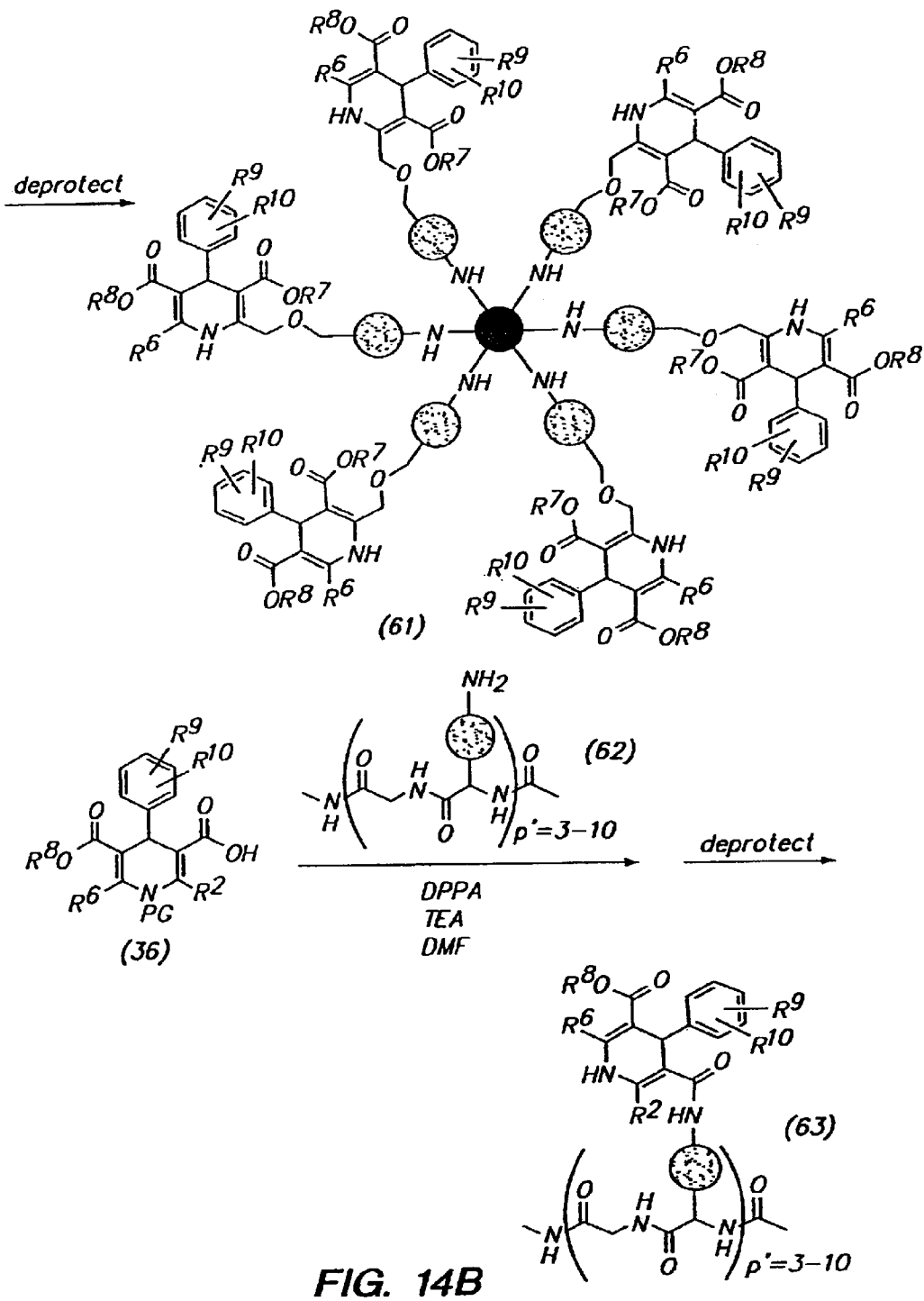

Compounds of Formula I of higher order valency, i.e. p>2, can be prepared by simple extension of the above strategies. As shown in FIG. 14 (Appendix), compounds (58) and (61) are prepared by coupling ligands to a central core bearing multiple functional groups. The reaction conditions are the same as described above for the preparation of bivalent compounds, with appropriate adjustments made in the molar quantities of ligand and reagents.

Compound (36), synthesized as described above with reference to FIG. 5. is coupled to a polypeptide core with a sidechain spacer (62) to make (63). Solid phase peptide synthesis can be used to produce a wide variety of peptidic core molecules. Techniques well known to those skilled in the art (including combinatorial methods) are used to vary the distance between ligand attachment sites on the core molecule, the number of attachment sites available for coupling, and the chemical properties of the core molecule. Orthogonal protecting groups are used to selectively protect functional groups on the core molecule, thus allowing ancillary groups to be inserted into the linker of the multibinding compound and/or the preparation of "heterovalomers" (i.e., multibinding compounds with nonidentical ligands). All of the synthetic strategies described above employ a step in which the ligand, attached to spacers or not, is symmetrically linked to functionally equivalent positions on a central core. Compounds of Formula I can also be synthesized using an asymmetric linear approach. This strategy is preferred when linking two or more ligands at different points of connectivity (see, e.g., FIG. 15) or when preparing heterovalomers (see, e.g., FIGS. 16 and 17).

Figure 15:
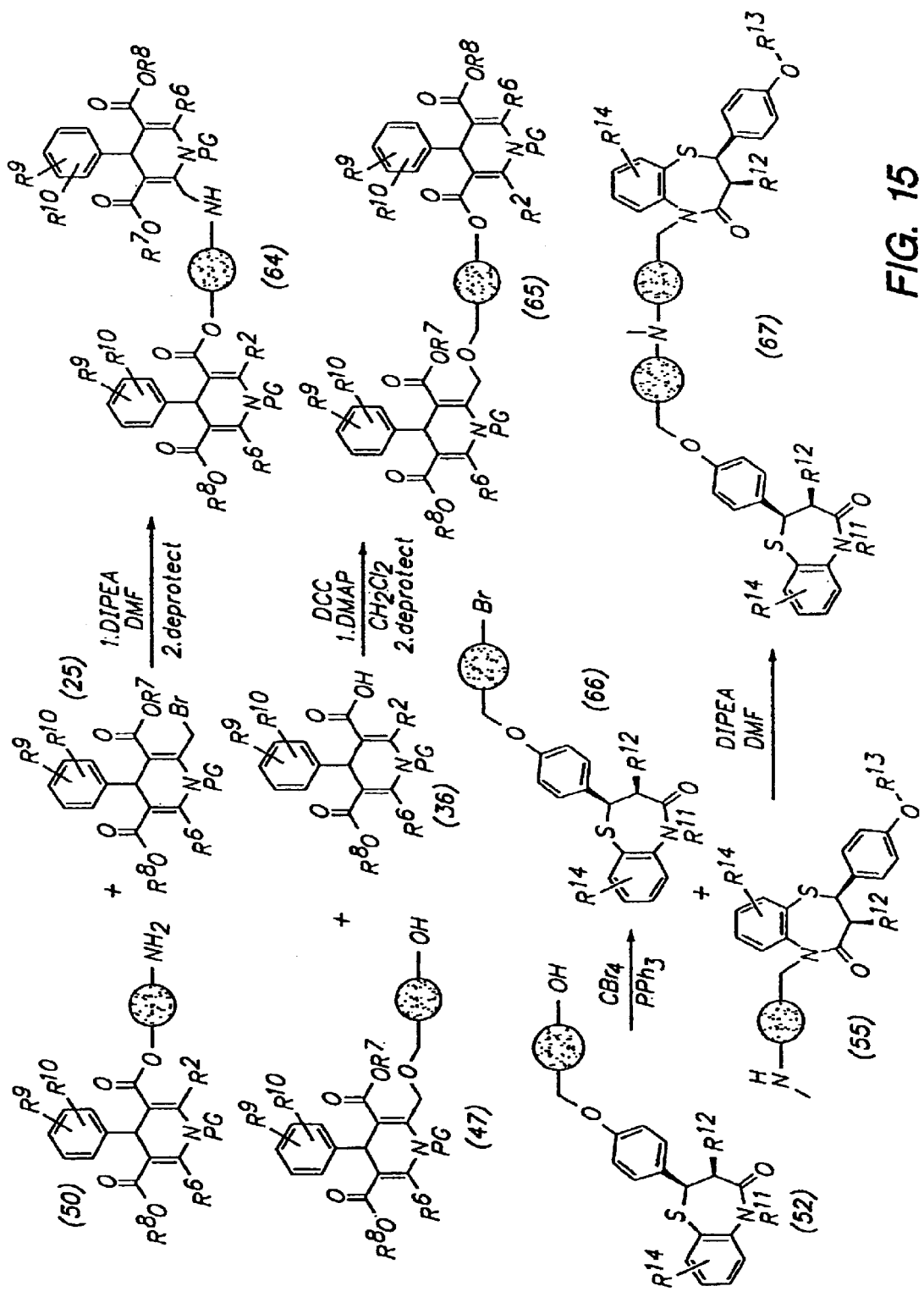

FIG. 15 illustrates the preparation of bivalent dihydropyridine compounds of formulae (64) and (65), wherein $R^2$ of a first ligand is attached through a linker to $R^7$ of a second ligand, and the preparation of a bivalent benzothiazepine compound of formula (67), wherein the linker is attached between $R^{11}$ of a first ligand and $R^{13}$ of a second ligand. The coupling steps are carried out as described previously.

Figure 16A:
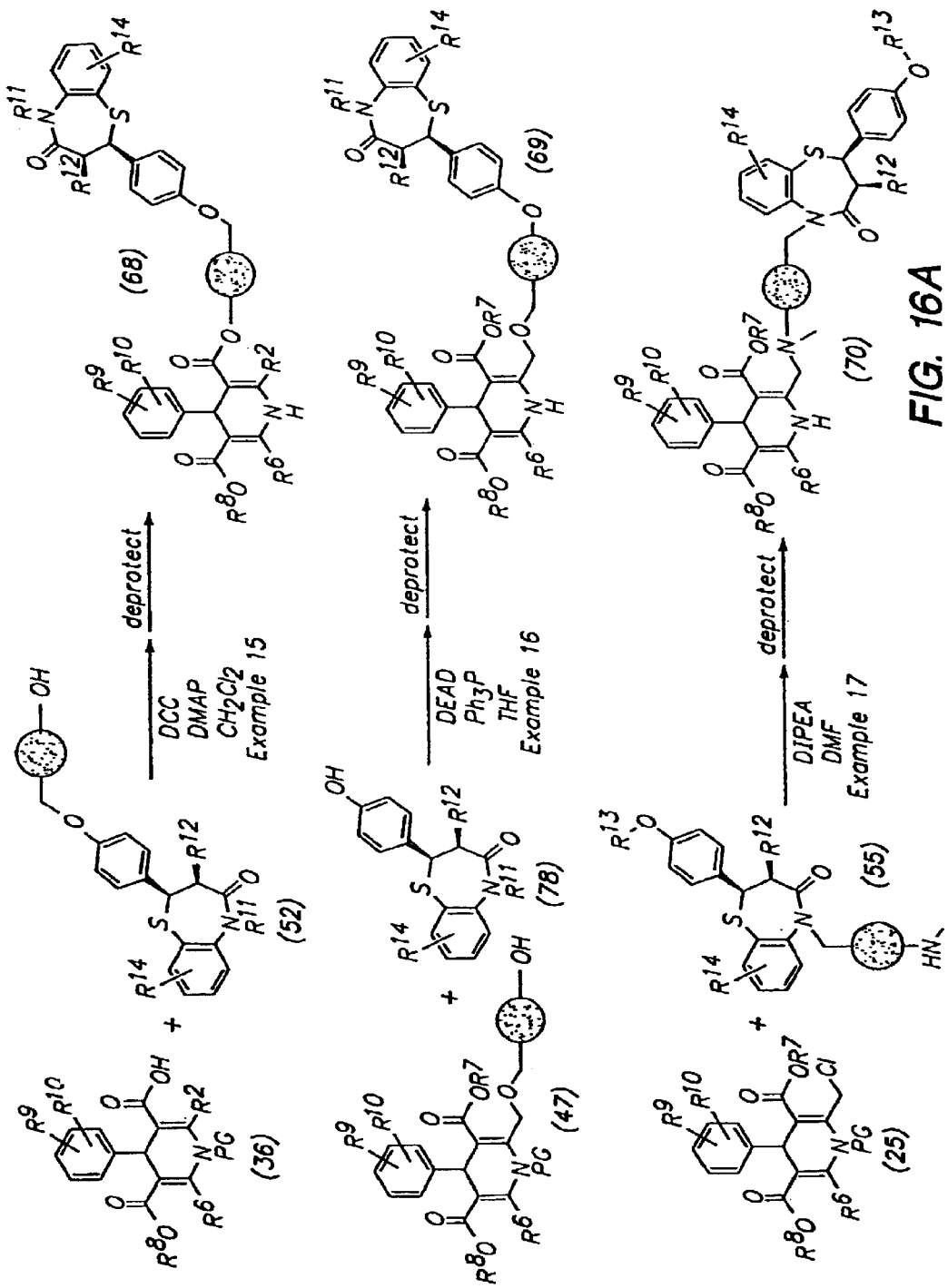
Figure 16B:
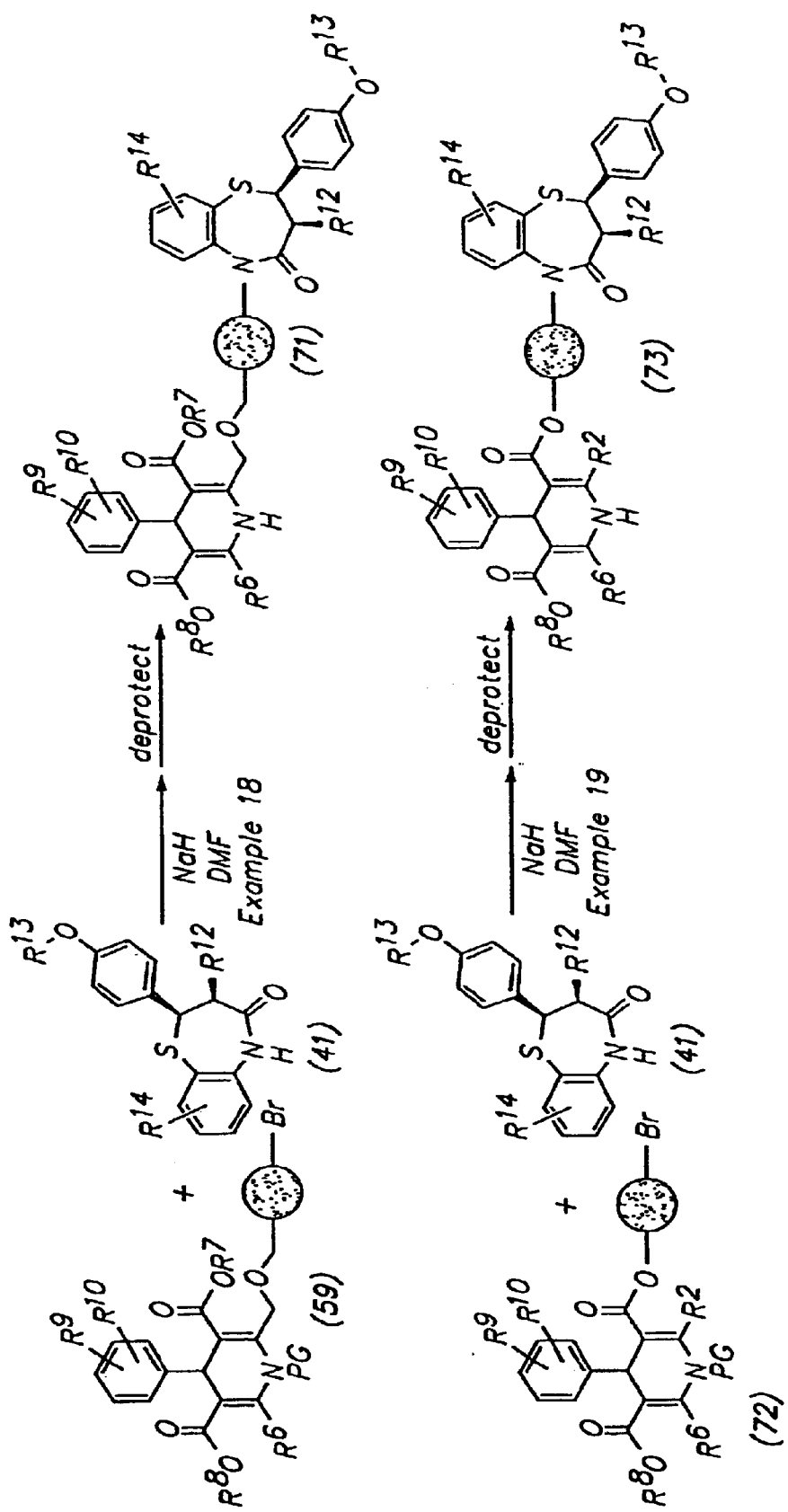
Figure 17:
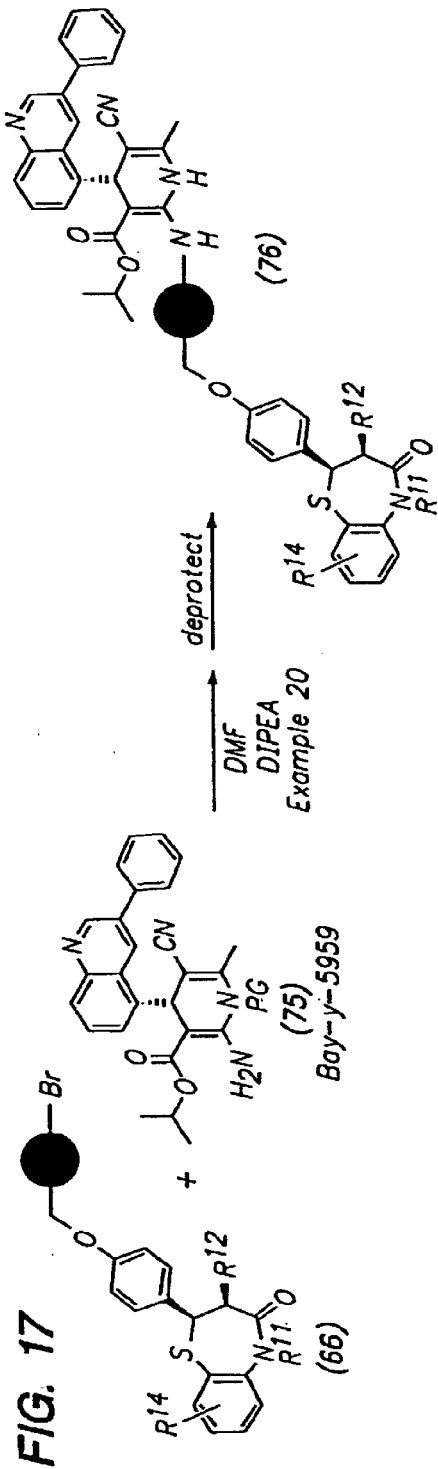

A linear strategy can also be used to prepare heterovalomers, as shown in FIGS. 16 and 17. Heterovalomers comprising different chemical classes of $Ca^{++}$ channel ligands (e.g., dihydropyridines and benzothiazepines), different ligands within the same chemical class (e.g. amlodipine and isradipine) and different enantiomers of a ligand (e.g., the (+) and (−) enantiomers of a dihydropyridine) are all encompassed by the present invention.

FIG. 16 illustrates methods of preparing bivalent compounds comprising dihydropyridine and benzothiazepine ligands in which the orientation of the ligands is varied.

FIG. 17 illustrates the preparation of a mixed agonist/antagonist heterovalomer. In this example, the compound of formula (66), a $Ca^{++}$ channel antagonist with an attached spacer, is coupled to the compound of formula (75), a $Ca^{++}$ channel agonist, and deprotected to yield a compound of formula (76).

Figure 18:
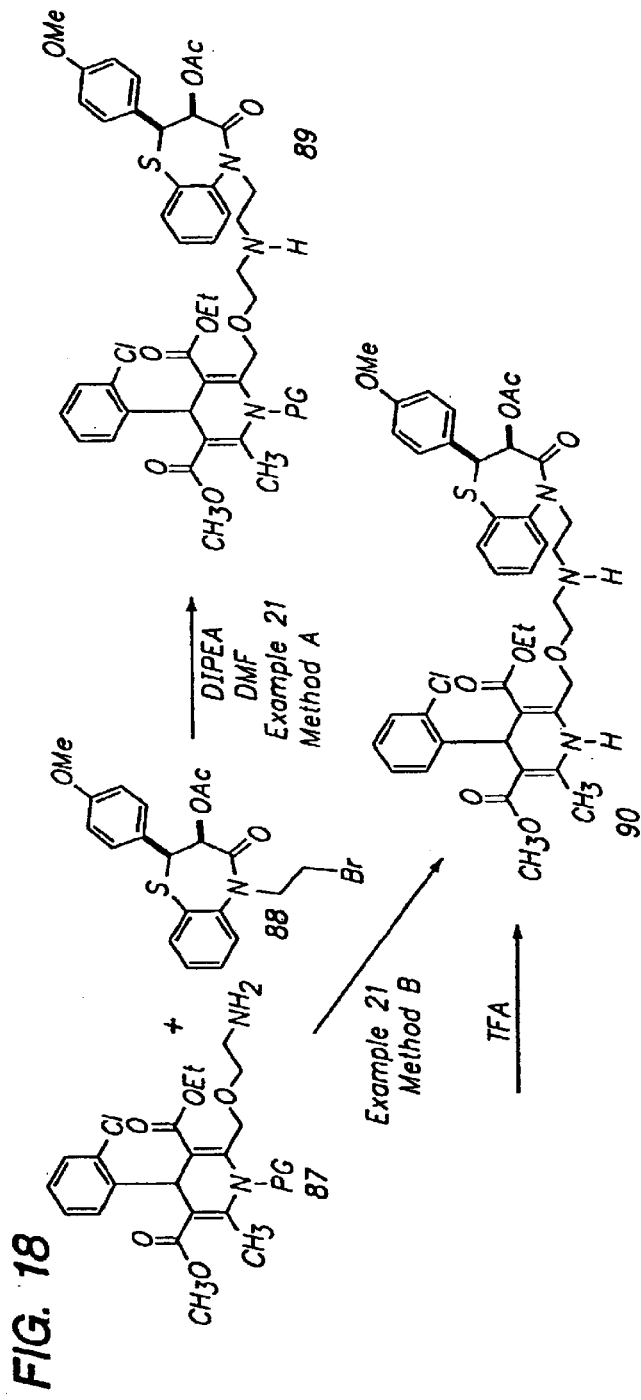
Figure 19:
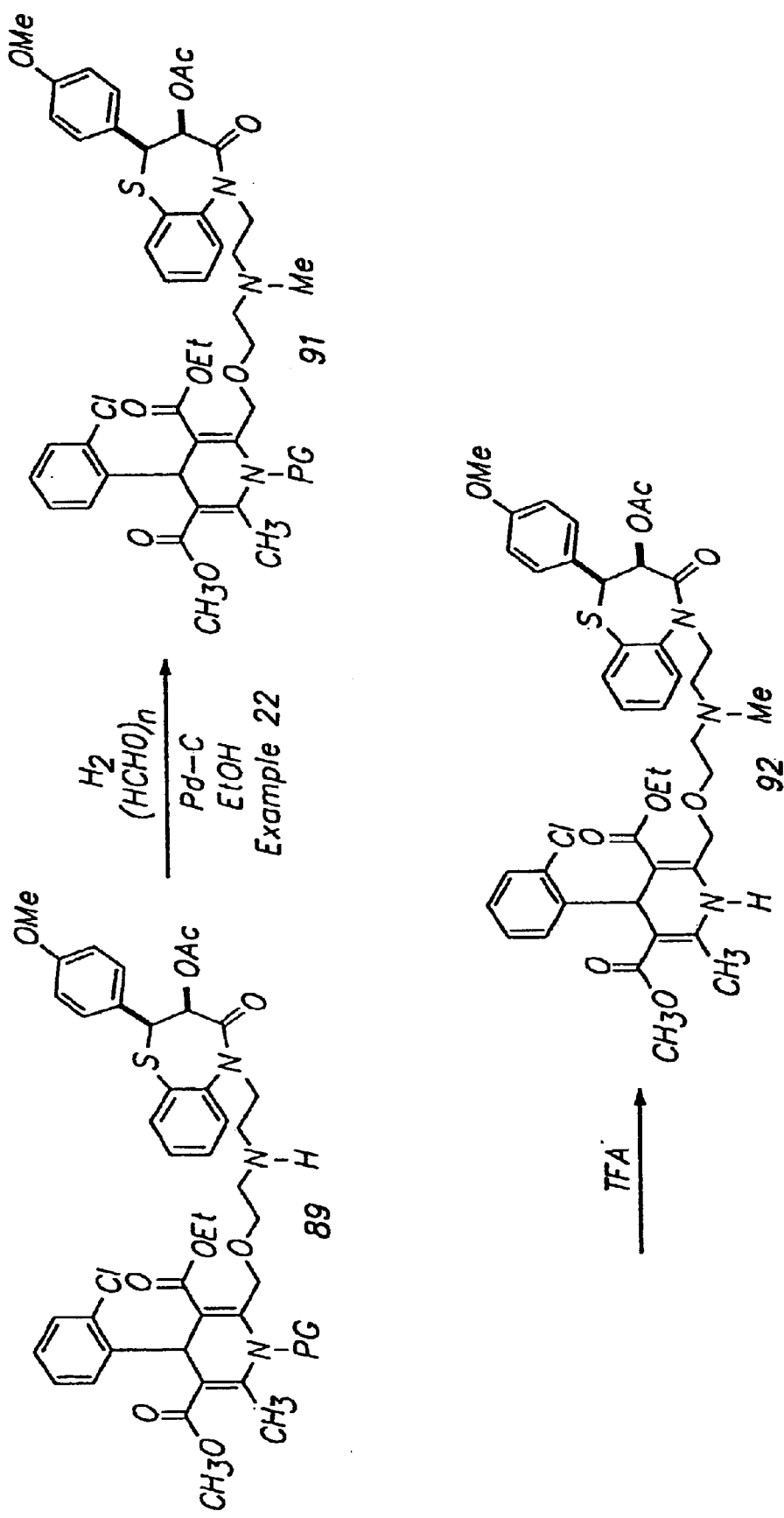
Figure 20:
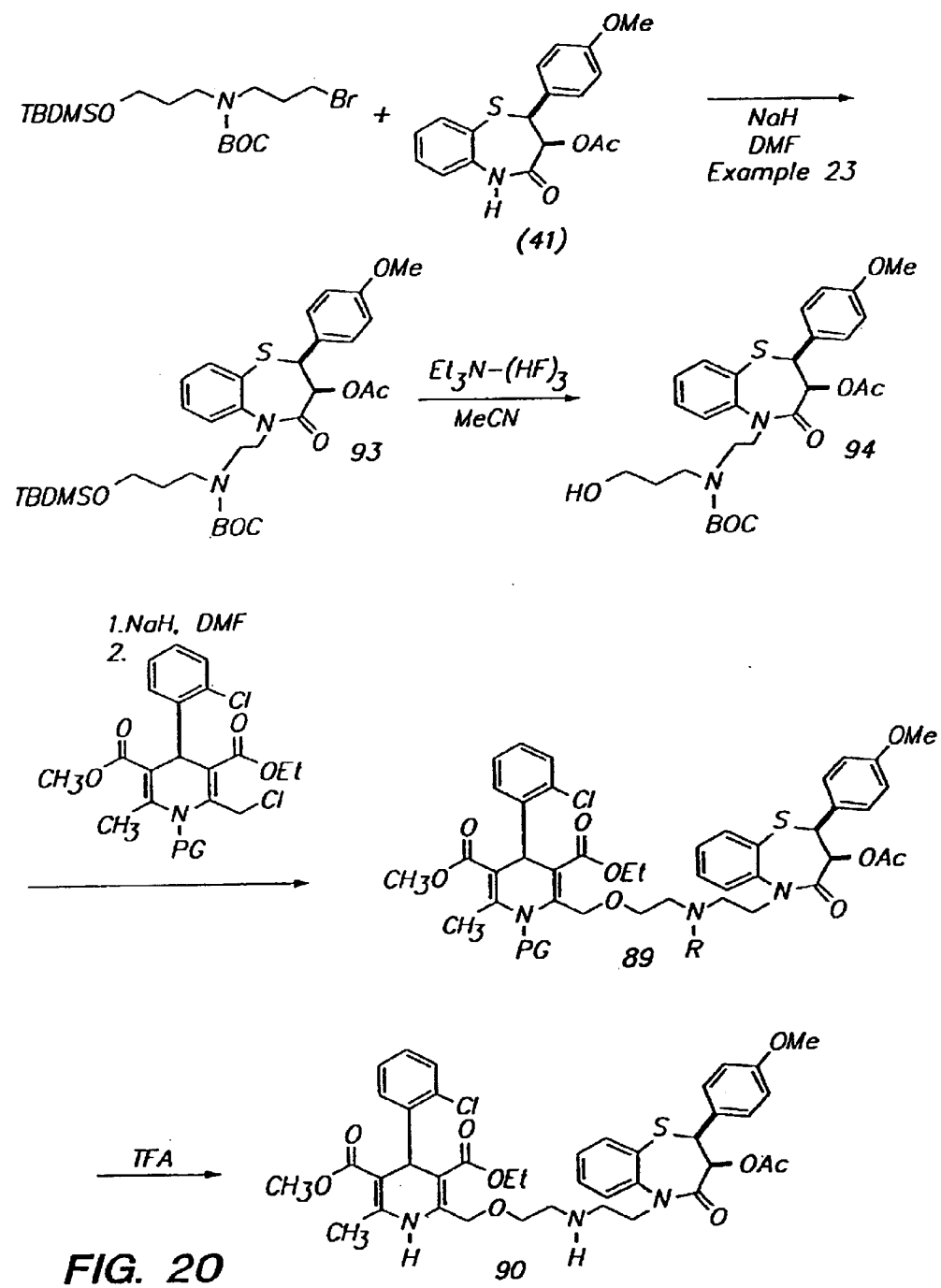
Figure 21:
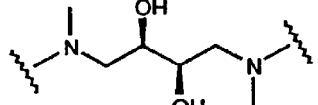
FIG. 21 is a table of 741 calcium channel antagonists according to the present invention.
Figure 21:
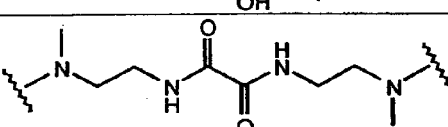
Figure 21:
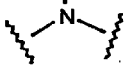
Figure 21:
Figure 21:
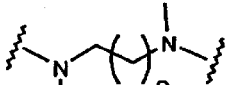
Figure 21:
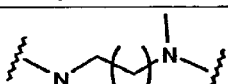
Figure 21:
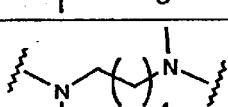
Figure 21:
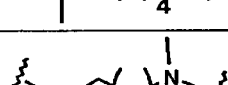
Figure 21:
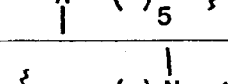
Figure 21:
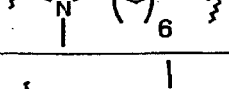
Figure 21:
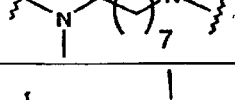

FIGS. 18–20 illustrate alternate methods of preparing bivalent compounds comprising dihydropyridine and benzothiazepine derivatives.

Isolation and Purification of the Compounds

Isolation and purification of the compounds and intermediates described herein can be effected, if desired, by any suitable separation or purification such as, for example, filtration, extraction, crystallization, column chromatography, thin-layer chromatography, thick-layer chromatography, preparative low or high-pressure liquid chromatography or a combination of these procedures. Characterization is preferably by NMR and mass spectroscopy.

Combinatorial Libraries

The methods described above lend themselves to combinatorial approaches for identifying multimeric compounds which possess multibinding properties.

Specifically, factors such as the proper juxtaposition of the individual ligands of a multibinding compound with respect to the relevant array of binding sites on a target or targets is important in optimizing the interaction of the multibinding compound with its target(s) and to maximize the biological advantage through multivalency. One approach is to identify a library of candidate multibinding compounds with properties spanning the multibinding parameters that are relevant for a particular target. These parameters include: (1) the identity of ligand(s), (2) the orientation of ligands, (3) the valency of the construct, (4) linker length, (5) linker geometry, (6) linker physical properties, and (7) linker chemical functional groups. Libraries of multimeric compounds potentially possessing multibinding properties (i.e., candidate multibinding compounds) and comprising a multiplicity of such variables are prepared and these libraries are then evaluated via conventional assays corresponding to the ligand selected and the multibinding parameters desired. Considerations relevant to each of these variables are set forth below:

Selection of ligand(s):

A single ligand or set of ligands is (are) selected for incorporation into the libraries of candidate multibinding compounds which library is directed against a particular biological target or targets. The only requirement for the ligands chosen is that they are capable of interacting with the selected target(s). Thus, ligands may be known drugs, modified forms of known drugs, substructures of known drugs or substrates of modified forms of known drugs (which are competent to interact with the target), or other compounds. Ligands are preferably chosen based on known favorable properties that may be projected to be carried over to or amplified in multibinding forms. Favorable properties include demonstrated safety and efficacy in human patients, appropriate PK/ADME profiles, synthetic accessibility, and desirable physical properties such as solubility, log P. etc. However, it is crucial to note that ligands which display an unfavorable property from among the previous list may obtain a more favorable property through the process of multibinding compound formation; i.e., ligands should not necessarily be excluded on such a basis. For example, a ligand that is not sufficiently potent at a particular target so as to be efficacious in a human patient may become highly potent and efficacious when presented in multibinding form. A ligand that is potent and efficacious but not of utility because of a non-mechanism-related toxic side effect may have increased therapeutic index (increased potency relative to toxicity) as a multibinding compound. Compounds that exhibit short in vivo half-lives may have extended half-lives as multibinding compounds. Physical properties of ligands that limit their usefulness (e.g. poor bioavailability due to low solubility, hydrophobicity, hydrophilicity) may be rationally modulated in multibinding forms, providing compounds with physical properties consistent with the desired utility.

Orientation: Selection of Ligand Attachment Points and Linking Chemistry

Several points are chosen on each ligand at which to attach the ligand to the linker. The selected points on the ligand/linker for attachment are functionalized to contain complementary reactive functional groups. This permits probing the effects of presenting the ligands to their receptor(s) in multiple relative orientations, an important multibinding design parameter. The only requirement for choosing attachment points is that attaching to at least one of these points does not abrogate activity of the ligand. Such points for attachment can be identified by structural information when available. For example, inspection of a co-crystal structure of a protease inhibitor bound to its target allows one to identify one or more sites where linker attachment will not preclude the enzyme:inhibitor interaction. Alternatively, evaluation of ligand/target binding by nuclear magnetic resonance will permit the identification of sites non-essential for ligand/target binding. See, for example, Fesik, et al., U.S. Pat. No. 5,891,643. When such structural information is not available, utilization of structure-activity relationships (SAR) for ligands will suggest positions where substantial structural variations are and are not allowed. In the absence of both structural and SAR information, a library is merely selected with multiple points of attachment to allow presentation of the ligand in multiple distinct orientations. Subsequent evaluation of this library will indicate what positions are suitable for attachment.

It is important to emphasize that positions of attachment that do abrogate the activity of the monomeric ligand may also be advantageously included in candidate multibinding compounds in the library provided that such compounds bear at least one ligand attached in a manner which does not abrogate intrinsic activity. This selection derives from, for example, heterobivalent interactions within the context of a single target molecule. For example, consider a receptor antagonist ligand bound to its target receptor, and then consider modifying this ligand by attaching to it a second copy of the same ligand with a linker which allows the second ligand to interact with the same receptor molecule at sites proximal to the antagonist binding site, which include elements of the receptor that are not part of the formal antagonist binding site and/or elements of the matrix surrounding the receptor such as the membrane. Here, the most favorable orientation for interaction of the second ligand molecule with the receptor/matrix may be achieved by attaching it to the linker at a position which abrogates activity of the ligand at the formal antagonist binding site. Another way to consider this is that the SAR of individual ligands within the context of a multibinding structure is often different from the SAR of those same ligands in momomeric form.

The foregoing discussion focused on bivalent interactions of dimeric compounds bearing two copies of the same ligand joined to a single linker through different attachment points, one of which may abrogate the binding/activity of the monomeric ligand. It should also be understood that bivalent advantage may also be attained with heterodimeric constructs bearing two different ligands that bind to common or different targets. For example, a $5HT_4$ receptor antagonist and a bladder-selective muscarinic $M_3$ antagonist may be joined to a linker through attachment points which do not abrogate the binding affinity of the monomeric ligands for their respective receptor sites. The dimeric compound may achieve enhanced affinity for both receptors due to favorable interactions between the $5HT_4$ ligand and elements of the $M_3$ receptor proximal to the formal $M_3$ antagonist binding site and between the $M_3$ ligand and elements of the $5HT_4$ receptor proximal to the formal $5HT_4$ antagonist binding site. Thus, the dimeric compound may be more potent and selective antagonist of overactive bladder and a superior therapy for urinary urge incontinence.

Once the ligand attachment points have been chosen, one identifies the types of chemical linkages that are possible at those points. The most preferred types of chemical linkages are those that are compatible with the overall structure of the ligand (or protected forms of the ligand) readily and generally formed, stable and intrinsically inocuous under typical chemical and physiological conditions, and compatible with a large number of available linkers. Amide bonds, ethers, amines, carbamates, ureas, and sulfonamides are but a few examples of preferred linkages.

Linkers: Spanning Relevant Multibinding Parameters through Selection of Valency, Linker Length, Linker Geometry, Rigidity, Physical Properties, and Chemical Functional Groups In the library of linkers employed to generate the library of candidate multibinding compounds, the selection of linkers employed in this library of linkers takes into consideration the following factors:

Valency:

In most instances the library of linkers is initiated with divalent linkers. The choice of ligands and proper juxtaposition of two ligands relative to their binding sites permits such molecules to exhibit target binding affinities and specificities more than sufficient to confer biological advantage. Furthermore, divalent linkers or constructs are also typically of modest size such that they retain the desirable biodistribution properties of small molecules.

Linker Length:

Linkers are chosen in a range of lengths to allow the spanning of a range of inter-ligand distances that encompass the distance preferable for a given divalent interaction. In some instances the preferred distance can be estimated rather precisely from high-resolution structural information of targets, typically enzymes and soluble receptor targets. In other instances where high-resolution structural information is not available (such as 7TM G-protein coupled receptors), one can make use of simple models to estimate the maximum distance between binding sites either on adjacent receptors or at different locations on the same receptor. In situations where two binding sites are present on the same target (or target subunit for multisubunit targets), preferred linker distances are 2–20, with more preferred linker distances of 3–12. In situations where two binding sites reside on separate (e.g., protein) target sites, preferred linker distances are 20–100, with more preferred distances of 30–70

Linker Geometry and Rigidity:

The combination of ligand attachment site, linker length, linker geometry, and linker rigidity determine the possible ways in which the ligands of candidate multibinding compounds may be displayed in three dimensions and thereby presented to their binding sites. Linker geometry and rigidity are nominally determined by chemical composition and bonding pattern, which may be controlled and are systematically varied as another spanning function in a multibinding array. For example, linker geometry is varied by attaching two ligands to the ortho, meta, and para positions of a benzene ring, or in cis- or trans-arrangements at the 1,1- vs. 1,2- vs. 1,3- vs. 1,4-positions around a cyclohexane core or in cis- or trans-arrangements at a point of ethylene unsaturation. Linker rigidity is varied by controlling the number and relative energies of different conformational states possible for the linker. For example, a divalent compound bearing two ligands joined by 1,8-octyl linker has many more degrees of freedom, and is therefore less rigid than a compound in which the two ligands are attached to the 4,4' positions of a biphenyl linker.

Linker Physical Properties:

The physical properties of linkers are nominally determined by the chemical constitution and bonding patterns of the linker, and linker physical properties impact the overall physical properties of the candidate multibinding compounds in which they are included. A range of linker compositions is typically selected to provide a range of physical properties (hydrophobicity, hydrophilicity, amphiphilicity, polarization, acidity, and basicity) in the candidate multibinding compounds. The particular choice of linker physical properties is made within the context of the physical properties of the ligands they join and preferably the goal is to generate molecules with favorable PK/ADME properties. For example, linkers can be selected to avoid those that are too hydrophilic or too hydrophobic to be readily absorbed and/or distributed in vivo.

Linker Chemical Functional Groups:

Linker chemical functional groups are selected to be compatible with the chemistry chosen to connect linkers to the ligands and to impart the range of physical properties sufficient to span initial examination of this parameter.

Combinatorial Synthesis:

Having chosen a set of n ligands (n being determined by the sum of the number of different attachment points for each ligand chosen) and m linkers by the process outlined above, a library of (n!)m candidate divalent multibinding compounds is prepared which spans the relevant multibinding design parameters for a particular target. For example, an array generated from two ligands, one which has two attachment points (A1, A2) and one which has three attachment points (B1, B2, B3) joined in all possible combinations provide for at least 15 possible combinations of multibinding compounds:

| A1-A1 | A1-A2 | A1-B1 | A1-B2 | A1-B3 | A2-A2 | A2-B1 | A2-B2 |
| A2-B3 | B1-B1 | B1-B2 | B1-B3 | B2-B2 | B2-B3 | B3-B3 | |

When each of these combinations is joined by 10 different linkers, a library of 150 candidate multibinding compounds results.

Given the combinatorial nature of the library, common chemistries are preferably used to join the reactive functionaries on the ligands with complementary reactive functionalities on the linkers. The library therefore lends itself to efficient parallel synthetic methods. The combinatorial library can employ solid phase chemistries well known in the art wherein the ligand and/or linker is attached to a solid support. Alternatively and preferably, the combinatorial libary is prepared in the solution phase. After synthesis, candidate multibinding compounds are optionally purified before assaying for activity by, for example, chromatographic methods (e.g., HPLC).

Analysis of Array by Biochemical, Analytical, Pharmacological, and Computational Methods:

Various methods are used to characterize the properties and activities of the candidate multibinding compounds in the library to determine which compounds possess multibinding properties. Physical constants such as solubility under various solvent conditions and logD/clog D values can be determined. A combination of NMR spectroscopy and computational methods is used to determine low-energy conformations of the candidate multibinding compounds in fluid media. The ability of the members of the library to bind to the desired target and other targets is determined by various standard methods, which include radioligand displacement assays for receptor and ion channel targets, and kinetic inhibition analysis for many enzyme targets. In vitro efficacy, such as for receptor agonists and antagonists, ion channel blockers, and antimicrobial activity, can also be determined. Pharmacological data, including oral absorption, everted gut penetration, other pharmacokinetic parameters and efficacy data can be determined in appropriate models. In this way, key structure-activity relationships are obtained for multibinding design parameters which are then used to direct future work.

The members of the library which exhibit multibinding properties, as defined herein, can be readily determined by conventional methods. First those members which exhibit multibinding properties are identified by conventional methods as described above including conventional assays (both in vitro and in vivo).

Second, ascertaining the structure of those compounds which exhibit multibinding properties can be accomplished via art recognized procedures. For example, each member of the library can be encrypted or tagged with appropriate information allowing determination of the structure of relevant members at a later time. See, for example, Dower, et al., International Patent Application Publication No. WO 93/06121; Brenner, et al., Proc. Natl. Acad. Sci., USA, 89:5181 (1992); Gallop, et al., U.S. Pat. No. 5,846,839; each of which are incorporated herein by reference in its entirety. Alternatively, the structure of relevant multivalent compounds can also be determined from soluble and untagged libraries of candidate multivalent compounds by methods known in the art such as those described by Hindsgaul, et al., Canadian Patent Application No. 2,240,325 which was published on Jul. 11, 1998. Such methods couple frontal affinity chromatography with mass spectroscopy to determine both the structure and relative binding affinities of candidate multibinding compounds to receptors.

The process set forth above for dimeric candidate multibinding compounds can, of course, be extended to trimeric candidate compounds and higher analogs thereof.

Follow-Up Synthesis and Analysis of Additional Array(s):

Based on the information obtained through analysis of the initial library, an optional component of the process is to ascertain one or more promising multibinding "lead" compounds as defined by particular relative ligand orientations, linker lengths, linker geometries, etc. Additional libraries can then be generated around these leads to provide for further information regarding structure to activity relationships. These arrays typically bear more focused variations in linker structure in an effort to further optimize target affinity and/or activity at the target (antagonism, partial agonism, etc.), and/or alter physical properties. By iterative redesign/analysis using the novel principles of multibinding design along with classical medicinal chemistry, biochemistry, and pharmacology approaches, one is able to prepare and identify optimal multibinding compounds that exhibit biological advantage towards their targets and as therapeutic agents.

To further elaborate upon this procedure, suitable divalent linkers include, by way of example only, those derived from dicarboxylic acids, disulfonylhalides, dialdehydes, diketones, dihalides, diisocyanates, diamines, diols, mixtures of carboxylic acids, sulfonylhalides, aldehydes, ketones, halides, isocyanates, amines and diols. In each case, the carboxylic acid, sulfonylhalide, aldehyde, ketone, halide, isocyanate, amine and diol functional group is reacted with a complementary functionality on the ligand to form a covalent linkage. Such complementary functionality is well known in the art as illustrated in the following table:

| COMPLEMENTARY BINDING CHEMISTRIES | | |
| --- | --- | --- |
| First Reactive Group | Second Reactive Group | Linkage |
| hydroxyl | isocyanate | urethane |
| amine | epoxide | -amine |
| hydroxyamine | sulfonyl halide | sulfonamide |
| carboxyl acid | amine | amide |
| hydroxyl | alkyl/aryl halide | ether |
| aldehyde | amine/NaCNBH$_4$ | amine |
| ketone | amine/NaCNBH$_4$ | amine |
| amine | isocyanate | urea |

The following table illustrates, by way of example, starting materials (identified as X-1 through X-418) that can be used to prepare linkers incorporated in the multibinding compounds of this invention utilizing the chemistry described above. For example, 1,10-decanedicarboxylic acid, X1, can be reacted with 2 equivalents of a ligand carrying an amino group in the presence of a coupling reagent such as DCC to provide a bivalent multibinding compound of formula (I) wherein the ligands are linked via a 1,10-decanediamido linking group.

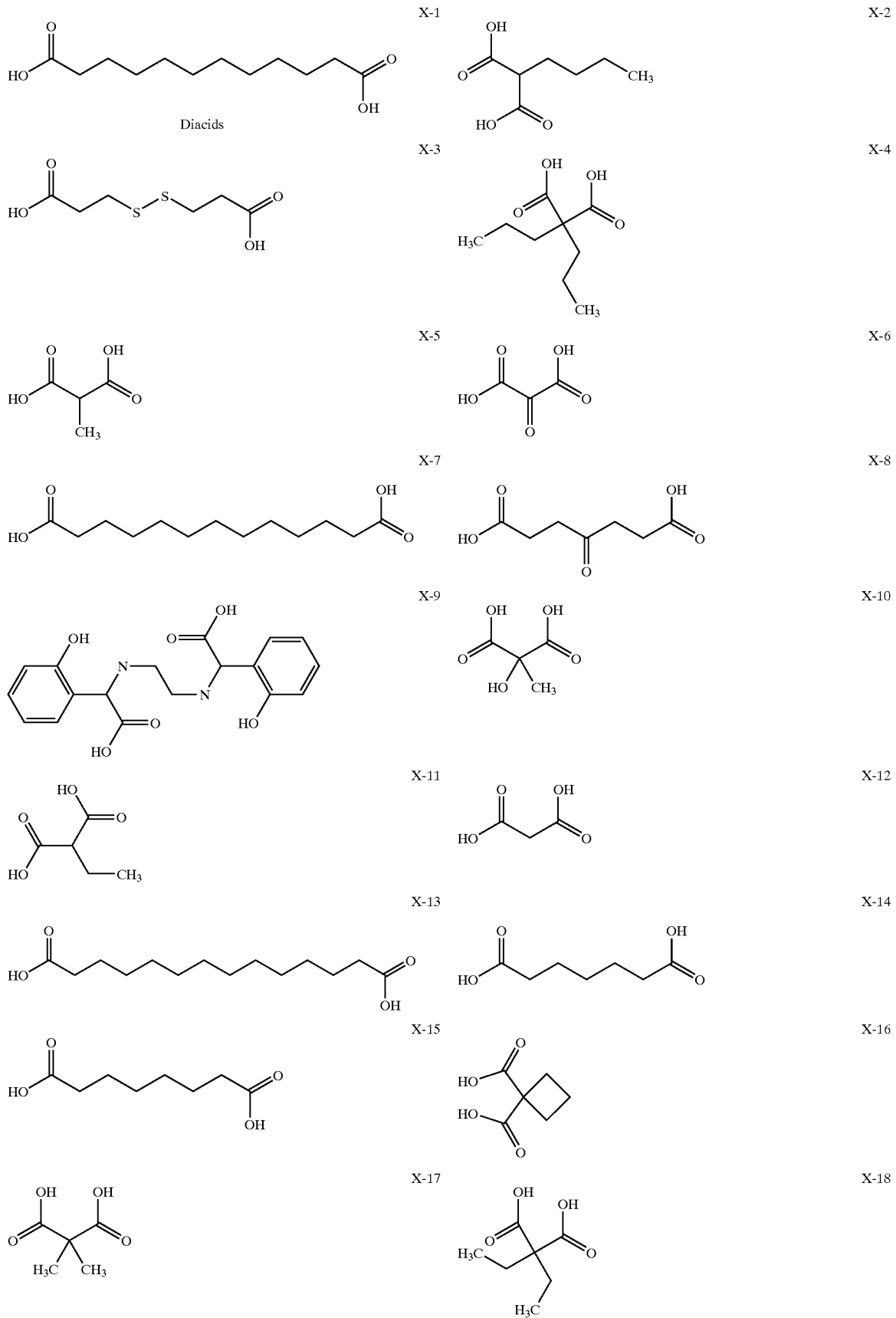

-continued
X-19
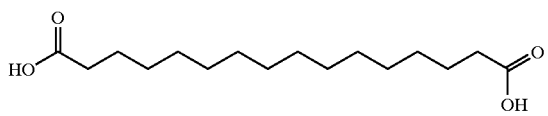
X-20
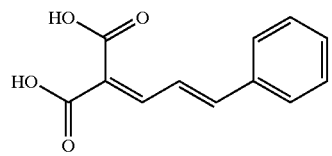
X-21
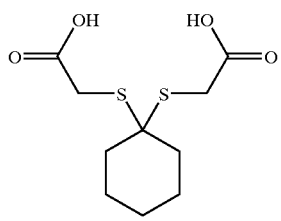
X-22
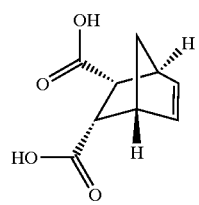
X-23
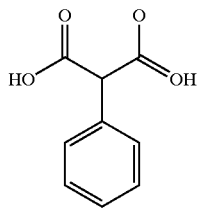
X-24
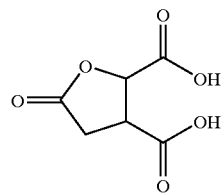
X-25
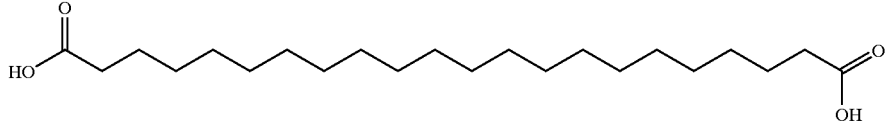
X-26
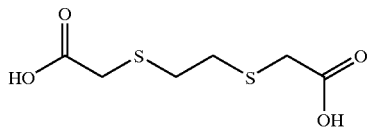
X-27
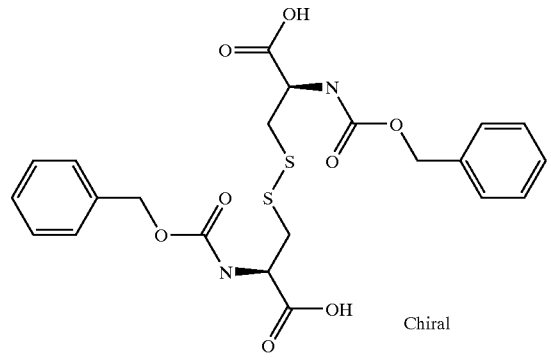
Chiral
X-28
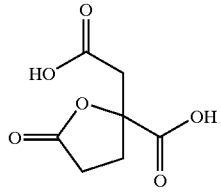
X-29
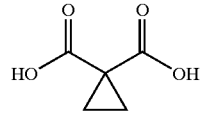
X-30
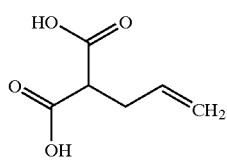
X-31
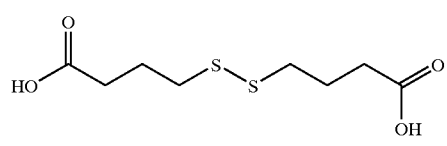

-continued
X-32
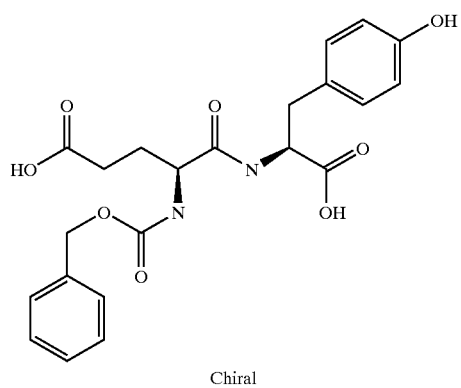
Chiral
X-33
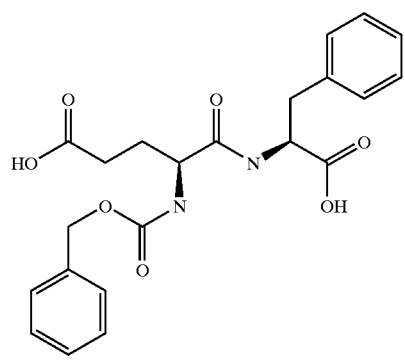
Chiral
X-34
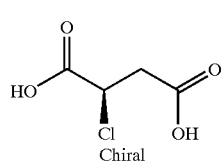
Chiral
X-35
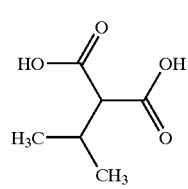
X-36
X-37
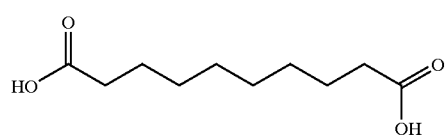
X-38
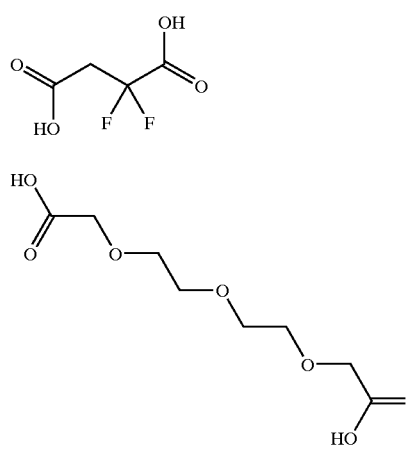
X-39
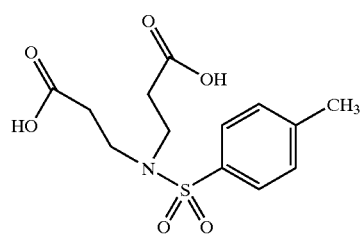
X-40
X-41
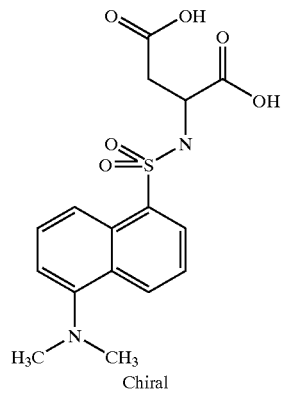
Chiral
X-42
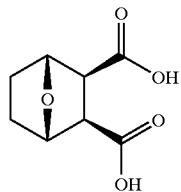
X-43
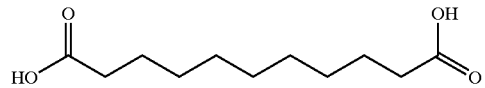
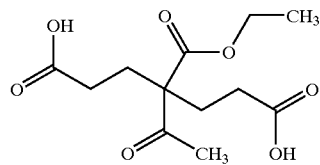

-continued
| | |
|---|---|
| X-44 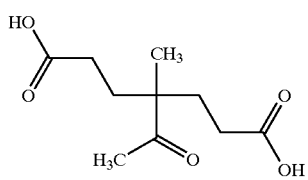 | X-45 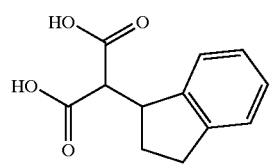 |
| X-46 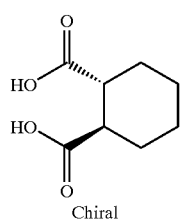 | X-47 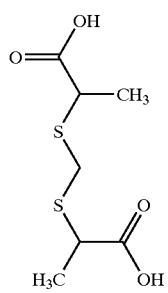 |
| X-48 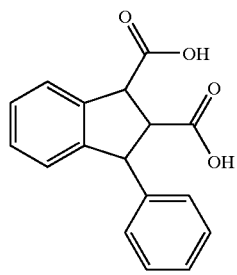 | X-49 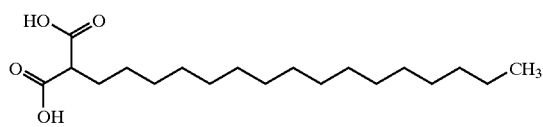 |
| X-50 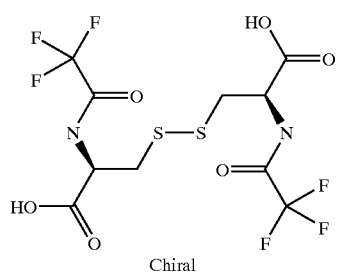 | X-51 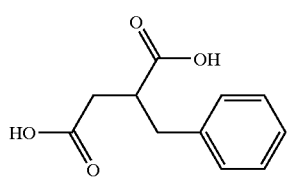 |
| X-52 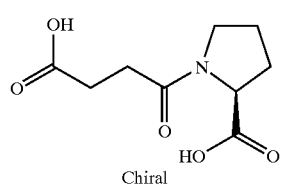 | X-53 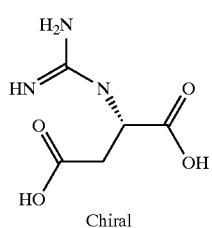 |
| X-54 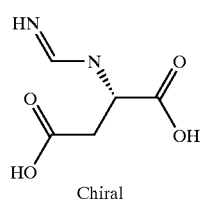 | X-55 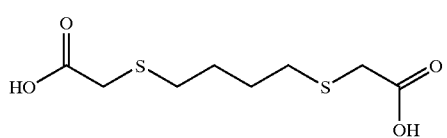 |

-continued
X-56 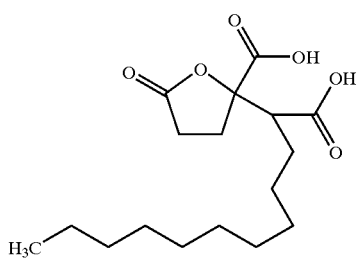
X-57 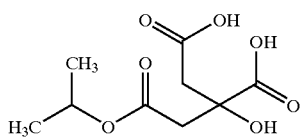
X-58 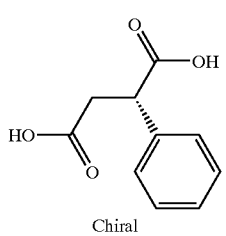
Chiral
X-59 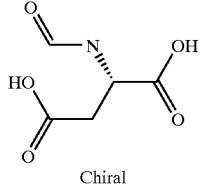
Chiral
X-60 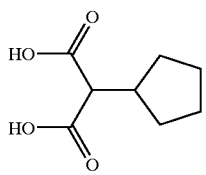
X-61 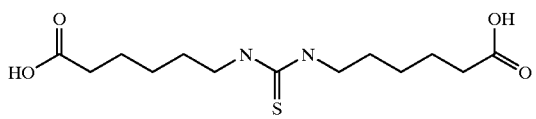
X-62 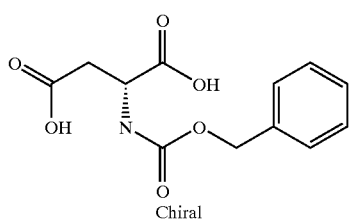
Chiral
X-63 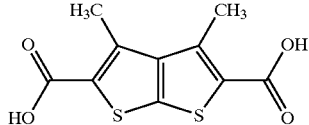
X-64 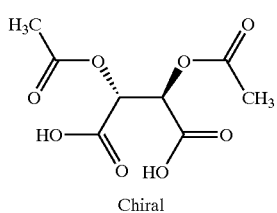
Chiral
X-65 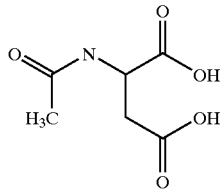
X-66 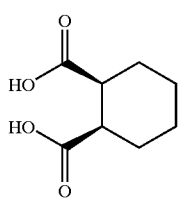
X-67 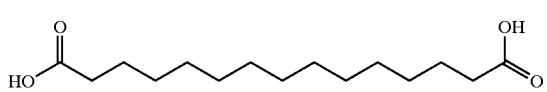
X-68 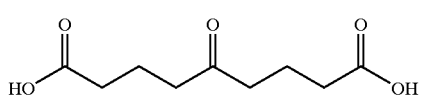
X-69 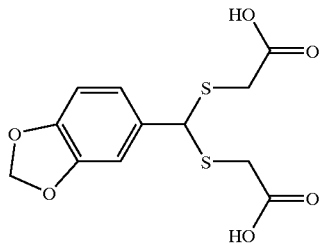

-continued
X-70
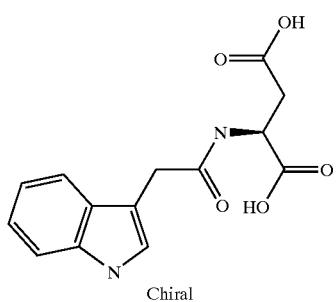
Chiral
X-71
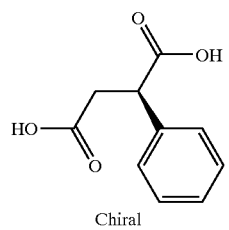
Chiral
X-72
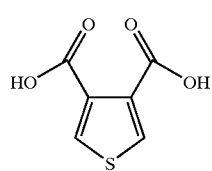
X-73
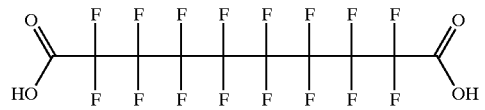
X-74
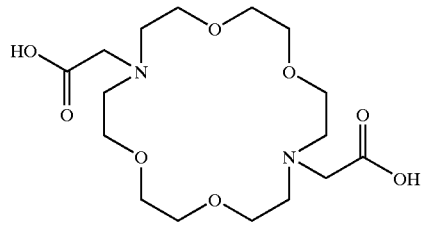
X-75
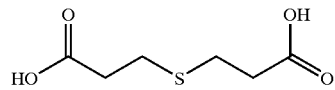
X-76
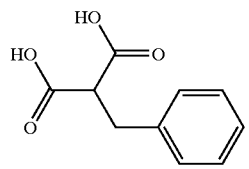
X-77
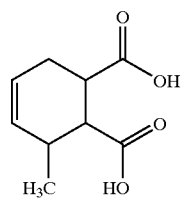
X-78
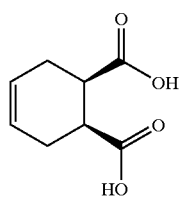
X-79
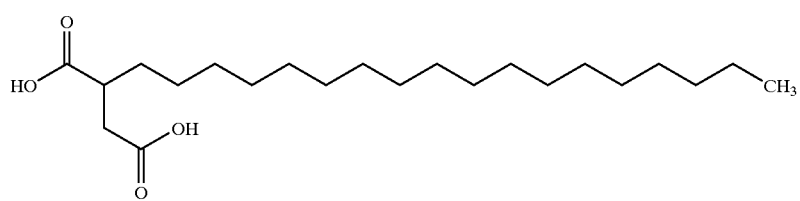
X-80
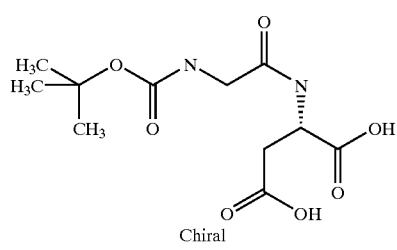
Chiral
X-81
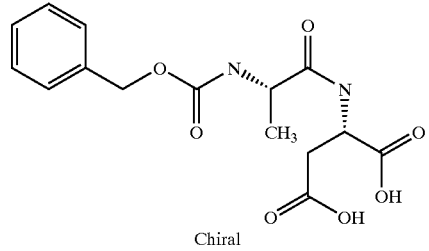
Chiral -continued
X-82
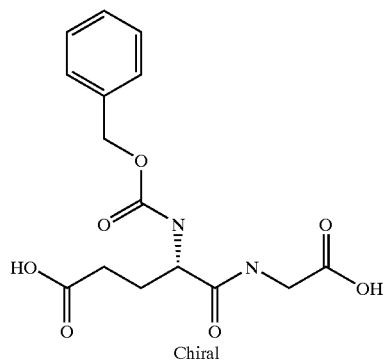
X-83
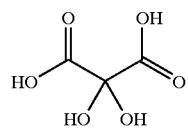
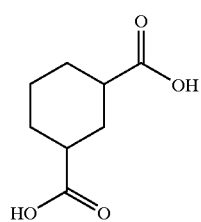
X-84
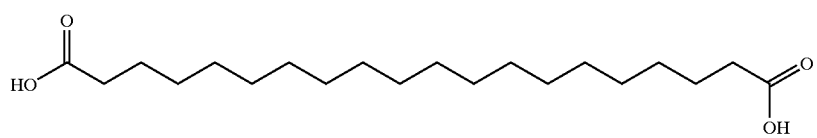
X-85
X-86
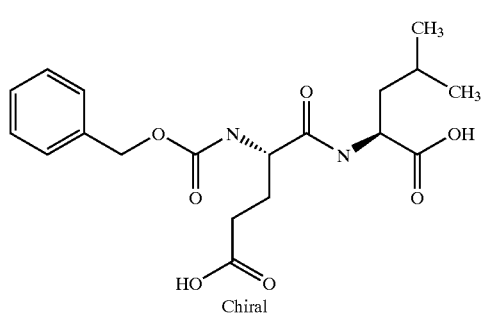
X-87
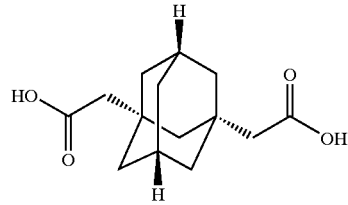
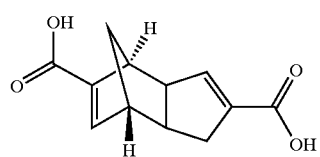
X-88
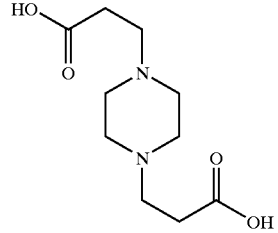
X-89
X-90
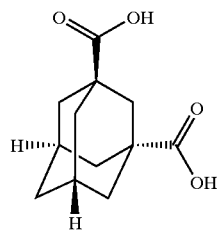
X-91
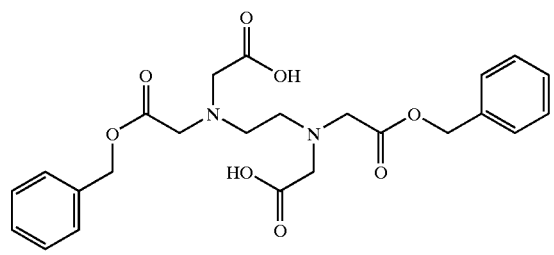

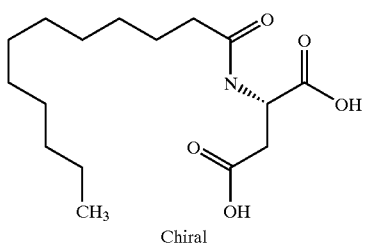
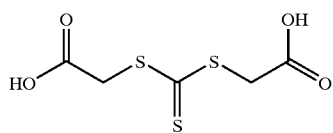
X-92
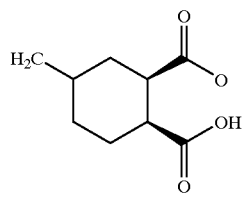
X-93
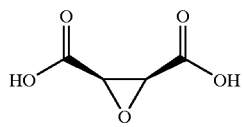
X-94
X-95
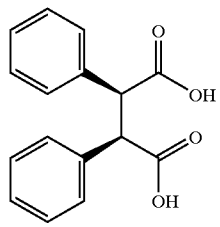
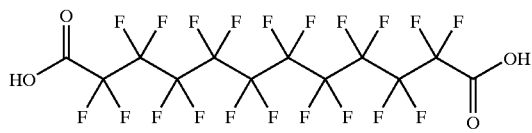
X-96
X-97
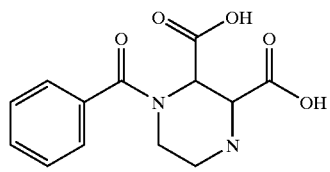
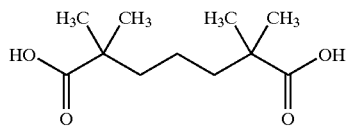
X-98
X-99
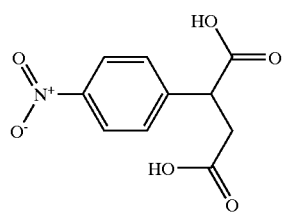
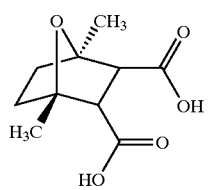
X-100
X-101
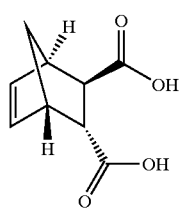
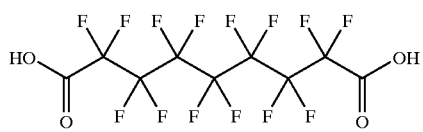
X-102
X-10-3
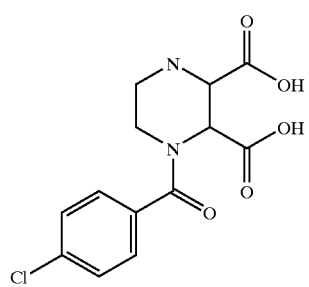
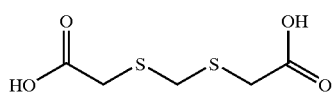
X-104
X-105

X-106 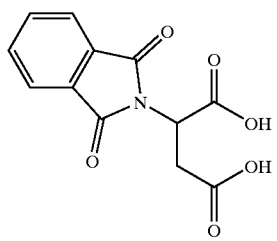
X-107 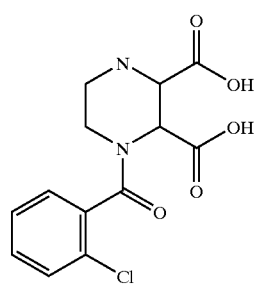
X-108 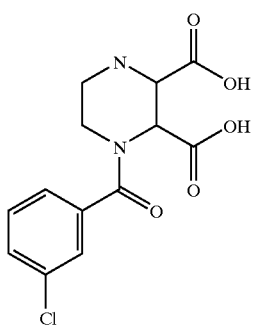
X-109 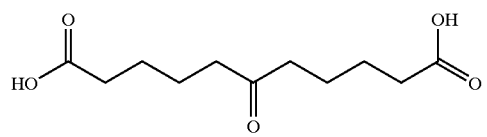
X-110 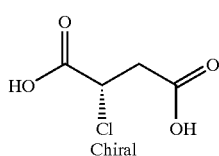
X-111 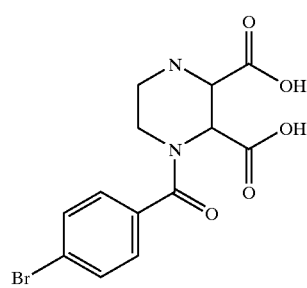
X-112 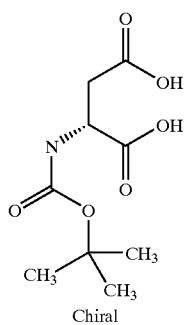
X-113 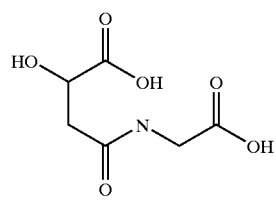
X-114 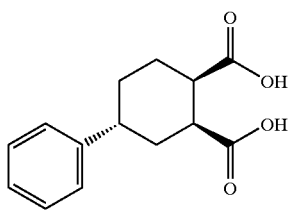
X-115 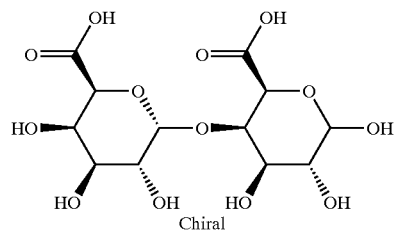

-continued
X-116
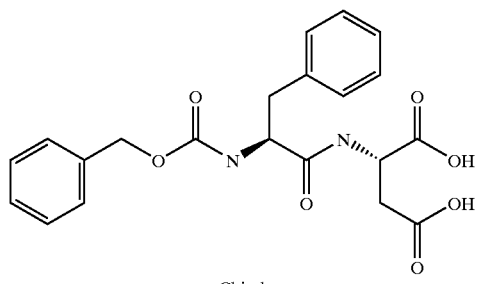
Chiral
X-117
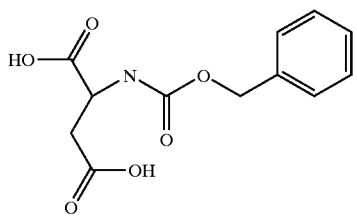
X-118
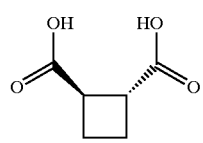
X-119
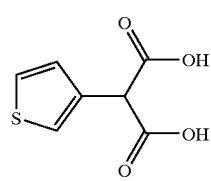
X-120
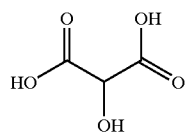
X-121
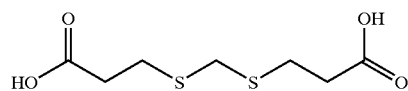
X-122
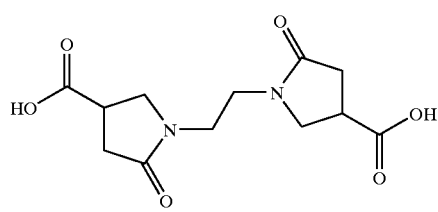
X-123
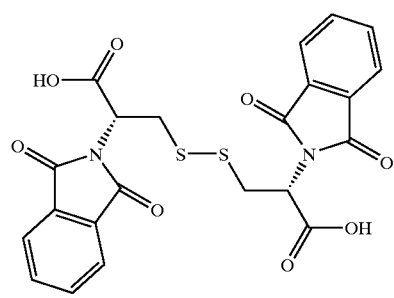
Chiral
X-124
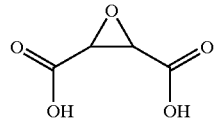
X-125
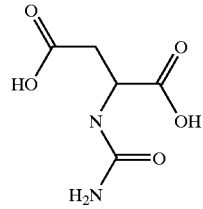
X-126
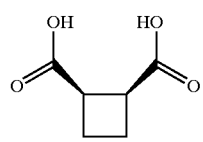
X-127
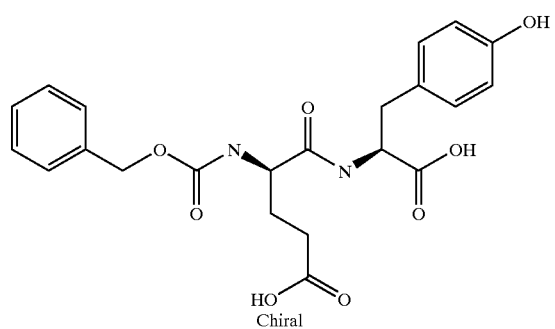
Chiral X-128
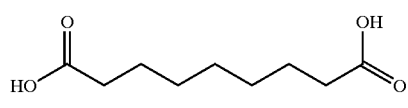
X-129
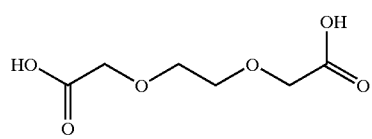
X-130
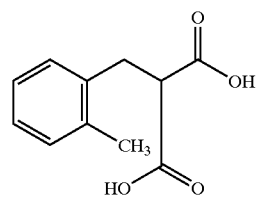
X-131
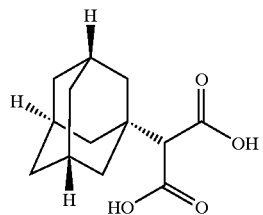
X-132
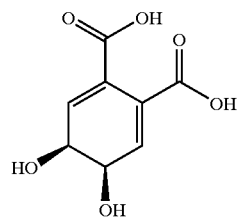
X-133
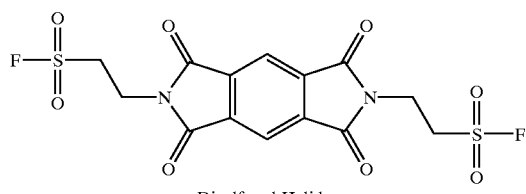
Disulfonyl Halides
X-134
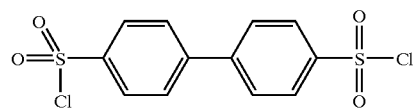
X-135
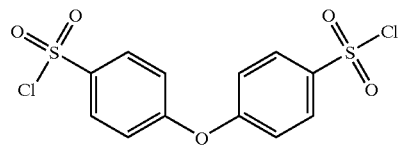
X-136
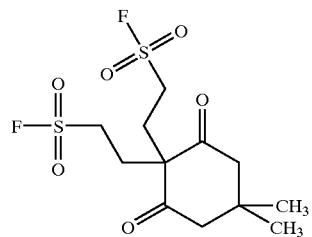
X-137
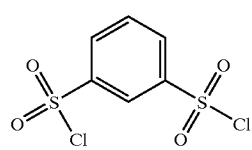
X-138
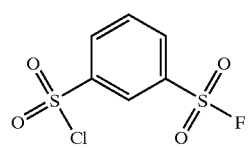
X-139
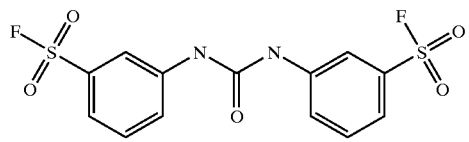
X-140
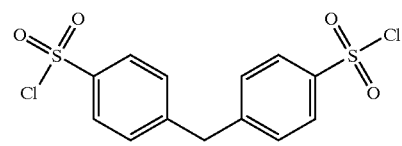
X-141
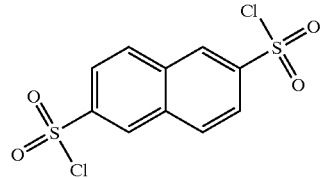

X-142 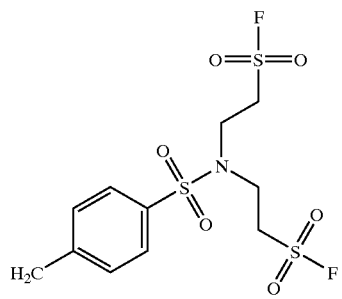
X-143 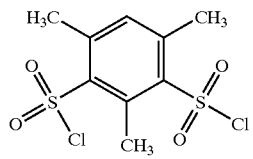
X-144
X-145 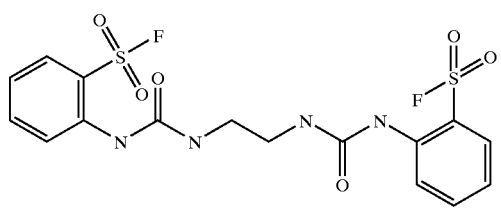
X-146
X-147 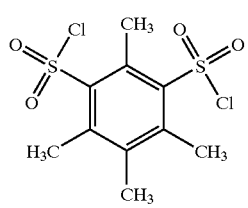
X-148
X-149 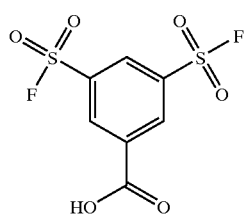
X-150
X-151 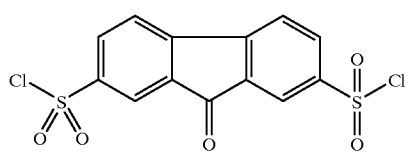
X-152
X-153
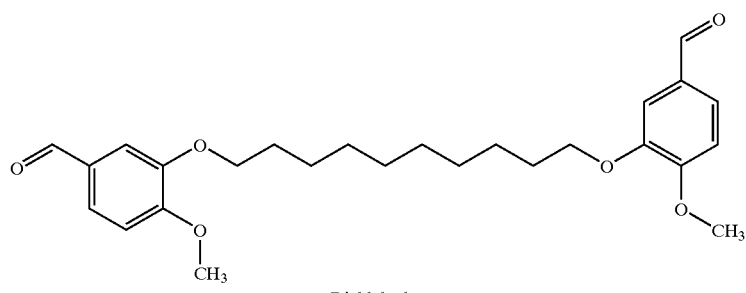
Dialdehydes -continued
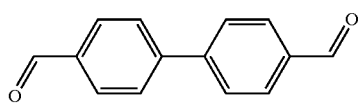
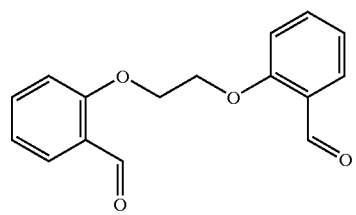
X-154
X-155
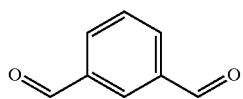
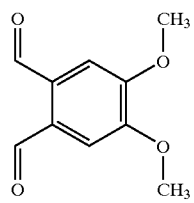
X-156
X-157
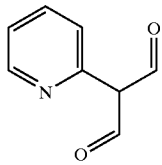
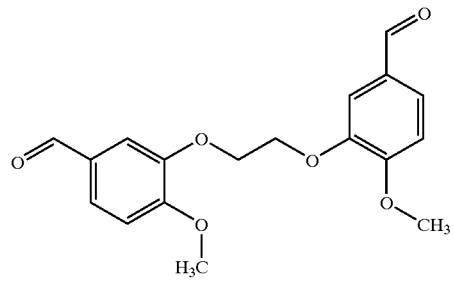
X-158
X-159
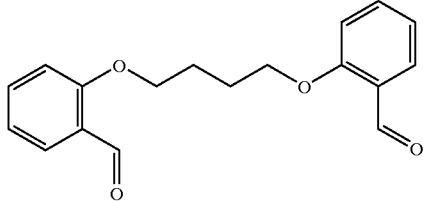
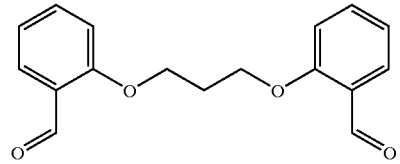
X-160
X-161
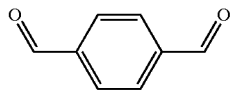
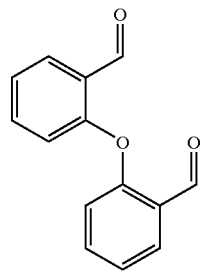
X-162
X-163
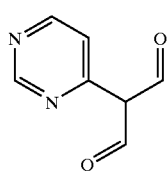
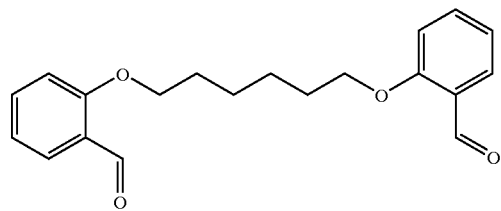
X-164
X-165
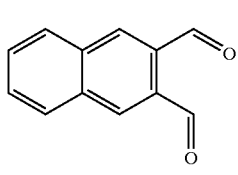
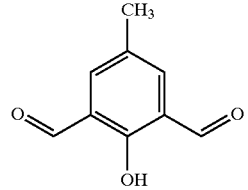
X-166
X-167

-continued
X-168 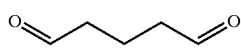
X-169 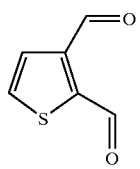
X-170 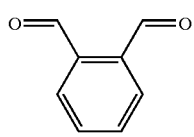
X-171 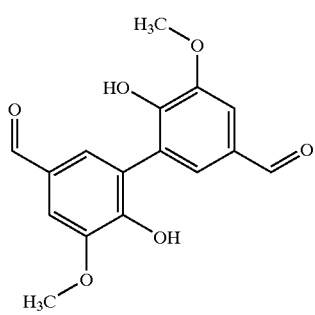
X-172 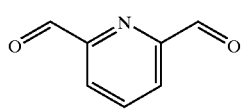
X-173 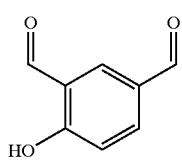
X-174 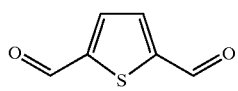
X-175 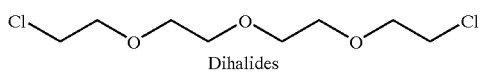
Dihalides
X-176 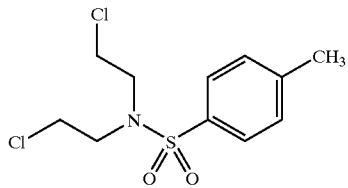
X-177 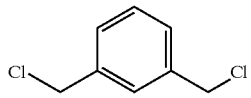
X-178 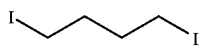
X-179 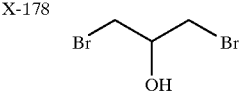
X-180 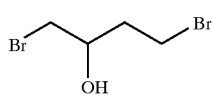
X-181 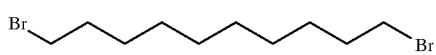
X-182 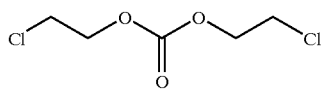
X-183 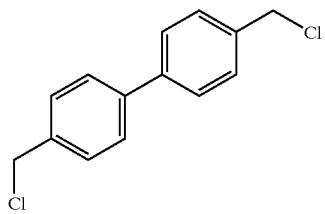
X-184 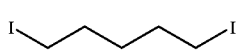
X-185 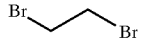
X-186 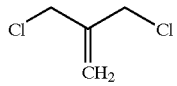
X-187 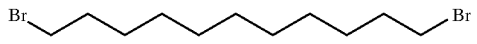

-continued
X-188 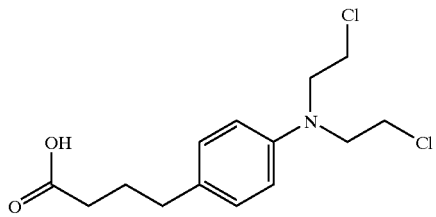 X-189 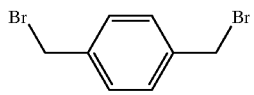
X-190 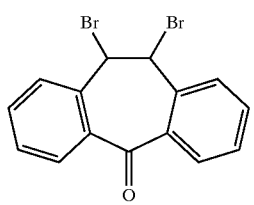 X-191 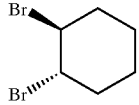
X-192 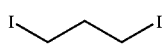 X-193 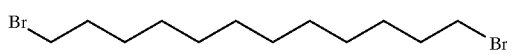
X-194 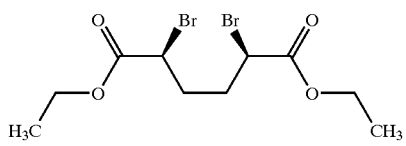 X-195 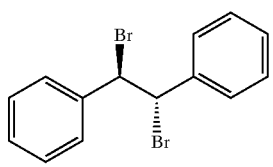
X-196 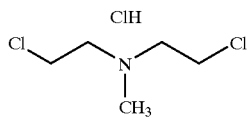 X-197 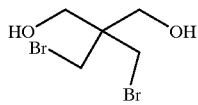
X-198 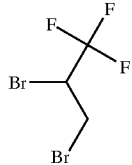 X-199 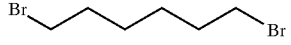
X-200 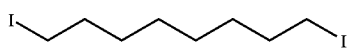 X-201 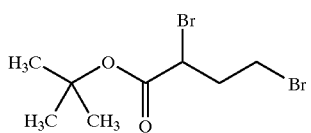
X-202 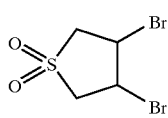 X-203 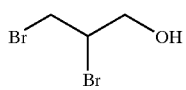
X-204 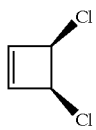 X-205 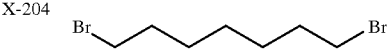
X-206 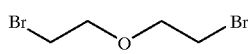 X-207 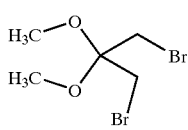

-continued
X-208 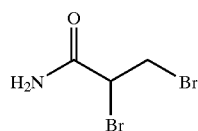
X-209 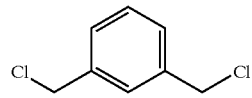
X-210 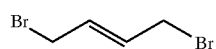
X-211 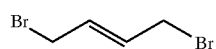
X-212 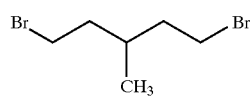
X-213 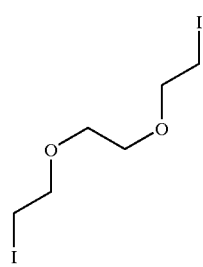
X-214 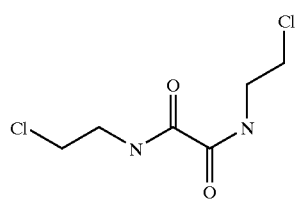
X-215 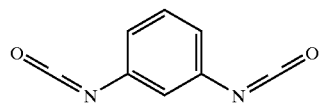
X-216 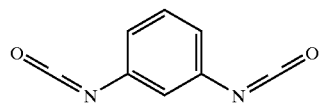
X-217 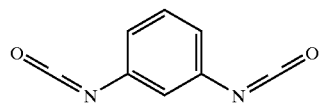
X-218 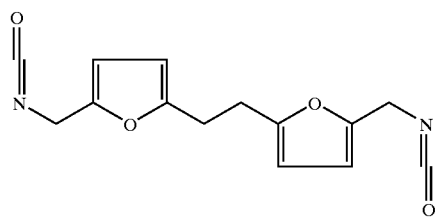
X-219 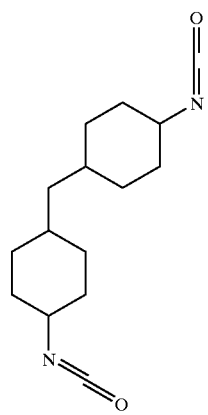
X-220 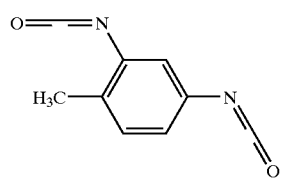
X-221 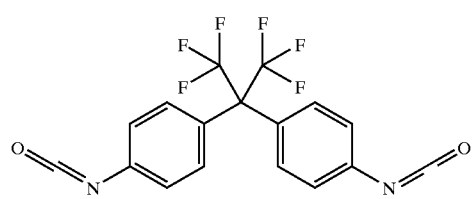

-continued
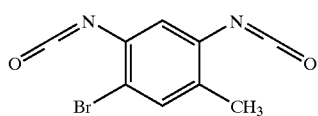
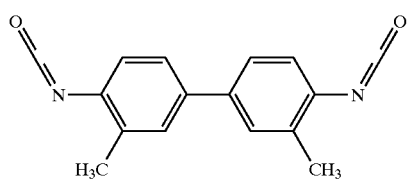
X-222  X-223
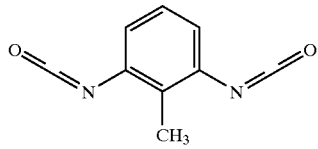
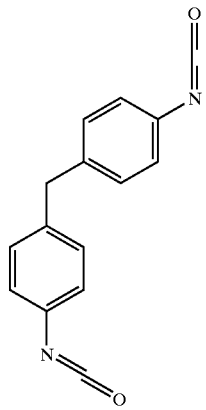
X-224  X-225
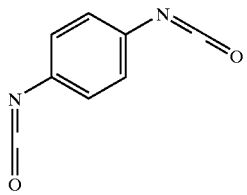
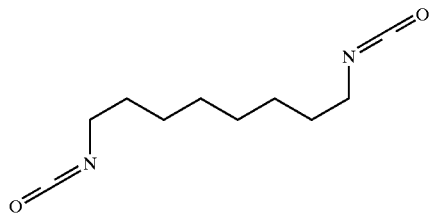
X-226  X-227
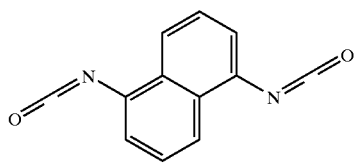
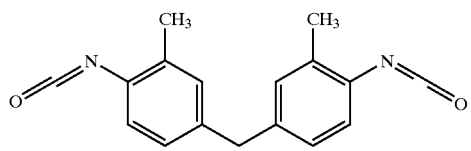
X-228  X-229
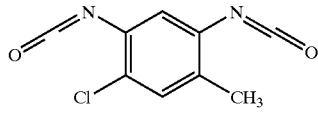
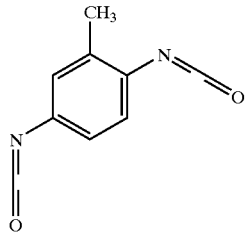
X-230  X-231
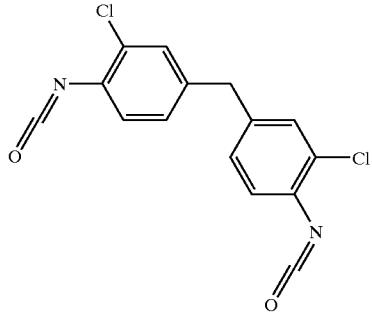
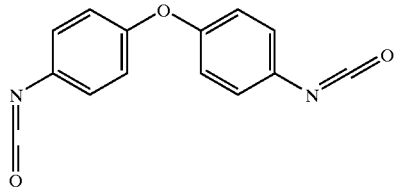
X-232  X-233

-continued
| | |
|---|---|
| X-234 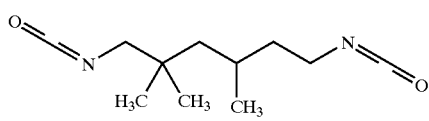 | X-235 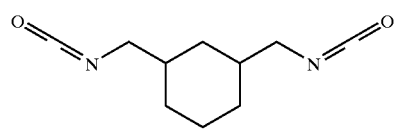 |
| X-236 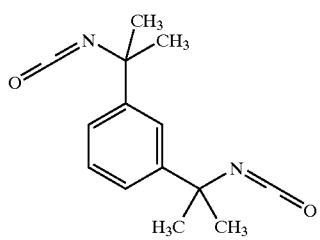 | X-237 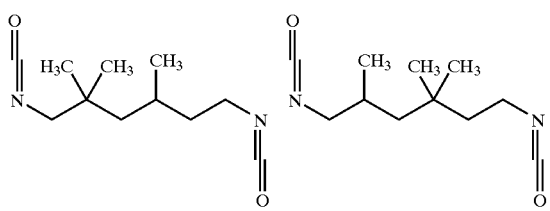 |
| X-238 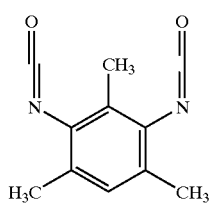 | X-239 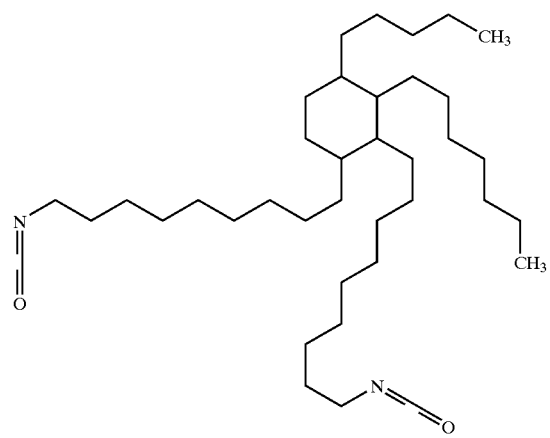 |
| X-240 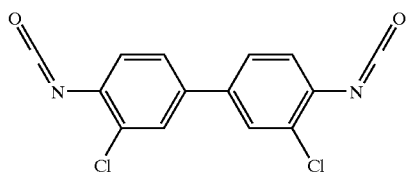 | X-241 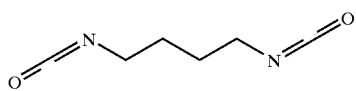 |
| X-242 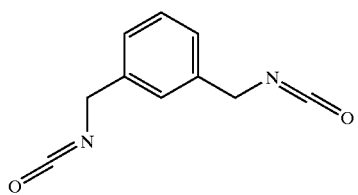 | X-243 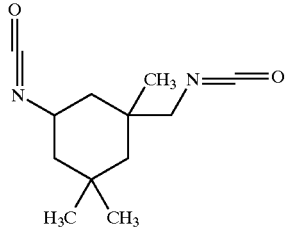 |
| X-244 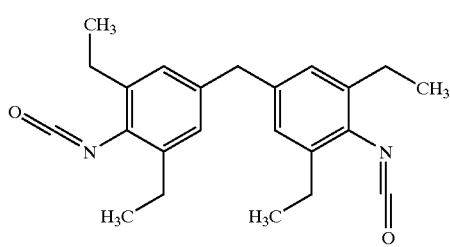 | X-245 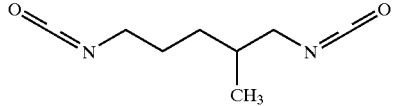 |

X-246 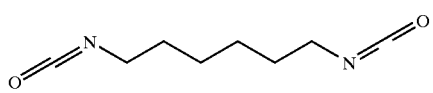
X-247 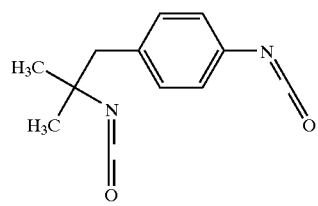
X-248 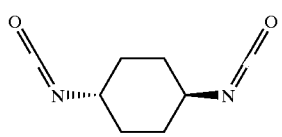
X-249 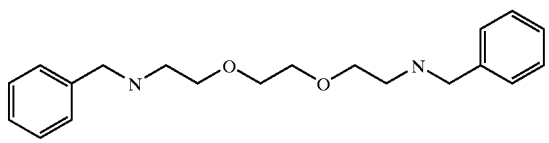
Diamines
X-250 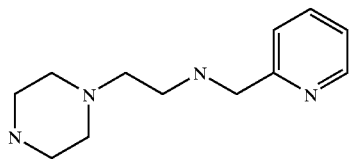
X-251 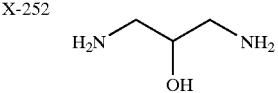
X-252 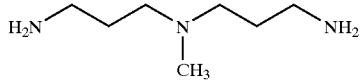
X-253
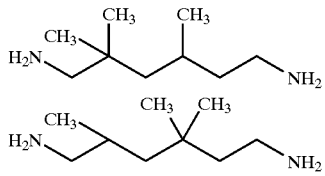
X-254 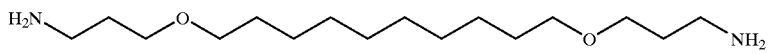
X-255 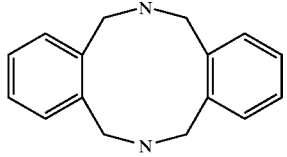
X-256 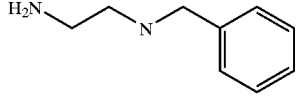
X-257
X-258 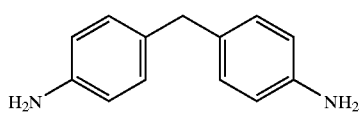
X-259 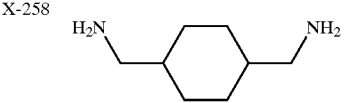
X-260 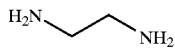
X-261 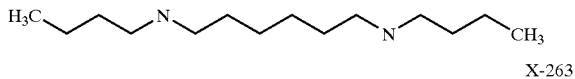
X-262 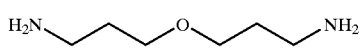
X-263 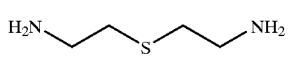
X-264 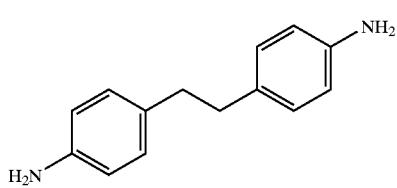
X-265

-continued
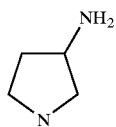
X-266
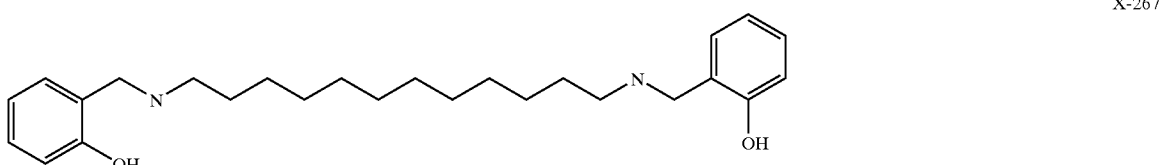
X-267
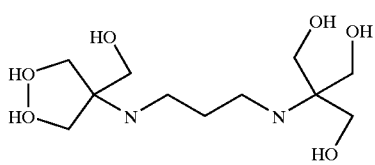
X-268
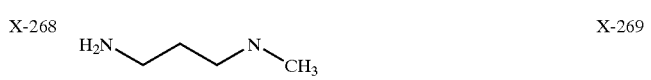
X-269
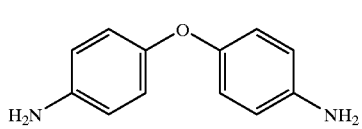
X-270
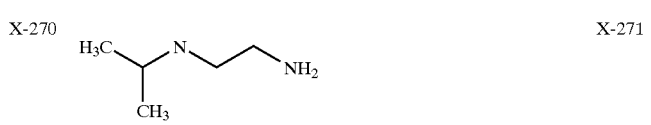
X-271
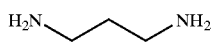
X-272
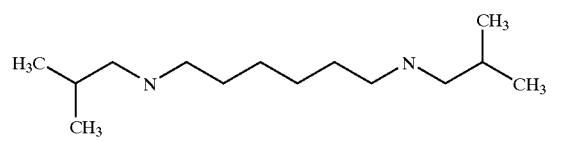
X-273
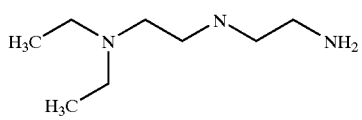
X-274
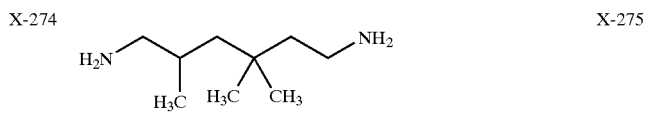
X-275
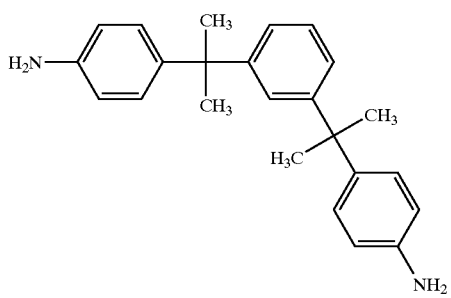
X-276
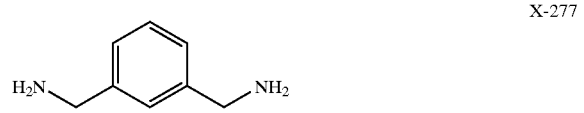
X-277
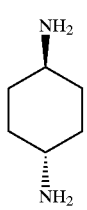
X-278
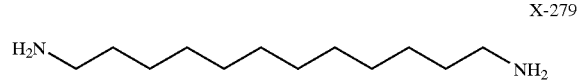
X-279
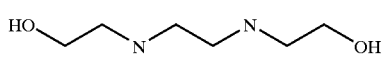
X-280
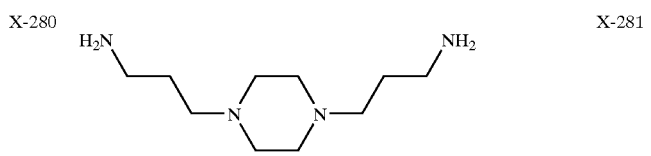
X-281

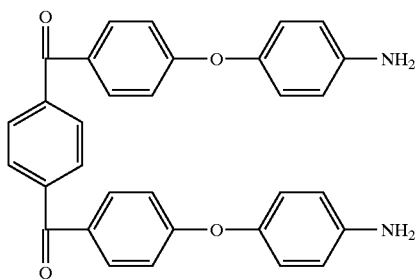
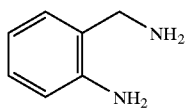
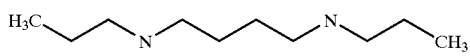
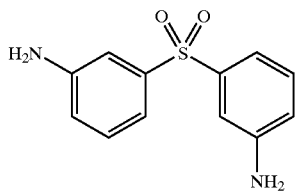
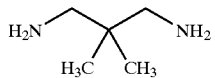
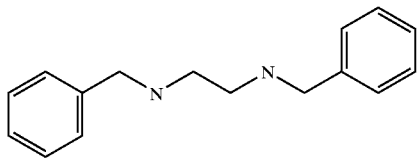
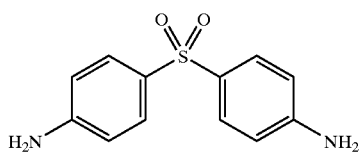
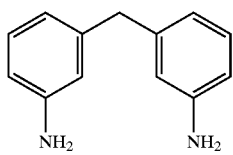
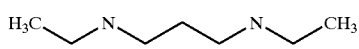
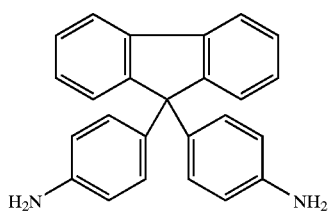
X-282
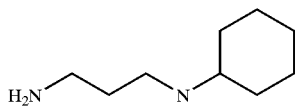
X-283
X-284
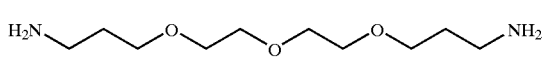
X-285
X-286  X-287
X-288 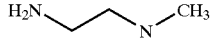 X-289
X-290
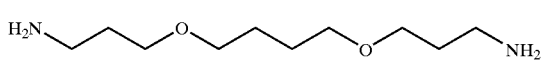
X-291
X-292  X-293
X-294
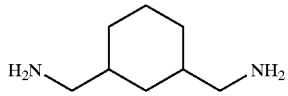
X-295
X-296
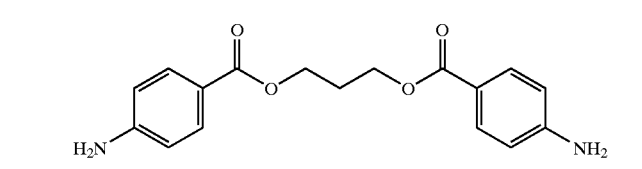
X-297
X-298  X-299
X-300 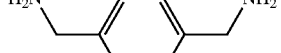 X-301

-continued
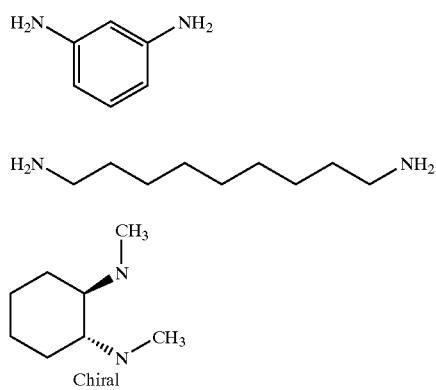
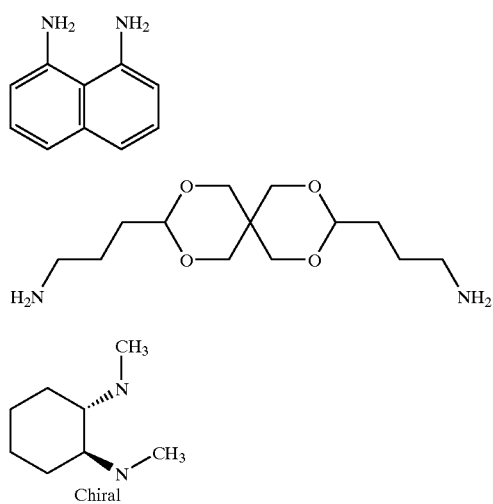
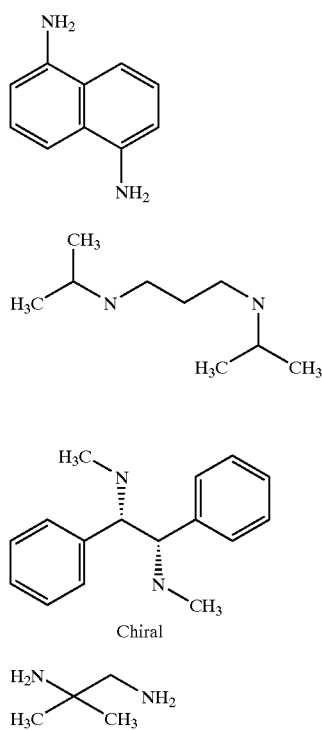

-continued
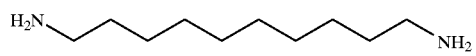
X-322
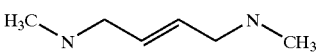
X-323
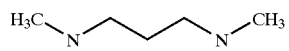
X-324
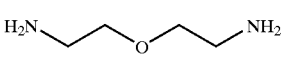
X-325
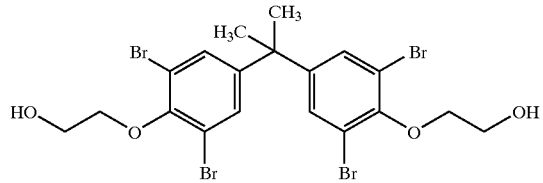
X-326
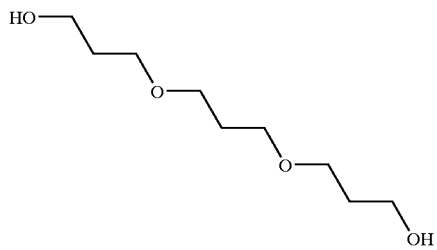
X-327
Diols
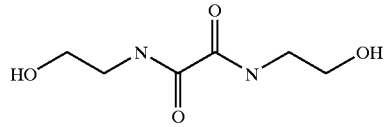
X-328
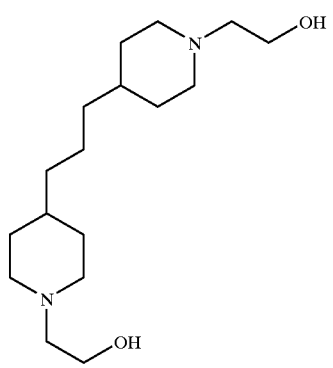
X-329
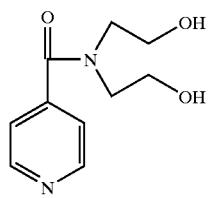
X-330
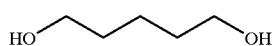
X-331
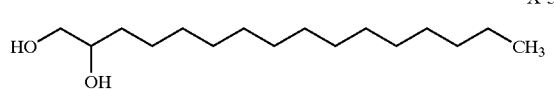
X-332
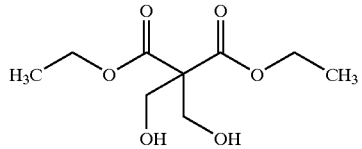
X-333
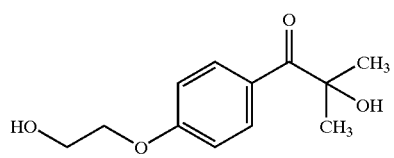
X-334
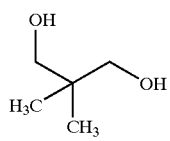
X-335
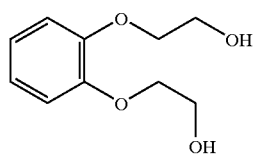
X-336
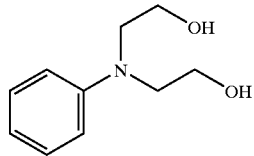
X-337
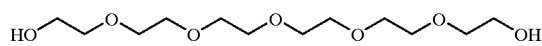
X-338
X-339
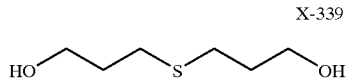

-continued
X-340 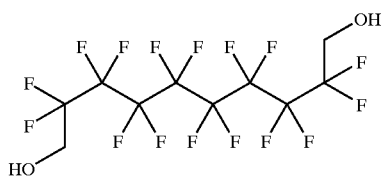
X-341 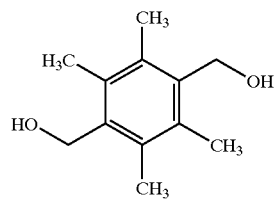
X-342 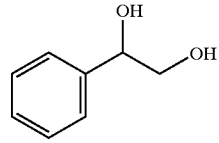
X-343 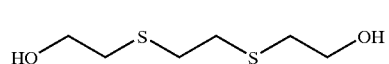
X-344 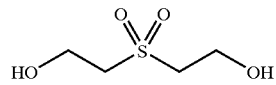
X-345 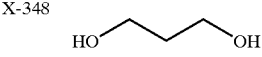
X-346 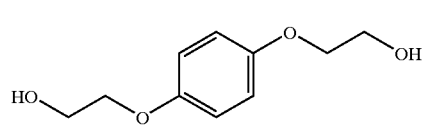
X-347 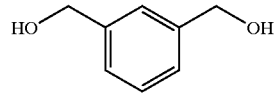
X-348 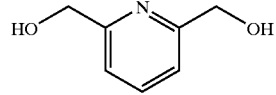
X-349 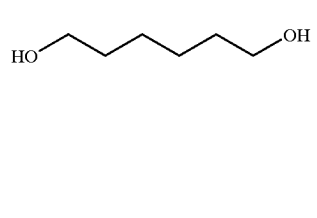
X-350 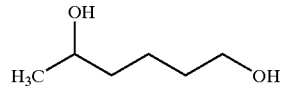
X-351 
X-352 
X-353 
X-354 
X-355 
X-356 
X-357 
X-358 
X-359

-continued
| | |
|---|---|
| X-360 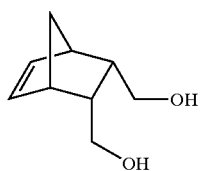 | X-361 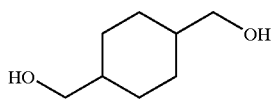 |
| X-362  | X-363 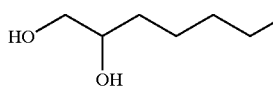 |
| X-364 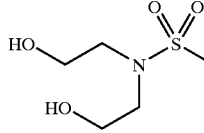 | X-365 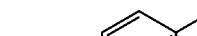 |
| X-366  | X-367 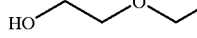 |
| X-368  | X-369  |
| X-370  | X-371 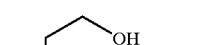 |
| X-372  | X-373 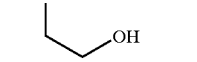 |
| X-374  | X-375 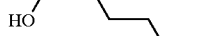 |
| X-376  | X-377 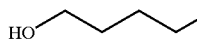 |

-continued
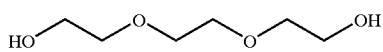
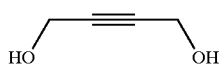
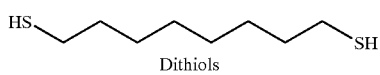
Dithiols
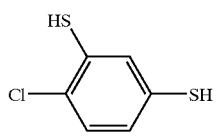
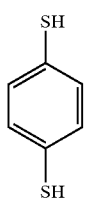
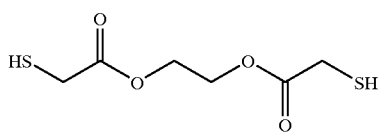
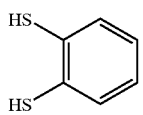
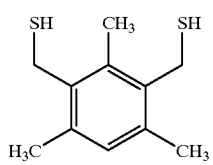
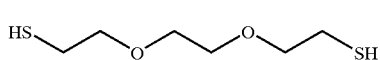
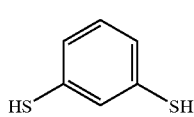
X-378  X-379
X-380 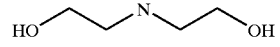 X-381
X-382 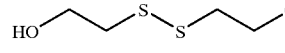 X-383
X-384  X-385
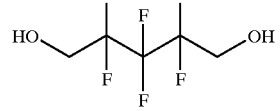
X-386 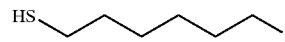 X-387
X-388 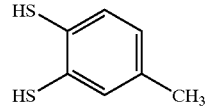 X-389
X-390  X-391
X-392 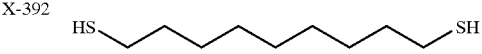 X-393
X-394 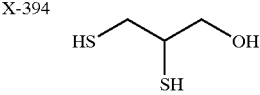 X-395
X-396 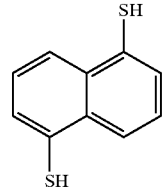 X-397
X-398 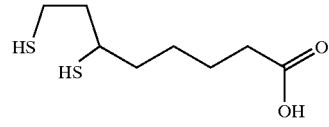 X-399
X-400 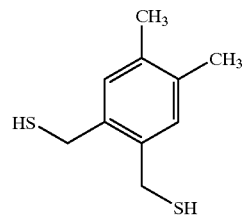 X-401

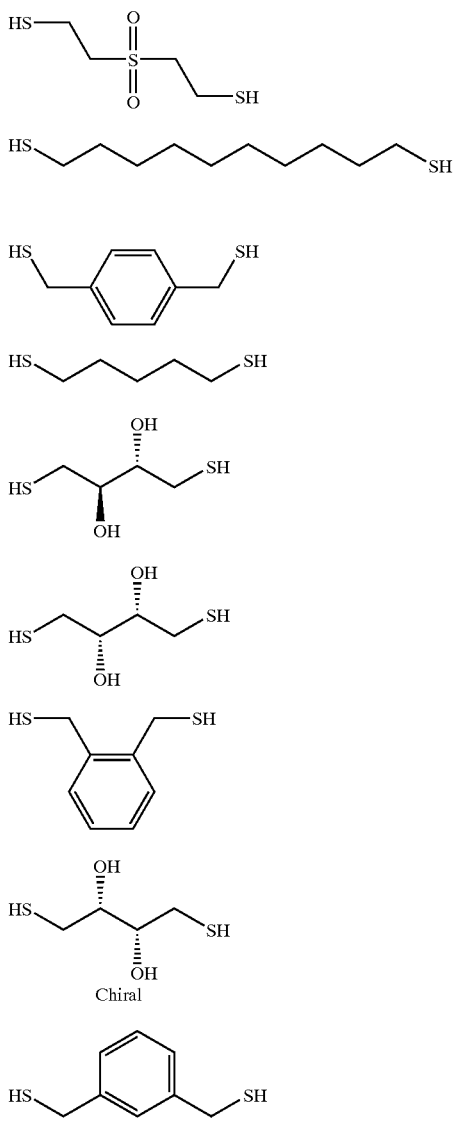

Representative ligands for use in this invention include, by way of example, L-1 through L-21, wherein L-1=verapamil, L-2=diltiazem, L-3=benziazem, L-4=clentiazem, L-5=nicardipine, L-6=nifedipine, L-7=nilvadipine, L-8=nitredipine, L-9=nimodipine, L-10=isradipine, L-11=lacidipine, L-12=amlodipine, L-13 nisoldipine, L-14=isradipine, L-15=mibefrodil, L-16=amlodipine, L-17=felodipine, L-18=nimodipine, L-19-bepridil, L-20=SQ32,910, and L-21-SQ32,248.

Combinations of ligands (L) and linkers (X) per this invention include, by way example only, homo- and heterodimers wherein a first ligand is selected from L-1 through L-21 above and the second ligand and linker is selected from the following:

| L-1/X-1- | L-1/X-2- | L-1/X-3- | L-1/X-4- | L-1/X-5- | L-1/X-6- |
|---|---|---|---|---|---|
| L-1/X-7- | L-1/X-8- | L-1/X-9- | L-1/X-10- | L-1/X-11- | L-1/X-12- |
| L-1/X-13- | L-1/X-14- | L-1/X-15- | L-1/X-16- | L-1/X-17- | L-1/X-18- |
| L-1/X-19- | L-1/X-20- | L-1/X-21- | L-1/X-22- | L-1/X-23- | L-1/X-24- |
| L-1/X-25- | L-1/X-26- | L-1/X-27- | L-1/X-28- | L-1/X-29- | L-1/X-30- |
| L-1/X-31- | L-1/X-32- | L-1/X-33- | L-1/X-34- | L-1/X-35- | L-1/X-36- |
| L-1/X-37- | L-1/X-38- | L-1/X-39- | L-1/X-40- | L-1/X-41- | L-1/X-42- |
| L-1/X-43- | L-1/X-44- | L-1/X-45- | L-1/X-46- | L-1/X-47- | L-1/X-48- |
| L-1/X-49- | L-1/X-50- | L-1/X-51- | L-1/X-52- | L-1/X-53- | L-1/X-54- |
| L-1/X-55- | L-1/X-56- | L-1/X-57- | L-1/X-58- | L-1/X-59- | L-1/X-60- |
| L-1/X-61- | L-1/X-62- | L-1/X-63- | L-1/X-64- | L-1/X-65- | L-1/X-66- |
| L-1/X-67- | L-1/X-68- | L-1/X-69- | L-1/X-70- | L-1/X-71- | L-1/X-72- |

-continued

| | | | | | |
|---|---|---|---|---|---|
| L-1/X-73- | L-1/X-74- | L-1/X-75- | L-1/X-76- | L-1/X-77- | L-1/X-78- |
| L-1/X-79- | L-1/X-80- | L-1/X-81- | L-1/X-82- | L-1/X-83- | L-1/X-84- |
| L-1/X-85- | L-1/X-86- | L-1/X-87- | L-1/X-88- | L-1/X-89- | L-1/X-90- |
| L-1/X-91- | L-1/X-92- | L-1/X-93- | L-1/X-94- | L-1/X-95- | L-1/X-96- |
| L-1/X-97- | L-1/X-98- | L-1/X-99- | L-1/X-100- | L-1/X-101- | L-1/X-102- |
| L-1/X-103- | L-1/X-104- | L-1/X-105- | L-1/X-106- | L-1/X-107- | L-1/X-108- |
| L-1/X-109- | L-1/X-110- | L-1/X-111- | L-1/X-112- | L-1/X-113- | L-1/X-114- |
| L-1/X-115- | L-1/X-116- | L-1/X-117- | L-1/X-118- | L-1/X-119- | L-1/X-120- |
| L-1/X-121- | L-1/X-122- | L-1/X-123- | L-1/X-124- | L-1/X-125- | L-1/X-126- |
| L-1/X-127- | L-1/X-128- | L-1/X-129- | L-1/X-130- | L-1/X-131- | L-1/X-132- |
| L-1/X-133- | L-1/X-134- | L-1/X-135- | L-1/X-136- | L-1/X-137- | L-1/X-138- |
| L-1/X-139- | L-1/X-140- | L-1/X-141- | L-1/X-142- | L-1/X-143- | L-1/X-144- |
| L-1/X-145- | L-1/X-146- | L-1/X-147- | L-1/X-148- | L-1/X-149- | L-1/X-150- |
| L-1/X-151- | L-1/X-152- | L-1/X-153- | L-1/X-154- | L-1/X-155- | L-1/X-156- |
| L-1/X-157- | L-1/X-158- | L-1/X-159- | L-1/X-160- | L-1/X-161- | L-1/X-162- |
| L-1/X-163- | L-1/X-164- | L-1/X-165- | L-1/X-166- | L-1/X-167- | L-1/X-168- |
| L-1/X-169- | L-1/X-170- | L-1/X-171- | L-1/X-172- | | |
| L-1/X-173- | L-1/X-174- | L-1/X-175- | L-1/X-176- | L-1/X-177- | L-1/X-178- |
| L-1/X-179- | L-1/X-180- | L-1/X-181- | L-1/X-182- | L-1/X-183- | L-1/X-184- |
| L-1/X-185- | L-1/X-186- | L-1/X-187- | L-1/X-188- | L-1/X-189- | L-1/X-190- |
| L-1/X-191- | L-1/X-192- | L-1/X-193- | L-1/X-194- | L-1/X-195- | L-1/X-196- |
| L-1/X-197- | L-1/X-198- | L-1/X-199- | L-1/X-200- | L-1/X-201- | L-1/X-202- |
| L-1/X-203- | L-1/X-204- | L-1/X-205- | L-1/X-206- | L-1/X-207- | L-1/X-208- |
| L-1/X-209- | L-1/X-210- | L-1/X-211- | L-1/X-212- | L-1/X-213- | L-1/X-214- |
| L-1/X-215- | L-1/X-216- | L-1/X-217- | L-1/X-218- | L-1/X-219- | L-1/X-220- |
| L-1/X-221- | L-1/X-222- | L-1/X-223- | L-1/X-224- | L-1/X-225- | L-1/X-226- |
| L-1/X-227- | L-1/X-228- | L-1/X-229- | L-1/X-230- | L-1/X-231- | L-1/X-232- |
| L-1/X-233- | L-1/X-234- | L-1/X-235- | L-1/X-236- | L-1/X-237- | L-1/X-238- |
| L-1/X-239- | L-1/X-240- | L-1/X-241- | L-1/X-242- | L-1/X-243- | L-1/X-244- |
| L-1/X-245- | L-1/X-246- | L-1/X-247- | L-1/X-248- | L-1/X-249- | L-1/X-250- |
| L-1/X-251- | L-1/X-252- | L-1/X-253- | L-1/X-254- | L-1/X-255- | L-1/X-256- |
| L-1/X-257- | L-1/X-258- | L-1/X-259- | L-1/X-260- | L-1/X-261- | L-1/X-262- |
| L-1/X-263- | L-1/X-264- | L-1/X-265- | L-1/X-266- | L-1/X-267- | L-1/X-268- |
| L-1/X-269- | L-1/X-270- | L-1/X-271- | L-1/X-272- | L-1/X-273- | L-1/X-274- |
| L-1/X-275- | L-1/X-276- | L-1/X-277- | L-1/X-278- | L-1/X-279- | L-1/X-280- |
| L-1/X-281- | L-1/X-282- | L-1/X-283- | L-1/X-284- | L-1/X-285- | L-1/X-286- |
| L-1/X-287- | L-1/X-288- | L-1/X-289- | L-1/X-290- | L-1/X-291- | L-1/X-292- |
| L-1/X-293- | L-1/X-294- | L-1/X-295- | L-1/X-296- | L-1/X-297- | L-1/X-298- |
| L-1/X-299- | L-1/X-300- | L-1/X-301- | L-1/X-302- | L-1/X-303- | L-1/X-304- |
| L-1/X-305- | L-1/X-306- | L-1/X-307- | L-1/X-308- | L-1/X-309- | L-1/X-310- |
| L-1/X-311- | L-1/X-312- | L-1/X-313- | L-1/X-314- | L-1/X-315- | L-1/X-316- |
| L-1/X-317- | L-1/X-318- | L-1/X-319- | L-1/X-320- | L-1/X-321- | L-1/X-322- |
| L-1/X-323- | L-1/X-324- | L-1/X-325- | L-1/X-326- | L-1/X-327- | L-1/X-328- |
| L-1/X-329- | L-1/X-330- | L-1/X-331- | L-1/X-332- | L-1/X-333- | L-1/X-334- |
| L-1/X-335- | L-1/X-336- | L-1/X-337- | L-1/X-338- | L-1/X-339- | L-1/X-340- |
| L-1/X-341- | L-1/X-342- | L-1/X-343- | L-1/X-344- | L-1/X-345- | L-1/X-346- |
| L-1/X-347- | L-1/X-348- | L-1/X-349- | L-1/X-350- | L-1/X-351- | L-1/X-352- |
| L-1/X-353- | L-1/X-354- | L-1/X-355- | L-1/X-356- | L-1/X-357- | L-1/X-358- |
| L-1/X-359- | L-1/X-360- | L-1/X-361- | L-1/X-362- | L-1/X-363- | L-1/X-364- |
| L-1/X-365- | L-1/X-366- | L-1/X-367- | L-1/X-368- | L-1/X-369- | L-1/X-370- |
| L-1/X-371- | L-1/X-372- | L-1/X-373- | L-1/X-374- | L-1/X-375- | L-1/X-376- |
| L-1/X-377- | L-1/X-378- | L-1/X-379- | L-1/X-380- | L-1/X-381- | L-1/X-382- |
| L-1/X-383- | L-1/X-384- | L-1/X-385- | L-1/X-386- | L-1/X-387- | L-1/X-388- |
| L-1/X-389- | L-1/X-390- | L-1/X-391- | L-1/X-392- | L-1/X-393- | L-1/X-394- |
| L-1/X-395- | L-1/X-396- | L-1/X-397- | L-1/X-398- | L-1/X-399- | L-1/X-400- |
| L-1/X-401- | L-1/X-402- | L-1/X-403- | L-1/X-404- | L-1/X-405- | L-1/X-406- |
| L-1/X-407- | L-1/X-408- | L-1/X-409- | L-1/X-410- | L-1/X-411- | L-1/X-412- |
| L-1/X-413- | L-1/X-414- | L-1/X-415- | L-1/X-416- | L-1/X-417- | L-1/X-418- |
| L-2/X-1- | L-2/X-2- | L-2/X-3- | L-2/X-4- | L-2/X-5- | L-2/X-6- |
| L-2/X-7- | L-2/X-8- | L-2/X-9- | L-2/X-10- | L-2/X-11- | L-2/X-12- |
| L-2/X-13- | L-2/X-14- | L-2/X-15- | L-2/X-16- | L-2/X-17- | L-2/X-18- |
| L-2/X-19- | L-2/X-20- | L-2/X-21- | L-2/X-22- | L-2/X-23- | L-2/X-24- |
| L-2/X-25- | L-2/X-26- | L-2/X-27- | L-2/X-28- | L-2/X-29- | L-2/X-30- |
| L-2/X-31- | L-2/X-32- | L-2/X-33- | L-2/X-34- | L-2/X-35- | L-2/X-36- |
| L-2/X-37- | L-2/X-38- | L-2/X-39- | L-2/X-40- | L-2/X-41- | L-2/X-42- |
| L-2/X-43- | L-2/X-44- | L-2/X-45- | L-2/X-46- | L-2/X-47- | L-2/X-48- |
| L-2/X-49- | L-2/X-50- | L-2/X-51- | L-2/X-52- | L-2/X-53- | L-2/X-54- |
| L-2/X-55- | L-2/X-56- | L-2/X-57- | L-2/X-58- | L-2/X-59- | L-2/X-60- |
| L-2/X-61- | L-2/X-62- | L-2/X-63- | L-2/X-64- | L-2/X-65- | L-2/X-66- |
| L-2/X-67- | L-2/X-68- | L-2/X-69- | L-2/X-70- | L-2/X-71- | L-2/X-72- |
| L-2/X-73- | L-2/X-74- | L-2/X-75- | L-2/X-76- | L-2/X-77- | L-2/X-78- |
| L-2/X-79- | L-2/X-80- | L-2/X-81- | L-2/X-82- | L-2/X-83- | L-2/X-84- |
| L-2/X-85- | L-2/X-86- | L-2/X-87- | L-2/X-88- | L-2/X-89- | L-2/X-90- |
| L-2/X-91- | L-2/X-92- | L-2/X-93- | L-2/X-94- | L-2/X-95- | L-2/X-96- |
| L-2/X-97- | L-2/X-98- | L-2/X-99- | L-2/X-100- | L-2/X-101- | L-2/X-102- |
| L-2/X-103- | L-2/X-104- | L-2/X-105- | L-2/X-106- | L-2/X-107- | L-2/X-108- |
| L-2/X-109- | L-2/X-110- | L-2/X-111- | L-2/X-112- | L-2/X-113- | L-2/X-114- |
| L-2/X-115- | L-2/X-116- | L-2/X-117- | L-2/X-118- | L-2/X-119- | L-2/X-120- |
| L-2/X-121- | L-2/X-122- | L-2/X-123- | L-2/X-124- | L-2/X-125- | L-2/X-126- |

-continued

| | | | | | |
|---|---|---|---|---|---|
| L-2/X-127- | L-2/X-128- | L-2/X-129- | L-2/X-130- | L-2/X-131- | L-2/X-132- |
| L-2/X-133- | L-2/X-134- | L-2/X-135- | L-2/X-136- | L-2/X-137- | L-2/X-138- |
| L-2/X-139- | L-2/X-140- | L-2/X-141- | L-2/X-142- | L-2/X-143- | L-2/X-144- |
| L-2/X-145- | L-2/X-146- | L-2/X-147- | L-2/X-148- | L-2/X-149- | L-2/X-150- |
| L-2/X-151- | L-2/X-152- | L-2/X-153- | L-2/X-154- | L-2/X-155- | L-2/X-156- |
| L-2/X-157- | L-2/X-158- | L-2/X-159- | L-2/X-160- | L-2/X-161- | L-2/X-162- |
| L-2/X-163- | L-2/X-164- | L-2/X-165- | L-2/X-166- | L-2/X-167- | L-2/X-168- |
| L-2/X-169- | L-2/X-170- | L-2/X-171- | L-2/X-172- | | |
| L-2/X-173- | L-2/X-174- | L-2/X-175- | L-2/X-176- | L-2/X-177- | L-2/X-178- |
| L-2/X-179- | L-2/X-180- | L-2/X-181- | L-2/X-182- | L-2/X-183- | L-2/X-184- |
| L-2/X-185- | L-2/X-186- | L-2/X-187- | L-2/X-188- | L-2/X-189- | L-2/X-190- |
| L-2/X-191- | L-2/X-192- | L-2/X-193- | L-2/X-194- | L-2/X-195- | L-2/X-196- |
| L-2/X-197- | L-2/X-198- | L-2/X-199- | L-2/X-200- | L-2/X-201- | L-2/X-202- |
| L-2/X-203- | L-2/X-204- | L-2/X-205- | L-2/X-206- | L-2/X-207- | L-2/X-208- |
| L-2/X-209- | L-2/X-210- | L-2/X-211- | L-2/X-212- | L-2/X-213- | L-2/X-214- |
| L-2/X-215- | L-2/X-216- | L-2/X-217- | L-2/X-218- | L-2/X-219- | L-2/X-220- |
| L-2/X-221- | L-2/X-222- | L-2/X-223- | L-2/X-224- | L-2/X-225- | L-2/X-226- |
| L-2/X-227- | L-2/X-228- | L-2/X-229- | L-2/X-230- | L-2/X-231- | L-2/X-232- |
| L-2/X-233- | L-2/X-234- | L-2/X-235- | L-2/X-236- | L-2/X-237- | L-2/X-238- |
| L-2/X-239- | L-2/X-240- | L-2/X-241- | L-2/X-242- | L-2/X-243- | L-2/X-244- |
| L-2/X-245- | L-2/X-246- | L-2/X-247- | L-2/X-248- | L-2/X-249- | L-2/X-250- |
| L-2/X-251- | L-2/X-252- | L-2/X-253- | L-2/X-254- | L-2/X-255- | L-2/X-256- |
| L-2/X-257- | L-2/X-258- | L-2/X-259- | L-2/X-260- | L-2/X-261- | L-2/X-262- |
| L-2/X-263- | L-2/X-264- | L-2/X-265- | L-2/X-266- | L-2/X-267- | L-2/X-268- |
| L-2/X-269- | L-2/X-270- | L-2/X-271- | L-2/X-272- | L-2/X-273- | L-2/X-274- |
| L-2/X-275- | L-2/X-276- | L-2/X-277- | L-2/X-278- | L-2/X-279- | L-2/X-280- |
| L-2/X-281- | L-2/X-282- | L-2/X-283- | L-2/X-284- | L-2/X-285- | L-2/X-286- |
| L-2/X-287- | L-2/X-288- | L-2/X-289- | L-2/X-290- | L-2/X-291- | L-2/X-292- |
| L-2/X-293- | L-2/X-294- | L-2/X-295- | L-2/X-296- | L-2/X-297- | L-2/X-298- |
| L-2/X-299- | L-2/X-300- | L-2/X-301- | L-2/X-302- | L-2/X-303- | L-2/X-304- |
| L-2/X-305- | L-2/X-306- | L-2/X-307- | L-2/X-308- | L-2/X-309- | L-2/X-310- |
| L-2/X-311- | L-2/X-312- | L-2/X-313- | L-2/X-314- | L-2/X-315- | L-2/X-316- |
| L-2/X-317- | L-2/X-318- | L-2/X-319- | L-2/X-320- | L-2/X-321- | L-2/X-322- |
| L-2/X-323- | L-2/X-324- | L-2/X-325- | L-2/X-326- | L-2/X-327- | L-2/X-328- |
| L-2/X-329- | L-2/X-330- | L-2/X-331- | L-2/X-332- | L-2/X-333- | L-2/X-334- |
| L-2/X-335- | L-2/X-336- | L-2/X-337- | L-2/X-338- | L-2/X-339- | L-2/X-340- |
| L-2/X-341- | L-2/X-342- | L-2/X-343- | L-2/X-344- | L-2/X-345- | L-2/X-346- |
| L-2/X-347- | L-2/X-348- | L-2/X-349- | L-2/X-350- | L-2/X-351- | L-2/X-352- |
| L-2/X-353- | L-2/X-354- | L-2/X-355- | L-2/X-356- | L-2/X-357- | L-2/X-358- |
| L-2/X-359- | L-2/X-360- | L-2/X-361- | L-2/X-362- | L-2/X-363- | L-2/X-364- |
| L-2/X-365- | L-2/X-366- | L-2/X-367- | L-2/X-368- | L-2/X-369- | L-2/X-370- |
| L-2/X-371- | L-2/X-372- | L-2/X-373- | L-2/X-374- | L-2/X-375- | L-2/X-376- |
| L-2/X-377- | L-2/X-378- | L-2/X-379- | L-2/X-380- | L-2/X-381- | L-2/X-382- |
| L-2/X-383- | L-2/X-384- | L-2/X-385- | L-2/X-386- | L-2/X-387- | L-2/X-388- |
| L-2/X-389- | L-2/X-390- | L-2/X-391- | L-2/X-392- | L-2/X-393- | L-2/X-394- |
| L-2/X-395- | L-2/X-396- | L-2/X-397- | L-2/X-398- | L-2/X-399- | L-2/X-400- |
| L-2/X-401- | L-2/X-402- | L-2/X-403- | L-2/X-404- | L-2/X-405- | L-2/X-406- |
| L-2/X-407- | L-2/X-408- | L-2/X-409- | L-2/X-410- | L-2/X-411- | L-2/X-412- |
| L-2/X-413- | L-2/X-414- | L-2/X-415- | L-2/X-416- | L-2/X-417- | L-2/X-418- | and so on.

and so on.

Utility and Testing

The multibinding compounds of this invention can be used to modulate calcium channels in various tissues including heart, muscle, and neurons. They will typically be used for the treatment of diseases and conditions in mammals that involve or are mediated by $Ca^{++}$ channels, such as hypertension, cardiac arrythmias, angina pectoris, cerebral ischemia, congestive heart failure, migraine, Raynaud's disease, asthma and bronchospasm, renal impairment and acute renal failure due to prolonged renal ischemia, retinal ischemia, and pain.

The multibinding compounds of this invention are tested in well-known and reliable assays and their activities are compared with those of the corresponding unlinked (i.e., monovalent) ligands.

Binding affinity to calcium channels: The binding affinity is determined by a radioligand competitive displacement assay, essentially as described in Eltze et al, *Chirality* 2: 233–240 (1990). The ability of the present compounds to displace (+)-[$^3$H] isradipine or a similar radioactive ligand from calcium binding sites of guinea pig skeletal muscle T-tubule membranes is measured in vitro. The binding affinity, calculated from competition curves, is compared with that of the monovalent ligand and/or monovalent linker-ligand conjugate.

$Ca^{++}$ channel activity: The effects of compounds of this invention on channel activity are determined by measurement of whole-cell $Ba^{++}$ currents in voltage-clamped Xenopus oocytes that express various types of voltage-gated $Ca^{++}$ channels, as described in *Bezprozvanny and Tsien, Molec. Pharmacol.* 48: 540–549 (1995).

Antivasoconstrictor activity: Antivasoconstrictor activity is determined as described in Brittain et al, *Physiologist* 28: 325 (1985) as the concentration of a compound required to produce 50% vasorelaxation in KCl-contracted rabbit thoracic aorta strips in the presence of calcium. Alternatively, the concentration of a compound required to inhibit coronary vasoconstriction induced by a thromboxane mimetic (U-46619, i.e., 9,11-methanoepoxy-PGH$_2$) in guinea pig Langendorff heart preparation is measured as described in Eltze et al, *Chirality* 2: 233–240 (1990).

Antihypertensive activity: Antihypertensive activity is determined in male spontaneously hypertensive rats by measurement of mean arterial blood pressure (Rovnyak et al, *J. Med. Chem.* 35: 3254–3263 (1992)).

Tissue selectivity: Selectivity for vascular smooth muscle as compared with cardiac muscle can be assessed by comparing the concentration of a multibinding compound that produces a 50% increase in coronary blood flow in an isolated guinea-pig heart with that required to inhibit myocardial contractility. See, e.g., Osterrieder, W and Holck, M., *J. Cardiovasc. Pharmacol.* 13: 754–9 (1989; and Cremers et al, *J. Cardiovasc. Pharmacol.* 29: 692–696 (1997).

Pharmaceutical Formulations

When employed as pharmaceuticals, the compounds of Formula I are usually administered in the form of pharmaceutical compositions. This invention therefore provides pharmaceutical compositions which contain, as the active ingredient, one or more of the compounds of Formula I above or a pharmaceutically acceptable salt thereof and one or more pharmaceutically acceptable excipients, carriers, diluents, permeation enhancers, solubilizers and adjuvants. The compounds may be administered alone or in combination with other therapeutic agents (e.g., other antihypertensive drugs, diuretics and the like). Such compositions are prepared in a manner well known in the pharmaceutical art (see, e.g., *Remington's Pharmaceutical Sciences*, Mace Publishing Co., Philadelphia, Pa. 17$^{th}$ Ed. (1985) and *"Modem Pharmaceutics"*, Marcel Dekker, Inc. 3$^{rd}$ Ed. (G. S. Banker & C. T. Rhodes, Eds.).

The compounds of Formula I may be administered by any of the accepted modes of administration of agents having similar utilities, for example, by oral, parenteral, rectal, buccal, intranasal or transdermal routes. The most suitable route will depend on the nature and severity of the condition being treated. Oral administration is a preferred route for the compounds of this invention. In making the compositions of this invention, the active ingredient is usually diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. Pharmaceutically acceptable salts of the active agents may be prepared using standard procedures known to those skilled in the art of synthetic organic chemistry and described, e.g., by J. March, *Advanced Organic Chemistry: Reactions, Mechanisms and Structure*, 4$^{th}$ Ed. (New York: Wiley-Interscience, 1992).

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents.

The compositions of the invention can be formulated so as to provide quick, sustained or delayed release of the active ingredient after administration to the patient by employing procedures known in the art. Controlled release drug delivery systems for oral administration include osmotic pump systems and dissolutional systems containing polymer-coated reservoirs or drug-polymer matrix formulations. Examples of controlled release systems are given in U.S. Pat. Nos. 3,845,770; 4,326,525; 4,902514; and 5,616,345. Another preferred formulation for use in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. Nos. 5,023,252, 4,992,445 and 5,001,139. Such patches may be constructed for continuous, pulsatile, or on demand delivery of pharmaceutical agents.

The compositions are preferably formulated in a unit dosage form. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient (e.g., a tablet, capsule, ampoule). The active compound is effective over a wide dosage range and is generally administered in a pharmaceutically effective amount. Preferably, for oral administration, each dosage unit contains from 1–250 mg of a compound of Formula I, and for parenteral administration, preferably from 0.1 to 60 mg of a compound of Formula I or a pharmaceutically acceptable salt thereof. It will be understood, however, that the amount of the compound actually administered will be determined by a physician, in the light of the relevant circumstances, including the condition to be treated, the chosen route of administration, the actual compound administered and its relative activity, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions, suitably flavored syrups, aqueous or oil suspensions, and flavored emulsions with edible oils such as corn oil, cottonseed oil, sesame oil, coconut oil, or peanut oil, as well as elixirs and similar pharmaceutical vehicles.

Compositions for inhalation or insulation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be inhaled directly from the nebulizing device or the nebulizing device may be attached to a face mask tent, or intermittent positive pressure breathing machine. Solution, suspension, or powder compositions may be administered, preferably orally or nasally, from devices which deliver the formulation in an appropriate manner.

The following formulation examples illustrate representative pharmaceutical compositions of the present invention.

FORMULATION EXAMPLE 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
| --- | --- |
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
| --- | --- |
| Active Ingredient | 5 |
| Lactose | 95 |

The active ingredient is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
| --- | --- |
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
| --- | --- |
| Active Ingredient | 40.0 mg |
| Starch | 109.0 mg |
| Magnesium stearate | 1.0 mg |
| Total | 150.0 mg |

The active ingredient, starch, and magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
| --- | --- |
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) | |
| Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, starch, and magnesium stearate are blended, passed through a No. 20 mesh U.S. sieve, and filled into hard gelatin capsules in 425.0 mg quantities.

FORMULATION EXAMPLE 9

A subcutaneous formulation may be prepared as follows:

| Ingredient | Quantity |
|---|---|
| Active Ingredient | 5.0 mg |
| Corn Oil | 1.0 mL |

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

SYNTHETIC EXAMPLES

Example 1

(See FIG. 4)

Preparation of a Formula I compound wherein p is 2, q is 1, and the ligand, L, is the amlodipine moiety linked via the side chain amine to the linker, X.

Method A

Step 1

A solution of N-BOC-amlodipine [structure 9, where PG is t-butyloxycarbonyl (BOC); $R^6$ and $R^8$ are methyl; $R^7$ is ethyl; $R^9$ is 2-Cl; and $R^{10}$ is H] (2 mmol), the linker molecule 1,6-dibromohexane (1 mmol), and diisopropylethylamine (0.2 mL) in DMF (3 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound is obtained by purification of the crude product by use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 11, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-amlodipine in the above example with other ligands of structure 9 and/or by replacing 1,6-dibromohexane with other linker molecules, other compounds of Formula I are prepared.

Method B

A solution of amlodipine [structure 9, where PG is H; $R^6$ and $R^8$ are methyl; $R^7$ is ethyl; $R^9$ is 2-Cl; and $R^{10}$ is H] (2 mmol), the linker molecule 1,6-dibromohexane (1 mmol), and diisopropylethylamine (0.2 mL) in DMF (3 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound of Formula I (structure 11, where $R^6$ and $R^8$ are methyl; $R^7$ is ethyl; $R^9$ is 2-Cl; and $R^{10}$ is H) is obtained by purification of the crude product by use of HPLC.

In similar manner, by replacing amlodipine in the above example with other ligands of structure 9 and/or by replacing 1,6-dibromohexane with other linker molecules, other compounds of Formula I are prepared.

Example 2

See FIG. 4

Preparation of a Formula I compound wherein p is 2, q is 1, and the ligand, L, is the amlodipine moiety linked via the side chain amine to the linker, X, through an amide bond Method A
Step 1

A solution of N-BOC-amlodipine [structure 9, where PG is t-butyloxycarbonyl (BOC); $R^6$ and $R^8$ are methyl; $R^7$ is ethyl; $R^9$ is 2-Cl; and $R^{10}$ is H] (2 mmol), the linker molecule 3,6-dioxaoctanedioic acid (1 mmol) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 14, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-amlodipine in the above example with other ligands of structure 9 and/or by replacing 3,6-dioxaoctanedioic acid with other linker molecules, other compounds of Formula I are prepared.

Method B

A solution of amlodipine [structure 9, where PG is H; $R^6$ and $R^8$ are methyl; $R^7$ is ethyl; $R^9$ is 2-Cl; and $R^{10}$ is H] (2 mmol), the linker molecule 3,6-dioxaoctanedioic acid (1 mmol) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound (structure 14, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing amlodipine in the above example with other ligands of structure 9 and/or by replacing 3,6-dioxaoctanedioic acid with other linker molecules, other compounds of Formula I are prepared.

Example 3

See FIG. 4

Preparation of a Formula I compound wherein p is 2, q is 1, and the ligand, L, is the amlodipine moiety linked via the side chain amine to the linker, X, through a urea bond Method A
Step 1

A solution of the linker molecule 1,4-diisocyanatobutane (1 mmol) in $CH_2Cl_2$ (5 mL) containing $Et_3N$ (0.2 mL) is stirred and cooled in an ice-water bath under an inert atmosphere. To this is added dropwise a solution of N-BOC-amlodipine [structure 9, where PG is t-butyloxycarbonyl (BOC); $R^6$ and $R^8$ are methyl; $R^7$ is ethyl; $R^9$ is 2-Cl; and $R^{10}$ is H] (2 mmol) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 16, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-amlodipine in the above example with other ligands of structure 9 and/or by replacing 1,4-diisocyanatobutane with other linker molecules, other compounds of Formula I are prepared.

Method B

A solution of the linker molecule 1,4-diisocyanatobutane (1 mmol) in $CH_2Cl_2$ (5 mL) containing $Et_3N$ (0.2 mL) is stirred and cooled in an ice-water bath under an inert atmosphere. To this is added dropwise a solution of amlodipine [structure 9, where PG is H; $R^6$ and $R^8$ are methyl; $R^7$ is ethyl; $R^9$ is 2-Cl; and $R^{10}$ is H] (2 mmol) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired Formula I compound (structure 16, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing amlodipine in the above example with other ligands of structure 9 and/or by replacing 1,4-diisocyanatobutane with other linker molecules, other compounds of Formula I are prepared.

Example 4

See FIG. 4

Preparation of a Formula I compound wherein p is 2, q is 1, and the ligand, L, is the amlodipine moiety linked via the side chain amine to the linker, X, through a sulfonamide bond.

Method A
Step 1

A solution of the linker molecule benzene-1,4-bis-sulfonyl chloride (1 mmol) in $CH_2Cl_2$ (5 mL) containing $Et_3N$ (0.2 mL) is stirred and cooled in an ice-water bath under an inert atmosphere. To this is added dropwise a solution of N-BOC-amlodipine [structure 9, where PG is t-butyloxycarbonyl (BOC); $R^6$ and $R^8$ are methyl; $R^7$ is ethyl; $R^9$ is 2-Cl; and $R^{10}$ is H] (2 mmol) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 18, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-amlodipine in the above example with other ligands of structure 9 and/or by replacing benzene-1,4-bissulfonyl chloride with other linker molecules, other compounds of Formula I are prepared.

Method B

A solution of the linker molecule benzene-1,4-bissulfonyl chloride (1 mmol) in $CH_2Cl_2$ (5 mL) containing $Et_3N$ (0.2 mL) is stirred and cooled in an ice-water bath under an inert atmosphere. To this is added dropwise a solution of amlodipine [structure 9, where PG is H; $R^6$ and $R^8$ are methyl; $R^7$ is ethyl; $R^9$ is 2-Cl; and $R^{10}$ is H] (2 mmol) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired Formula I compound (structure 18, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing amlodipine in the above example with other ligands of structure 9 and/or by replacing benzene-1,4-bissulfonyl chloride with other linker molecules, other compounds of Formula I are prepared.

Example 5

See FIG. 5

Preparation of a Formula I compound wherein p is 2, q is 1, and the ligand, L, is the 1,4-dihydropyridine moiety linked via the 2-hydroxymethyl group to the linker, X, through an ether bond.

Method A

Step 1

To a mixture of sodium hydride (3.1 mmol) and dry THF (2 mL) stirred under an inert atmosphere and protected from the atmosphere with a drying tube is added a solution of the linker molecule 1,4-dihydroxymethylbenzene (1 mmol) in dry THF (2 mL). To this is added a solution of N-BOC-1,4-dihydropyridine [structure 25, where PG is t-butyloxycarbonyl (BOC); $R^6$ and $R^8$ are methyl; $R^7$ is ethyl; $R^9$ is 2-Cl; and $R^{10}$ is H] (2 mmol) in dry THF (2 mL). A solution of is added and the resulting mixture is stirred at RT. The progress of the reaction is followed by Uc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound is obtained by purification of the crude product by use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 22, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-1,4-dihydropyridine in the above example with other ligands of structure 21 and/or by replacing 1,4-dihydroxymethylbenzene-with other linker molecules, other compounds of Formula I are prepared.

Method B

Step 1

To a mixture of sodium hydride (3.1 mmol) and dry THF (2 mL) stirred under an inert atmosphere and protected from the atmosphere with a drying tube is added a solution of the linker molecule 1,4-dihydroxymethylbenzene (1 mmol) in dry THF (2 mL). To this is added a solution of 1,4-dihydropyridine [structure 25, where PG is H; $R^6$ and $R^8$ are methyl; $R^7$ is ethyl; $R^9$ is 2-Cl; and $R^{10}$ is H] (2 mmol) in dry THF (2 mL). A solution of is added and the resulting mixture is stirred at RT. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound of Formula I (structure 22, where $R^6$ and $R^8$ are methyl; $R^7$ is ethyl; $R^9$ is 2-Cl; and $R^{10}$ is H) is obtained by purification of the crude product by use of HPLC.

In similar manner, by replacing 1,4-dihydropyridine in the above example with other ligands of structure 25 and/or by replacing 1,4-dihydroxymethylbenzene with other linker molecules, other compounds of Formula I are prepared.

Example 6

See FIG. 5

Preparation of a Formula I compound wherein p is 2, q is 1, and the ligand, L, is the 1,4-dihydropyridine moiety linked via the 2-hydroxymethyl group to the linker, X, through an ester bond Method A Step 1

A solution of N-BOC-1,4dihydropyridine [structure 21, where PG is t-butyloxycarbonyl (BOC); $R^6$ and $R^8$ are methyl; $R^7$ is ethyl; $R^9$ is 2-Cl; and R is H] (2 mmol), the linker molecule benzene-1,4-bisacetic acid (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 23, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-1,4-dihydropyridine in the above example with other ligands of structure 21 and/or by replacing benzene-1,4-bisacetic acid with other linker molecules, other compounds of Formula I are prepared.

Method B

A solution of 1,4-dihydropyridine [structure 21, where PG is H; $R^6$ and $R^8$ are methyl; $R^7$ is ethyl; $R^9$ is 2-Cl; and $R^{10}$ is H] (2 mmol), the linker molecule benzene-1,4-bisacetic acid (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound of Formula I (structure 23, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing 1,4-dihydropyridine in the above example with other ligands of structure 21 and/or by replacing benzene-1,4-bisacetic acid with other linker molecules, other compounds of Formula I are prepared.

Example 7

See FIG. 5

Preparation of a Formula I compound wherein p is 2, q is 1, and the ligand, L, is the 1,4-dihydropyridine moiety linked via the 2-hydroxymethyl group to the linker, X, through a carbamate bond Method A Step 1

A solution of the linker molecule trans-1,4-cyclohexylisocyanate (1 mmol) in $CH_2Cl_2$ (5 mL) containing $Et_3N$ (0.2 mL) is stirred and cooled in an ice-water bath under an inert atmosphere. To this is added dropwise a solution of N-BOC-1,4dihydropyridine [structure 21, where PG is t-butyloxycarbonyl (BOC); $R^6$ and $R^8$ are methyl; $R^7$ is ethyl; $R^9$ is 2-Cl; and $R^{10}$ is H] (2 mmol) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 24, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing N-BOC-1,4-dihydropyridine in the above example with other ligands of structure 21 and/or by replacing trans-1,4-cyclohexylisocyanate with other linker molecules, other compounds of Formula I are prepared.

Method B

A solution of the linker molecule trans-1,4cyclohexylisocyanate (1 mmol) in $CH_2Cl_2$(5 mL) containing $Et_3N$ (0.2 mL) is stirred and cooled in an ice-water bath under an inert atmosphere. To this is added dropwise a solution of1,4-dihydropyridine [structure 21, where PG is H; $R^6$ and $R^8$ are methyl; $R^7$ is ethyl; $R^9$ is 2-Cl; and $R^{10}$ is H] (2 mmol) in $CH_2Cl_2$ (5 mL). After addition is complete, the cooling bath is removed and the reaction solution is allowed to warm to room temperature. The progress of the reaction is followed by tlc and when reaction has occurred, the reaction solution is quenched in cold 5% aqueous $Na_2CO_3$. The layers are separated and the organic layer is washed with aqueous $Na_2CO_3$, with water and is dried ($Na_2SO_4$), filtered and concentrated under reduced pressure to give the crude product. The desired compound of Formula I (structure 24, where $R^6$ and $R^8$ are methyl; $R^7$ is ethyl; $R^9$ is 2-Cl; and $R^{10}$ is H) is obtained by purification of the crude product with the use of HPLC.

In similar manner, by replacing 1,4-dihydropyridine in the above example with other ligands of structure 21 and/or by replacing trans-1,4-cyclohexylisocyanate with other linker molecules, other compounds of Formula I are prepared.

Example 8

See FIG. 8

Preparation of a Formula I compound wherein p is 2, q is 1, and the ligand, L, is the 1,4-dihydropyridine moiety linked via the 3-carboxyl group to the linker, X, through an ester bond Method A Step 1

A solution of N-BOC-1,4-dihydropyridine (structure 36, where PG is t-butyloxycarbonyl (BOC); $R^2$, $R^6$ and $R^8$ are methyl; $R^9$ is 2-Cl; and $R^{10}$ is H] (2 mmol), the linker molecule 1,4-bis(hydroxymethyl)benzene (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the ms reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 37, where $R^2$, $R^6$ and $R^8$ are methyl; $R^9$ is 2-Cl; and $R^{10}$ is H) is obtained by purification of the crude product with the use of HPLC.

In similar manner, by replacing N-BOC-1,4-dihydropyridine in the above example with other ligands of structure 36 and/or by replacing 1,4-bis(hydroxymethyl)benzene with other linker molecules, other compounds of Formula I are prepared.

Method B

A solution of dihydropyridine (structure 36, where PG is H; $R^2$, $R^6$ and $R^8$ are methyl; $R^9$ is 2-Cl; and $R^{10}$ is H] (2 mmol), the linker molecule 1,4-bis(hydroxymethyl)benzene (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound of Formula I (structure 37, where $R^2$, $R^6$ and $R^8$ are methyl; $R^9$ is 2-Cl; and $R^{10}$ is H) is obtained by purification of the crude product with the use of HPLC.

In similar manner, by replacing 1,4-dihydropyridine in the above example with other ligands of structure 36 and/or by replacing 1,4-bis(hydroxymethyl)benzene with other linker molecules, other compounds of Formula I are prepared.

Example 9

See FIG. 8

Preparation of a Formula I compound wherein p is 2, q is 1, and the ligand, L, is the 1,4-dihydropyridine moiety linked via the 3-carboxyl group to the linker, X, through an amide bond.

Method A

Step 1

A solution of N-BOC-1,4-dihydropyridine (structure 36, where PG is t-butyloxycarbonyl (BOC); $R^2$, $R^6$ and $R^8$ are methyl; $R^9$ is 2-Cl; and $R^{10}$ is H] (2 mmol), the linker molecule 1,5diaminopentane (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by Uc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by Uc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I (structure 37a, where $R^2$, $R^6$ and $R^8$ are methyl; $R^9$ is 2-Cl; and $R^{10}$ is H) is obtained by purification of the crude product with the use of HPLC.

In similar manner, by replacing N-BOC-1,4-dihydropyridine in the above example with other ligands of structure 36 and/or by replacing 1,5-diaminopentane with other linker molecules, other compounds of Formula I are prepared.

Method B

A solution of dihydropyridine (structure 36, where PG is H; $R^2$, $R^6$ and $R^8$ are methyl; $R^9$ is 2-Cl; and $R^{10}$ is H] (2 mmol), the linker molecule 1,5-diaminopentane (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired Formula I compound (structure 37a, where $R^2$, $R^6$ and $R^8$ are methyl; $R^9$ is 2-Cl; and $R^{10}$ is H) is obtained by purification of the crude product with the use of HPLC.

In similar manner, by replacing dihydropyridine in the above example with other ligands of structure 36 and/or by replacing 1,5-diaminopentane with other linker molecules, other compounds of Formula I are prepared.

Example 10

See FIG. 10

Preparation of a Formula I compound wherein p is 2, q is 1, and the ligand, L, is the benzothiazepine moiety linked via the nitrogen of the amide group to the linker, X A mixture of NaH (2.1 mmol) and DMF (1 mL) is prepared under an inert atmosphere in a flask equipped with a stirring bar and a drying tube. To this is added first a solution of benzothiazepine (structure 41, where $R^{12}$ is OAc; $R^{13}$ is Me; and $R^{14}$ is H) (2 mmol) in DMF (5 mL) and then the linker molecule 1,8-dibromooctane (1 mmol). The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound of Formula I (structure 42, where $R^{12}$ is OAc; $R^{13}$ is Me; and $R^{14}$ is H) is obtained by purification of the crude product by use of HPLC.

In similar manner, by replacing the benzothiazepine in the above example with other ligands of structure 41 and/or by replacing 1,8-dibromooctane with other linker molecules, other compounds of Formula I are prepared.

Example 11

See FIG. 10

Preparation of a Formula I compound wherein p is 2, q is 1, and the ligand, L, is the benzothiazepine moiety linked via the 3-hydroxyl group to the linker, X.

Step 1

A solution of the benzothiazepine (structure 43, where PG=Ac; $R^{11}$ is 2-(N,N-dimethylamino)ethyl; $R^{13}$ is methyl; and $R^{14}$ is H) (1 mmol) in methanol (5 mL) is stirred with potassium carbonate. The progress of the reaction is followed by tlc. After reaction occurs, the mixture is filtered to remove solids and the filtrate is concentrated to give the crude product. The desired compound (structure 44) is obtained by purification of the crude product with the use of HPLC.

Step 2

A solution of the linker molecule benzene-1,4-bisacetyl chloride (2 mmol) in methylene chloride is added slowly to a solution of the benzothiazepine [structure 44, where $R^{11}$ is 2-(N,N-dimethylamino)ethyl; $R^{13}$ is methyl; and $R^{14}$ is H] (2 mmols) in methylene chloride (5 mL) and pyridine (0.5 mL) in a flask equipped with a magnetic stirrer and a drying tube and which is cooled in an ice-water bath. The course of the reaction is followed by thin layer chromatography. After reaction occurs, the reaction solution is quenched in water and the aqueous mixture is extracted with ethyl acetate. The organic layer is washed with aqueous $Na_2CO_3$ with water, and is dried ($Na_2SO_4$), filtered and concentrated under reduced pressure to give the crude product. The desired compound of Formula I [structure 45, where $R^{11}$ is 2-(N,N-dimethylamino)ethyl; $R^{13}$ is methyl; and $R^{14}$ is H] is obtained by purification of the crude product by use of HPLC.

In similar manner, by replacing the benzothiazepine in the above example with other ligands of structure 44 and/or by replacing benzene-1,4-bisacetyl chloride with other linker molecules, other compounds of Formula I are prepared.

Example 12

See FIG. 10

Preparation of a Formula I compound wherein p is 2, q is 1, and the ligand, L, is the benzothiazepine moiety linked via the oxygen of the phenolic group to the linker, X Step 1

A solution of the benzothiazepine [structure 77, where $R^{11}$ is 2-(N,N-dimethylamino)ethyl; $R^{12}$ is OAc; and $R^{14}$ is H] (2 mmols) in methylene chloride (5 mL) is stirred and cooled to −78° C. under and inert atmosphere. $BBr_3$ (5 mmol) is added and stirring is continued as the cooling bath is removed and the temperature of the reaction solution is allowed to rise to room temperature. The course of the reaction is followed by thin layer chromatography. After reaction occurs, the reaction solution is diluted with methylene chloride and washed with cold aqueous $Na_2CO_3$ and with half-saturated brine. The organic layer is dried ($Na_2SO_4$), filtered and concentrated under reduced pressure to give the crude product. The desired compound [structure 78, where $R^{11}$ is 2-(N,N-dimethylamino)ethyl; $R^{12}$ is OAc; and $R^{14}$ is H] is obtained by purification of the crude product by use of HPLC.

Step 2

A solution of the benzothiazepine [structure 78, where $R^{11}$ is 2-(N,N-dimethylamino)ethyl; $R^{12}$ is OAc; and $R^{14}$ is H] (2 mmols) and linker molecule 1,4bisiodomethylbenzene (1 mmol) in acetone (5 mL) containing $K_2CO_3$ is stirred and heated at reflux temperature under an inert atmosphere. The course of the reaction is followed by thin layer chromatography. After reaction occurs, the reaction solution is diluted with ethyl acetate and washed with water and with aqueous $Na_2CO_3$. The organic layer is dried ($Na_2SO_4$), filtered and concentrated under reduced pressure to give the crude product. The desired compound of Formula I [structure 79, where $R^{11}$ is 2-(N,N-dimethylamino)ethyl; $R^{12}$ is OAc; and $R^{14}$ is H] is obtained by purification of the crude product by use of HPLC.

In similar manner, by replacing the benzothiazepine in the above example with other ligands of structure 78 and/or by replacing 1,4-bisiodomethylbenzene with other linker molecules, other compounds of Formula I are prepared.

Example 13

See FIG. 11

Preparation of a Formula I compound wherein p is 2, q is 1, and the ligand, L, is the verapamil moiety linked via the nitrogen of the amine group to the linker, X.

A solution of N-desmethyl-verapamil (structure 82) (2 mmol), the linker molecule 1,4-diiodobutane (1 mmol), and diisopropylethylamine (0.2 mL) in DMF (3 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound of Formula I (structure 83) is obtained by purification of the crude product by use of HPLC.

Example 14

See FIG. 11

Preparation of a Formula I compound wherein p is 2, q is 1, and the ligand, L, is the verapamil moiety linked via an oxygen atom to the linker, X.

A solution of the O-desmethyl-verapamil (structure 85) (2 mmols) and linker molecule 1,2-bis-(2-iodoethoxy)ethane (1 mmol) in acetone (5 mL) containing $K_2CO_3$ is stirred and heated at reflux temperature under an inert atmosphere. The course of the reaction is followed by thin layer chromatography. After reaction occurs, the reaction solution is diluted with ethyl acetate and washed with water and with aqueous $Na_2CO_3$. The organic layer is dried ($Na_2SO_4$), filtered and concentrated under reduced pressure to give the crude product. The desired Formula I compound (structure 86) is obtained by purification of the crude product by use of HPLC.

Example 15

See FIG. 16

Preparation of a Formula I compound wherein p is 2, q is 1, and one ligand, $L_1$, is the 1,4-dihydropyridine moiety linked via the 3-carboxyl group to the linker, X, and the second ligand, $L_2$, is the benzothioazepine moiety linked to linker, X, via the hydroxyl function of the phenolic ring.

Method A

Step 1

A solution of the benzothiazepine [structure 78, where $R^{11}$ is 2-(N,N-dimethylamino)ethyl; $R^{12}$ is OAc; and $R^{14}$ is H (see FIG. 13)] (1 mmols) and linker molecule 1-iodomethyl-4-benzyloxybenzene (1 mmol) in acetone (5 mL) containing $K_2CO_3$ is stirred and heated at reflux temperature under an inert atmosphere. The course of the reaction is followed by thin layer chromatography. After reaction occurs, the reaction solution is diluted with ethyl acetate and washed with water and with aqueous $Na_2CO_3$. The organic layer is dried ($Na_2SO_4$), filtered and concentrated under reduced pressure to give the crude product. The desired compound is obtained by purification of the crude product by use of HPLC.

Step 2

Ammonium formate (96 mg, 1.5 mmol) and 10% Pd—C (50 mg) are added to a solution of the compound obtained in the preceding reaction in methanol (3 mL) and THF (2 mL). The mixture is stirred at room temperature and the progress of the reaction is monitored by tlc. After reaction is complete, the mixture is filtered through Celite, the filter pad is rinsed with EtOAc, the combined organic layers are washed successively with aq. $NaHCO_3$ and with half-saturated brine, then filtered and concentrated under reduced pressure to give the crude product. The desired compound [(see FIG. 13 and 16) structure 52, where $R^{11}$ is 2-(N,N-dimethylamino)ethyl; $R^{12}$ is OAc; and $R^{14}$ is H] is obtained by purification of the crude product with the use of HPLC.

Step 3

A solution of N-BOC-1,4-dihydropyridine (structure 36, where PG is t-butyloxycarbonyl (BOC); $R^2$ is 2-(N-BOC-amino)ethoxymethyl; $R^6$ and $R^8$ are methyl; $R^9$ is 2-Cl; and $R^{10}$ is H] (1 mmol), the compound [structure 52, where $R^{11}$ is 2-(N,N-dimethylamino)ethyl; $R^{12}$ is Oac; and $R^{14}$ is H] (1 mmol) obtained in the preceding reaction (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound is obtained by purification of the crude product with the use of HPLC.

Step 4

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I [structure 68, where $R^2$ is (2-amino)ethoxymethyl; $R^6$ and $R^8$ are methyl; $R^9$ is 2-Cl; $R^{10}$ and $R^{14}$ are H; $R^{11}$ is 2-(N,N-dimethylamino)ethyl; and $R^{12}$ is OAc] is obtained by purification of the crude product with the use of HPLC.

In similar manner, by replacing the 1,4dihydropyridine of the above example with other ligands of structure 36 and/or the benzothiazepine in the above example with other ligands of structure 52 and/or by replacing 1-iodomethyl-4-benzyloxybenzene with other linker molecules, other compounds of Formula I are prepared.

Method B

Step 1

A solution of dihydropyridine (structure 36, where PG is H; $R^2$ is 2-(N-BOC-amino)ethoxymethyl; $R^6$ and $R^8$ are methyl; $R^9$ is 2-Cl; and $R^{10}$ is H] (1 mmol), the compound [structure 52, where $R^{11}$ is 2-(N,N-dimethylamino) ethyl; $R^{12}$ is OAc; and $R^{14}$ is H] (1 mmol) obtained in the preceding reaction (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound is obtained by purification of the crude product with the use of HPLC.

Step 2

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired Formula I compound [structure 68, where $R^2$ is (2-amino)ethoxymethyl; $R^6$ and $R^8$ are methyl; $R^9$ is 2-Cl; $R^{10}$ and $R^{14}$ are H; $R^{11}$ is 2-(N,N-dimethylamino)ethyl; and $R^{12}$ is OAc] is obtained by purification of the crude product with the use of HPLC.

Example 16

See FIG. 16

Preparation of a Formula I compound wherein p is 2, q is 1, and one ligand, $L_1$, is the 1,4-dihydropyridine moiety linked via the 2-hydroxymethyl group to the linker, X, and the second ligand, $L_2$, is the benzothioazepine moiety linked to X via the hydroxyl function of the phenolic ring Method A Step 1

A mixture of NaH (1.1 mmol) and DMF (1 mL) is prepared under an inert atmosphere in a flask equipped with a stirring bar and a drying tube. To this is added a solution of the linker molecule 1-hydroxymethyl-4-benzyloxybenzene (1 mmol) in dry DMF (5 mL) and the resulting mixture is stirred for 1 hour. Then a solution of the N-BOC-1,4-dihydropyridine [(see FIG. 12) structure 21, where PG is t-butyloxycarbonyl (BOC); $R^6$ and $R^8$ are methyl; $R^7$ is ethyl; $R^9$ is 2-Cl; and $R^{10}$ is H] (1 mmol) in dry DMF (2 mL) is added. The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound is obtained by purification of the crude product by use of HPLC.

Step 2

Ammonium formate (96 mg, 1.5 mmol) and 10% Pd—C (50 mg) are added to a solution of the compound obtained in the preceding reaction in methanol (3 mL) and THF (2 mL). The mixture is stirred at room temperature and the progress of the reaction is monitored by tlc. After reaction is complete, the mixture is filtered through Celite, the filter pad is rinsed with EtOAc, the combined organic layers are washed successively with aq. $NaHCO_3$ and with half-saturated brine, then filtered and concentrated under reduced pressure to give the crude product. The desired compound [(see FIG. 12 and 16) structure 47, where PG is t-butyloxycarbonyl (BOC); $R^6$ and $R^8$ are methyl; $R^7$ is ethyl; $R^9$ is 2-Cl; and $R^{10}$ is H] is obtained by purification of the crude product with the use of HPLC.

Step 3

Diethyl azodicarboxylate (1 mmol) is added dropwise via a syringe to a stirred solution of triphenylphosphine (1 mmol) in THF (5 mL) at room temperature. To this is added a solution of the compound obtained in the preceding reaction (structure 47, where PG is t-butyloxycarbonyl (BOC); $R^6$ and $R^8$ are methyl; $R^7$ is ethyl; $R^9$ is 2-Cl; and $R^{10}$ is H) (1 mmol) and the benzothiazepine [structure 78, where $R^{11}$ is 2-(N,N-dimethylamino)ethyl; $R^{12}$ is OAc; and $R^{14}$ is H] (1 mmol) in THF (3 mL). The resulting solution is stirred at RT and the progress of the reaction is followed by tlc. After reaction occurs, solvent is removed by evaporation under reduced pressure and the residue is purified by HPLC, giving the desired compound.

Step 4

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I [structure 69, where $R^6$ and $R^8$ are methyl; $R^7$ is ethyl; $R^9$ is 2-Cl; $R^{10}$ and $R^{14}$ are H: $R^{11}$ is 2-(N,N-dimethylamino)ethyl; and $R^{12}$ is OAc] is obtained by purification of the crude product with the use of HPLC.

In similar manner, by replacing the 1,4dihydropyridine of the above example with other ligands of structure 47 and/or the benzothiazepine in the above example with other ligands of structure 78 and/or by replacing 1-bromomethyl-4-benzyloxybenzene with other linker molecules, other compounds of Formula I are prepared.

Method B

Step 1

A mixture of NaH (2.1 mmol) and DMF (1 mL) is prepared under an inert atmosphere in a flask equipped with a stirring bar and a drying tube. To this is added a solution of the linker molecule 1-hydroxymethyl-4-benzyloxybenzene (1 mmol) in dry DMF (5 mL) and the resulting mixture is stirred for 1 hour. Then a solution of the 1,4-dihydropyridine [(see FIG. 12) structure 21, where PG is H; $R^6$ and $R^8$ are methyl; $R^7$ is ethyl; $R^9$ is 2-Cl; and $R^{10}$ is H] (1 mmol) in dry DMF (2 mL) is added. The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound is obtained by purification of the crude product by use of HPLC.

Step 2

Ammonium formate (96 mg, 1.5 mmol) and 10% Pd—C (50 mg) are added to a solution of the compound obtained in the preceding reaction in methanol (3 mL) and THF (2 mL). The mixture is stirred at room temperature and the progress of the reaction is monitored by tlc. After reaction is complete, the mixture is filtered through Celite, the filter pad is rinsed with EtOAc, the combined organic layers are washed successively with aq. $NaHCO_3$ and with half-saturated brine, then filtered and concentrated under reduced pressure to give the crude product. The desired compound [(see FIGS. 12 and 16) structure 47, where PG is H; $R^6$ and $R^8$ are methyl; $R^7$ is ethyl; $R^9$ is 2-Cl; and $R^{10}$ is H] is obtained by purification of the crude product with the use of HPLC.

Step 3

Diethyl azodicarboxylate (1 mmol) is added dropwise via a syringe to a stirred solution of triphenylphosphine (1 mmol) in THF (5 mL) at room temperature. To this is added a solution of the compound obtained in the preceding reaction (structure 47, where PG is H; R6 and $R^8$ are methyl; $R^7$ is ethyl; $R^9$ is 2-Cl; and $R^{10}$ is H) (1 mmol) and the benzothiazepine [structure 78, where $R^{11}$ is 2-(N,N-dimethylamino)ethyl; $R^{12}$ is OAc; and $R^{14}$ is H] (1 mmol) in THF (3 mL). The resulting solution is stirred at RT and the progress of the reaction is followed by tlc. After reaction occurs, solvent is removed by evaporation under reduced pressure and the residue is purified by HPLC, giving the desired compound of Formula I [structure 69, where $R^6$ and $R^8$ are methyl; $R^7$ is ethyl; $R^9$ is 2-Cl; $R^{10}$ and $R^{14}$ are H; $R^{11}$ is 2-(N,N-dimethylamino)ethyl; and $R^{12}$ is OAc].

Example 17

See FIG. 16

Preparation of a Formula I compound wherein p is 2, q is 1, and one ligand, $L_1$, is the 1,4-dihydropyridine moiety linked via a 2-aminomethyl group to the linker, X, and the second ligand, $L_2$, is the benzothioazepine moiety linked to X via the amide nitrogen of the thioazepine ring.

Method A

Step 1

A mixture of NaH (1.1 mmol) and DMF (1 mL) is prepared under an inert atmosphere in a flask equipped with a stirring bar and a drying tube. To this is first added a solution of the benzothiazepine (see FIG. 13 structure 41, where $R^{12}$ is OAc; $R^{13}$ is methyl; and $R^{14}$ is H) (1 mmol) (1 mmol) in dry DMF (3 mL) followed by the linker molecule 1-bromomethyl-4-(N-Cbz-N-methyl)aminobenzene (1 mmol) in dry DMF (1 mL). The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound is obtained by purification of the crude product by use of HPLC.

Step 2

Ammonium formate (96 mg, 1.5 mmol) and 10% Pd—C (50 mg) are added to a solution of the compound obtained in the preceding reaction in methanol (3 mL) and THF (2 mL). The mixture is stirred at room temperature and the progress of the reaction is monitored by tlc. After reaction is complete, the mixture is filtered through Celite, the filter pad is rinsed with EtOAc, the combined organic layers are washed successively with aq. $NaHCO_3$ and with half-saturated brine, then filtered and concentrated under reduced pressure to give the crude product. The desired compound [(see FIGS. 13 and 16) structure 55, where $R^{12}$ is OAc; $R^{13}$ is methyl; and $R^{14}$ is H] is obtained by purification of the crude product with the use of HPLC.

Step3

A solution of the compound (structure 55, where $R^{12}$ is OAc; $R^{13}$ is methyl; and $R^{14}$ is H) from the preceding reaction (1 mmol) and the N-BOC-1,4-dihydropyridine [structure 25 (Alker, D.; Swanson, A. G. *Tetrahedron Lett.* 1990, 31, 1479–1482), where PG is t-butyloxycarbonyl (BOC); $R^6$ and $R^8$ are methyl; $R^7$ is ethyl; $R^9$ is 2-Cl; and $R^{10}$ is H] (1 mmol) and diisopropylethylamine (0.2 mL) in DMF (3 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The organic extract solution is dried (Na$_2$SO$_4$), filtered and concentrated under reduced pressure to give the crude product. The desired compound is obtained by purification of the crude product by use of HPLC.

Step 4

A solution of the product from the preceding reaction and trifluoroacetic acid (3 mL) in CH$_2$Cl$_2$ (5 mL) is stirred at room temperature. The progress of the reaction is followed by tlc. After reaction occurs, more CH$_2$Cl$_2$ is added and the solution is washed with aqueous Na$_2$CO$_3$ and with H$_2$O. The organic layer is dried (Na$_2$SO$_4$), filtered and concentrated under reduced pressure to give the crude product. The desired compound of Formula I [structure 70, where R$^6$ and R$^8$ are methyl; R$^7$ is ethyl; R$^9$ is 2-Cl; R$^{10}$ and R$^{14}$ are H; R$^{12}$ is Oac; and R$^{13}$ is methyl] is obtained by purification of the crude product with the use of HPLC.

In similar manner, by replacing the 1,4-dihydropyridine of the above example with other ligands of structure 25 and/or the benzothiazepine in the above example with other ligands of structure 55 and/or by replacing 1-bromomethyl-4-(N-Cbz-N-methyl)aminobenzene [in step (1) of this example] with other linker molecules, other compounds of Formula I are prepared.

Method B

A solution of the compound (structure 55, where R$^{12}$ is OAc; R$^{13}$ is methyl; and R$^{14}$ is H) from the preceding reaction (1 mmol) and the 1,4-dihydropyridine [structure 25 (Alker, D.; Swanson, A. G. Tetrahedron Lett. 1990, 31, 1479–1482), where PG is H; R$^6$ and R$^8$ are methyl; R$^7$ is ethyl; R$^9$ is 2-Cl; and R$^{10}$ is H] (1 mmol) and diisopropylethylamine (0.2 mL) in DMF (3 mL) is stirred and warmed under an inert atmosphere. The progress of the reaction is followed by tlc and when reaction is complete, the solution is poured into aqueous 5% NaHCO$_3$ and the aqueous mixture is extracted with methylene chloride. The organic extract solution is dried (Na$_2$SO$_4$), filtered and concentrated under reduced pressure to give the crude product. The desired Formula I compound [structure 70, where R$^6$ and R$^8$ are methyl; R$^7$ is ethyl; R$^9$ is 2-Cl; R$^{10}$ and R$^{14}$ are H; R$^{12}$ is Oac; and R$^{13}$ is methyl] is obtained by purification of the crude product by use of HPLC.

Example 18

See FIG. 16

Preparation of a Formula I compound wherein p is 2, q is 1, and one ligand, L$_1$, is the 1,4-dihydropyridine moiety linked via a 2-hydroxymethyl group to the linker, X, and the second ligand, L$_2$, is the benzothioazepine moiety linked to X via the amide nitrogen of the thioazepine ring Method A Step 1

A solution, cooled to the temperature of an ice-water bath, containing the N-BOC-1,4-dihydropyridine (structure 47 [see example 16, method A, step 2)] where PG is BOC; R$^6$ and R$^8$ are methyl; R$^7$ is ethyl; R$^9$ is 2-Cl; and R$^{10}$ is H} (1 mmol), triphenylphosphine (1.5 mmol), and carbon tetrabromide (2 mmol) in CH$_2$Cl$_2$ (10 mL) is prepared and is stirred. The cooling bath is removed and the solution is stirred at room temperature. The progress of the reaction is followed by tlc and after reaction occurs, the solution is diluted with additional CH$_2$Cl$_2$, washed with aqueous 5% NaHCO$_3$, with water and with half-saturated brine. The organic layer is separated, dried (Na$_2$SO$_4$), filtered and concentrated under reduced pressure to give the crude product. The desired compound (structure 59 where PG is t-butyloxycarbonyl (BOC); R$^6$ and R$^8$ are methyl; R$^7$ is ethyl; R$^9$ is 2-Cl; and R$^{10}$ is H) is obtained by purification of the crude product by use of HPLC.

Step 2

A mixture of NaH (1.1 mmol) and DMF (1 mL) is prepared under an inert atmosphere in a flask equipped with a stirring bar and a drying tube. To this is added a solution of the N-BOC-1,4-dihydropyridine [structure 59, where PG is t-butyloxycarbonyl (BOC); R$^6$ and R$^8$ are methyl; R$^7$ is ethyl; R$^9$ is 2-Cl; and R$^{10}$ is H] (1 mmol) in DMF (3 mL) followed by a solution of the benzothiazepine (structure 41, where R$^{12}$ is OAc; R$^{13}$ is methyl; and R$^{14}$ is H) (1 mmol) in dry DMF (3 mL). The resulting mixture is stirred and the course of the reaction is followed by thin layer chromatography. After reaction occurs, the reaction is quenched with cold dilute aq. Na$_2$CO$_3$ and extracted with methylene chloride. The organic layer is dried (Na$_2$SO$_4$), filtered and concentrated under reduced pressure to give the crude product. The desired compound is obtained by purification of the crude product by use of HPLC.

Step 3

A solution of the product from the preceding reaction and trifluoroacetic acid (3 mL) in CH$_2$Cl$_2$ (5 mL) is stirred at room temperature. The progress of the reaction is followed by tlc. After reaction occurs, more CH$_2$Cl$_2$ is added and the solution is washed with aqueous Na$_2$CO$_3$ and with H$_2$O. The organic layer is dried (Na$_2$SO$_4$), filtered and concentrated under reduced pressure to give the crude product. The desired compound of Formula I [structure 71, where R$^6$, R$^8$ and R$^{13}$ are methyl; R$^7$ is ethyl; R$^9$ is 2-Cl; R$^{10}$ and R$^{14}$ are H; R$^{12}$ is OAc] is obtained by purification of the crude product with the use of HPLC.

In similar manner, by replacing the 1,4-dihydropyridine of the above example with other ligands of structure 59 and/or the benzothiazepine in the above example with other ligands of structure 41 and/or by replacing 1-bromomethyl-4-benzyloxybenzene [in example 16] with other linker molecules, other compounds of Formula I are prepared.

Method B

Step 1

A solution, cooled to the temperature of an ice-water bath, containing the 1,4-dihydropyridine {structure 47 [see example 16, method B, step 2] where PG is H; R$^6$ and R$^8$ are methyl; R$^7$ is ethyl; R$^9$ is 2-Cl; and R$^{10}$ is H} (1 mmol), triphenylphosphine (1.5 mmol), and carbon tetrabromide (2 mmol) in CH$_2$Cl$_2$ (10 mL) is prepared and is stirred. The cooling bath is removed and the solution is stirred at room temperature. The progress of the reaction is followed by tlc and after reaction occurs, the solution is diluted with additional CH$_2$Cl$_2$, washed with aqueous 5% NaHCO$_3$, with water and with half-saturated brine. The organic layer is separated, dried (Na$_2$SO$_4$), filtered and concentrated under reduced pressure to give the crude product. The desired compound (structure 59 where PG is H; R$^6$ and R$^8$ are methyl; R$^7$ is ethyl; R$^9$ is 2-Cl; and R$^{10}$ is H) is obtained by purification of the crude product by use of HPLC.

Step 2

A mixture of NaH (1.1 mmol) and DMF (1 mL) is prepared under an inert atmosphere in a flask equipped with a stirring bar and a drying tube. To this is added a solution of the 1,4-dihydropyridine [structure 59, where PG is H; R$^6$ and R$^8$ are methyl; R$^7$ is ethyl; R$^9$ is 2-Cl; and R$^{10}$ is H] (1 mmol) in DMF (3 mL) followed by a solution of the benzothiazepine (structure 41, where R$^{12}$ is OAc; R$^{13}$ is methyl; and R$^{14}$ is H) (1 mmol) in dry DMF (3 mL). The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound of Formula I [structure 71, where $R^6$, $R^8$, and $R^{13}$ are methyl; $R^7$ is ethyl; $R^9$ is 2-Cl; $R^{10}$ and $R^{14}$ are H; $Ra^{12}$ is OAc] is obtained by purification of the crude product by use of HPLC.

In similar manner, by replacing the 1,4-dihydropyridine of the above example with other ligands of structure 59 and/or the benzothiazepine in the above example with other ligands of structure 41 and/or by replacing 1-bromomethyl-4-benzyloxybenzene [in example 16, Method A, Part A(1.)] with other linker molecules, other compounds of Formula I are prepared.

Example 19

See FIG. 16

Preparation of a Formula I compound wherein p is 2, q is 1, and one ligand, $L_1$, is the 1,4-dihydropyridine moiety linked via the 3-carboxyl group to the linker, X, and the second ligand, $L_2$, is the benzothioazepine moiety linked toX via the amide nitrogen of the thioazepine ring.
Method A
Step 1

A solution of N-BOC-1,4-dihydropyridine (structure 36, where PG is t-butyloxycarbonyl (BOC); $R^2$, $R^6$ and $R^8$ are methyl; $R^9$ is 2-Cl; and $R^{10}$ is H] (1 mmol), the linker molecule 1-hydroxymethyl-4-bromomethylbenzene (1 mmol), and 4-dimethylaminopyridine (10 mg) in $CH_2C_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound (structure 72, where PG is t-butyloxycarbonyl (BOC); $R^2$, $R^6$ and $R^8$ are methyl; $R^9$ is 2-Cl; and $R^{10}$ is H) is obtained by purification of the crude product with the use of HPLC.
Step 2

A mixture of NaH (1.1 mmol) and DMF (1 mL) is prepared under an inert atmosphere in a flask equipped with a stirring bar and a drying tube. To this is added a solution of the benzothiazepine (structure 41, where $R^{12}$ is OAc; $R^{13}$ is methyl; and $R^{14}$ is H) (1 mmol) in dry DMF (3 mL) followed by a solution of the N-BOC-1,4-dihydropyridine [structure 72, where PG is t-butyloxycarbonyl (BOC); $R^2$, $R^6$ and $R^8$ are methyl; $R^9$ is 2-Cl; and $R^{10}$ is H] (1 mmol) in DMF (3 mL). The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound is obtained by purification of the crude product by use of HPLC.
Step 3

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I [structure 73, where $R^2$, $R^6$, $R^8$ and $R^{13}$ are methyl; $R^9$ is 2-Cl; $R^{10}$ and $R^{14}$ are H; and $R^{12}$ is OAc] is obtained by purification of the crude product with the use of HPLC.

In similar manner, by replacing the 1,4-dihydropyridine of the above example with other ligands of structure 72 and/or the benzothiazepine in the above example with other ligands of structure 41 and/or by replacing 1-hydroxymethyl-4-bromomethylbenzene with other linker molecules, other compounds of Formula I are prepared.
Method B
Step 1

A solution of 1,4-dihydropyridine (structure 36, where PG is H; $R^2$, $R^6$ and $R^8$ are methyl; $R^9$ is 2-Cl; and $R^{10}$ is H] (1 mmol), the linker molecule 1-hydroxymethyl-4-bromomethylbenzene (1 mmol), and 4-dimethylaminopyridine (10 mg) in $CH_2Cl_2$ (5 mL) is prepared under argon in a flask equipped with magnetic stirrer and a drying tube. To this solution is added dicyclohexylcarbodiimide (solid, 2.2 mmol). The progress of the reaction is followed by tlc and after reaction occurs, the reaction solution is quenched in water, aqueous sodium bicarbonate is added and the aqueous mixture is extracted with methylene chloride. The organic layer is washed with aqueous $Na_2CO_3$ and with $H_2O$, dried ($Na_2SO_4$), filtered and concentrated under reduced pressure to give the crude product. The desired compound (structure 72, where PG is H; $R^2$, $R^6$ and $R^8$ are methyl; $R^9$ is 2-Cl; and $R^{10}$ is H) is obtained by purification of the crude product with the use of HPLC.
Step 2

A mixture of NaH (1.1 mmol) and DMF (1 mL) is prepared under an inert atmosphere in a flask equipped with a stirring bar and a drying tube. To this is added a solution of the benzothiazepine (structure 41, where $R^{12}$ is OAc; $R^{13}$ is methyl; and $R^{14}$ is H) (1 mmol) in dry DMF (3 mL) followed by a solution of the dihydropyridine [structure 72, where PG is H; $R^2$, $R^6$ and $R^8$ are methyl; $R^9$ is 2-Cl; and $R^{10}$ is H] (1 mmol) in DMF (3 mL). The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired Formula I compound [structure 73, where $R^2$, $R^6$, $R^8$ and $R^{13}$ are methyl; $R^9$ is 2-Cl; $R^{10}$ and $R^{14}$ are H; and $R^{12}$ is OAc] is obtained by purification of the crude product by use of HPLC.

In similar manner, by replacing the 1,4-dihydropyridine of the above example with other ligands of structure 72 and/or the benzothiazepine in the above example with other ligands of structure 41 and/or by replacing 1-hydroxymethyl-4-bromomethylbenzene with other linker molecules, other compounds of Formula I are prepared.

Example 20

See FIG. 17

Preparation of a Formula I compound wherein p is 2, q is 7, and one ligand, $L_1$, is the 1,4-dihydropyridine moiety linked via a 6-amino group to the linker, X, and the second ligand, $L_2$, is the benzthioazepine moiety linked to X via the hydroxyl function of the phenolic ring.

Method A
Step 1

A solution, cooled to the temperature of an ice-water bath, containing the benzothioazepine {structure 52 [see example 9], where $R^{11}$ is 2-(N,N-dimethylamino)ethyl; $R^{12}$ is OAc; and $R^{14}$ is H} (1 mmol), triphenylphosphine (1.5 mmol), and carbon tetrabromide (2 mmol) in $CH_2Cl_2$ (10 mL) is prepared and is stirred. The cooling bath is removed and the solution is stirred at room temperature. The progress of the reaction is followed by tlc and after reaction occurs, the solution is diluted with additional $CH_2Cl_2$, washed with aqueous 5% $NaHCO_3$, with water and with half-saturated brine. The organic layer is separated, dried ($Na_2SO_4$), filtered and concentrated under reduced pressure to give the crude product. The desired compound [structure 66 where $R^{11}$ is 2-(N,N-dimethylamino)ethyl; $R^{12}$ is OAc; and $R^{14}$ is H] is obtained by purification of the crude product by use of HPLC.

Step 2

A solution of the compound [structure 66 where $R^{11}$ is 2-(N,N-dimethylamino)-ethyl; $R^{12}$ is OAc; and $R^{14}$ is H] (1 mmol) prepared in the preceding reaction, the N-BOC-1,4-dihydropyridine [structure 75, where PG is t-butyloxycarbonyl (BOC)] (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound is obtained by purification of the crude product by use of HPLC.

Step 3

A solution of the product from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound of Formula I [structure 76, where $R^{11}$ is 2-(N,N-dimethylamino)ethyl; $R^{12}$ is OAc; and $R^{14}$ is H] is obtained by purification of the crude product with the use of HPLC.

In similar manner, by replacing the benzothiazepine in the above example with other ligands of structure 66 and/or by replacing the linker molecule used to prepare 52 with other linker molecules, other compounds of Formula I are prepared.

Method B
Step 1

A solution, cooled to the temperature of an ice-water bath, containing the benzothioazepine {structure 52 [see example 9, method A, step 2], where $R^{11}$ is 2-(N,N-dimethylamino)ethyl; $R^{12}$ is OAc; and $R^{14}$ is H} (1 mmol), triphenylphosphine (1.5 mmol), and carbon tetrabromide (2 mmol) in $CH_2Cl_2$ (10 mL) is prepared and is stirred. The cooling bath is removed and the solution is stirred at room temperature. The progress of the reaction is followed by tlc and after reaction occurs, the solution is diluted with additional $CH_2Cl_2$, washed with aqueous 5% $NaHCO_3$, with water and with half-saturated brine. The organic layer is separated, dried ($Na_2SO_4$), filtered and concentrated under reduced pressure to give the crude product. The desired compound [structure 66 where $R^{11}$ is 2-(N,N-dimethylamino)ethyl; $R^{12}$ is OAc; and $R^{14}$ is H] is obtained by purification of the crude product by use of HPLC.

Step 2

A solution of the compound [structure 66 where $R^{10}$ is 2-(N,N-dimethylamino)ethyl; $R^{12}$ is OAc; and $R^{14}$ is H] (1 mmol) prepared in the preceding reaction, the dihydropyridine [structure 75, where PG is H] (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired Formula I compound [structure 76, where $R^{11}$ is 2-(N,N-dimethylamino)ethyl; $R^{12}$ is OAc; and $R^{14}$ is H]compound is obtained by purification of the crude product by use of HPLC.

In similar manner, by replacing the benzothiazepine in the above example with other ligands of structure 66 and/or by replacing the linker molecule used to prepare 52 with other linker molecules, other compounds of Formula I are prepared.

Example 21

See FIG. 18

Preparation of a compound in which ligand, $L_1$, is linked directly to ligand, $L_2$, where $L_1$ is the amlodipine moiety and $L_2$ is the diltiazem moiety and where R=H.

Method A
Step 1

A mixture of NaH (1.1 mmol) and DMF (1 mL) is prepared under an inert atmosphere in a flask equipped with a stirring bar and a drying tube. To this is added a solution of the benzothiazepine (structure 41 where $R^{12}$ is OAc; $R^{13}$ is methyl; and $R^{14}$ is H) (1 mmol) in dry DMF (3 mL) followed by 1,2-dibromoethane (10 mmol). The resulting mixture is stirred and the course of the reaction is followed by thin layer chromatography. After reaction occurs, the reaction is quenched with cold dilute aq. $Na_2CO_3$ and extracted with methylene chloride. The organic layer is dried ($Na_2SO_4$), filtered and concentrated under reduced pressure to give the crude product. The desired compound (structure 88) is obtained by purification of the crude product by use of HPLC.

Step 2

A solution of the compound (structure 88) (1 mmol) prepared in the preceding reaction, N-BOC-amlodipine [structure 87, where PG is t-butyloxycarbonyl (BOC)] (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound (structure 89) is obtained by purification of the crude product by use of HPLC.

Step 3

A solution of the product (structure 89) from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound (structure 90) is obtained by purification of the crude product with the use of HPLC.

Method B

A solution of the compound (structure 88) (1 mmol) prepared in the preceding reaction, amlodipine (structure 87, where PG is H) (1 mmol), and diisopropylethylamine (0.2 mL) in DMF (5 mL) is stirred and warmed under an inert atmosphere. The progress of the reaction is followed by tlc and when reaction is complete, the solution is poured into aqueous 5% $NaHCO_3$ and the aqueous mixture is extracted with methylene chloride. The organic extract solution is dried ($Na_2SO_4$), filtered and concentrated under reduced pressure to give the crude product. The desired compound (structure 90) is obtained by purification of the crude product by use of HPLC.

Example 22

See FIG. 19

Preparation of a compound in which ligand, $L_1$, is linked directly to ligand, $L_2$, where $L^1$ is the amlodipine moiety and $L_2$ is the diltiazem moiety
Method A
Step 1

A solution of compound (structure 89) (1 mmol) and paraformaldehyde (2 mmols) in methanol (4 mL) is stirred and is acidified with acetic acid to pH 6.6 (pH meter) under a nitrogen atmosphere. Sodium cyanoborohydride (1.1 mmol) is then added and stirring is continued. The course of the reaction is followed by thin layer chromatography. After reaction occurs, the reaction solution is quenched in water and the pH of the aqueous mixture is adjusted to greater than 10 with aqueous NaOH. The mixture is extracted with ether, the organic extracts are washed with half-saturated saline, dried ($Na_2SO_4$), filtered and concentrated under reduced pressure to give the crude product. The desired compound (structure 91) is obtained by purification of the crude product by use of HPLC.
Step 2

A solution of the product (structure 91) from the preceding reaction and trifluoroacetic acid (3 mL) in $CH_2Cl_2$ (5 mL) is stirred at room temperature. The progress of the reaction is followed by tlc. After reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired compound (structure 92) is obtained by purification of the crude product with the use of HPLC.
Method B
Step 1

A solution of the compound (structure 89) (1 mmol) and paraformaldehyde (5 mmol) in ethanol (5 mL) is stirred with 10% Pd—C (20 mg) under a hydrogen atmosphere. The progress of the reaction is followed by tlc. After reaction occurs, the mixture is filtered through Celite, the filter pad is washed with ethanol, and the filtrates are concentrated under reduced pressure. The desired compound (structure 91) is obtained by purification of the crude product with the use of HPLC and is converted to structure 92 as described above in Method A.
(Method C)

A solution of the compound (structure 89) (1 mmol) in ether (5 mL) is added slowly to a vigorously stirred mixture of a solution methyl iodide (1 mmol) in ether (5 mL) and a solution of $Na_2CO_3$ in $H_2O$ (1 mL). The progress of the reaction is followed by tlc. After reaction is complete, the mixture is washed with additional aqueous $Na_2CO_3$ and with $H_2O$, the organic layer is dried ($Na_2SO_4$), filtered and concentrated under reduced pressure to give the crude product. The desired compound (structure 91) is obtained by purification of the crude product with the use of HPLC. The compound (structure 91) is converted to structure 92 as described above in Method A.
(Method D)

A solution of the compound (structure 90) (1 mmol) and paraformaldehyde (5 mmol) in ethanol (5 mL) is stirred with 10% Pd—C (20 mg) under a hydrogen atmosphere. The progress of the reaction is followed by tlc. After reaction occurs, the mixture is filtered through Celite, the filter pad is washed with ethanol, and the filtrates are concentrated under reduced pressure. The desired compound (structure 92) is obtained by purification of the crude product with the use of HPLC.

Example 23

See FIG. 20

Preparation of a compound in which ligand, $L_1$, is linked directly to ligand, $L_2$, where $L^1$ is the amlodipine moiety and $L_2$ is the diltiazem moiety and where R=H.
Step 1

A mixture of ethanolamine (0.1 mol), di-tert-butylcarbonate (0.15 mol), dioxane (50 mL) and aq. 2 N NaOH (25 mL) is stirred at RT for 24 hr. The dioxane is removed by evaporation under reduced pressure. Water (50 mL) is added to the aqueous mixture and the mixture is extracted with $CH_2Cl_2$ (4×25 mL). The combined organic layers are dried ($Na_2SO_4$), filtered and concentrated under reduced pressure to give the crude product. Pure N-BOC-ethanolamine is obtained by purification of the crude product with the use of flash chromatography over silica gel.
Step 2 t-Butyldimethylsilyl chloride(0.4 mol) is added to a solution of N-BOC-ethanolamine (0.1 mole) and imidazole (0.1 mol) in dry pyridine (75 mL) and the resulting solution is stirred at RT. The progress of the reaction is followed by tlc. When reaction is complete, water (5 mL) is added to the solution which is then concentrated by evaporation under reduced pressure (>25 mm Hg, 30° C.). The residue is dissolved in EtOAc and the solution is extracted with saturated aq. $CuSO_4$ to remove residual pyridine. The EtOAc solution is washed with water, dried ($Na_2SO_4$), filtered and concentrated under reduced pressure to give the crude product. The pure product, N-BOC-ethanolamine-O-TBDMS, is obtained by purification of the crude product by flash chromatography over silica gel.
Step 3

A solution of N-BOC-ethanolamine-O-TBDMS (0.05 mol) in dry DMF (3 mL) is added dropwise to a stirred mixture of NaH (0.05 mol) and dry DMF (10 mL) under an inert atmosphere. The resulting mixture is stirred for 1 hr and then is tranferred by cannulation to a stirred solution of 1,2-dibromoethane (0.3 mol) in dry DMF (10 mL). The resulting solution is stirred and the progress of the reaction is followed by tlc. After reaction occurs, the reaction solution is quenched with aqueous 5% $NaHCO_3$ (100 mL) and brine (100 mL). The mixture is extracted with $CH_2Cl_2$ (4×25 mL) and the combined organic extracts are back-washed with water (3×). The organic layer is dried ($Na_2SO_4$), filtered and concentrated under reduced pressure to give the crude product. Pure N-BOC-N-(2-bromoethyl) ethanolamine-O-TBDMS is obtained by purification of the crude product with the use of flash chromatography over silica gel.
Step 4

A mixture of NaH (1.1 mmol) and dry DMF (1 mL) is prepared under an inert atmosphere in a flask equipped with a stirring bar and a drying tube. To this is added a solution of the benzothiazepine (structure 41 where $R^{12}$ is OAc; $R^{13}$ is methyl; and $R^{14}$ is H) (1 mmol) in dry DMF (3 mL). Then a solution of N-BOC-N-(2-bromoethyl)ethanolamine-O-TBDMS (1 mmol) in dry DMF (2 mL) is added and the resulting mixture is stirred and monitored for reaction by tlc. After reaction occurs, the reaction solution is quenched with aqueous 5% $NaHCO_3$ (25 mL) and brine (25 mL). The mixture is extracted with $CH_2Cl_2$ (4×20 mL) and the combined organic extracts are back-washed with water (3×). The organic layer is dried ($Na_2SO_4$), filtered and concentrated under reduced pressure to give the crude product. The desired compound (structure 93) is obtained by purification of the crude product with the use of HPLC.

Step 5

A solution of the product (structure 93) (1 mmol) from the preceding reaction and $Et_3N$-$(HF)_3$ in MeCN (5 mL) is stirred at room temperature. After reaction occurs as detected by tlc, the solution is diluted with EtOAc and then washed with water-brine. The organic layer is dried ($Na_2SO_4$), filtered and concentrated under reduced pressure to give the crude product. The desired compound (structure 94) is obtained by purification of the crude product with the use of HPLC.

Step 6

A mixture of NaH (2.1 mmol) and dry DMF (1 mL) is prepared under an inert atmosphere in a flask equipped with a stirring bar and a drying tube. To this is added a solution of the compound (structure 94) prepared in the preceding reaction (1 mmol) in dry DMF (3 mL). Then a solution of the 1,4-dihydropyridine 26 (where PG=H) (1 mmol) in dry DMF (2 mL) is added and the resulting mixture is stirred and monitored for reaction by tlc. After reaction occurs, the reaction solution is quenched water (25 mL) and brine (25 mL). The mixture is extracted with $CH_2Cl_2$ (4×20 mL) and the combined organic extracts are back-washed with water (3×). The organic layer is dried ($Na_2SO_4$), filtered and concentrated under reduced pressure to give the crude product. The desired compound (structure 89, where PG=H; R=BOC) is obtained by purification of the crude product with the use of HPLC.

Step 7

A solution of the product (structure 89, PG=H; R=BOC) from the preceding reaction and trifluoroacetic acid (3 mL) in $CH_2Cl_2$ (5 mL) is stirred at room temperature. The progress of the reaction is followed by tlc. After (D reaction occurs, more $CH_2Cl_2$ is added and the solution is washed with aqueous $Na_2CO_3$ and with $H_2O$. The organic layer is dried ($Na_2SO_4$), filtered and concentrated under reduced pressure to give the crude product. The desired Formula I compound (structure 90) is obtained by purification of the crude product with the use of HPLC.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective spirit and scope of the present invention. All such modifications are intended to be within the scope of the claims appended hereto.

All of the publications, patent applications and patents cited in this application are herein incorporated by reference in their entirety to the same extent as if each individual publication, patent application or patent was specifically and individually indicated to be incorporated by reference in its entirety.

What is claimed is:

1. A compound of the formula:

L-X-L or a pharmaceutically-acceptable salt thereof;
wherein one L is a ligand of formula (vi):

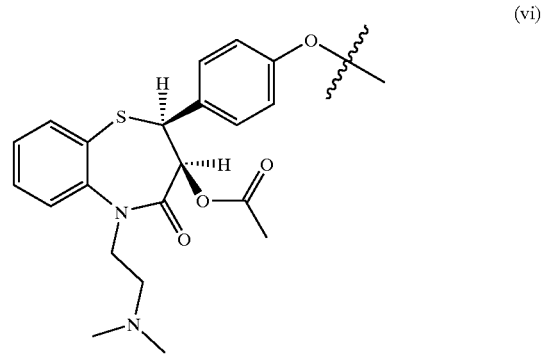

(vi)

and the other L is a ligand independently selected from the group consisting of formula (i), (ii), (iii), (iv), (v) and (vi):

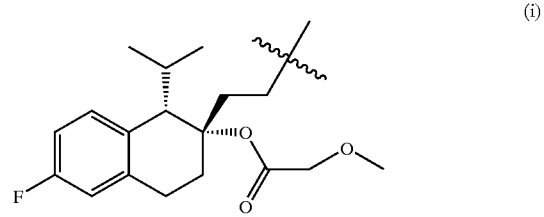

(i)

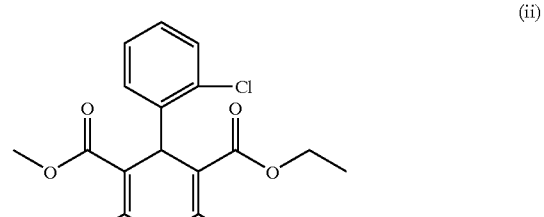

(ii)

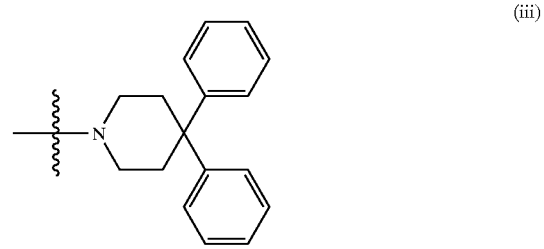

(iii)

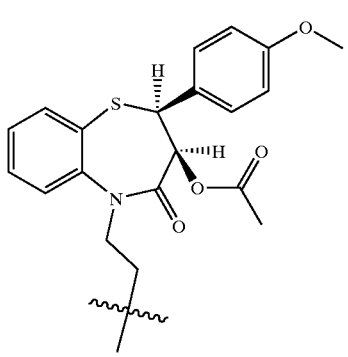

(iv)

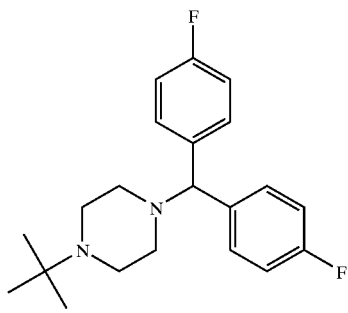

(v)

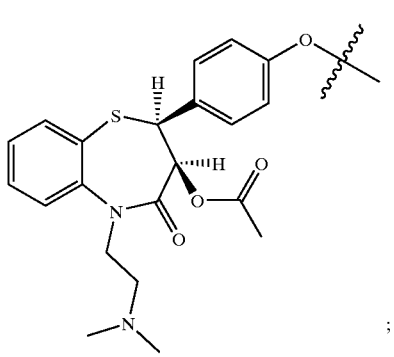

(vi)

and

X is a linker of the formula:

—X'-Z-(Y'-Z)$_m$-Y"-Z-X'— in which:

m is an integer from 0 to 20;

X' at each separate occurrence is —O—, —S—, —S(O)—, —S(O)2-, —NR—, —NRR', —C(O)—, —C(O)O—, —C(O)NH—, —C(S)—, —C(S)O—, —C(S)NH— or a covalent bond, where R and R' at each separate occurrence are as defined below for R' and R";

Z is at each separate occurrence selected from alkylene, substituted alkylene, alkylalkoxy, cycloalkylene, substituted cycloalkylene, alkenylene, substituted alkenylene, alkynylene, substituted alkynylene, cycloalkenylene, substituted cycloalkenylene, arylene, substituted arylene, heteroarylene, heterocyclene, substituted heterocyclene, crown compounds or a covalent bond;

Y' and Y" at each separate occurrence are selected from —S—S—, a covalent bond or a structure selected from the following group:

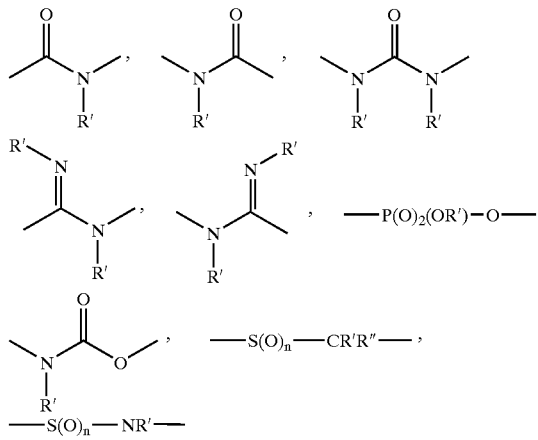

in which:

n is 0, 1 or 2; and

R' and R" at each separate occurrence are selected from hydrogen, alkyl, substituted alkyl, cycloalkyl, substituted cycloalkyl, alkenyl, substituted alkenyl, alkynyl, substituted alkynyl, aryl, heteroaryl or heterocyclic.

2. The compound according to claim 1, wherein the compound is of the following structure:

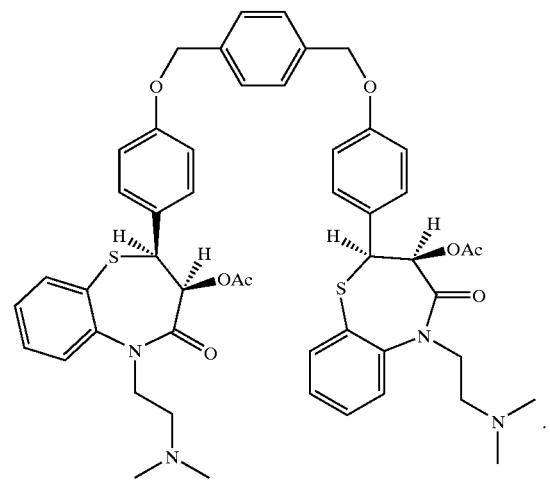

3. A pharmaceutical composition comprising a pharmaceutically acceptable excipient and a therapeutically effective amount of a compound of claim 1 or 2.

* * * * *